United States Patent
Wesche et al.

(10) Patent No.: US 11,807,692 B2
(45) Date of Patent: *Nov. 7, 2023

(54) DLL3 BINDING PROTEINS AND METHODS OF USE

(71) Applicant: Harpoon Therapeutics, Inc., South San Francisco, CA (US)

(72) Inventors: Holger Wesche, San Francisco, CA (US); Richard J. Austin, San Francisco, CA (US)

(73) Assignee: HARPOON THERAPEUTICS, INC., South San Francisco, CA (US)

( * ) Notice: Subject to any disclaimer, the term of this patent is extended or adjusted under 35 U.S.C. 154(b) by 482 days.

This patent is subject to a terminal disclaimer.

(21) Appl. No.: 16/999,773

(22) Filed: Aug. 21, 2020

(65) Prior Publication Data

US 2021/0047439 A1    Feb. 18, 2021

Related U.S. Application Data

(63) Continuation of application No. 16/583,070, filed on Sep. 25, 2019, now Pat. No. 10,815,311.

(60) Provisional application No. 62/877,227, filed on Jul. 22, 2019, provisional application No. 62/736,358, filed on Sep. 25, 2018, provisional application No. 62/736,368, filed on Sep. 25, 2018.

(51) Int. Cl.
| | |
|---|---|
| *C07K 16/28* | (2006.01) |
| *C07K 16/30* | (2006.01) |
| *A61K 39/395* | (2006.01) |
| *A61P 35/00* | (2006.01) |
| *C07K 16/46* | (2006.01) |
| *C07K 16/18* | (2006.01) |
| *A61K 39/00* | (2006.01) |

(52) U.S. Cl.
CPC ............ *C07K 16/468* (2013.01); *C07K 16/18* (2013.01); *C07K 16/2809* (2013.01); *C07K 16/30* (2013.01); *A61K 39/395* (2013.01); *A61K 2039/505* (2013.01); *A61P 35/00* (2018.01); *C07K 2317/24* (2013.01); *C07K 2317/31* (2013.01); *C07K 2317/565* (2013.01); *C07K 2317/569* (2013.01); *C07K 2317/622* (2013.01); *C07K 2317/76* (2013.01); *C07K 2317/92* (2013.01)

(58) Field of Classification Search
CPC .... C07K 16/18; C07K 16/28; C07K 16/2809; C07K 16/30; C07K 2317/24; C07K 2317/565; C07K 2317/62; C07K 2317/622; C07K 2317/73; C07K 2317/76; C07K 16/468; C07K 2317/31; C07K 2317/569; C07K 2317/22; A61K 2039/505

See application file for complete search history.

(56) References Cited

U.S. PATENT DOCUMENTS

| | | | |
|---|---|---|---|
| 4,816,567 | A | 3/1989 | Cabilly et al. |
| 4,943,533 | A | 7/1990 | Mendelsohn et al. |
| 5,061,620 | A | 10/1991 | Tsukamoto et al. |
| 5,199,942 | A | 4/1993 | Gillis |
| 5,225,539 | A | 7/1993 | Winter |
| 5,350,674 | A | 9/1994 | Boenisch et al. |
| 5,399,346 | A | 3/1995 | Anderson et al. |
| 5,530,101 | A | 6/1996 | Queen et al. |
| 5,565,332 | A | 10/1996 | Hoogenboom et al. |
| 5,580,859 | A | 12/1996 | Felgner et al. |
| 5,585,089 | A | 12/1996 | Queen et al. |
| 5,585,362 | A | 12/1996 | Wilson et al. |
| 5,589,466 | A | 12/1996 | Felgner et al. |
| 5,759,808 | A | 6/1998 | Casterman et al. |
| 5,766,886 | A | 6/1998 | Studnicka et al. |
| 5,773,292 | A | 6/1998 | Bander |
| 5,800,988 | A | 9/1998 | Casterman et al. |
| 5,811,097 | A | 9/1998 | Allison et al. |
| 5,840,526 | A | 11/1998 | Casterman et al. |
| 5,843,439 | A | 12/1998 | Anderson et al. |
| 5,844,093 | A | 12/1998 | Kettleborough et al. |
| 5,858,358 | A | 1/1999 | June et al. |
| 5,859,205 | A | 1/1999 | Adair et al. |
| 5,874,541 | A | 2/1999 | Casterman et al. |
| 5,883,223 | A | 3/1999 | Gray |

(Continued)

FOREIGN PATENT DOCUMENTS

| | | |
|---|---|---|
| CA | 2992797 A1 | 2/2017 |
| CA | 2994579 A1 | 2/2017 |

(Continued)

OTHER PUBLICATIONS

Muyldermans et al., Annu. Rev. Biochem., 82:775-97, 2013.*

(Continued)

*Primary Examiner* — Hong Sang
(74) *Attorney, Agent, or Firm* — WILSON SONSINI GOODRICH & ROSATI

(57) ABSTRACT

Provided herein are DLL3 binding proteins and DLL3 targeting multispecific proteins (e.g., DLL3 targeting trispecific protein) comprising a domain binding to CD3, a half-life extension domain, and a domain binding to DLL3 (such as a DLL3 binding protein as provided herein). Also provided are pharmaceutical compositions thereof, as well as nucleic acids, recombinant expression vectors and host cells for making such DLL3 binding proteins, DLL3 targeting trispecific proteins. Also disclosed are methods of using the disclosed DLL3 binding proteins, DLL3 targeting trispecific proteins in the prevention, and/or treatment diseases, conditions and disorders.

20 Claims, 64 Drawing Sheets

Specification includes a Sequence Listing.

(56) References Cited

U.S. PATENT DOCUMENTS

| | | | |
|---|---|---|---|
| 5,977,318 A | 11/1999 | Linsley et al. | |
| 6,005,079 A | 12/1999 | Casterman et al. | |
| 6,015,695 A | 1/2000 | Casterman et al. | |
| 6,051,227 A | 4/2000 | Allison et al. | |
| 6,107,090 A | 8/2000 | Bander | |
| 6,120,766 A | 9/2000 | Hale et al. | |
| 6,136,311 A | 10/2000 | Bander | |
| 6,210,669 B1 | 4/2001 | Aruffo et al. | |
| 6,303,121 B1 | 10/2001 | Kwon | |
| 6,326,193 B1 | 12/2001 | Liu et al. | |
| 6,331,415 B1 | 12/2001 | Cabilly et al. | |
| 6,352,694 B1 | 3/2002 | June et al. | |
| 6,355,476 B1 | 3/2002 | Kwon et al. | |
| 6,362,325 B1 | 3/2002 | Kwon | |
| 6,407,213 B1 | 6/2002 | Carter et al. | |
| 6,534,055 B1 | 3/2003 | June et al. | |
| 6,548,640 B1 | 4/2003 | Winter | |
| 6,569,997 B1 | 5/2003 | Kwon | |
| 6,670,453 B2 | 12/2003 | Frenken et al. | |
| 6,682,736 B1 | 1/2004 | Hanson et al. | |
| 6,692,964 B1 | 2/2004 | June et al. | |
| 6,759,518 B1 | 7/2004 | Kontermann et al. | |
| 6,767,711 B2 | 7/2004 | Bander | |
| 6,797,514 B2 | 9/2004 | Berenson et al. | |
| 6,808,710 B1 | 10/2004 | Wood et al. | |
| 6,867,041 B2 | 3/2005 | Berenson et al. | |
| 6,887,466 B2 | 5/2005 | June et al. | |
| 6,887,673 B2 | 5/2005 | Kunkel et al. | |
| 6,905,680 B2 | 6/2005 | June et al. | |
| 6,905,681 B1 | 6/2005 | June et al. | |
| 6,905,685 B2 | 6/2005 | Kwon | |
| 6,905,874 B2 | 6/2005 | Berenson et al. | |
| 6,974,863 B2 | 12/2005 | Kwon | |
| 6,984,720 B1 | 1/2006 | Korman et al. | |
| 7,034,121 B2 | 4/2006 | Carreno et al. | |
| 7,060,808 B1 | 6/2006 | Goldstein et al. | |
| 7,067,318 B2 | 6/2006 | June et al. | |
| 7,144,575 B2 | 12/2006 | June et al. | |
| 7,163,680 B2 | 1/2007 | Bander | |
| 7,172,869 B2 | 2/2007 | June et al. | |
| 7,175,843 B2 | 2/2007 | June et al. | |
| 7,214,493 B2 | 5/2007 | Kunkel et al. | |
| 7,232,566 B2 | 6/2007 | June et al. | |
| 7,247,301 B2 | 7/2007 | van de Winkel et al. | |
| 7,262,276 B2 | 8/2007 | Huang et al. | |
| 7,288,638 B2 | 10/2007 | Jure-Kunkel et al. | |
| 7,488,802 B2 | 2/2009 | Collins et al. | |
| 7,595,378 B2 | 9/2009 | van de Winkel et al. | |
| 7,605,238 B2 | 10/2009 | Korman et al. | |
| 7,666,414 B2 | 2/2010 | Bander | |
| 7,723,484 B2 | 5/2010 | Beidler et al. | |
| 7,807,162 B2 | 10/2010 | Silence | |
| 7,812,135 B2 | 10/2010 | Smith et al. | |
| 7,850,971 B2 | 12/2010 | Maddon et al. | |
| 7,939,072 B2 | 5/2011 | Yarden et al. | |
| 7,943,743 B2 | 5/2011 | Korman et al. | |
| 8,008,449 B2 | 8/2011 | Korman et al. | |
| 8,114,965 B2 | 2/2012 | Maddon et al. | |
| 8,153,768 B2 | 4/2012 | Kunz et al. | |
| 8,168,757 B2 | 5/2012 | Finnefrock et al. | |
| 8,188,223 B2 | 5/2012 | Beirnaert et al. | |
| 8,236,308 B2 | 8/2012 | Kischel et al. | |
| 8,354,509 B2 | 1/2013 | Carven et al. | |
| 8,388,967 B2 | 3/2013 | Smith et al. | |
| 8,470,330 B2 | 6/2013 | Schuelke et al. | |
| 8,552,156 B2 | 10/2013 | Takayanagi et al. | |
| 8,609,089 B2 | 12/2013 | Langermann et al. | |
| 8,623,356 B2 | 1/2014 | Christopherson et al. | |
| 8,629,244 B2 | 1/2014 | Kolkman et al. | |
| 8,703,135 B2 | 4/2014 | Beste et al. | |
| 8,709,424 B2 | 4/2014 | Schebye et al. | |
| 8,779,105 B2 | 7/2014 | Korman et al. | |
| 8,784,821 B1 | 7/2014 | Kufer et al. | |
| 8,846,042 B2 | 9/2014 | Zhou | |
| 8,900,587 B2 | 12/2014 | Carven et al. | |
| 8,907,071 B2 | 12/2014 | Sullivan et al. | |
| 8,937,164 B2 | 1/2015 | Descamps et al. | |
| 9,126,984 B2 | 9/2015 | Crosignani et al. | |
| 9,169,316 B2 | 10/2015 | Baty et al. | |
| 9,309,327 B2 | 4/2016 | Humphreys et al. | |
| 9,327,022 B2 | 5/2016 | Zhang et al. | |
| 9,340,621 B2 | 5/2016 | Kufer et al. | |
| 9,359,442 B2 | 6/2016 | Hoffee et al. | |
| 9,422,368 B2 | 8/2016 | Spee et al. | |
| 9,624,185 B1 | 4/2017 | Xu | |
| 9,642,918 B2 | 5/2017 | Bruederle et al. | |
| 9,708,412 B2 | 7/2017 | Baeuerle et al. | |
| 9,920,115 B2 | 3/2018 | Dubridge et al. | |
| 10,066,016 B2 | 9/2018 | Dubridge et al. | |
| 10,100,106 B2 | 10/2018 | Dubridge et al. | |
| 10,428,120 B2 | 10/2019 | Kontermann et al. | |
| 10,543,271 B2 | 1/2020 | Wesche et al. | |
| 10,544,221 B2 | 1/2020 | Dubridge et al. | |
| 10,730,954 B2 | 8/2020 | Wesche et al. | |
| 11,111,311 B2 * | 9/2021 | Yoshida | A61P 35/00 |
| 11,180,563 B2 | 11/2021 | Wesche et al. | |
| 2002/0015704 A1 | 2/2002 | Bander | |
| 2002/0051780 A1 | 5/2002 | Lindhofer et al. | |
| 2002/0081296 A1 | 6/2002 | Theill et al. | |
| 2003/0031673 A1 | 2/2003 | Bander | |
| 2003/0092892 A1 | 5/2003 | Frenken et al. | |
| 2004/0101519 A1 | 5/2004 | June et al. | |
| 2005/0042664 A1 | 2/2005 | Wu et al. | |
| 2005/0048617 A1 | 3/2005 | Wu et al. | |
| 2005/0095244 A1 | 5/2005 | Jure-Kunkel et al. | |
| 2005/0100543 A1 | 5/2005 | Hansen et al. | |
| 2005/0175606 A1 | 8/2005 | Huang et al. | |
| 2006/0034810 A1 | 2/2006 | Riley et al. | |
| 2006/0046971 A1 | 3/2006 | Stuhler et al. | |
| 2006/0121005 A1 | 6/2006 | Berenson et al. | |
| 2006/0228364 A1 | 10/2006 | Dennis et al. | |
| 2006/0252096 A1 | 11/2006 | Zha et al. | |
| 2007/0014794 A1 | 1/2007 | Carter et al. | |
| 2007/0178082 A1 | 8/2007 | Silence et al. | |
| 2007/0269422 A1 | 11/2007 | Beirnaert et al. | |
| 2008/0069772 A1 | 3/2008 | Stuhler et al. | |
| 2008/0260757 A1 | 10/2008 | Holt et al. | |
| 2009/0028880 A1 | 1/2009 | Beirnaert et al. | |
| 2009/0041789 A1 | 2/2009 | Elsaesser-Beile et al. | |
| 2009/0117108 A1 | 5/2009 | Wang et al. | |
| 2009/0136494 A1 | 5/2009 | Ponath et al. | |
| 2009/0252683 A1 | 10/2009 | Kischel et al. | |
| 2009/0259026 A1 | 10/2009 | Tomlinson et al. | |
| 2010/0022452 A1 | 1/2010 | Silence | |
| 2010/0028330 A1 | 2/2010 | Collins et al. | |
| 2010/0122358 A1 | 5/2010 | Brueggemann et al. | |
| 2010/0150918 A1 | 6/2010 | Kufer et al. | |
| 2010/0166734 A1 | 7/2010 | Dolk | |
| 2010/0189651 A1 | 7/2010 | Stagliano et al. | |
| 2010/0189727 A1 | 7/2010 | Rodeck et al. | |
| 2010/0266531 A1 | 10/2010 | Hsieh et al. | |
| 2010/0291112 A1 | 11/2010 | Kellner et al. | |
| 2010/0311119 A1 | 12/2010 | Hermans et al. | |
| 2011/0129458 A1 | 6/2011 | Dolk et al. | |
| 2011/0150892 A1 | 6/2011 | Thudium et al. | |
| 2011/0165621 A1 | 7/2011 | Dreier et al. | |
| 2011/0262439 A1 | 10/2011 | Kufer et al. | |
| 2011/0275787 A1 | 11/2011 | Kufer et al. | |
| 2011/0313135 A1 | 12/2011 | Vanhove et al. | |
| 2012/0039899 A1 | 2/2012 | Olsen et al. | |
| 2012/0039906 A1 | 2/2012 | Olive | |
| 2012/0114649 A1 | 5/2012 | Langermann et al. | |
| 2012/0231024 A1 | 9/2012 | Elsaesser-Beile et al. | |
| 2012/0237977 A1 | 9/2012 | Daugherty et al. | |
| 2012/0263677 A1 | 10/2012 | Eagle et al. | |
| 2012/0328619 A1 | 12/2012 | Fey et al. | |
| 2013/0017199 A1 | 1/2013 | Langermann | |
| 2013/0017200 A1 | 1/2013 | Scheer et al. | |
| 2013/0136744 A1 | 5/2013 | Bouche et al. | |
| 2013/0183321 A1 | 7/2013 | Smith et al. | |
| 2013/0197201 A1 | 8/2013 | Vasquez et al. | |
| 2013/0266568 A1 | 10/2013 | Brinkmann et al. | |
| 2013/0267686 A1 | 10/2013 | Brinkmann et al. | |
| 2013/0273055 A1 | 10/2013 | Borges et al. | |

(56) References Cited

U.S. PATENT DOCUMENTS

| | | |
|---|---|---|
| 2013/0330335 A1 | 12/2013 | Bremel et al. |
| 2014/0004121 A1 | 1/2014 | Fanslow, III et al. |
| 2014/0004575 A1 | 1/2014 | Ito et al. |
| 2014/0023664 A1 | 1/2014 | Lowman et al. |
| 2014/0044728 A1 | 2/2014 | Takayanagi et al. |
| 2014/0045195 A1 | 2/2014 | Daugherty et al. |
| 2014/0065152 A1 | 3/2014 | Kwon |
| 2014/0072565 A1 | 3/2014 | Kwon |
| 2014/0072566 A1 | 3/2014 | Kwon |
| 2014/0073767 A1 | 3/2014 | Lee et al. |
| 2014/0088295 A1 | 3/2014 | Smith et al. |
| 2014/0093511 A1 | 4/2014 | Lonberg et al. |
| 2014/0161828 A1 | 6/2014 | Armitage et al. |
| 2014/0205601 A1 | 7/2014 | Beirnaert et al. |
| 2014/0220002 A1 | 8/2014 | Ponte et al. |
| 2014/0242075 A1 | 8/2014 | Parren et al. |
| 2014/0302037 A1 | 10/2014 | Borges et al. |
| 2014/0322218 A1 | 10/2014 | Xiao et al. |
| 2014/0348841 A1 | 11/2014 | Schebye et al. |
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |
| 2015/0079109 A1 | 3/2015 | Li et al. |
| 2015/0093336 A1 | 4/2015 | Van Ginderachter et al. |
| 2015/0174268 A1 | 6/2015 | Li et al. |
| 2015/0183875 A1 | 7/2015 | Cobbold et al. |
| 2015/0225367 A1 | 8/2015 | Crosignani et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2016/0017058 A1 | 1/2016 | Kim et al. |
| 2016/0024174 A1 | 1/2016 | Odunsi et al. |
| 2016/0032011 A1 | 2/2016 | Zhang et al. |
| 2016/0032019 A1 | 2/2016 | Xiao et al. |
| 2016/0039942 A1 | 2/2016 | Cobbold et al. |
| 2016/0046724 A1 | 2/2016 | Brogdon et al. |
| 2016/0068605 A1 | 3/2016 | Nemeth et al. |
| 2016/0115241 A1 | 4/2016 | Yan et al. |
| 2016/0130331 A1 | 5/2016 | Stull et al. |
| 2016/0185875 A1 | 6/2016 | Cheng et al. |
| 2016/0194399 A1 | 7/2016 | Irving et al. |
| 2016/0215063 A1 | 7/2016 | Bernett et al. |
| 2016/0229913 A1 | 8/2016 | Bosques et al. |
| 2016/0251438 A1 | 9/2016 | Lucas et al. |
| 2016/0251440 A1 | 9/2016 | Roobrouck et al. |
| 2016/0257721 A1 | 9/2016 | Lieber et al. |
| 2016/0263087 A1 | 9/2016 | Crosignani et al. |
| 2016/0319040 A1 | 11/2016 | Dreier et al. |
| 2016/0340444 A1 | 11/2016 | Baeuerle et al. |
| 2016/0355842 A1 | 12/2016 | Parks et al. |
| 2017/0029502 A1 | 2/2017 | Raum et al. |
| 2017/0037130 A1 | 2/2017 | Raum et al. |
| 2017/0037149 A1 | 2/2017 | Raum et al. |
| 2017/0051068 A1 | 2/2017 | Pillarisetti et al. |
| 2017/0152316 A1 | 6/2017 | Cobbold et al. |
| 2017/0158771 A1 | 6/2017 | Glennie et al. |
| 2017/0204164 A1 | 7/2017 | Himmler et al. |
| 2017/0274094 A1 | 9/2017 | Stull et al. |
| 2017/0275373 A1 | 9/2017 | Kufer et al. |
| 2017/0298149 A1 | 10/2017 | Baeuerle et al. |
| 2017/0306014 A1 | 10/2017 | Cornen et al. |
| 2017/0334979 A1 | 11/2017 | Dubridge et al. |
| 2017/0334997 A1 | 11/2017 | Dubridge et al. |
| 2017/0349660 A1 | 12/2017 | Saville et al. |
| 2017/0362310 A1 | 12/2017 | Shoemaker |
| 2017/0369563 A1 | 12/2017 | Dubridge et al. |
| 2018/0016323 A1 | 1/2018 | Brandenburg et al. |
| 2018/0036306 A1 | 2/2018 | Jones et al. |
| 2018/0134789 A1 | 5/2018 | Baeuerle et al. |
| 2018/0148508 A1 | 5/2018 | Wang et al. |
| 2018/0161428 A1 | 6/2018 | Dubridge et al. |
| 2018/0162949 A1 | 6/2018 | Baeuerle et al. |
| 2018/0327511 A1 | 11/2018 | Satoh et al. |
| 2018/0346601 A1 | 12/2018 | Dettling et al. |
| 2019/0016811 A1 | 1/2019 | Lucas et al. |
| 2019/0023786 A1 | 1/2019 | Broderick et al. |
| 2019/0031749 A1 | 1/2019 | Dubridge et al. |
| 2019/0062427 A1 | 2/2019 | Rosenthal et al. |
| 2019/0092862 A1 | 3/2019 | Cui et al. |
| 2019/0112381 A1 | 4/2019 | Wesche et al. |
| 2019/0127483 A1 | 5/2019 | Li |
| 2019/0135930 A1 | 5/2019 | Wesche et al. |
| 2019/0225702 A1 | 7/2019 | Baeuerle et al. |
| 2020/0095340 A1 | 3/2020 | Wesche et al. |
| 2020/0115461 A1 | 4/2020 | Evnin et al. |
| 2020/0148771 A1 | 5/2020 | Paeuerle et al. |
| 2020/0155520 A1 | 5/2020 | Colburn et al. |
| 2020/0231672 A1 | 7/2020 | Dubridge et al. |
| 2020/0270362 A1 | 8/2020 | Wesche et al. |
| 2020/0289646 A1 | 9/2020 | Wesche et al. |
| 2020/0352998 A1 | 11/2020 | Albertson et al. |
| 2021/0171649 A1 | 6/2021 | Wesche et al. |
| 2021/0179735 A1 | 6/2021 | Baeuerle et al. |
| 2021/0269530 A1 | 9/2021 | Lin et al. |
| 2021/0284728 A1 | 9/2021 | Lin et al. |
| 2021/0292421 A1 | 9/2021 | Lin et al. |
| 2021/0355219 A1 | 11/2021 | Lin et al. |
| 2022/0017626 A1 | 1/2022 | Wesche et al. |
| 2022/0054544 A1 | 2/2022 | Lin et al. |
| 2022/0098311 A1 | 3/2022 | Wesche et al. |
| 2022/0112297 A1 | 4/2022 | Wesche et al. |
| 2022/0267462 A1 | 8/2022 | Wesche et al. |
| 2023/0257451 A1 | 8/2023 | Dubridge et al. |

FOREIGN PATENT DOCUMENTS

| | | |
|---|---|---|
| CN | 1563092 A | 1/2005 |
| CN | 101646689 A | 2/2010 |
| CN | 101809035 A | 8/2010 |
| CN | 105968201 A | 9/2016 |
| CN | 105968204 A | 9/2016 |
| CN | 108026174 A | 5/2018 |
| CN | 109593786 A | 4/2019 |
| EP | 0239400 A2 | 9/1987 |
| EP | 0519596 A1 | 12/1992 |
| EP | 0592106 A1 | 4/1994 |
| EP | 1378520 A1 | 1/2004 |
| EP | 1736484 A1 | 12/2006 |
| EP | 2336179 A1 | 6/2011 |
| EP | 2581113 A1 | 4/2013 |
| EP | 3146979 A1 | 3/2017 |
| EP | 3193929 B1 | 6/2019 |
| FR | 901228 A | 7/1945 |
| JP | 2005501517 A | 1/2005 |
| JP | 2005518789 A | 6/2005 |
| JP | 2007535915 A | 12/2007 |
| JP | 2008278814 A | 11/2008 |
| JP | 2015501135 A | 1/2015 |
| JP | 2015528003 A | 9/2015 |
| JP | 2016500655 A | 1/2016 |
| JP | 2019052750 A | 4/2019 |
| WO | WO-9109967 A1 | 7/1991 |
| WO | WO-9307105 A1 | 4/1993 |
| WO | WO-9404678 A1 | 3/1994 |
| WO | WO-9937681 A2 | 7/1999 |
| WO | WO-0043507 A1 | 7/2000 |
| WO | WO-0130381 A2 | 5/2001 |
| WO | WO-0190190 A2 | 11/2001 |
| WO | WO-0196584 A2 | 12/2001 |
| WO | WO-02055082 A1 | 7/2002 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004035607 A2 | 4/2004 |
| WO | WO-2004041867 A2 | 5/2004 |
| WO | WO-2004042404 A1 | 5/2004 |
| WO | WO-2004049794 A2 | 6/2004 |
| WO | WO-2004056312 A2 | 7/2004 |
| WO | WO-2004099249 A2 | 11/2004 |
| WO | WO-2005003168 A2 | 1/2005 |

(56) References Cited

FOREIGN PATENT DOCUMENTS

| | | |
|---|---|---|
| WO | WO-2005009465 A1 | 2/2005 |
| WO | WO-2005040220 A1 | 5/2005 |
| WO | WO-2005095456 A1 | 10/2005 |
| WO | WO-2006020258 A2 | 2/2006 |
| WO | WO-2006072625 A2 | 7/2006 |
| WO | WO-2006072626 A1 | 7/2006 |
| WO | WO-2006105021 A2 | 10/2006 |
| WO | WO-2006121168 A1 | 11/2006 |
| WO | WO-2006122786 A2 | 11/2006 |
| WO | WO-2006122787 A1 | 11/2006 |
| WO | WO-2007005874 A2 | 1/2007 |
| WO | WO-2007024715 A2 | 3/2007 |
| WO | WO-2007042261 A2 | 4/2007 |
| WO | WO-2007042573 A2 | 4/2007 |
| WO | WO-2007062466 A1 | 6/2007 |
| WO | WO-2007113648 A2 | 10/2007 |
| WO | WO-2007115230 A2 | 10/2007 |
| WO | WO-2008028977 A2 | 3/2008 |
| WO | WO-2008084106 A1 | 7/2008 |
| WO | WO-2009009116 A2 | 1/2009 |
| WO | WO-2009025846 A2 | 2/2009 |
| WO | WO-2009030285 A1 | 3/2009 |
| WO | WO-2009035577 A1 | 3/2009 |
| WO | WO-2009101611 A1 | 8/2009 |
| WO | WO-2009114335 A2 | 9/2009 |
| WO | WO-2009147248 A2 | 12/2009 |
| WO | WO-2010003118 A1 | 1/2010 |
| WO | WO-2010012557 A1 | 2/2010 |
| WO | WO-2010019570 A2 | 2/2010 |
| WO | WO-2010027827 A2 | 3/2010 |
| WO | WO-2010037836 A2 | 4/2010 |
| WO | WO-2010037837 A2 | 4/2010 |
| WO | WO-2010065939 A1 | 6/2010 |
| WO | WO-2010077634 A1 | 7/2010 |
| WO | WO-2010081173 A2 | 7/2010 |
| WO | WO-2011028683 A1 | 3/2011 |
| WO | WO-2011039368 A2 | 4/2011 |
| WO | WO-2011051327 A2 | 5/2011 |
| WO | WO-2011066342 A2 | 6/2011 |
| WO | WO-2011070024 A1 | 6/2011 |
| WO | WO-2011107553 A1 | 9/2011 |
| WO | WO-2011117423 A1 | 9/2011 |
| WO | WO-2011131407 A1 | 10/2011 |
| WO | WO-2011140249 A2 | 11/2011 |
| WO | WO-2011155607 A1 | 12/2011 |
| WO | WO-2012071411 A2 | 5/2012 |
| WO | WO-2012122444 A1 | 9/2012 |
| WO | WO-2012131053 A1 | 10/2012 |
| WO | WO-2012138475 A1 | 10/2012 |
| WO | WO-2012145493 A1 | 10/2012 |
| WO | WO-2012158818 A2 | 11/2012 |
| WO | WO-2012160448 A2 | 11/2012 |
| WO | WO-2012163805 A1 | 12/2012 |
| WO | WO-2012175400 A1 | 12/2012 |
| WO | WO-2013006490 A2 | 1/2013 |
| WO | WO-2013036130 A1 | 3/2013 |
| WO | WO-2013039954 A1 | 3/2013 |
| WO | WO-2013072406 A1 | 5/2013 |
| WO | WO-2013072415 A1 | 5/2013 |
| WO | WO-2013079174 A1 | 6/2013 |
| WO | WO-2013087699 A1 | 6/2013 |
| WO | WO-2013104804 A2 | 7/2013 |
| WO | WO-2013110531 A1 | 8/2013 |
| WO | WO-2013119716 A1 | 8/2013 |
| WO | WO-2013126712 A1 | 8/2013 |
| WO | WO-2013128027 A1 | 9/2013 |
| WO | WO-2013128194 A1 | 9/2013 |
| WO | WO-2013132044 A1 | 9/2013 |
| WO | WO-2013158856 A2 | 10/2013 |
| WO | WO-2013169264 A1 | 11/2013 |
| WO | WO-2013173223 A1 | 11/2013 |
| WO | WO-2014008218 A1 | 1/2014 |
| WO | WO-2014012085 A2 | 1/2014 |
| WO | WO-2014033304 A2 | 3/2014 |
| WO | WO-2014036357 A1 | 3/2014 |
| WO | WO-2014047231 A1 | 3/2014 |
| WO | WO-2014052064 A1 | 4/2014 |
| WO | WO-2014055648 A1 | 4/2014 |
| WO | WO-2014094122 A1 | 6/2014 |
| WO | WO-2014125273 A1 | 8/2014 |
| WO | WO-2014132072 A1 | 9/2014 |
| WO | WO-2014138306 A1 | 9/2014 |
| WO | WO-2014140358 A1 | 9/2014 |
| WO | WO-2014144689 A1 | 9/2014 |
| WO | WO-2014151910 A1 | 9/2014 |
| WO | WO-2014153270 A1 | 9/2014 |
| WO | WO-2015026684 A1 | 2/2015 |
| WO | WO-2015031667 A2 | 3/2015 |
| WO | WO-2015042246 A1 | 3/2015 |
| WO | WO-2015082499 A2 | 6/2015 |
| WO | WO-2015103072 A1 | 7/2015 |
| WO | WO-2015121812 A1 | 8/2015 |
| WO | WO-2015140717 A1 | 9/2015 |
| WO | WO-2015142675 A2 | 9/2015 |
| WO | WO-2015146437 A1 | 10/2015 |
| WO | WO-2015150097 A1 | 10/2015 |
| WO | WO-2015150447 A1 | 10/2015 |
| WO | WO-2015173764 A1 | 11/2015 |
| WO | WO-2015184099 A1 | 12/2015 |
| WO | WO-2015184207 A1 | 12/2015 |
| WO | WO-2015187835 A2 | 12/2015 |
| WO | WO-2016009029 A1 | 1/2016 |
| WO | WO-2016026772 A1 | 2/2016 |
| WO | WO-2016032334 A1 | 3/2016 |
| WO | WO-2016034044 A1 | 3/2016 |
| WO | WO-2016046778 A2 | 3/2016 |
| WO | WO-2016055551 A1 | 4/2016 |
| WO | WO-2016071283 A1 | 5/2016 |
| WO | WO-2016071293 A2 | 5/2016 |
| WO | WO-2016075099 A1 | 5/2016 |
| WO | WO-2016087531 A1 | 6/2016 |
| WO | WO-2016105450 A2 | 6/2016 |
| WO | WO-2016125017 A1 | 8/2016 |
| WO | WO-2016130819 A2 | 8/2016 |
| WO | WO-2016134333 A1 | 8/2016 |
| WO | WO-2016134335 A2 | 8/2016 |
| WO | WO-2016147144 A1 | 9/2016 |
| WO | WO-2016171999 A2 | 10/2016 |
| WO | WO-2016179003 A1 | 11/2016 |
| WO | WO-2016179518 A2 | 11/2016 |
| WO | WO-2016180982 A1 | 11/2016 |
| WO | WO-2016181348 A1 | 11/2016 |
| WO | WO-2016182064 A1 | 11/2016 |
| WO | WO-2016187101 A2 | 11/2016 |
| WO | WO-2016187594 A1 | 11/2016 |
| WO | WO-2016210447 A1 | 12/2016 |
| WO | WO-2017007700 A1 | 1/2017 |
| WO | WO-2017021349 A1 | 2/2017 |
| WO | WO-2017021356 A1 | 2/2017 |
| WO | WO-2017025038 A1 | 2/2017 |
| WO | WO-2017025698 A1 | 2/2017 |
| WO | WO-2017025868 A1 | 2/2017 |
| WO | WO-2017027392 A1 | 2/2017 |
| WO | WO-2017031104 A1 | 2/2017 |
| WO | WO-2017041749 A1 | 3/2017 |
| WO | WO-2017079528 A1 | 5/2017 |
| WO | WO-2017093969 A1 | 6/2017 |
| WO | WO-2017134134 A1 | 8/2017 |
| WO | WO-2017136549 A1 | 8/2017 |
| WO | WO-2017156178 A1 | 9/2017 |
| WO | WO-2017157305 A1 | 9/2017 |
| WO | WO-2017161206 A1 | 9/2017 |
| WO | WO-2017162587 A1 | 9/2017 |
| WO | WO-2017201488 A1 | 11/2017 |
| WO | WO-2017201493 A1 | 11/2017 |
| WO | WO-2017220988 A1 | 12/2017 |
| WO | WO-2018017863 A1 | 1/2018 |
| WO | WO-2018017864 A2 | 1/2018 |
| WO | WO-2018026953 A1 | 2/2018 |
| WO | WO-2018027203 A1 | 2/2018 |
| WO | WO-2018033798 A1 | 2/2018 |
| WO | WO-2018048975 A1 | 3/2018 |
| WO | WO-2018067993 A1 | 4/2018 |
| WO | WO-2018071777 A1 | 4/2018 |

(56) References Cited

FOREIGN PATENT DOCUMENTS

| | | |
|---|---|---|
| WO | WO-2018075359 A1 | 4/2018 |
| WO | WO-2018083204 A1 | 5/2018 |
| WO | WO-2018085469 A2 | 5/2018 |
| WO | WO-2018098354 A1 | 5/2018 |
| WO | WO-2018098356 A1 | 5/2018 |
| WO | WO-2018106529 A1 | 6/2018 |
| WO | WO-2018106588 A1 | 6/2018 |
| WO | WO-2018110555 A1 | 6/2018 |
| WO | WO-2018115859 A1 | 6/2018 |
| WO | WO-2018133877 A1 | 7/2018 |
| WO | WO-2018136725 A1 | 7/2018 |
| WO | WO-2018160671 A1 | 9/2018 |
| WO | WO-2018160754 A2 | 9/2018 |
| WO | WO-2018165619 A1 | 9/2018 |
| WO | WO-2018183366 A1 | 10/2018 |
| WO | WO-2018204717 A1 | 11/2018 |
| WO | WO-2018209298 A1 | 11/2018 |
| WO | WO-2018209304 A1 | 11/2018 |
| WO | WO-2018232020 A1 | 12/2018 |
| WO | WO-2019011852 A1 | 1/2019 |
| WO | WO-2019011855 A1 | 1/2019 |
| WO | WO-2019025983 A1 | 2/2019 |
| WO | WO-2019075359 A1 | 4/2019 |
| WO | WO-2019075378 A1 | 4/2019 |
| WO | WO-2019136305 A1 | 7/2019 |
| WO | WO-2019222278 A1 | 11/2019 |
| WO | WO-2019222282 A1 | 11/2019 |
| WO | WO-2019222283 A1 | 11/2019 |
| WO | WO-2019229701 A2 | 12/2019 |
| WO | WO-2019246004 A1 | 12/2019 |
| WO | WO-2020053263 A1 | 3/2020 |
| WO | WO-2020060593 A1 | 3/2020 |
| WO | WO-2020061482 A1 | 3/2020 |
| WO | WO-2020061526 A1 | 3/2020 |
| WO | WO-2020069028 A1 | 4/2020 |
| WO | WO-2020092792 A2 | 5/2020 |
| WO | WO-2020097403 A1 | 5/2020 |
| WO | WO-2019166650 A9 | 8/2020 |
| WO | WO-2020181145 A1 | 9/2020 |
| WO | WO-2020232303 A1 | 11/2020 |
| WO | WO-2020252349 A1 | 12/2020 |
| WO | WO-2020261093 A1 | 12/2020 |
| WO | WO-2020263830 A1 | 12/2020 |
| WO | WO-2021097060 A1 | 5/2021 |
| WO | WO-2021168303 A1 | 8/2021 |
| WO | WO-2021231434 A1 | 11/2021 |
| WO | WO-2022031884 A2 | 2/2022 |
| WO | WO-2022032006 A2 | 2/2022 |
| WO | WO-2022098909 A1 | 5/2022 |
| WO | WO-2022212732 A1 | 10/2022 |
| WO | WO-2022256498 A1 | 12/2022 |
| WO | WO-2022256499 A2 | 12/2022 |
| WO | WO-2022256500 A2 | 12/2022 |
| WO | WO-2022272033 A2 | 12/2022 |
| WO | WO-2023064945 A2 | 4/2023 |

OTHER PUBLICATIONS

Zabetakis et al., PLOS One, 2013, 8(10), 1-7.*
Saerens et al., J Mol. Biol., 2005, 352: 597-607.*
Vincke et al., J. Biol. Chem., 2009, 284(5): 3273-3284.*
Rabia et al., Biochem Eng J 2018, 137:365-374.*
PCT/US/2020/032985 International Search Report and Written Opinion dated Oct. 15, 2020.
Co-pending U.S. Appl. No. 17/030,118, inventors Dubridge; Robert et al., filed Sep. 23, 2020.
Co-pending U.S. Appl. No. 17/072,370, inventors Baeuerle; Patrick et al., filed Oct. 16, 2020.
Balzar et al. The biology of the 17-1A antigen (Ep-CAM). J. Mol. Med. 77:699-712 (1999).
Bluemel et al. Epitope distance to the target cell membrane and antigen size determine the potency of T cell-mediated lysis by BiTE antibodies specific for a large melanoma surface antigen. Cancer Immunol Immunother 59(8):1197-209 (2010).
Chaubal et al. Ep-CAM—a marker for the detection of disseminated tumor cells in patients suffering from SCCHN. Anticancer Res 19:2237-2242 (1999).
Davé et al. Fab-dsFv: A bispecific antibody format with extended serum half-life through albumin binding. MAbs 8(7):1319-1335 (2016).
Dickopf et al. Format and geometries matter: Structure-based design defines the functionality of bispecific antibodies. Comput Struct Biotechnol J 18:1221-1227 (2020).
Eyvazi et al. Antibody Based EpCAM Targeted Therapy of Cancer, Review and Update. Curr Cancer Drug Targets. 18(9):857-868 (2018).
Gastl et al. Ep-CAM overexpression in breast cancer as a predictor of survival. Lancet. 356:1981-1982 (2000).
Goettlinger et al. The epithelial cell surface antigen 17-1A, a target for antibody-mediated tumor therapy: its biochemical nature, tissue distribution and recognition by different monoclonal antibodies. Int J Cancer. 38:47-53 (1986).
Kim et al. Strategies and 1-17 Advancement in Antibody-Drug Conjugate Optimization for Targeted Cancer Therapeutics. Biomol Ther (Seoul) 23(6):493-509 (2015).
Koprowski et al. Colorectal carcinoma antigens detected by hybridoma antibodies. Somatic Cell Genet. 5:957-971 (1979).
Lehmann et al. Stability engineering of anti-EGFR scFv antibodies by rational design of a lambda-to-kappa swap of the VL framework using a structure-guided approach. MAbs 7(6):1058-1071 (2015).
Lin et al. Improved affinity of a chicken single-chain antibody to avian infectious bronchitis virus by site-directed mutagenesis of complementarity-determining region H3. African Journal of Biotechnology 10(79):18294-18302 (2011).
Litvinov et al. Epithelial cell adhesion molecule (Ep-CAM) modulates cell-cell interactions mediated by classic cadherins. J Cell Biol. 139:1337-1348 (1997).
Litvinov et al. Expression of Ep-CAM in cervical squamous epithelia correlates with an increased proliferation and the disappearance of markers for terminal differentiation. Am. J. Pathol. 148:865-75 (1996).
Lucchi et al. The Masking Game: Design of Activatable Antibodies and Mimetics for Selective Thera-peutics Cell Control. ACS Cent Sci 7(5):724-738 (2021).
McCall et al. Isolation and characterization of an anti-CD16 single-chain Fv fragment and construction of an anti-HER2/neu/anti-CD16 bispecific scFv that triggers CD16-dependent tumor cytolysis Mol Immunol. 36(7):433-46 (1999).
McCarthy et al. Altering the fine specificity of an anti-Legionella single chain antibody by a single amino acid insertion. J Immunol Methods 251(1-2):137-49 (2001).
Osta et al. EpCAM is overexpressed in breast cancer and is a potential target for breast cancer gene therapy. Cancer Res 64:5818-24 (2004).
PCT/US2021/058108 International Search Report and Written Opinion dated Apr. 1, 2022.
Piyathilake et al. The expression of Ep-CAM (17-1A) in squamous cell cancers of the lung. Hum Pathol. 31:482-487 (2000).
Quak et al. Production of a monoclonal antibody (K 931) to a squamous cell carcinoma associated antigen identified as the 17-1A antigen. Hybridoma 9:377-387 (1990).
Roda-Navarro et al. Understanding the Spatial Topology of Artificial Immunological Synapses Assembled in T Cell-Redirecting Strategies: A Major Issue in Cancer Immunotherapy. Front Cell Dev Biol 7:370 (2020).
Simon et al. Epithelial glycoprotein is a member of a family of epithelial cell surface antigens homologous to nidogen, a matrix adhesion protein. PNAS USA 87:2755-2759 (1990).
Trail et al. Antibody drug 1-17 conjugates for treatment of breast cancer: Novel targets and diverse approaches in ADC design. Pharmacol Ther 181:126-142 (2018).
Trebak et al. Oligomeric state of the colon carcinoma-associated glycoprotein GA733-2 (Ep-CAM/EGP40) and its role in GA733-mediated homotypic cell-cell adhesion. J Biol Chem. 276:2299-2309 (2001).
U.S. Appl. No. 16/339,263 Office Action dated Jan. 11, 2022.
U.S. Appl. No. 16/339,263 Office Action dated May 3, 2022.

(56) References Cited

OTHER PUBLICATIONS

U.S. Appl. No. 16/489,523 Office Action dated Feb. 14, 2022.
U.S. Appl. No. 16/773,843 Office Action dated Feb. 8, 2022.
Agata et al. Expression of the PD-1 antigen on the surface of stimulated mouse T and B lymphocytes. Int. Immunol 8:765-75 (1996).
Al-Lazikani et al. Standard conformations for the canonical structures of immunoglobulins. J. Mol Biology 273(4):927-948 (1997).
Almagro et al. Humanization of antibodies. Front Biosci 13:1619-1633 (2008).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1977).
Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Barrett et al. Treatment of advanced leukemia in mice with mRNA engineered T cells. Hum Gene Ther 22:1575-1586 (2011).
Batzer et al. Enhanced evolutionary PCR using oligonucleotides with inosine at the 3'-terminus. Nucleic Acids Res. 19(18):5081 (1991).
Baum et al. Antitumor activities of PSMAxCD3 diabodies by redirected T-cell lysis of prostate cancer cells. Immunotherapy 5(1):27-38 (2013).
Bedouelle et al. Diversity and junction residues as hotspots of binding energy in an antibody neutralizing the dengue virus. FEBS J 273(1):34-46 (2006).
Bendell et al. Abstract 5552: First-in-human phase I study of HPN424, a tri-specific half-life extended PSMA-targeting T-cell engager in patients with metastatic castration-resistant prostate cancer (mCRPC). J Clin Oncol 38(15):5552 (May 2020).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Bortoletto et al. Optimizing anti-CD3 affinity for effective T cell targeting against tumor cells. Eur J Immunol 32:3102-3107 (2002).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Brown et al. Tolerance of single, but not multiple, amino acid replacements in antibody VH CDR 2: a means of minimizing B cell wastage from somatic hypermutation? J Immunol 156(9):3285-3291 (1996).
Caldas et al. Design and synthesis of germline-based hemi-humanized single-chain Fv against the CD18 surface antigen. Protein Eng 13(5):353-360 (2000).
Caldas et al. Humanization of the anti-CD18 antibody 6.7: an unexpected effect of a framework residue in binding to antigen. Mol Immunol. 39(15):941-952 (2003).
Carter et al. Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Casset et al. A peptide mimetic of an anti-CD4 monoclonal antibody by rational design. Biochemical and Biophysical Research Communication 307:198-205 (2003).
Chang et al. Loop-sequence features and stability determinants in antibody variable domains by high-throughput experiments. Structure 22(1):9-21 (2014).
Chang et al. Molecular cloning of mesothelin, a differentiation antigen present on mesothelium, mesotheliomas, and ovarian cancers. PNAS USA 93:136-140 (1996).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Fusion protein linkers: Property, design and functionality. Advanced Drug Delivery Reviews 65:1357-1369 (2013).
Chen et al. Selection and analysis of an optimized anti-VEGF antibody: Crystal structure of an affinity-matured Fab in complex with antigen. J Mol Bio 293:865-881 (1999).
Chien et al. Significant structural and functional change of an antigen-binding site by a distant amino acid substitution: proposal of a structural mechanism. PNAS USA 86(14):5532-5536 (1989).
Cho et al. Targeting B Cell Maturation Antigen (BCMA) in Multiple Myeloma: Potential Uses of BCMA-Based Immunotherapy. Front Immunol 9:1821 (2018).
Choi et al. Engineering of Immunoglobulin Fc heterodimers using yeast surface-displayed combinatorial Fc library screening. PLOS One 10(12):e0145349 (2015).
Chothia et al. Canonical structures for the hypervariable regions of immunoglobulins. J Mol Biol 196(4):901-917 (1987).
Chothia, et al. Conformations of immunoglobulin hypervariable regions. Nature 342(6252):877-83 (1989).
Corso et al. Real-time detection of mesothelin in pancreatic cancer cell line supernatant using an acoustic wave immunosensor. Cancer Detect Prev 30:180-187 (2006).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
Dao et al. Targeting the intracellular WT1 oncogene product with a therapeutic human antibody. Sci Transl Med 5(176):176ra33 (2013).
De Genst et al. Antibody repertoire development in camelids. Dev Comp Immunol 30(1-2):187-198 (2006).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Dennis et al. Imaging Tumors with an Albumin-Binding Fab, a Novel Tumor-Targeting Agent. Cancer Res 67(1):254-61 (2007).
Document D28—Investigation of human CD38 variants binding to monoclonal antibodies. Submitted by Pfizer to the European Patent Register on Apr. 30, 2014 in connection with their opposition to the EP2155783 patent. (3 pages) (2014).
Document D78—CD38 N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).

(56) References Cited

OTHER PUBLICATIONS

Dong et al. B7-H1 pathway and its role in the evasion of tumor immunity. J Mol Med 81:281-287 (2003).
Elango et al. Optimized transfection of mRNA transcribed from a d(A/T)100 tail-containing vector. Biochim Biophys Res Commun 330:958-966 (2005).
Foote et al. Antibody Framework Residues Affecting the Conformation of the Hypervariable Loops. J. Mol. Biol. 224(2):487-99 (1992).
Frankel et al. Targeting T cells to tumor cells using bispecific antibodies. Curr Opin Chem Biol 17(3):385-392 (2013).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Giusti et al. Somatic diversification of S107 from an antiphosphocholine to an anti-DNA autoantibody is due to a single base change in its heavy chain variable region. PNAS USA 84(9):2926-30 (1987).
Goldman et al. Enhancing Stability of Camelid and Shark Single Domain Antibodies: An Overview. Front. Immunol. 8:865 (2017).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Grupp et al. Chimeric antigen receptor-modified T cells for acute lymphoid leukemia. NEJM 368:1509-1518 (2013).
Gubbels et al. Mesothelin-MUC16 binding is a high affinity, N-glycan dependent interaction that facilitates peritoneal metastasis of ovarian tumors. Mol Cancer 5:50 (2006).
Gussow et al. Chapter 5: Humanization of Monoclonal Antibodies. Methods in Enzymology 203:99-121 (1991).
Haanen et al. Selective expansion of cross-reactive CD8(+) memory T cells by viral variants. J Exp Med 190(9):1319-1328 (1999).
Harding et al. The immunogenicity of humanized and fully human antibodies: residual immunogenicity resides in the CDR regions. MAbs 2(3):256-265 (2010).
Harmsen et al. Properties, production, and applications of camelid single-domain antibody fragments. Appl. Microbiol. Biotechnol. 77:13-22 (2007).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prey 15:1014-1020 (2006).
Hipp et al. A novel BCMA/CD3 bispecific T-cell engager for the treatment of multiple myeloma induces selective lysis in vitro and in vivo. Leukemia 31(8):1743-1751 (2017).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Ho et al. Mesothelin is shed from tumor cells. Cancer Epidemiol Biomarkers Prey 15:1751 (2006).
Hollinger et al. "Diabodies": Small bivalent and bispecific antibody fragments . PNAS USA 90:6444 6448 (1993).
Holm et al. Functional mapping and single chain construction of the anti-cytokeratin 8 monoclonal antibody TS1. Mol Immunol 44(6):1075-1084 (2007).
Holt et al. Anti-serum albumin domain antibodies for extending the half-lives of short-lived drugs. Protein Eng Des Sel 21(5):283-288 (2008).
Hopp et al. The effects of affinity and valency of an albumin-binding domain (ABD) on the half-life of a single-chain diabody-ABD fusion protein. Protein Eng. Des. Sel. 23(11):827-34 (2010).
Huston et al. Protein engineering of antibody binding sites: recovery of specific activity in an anti-digoxin single-chain Fv analogue produced in *Escherichia coli*. PNAS USA 85(16):5879-5883 (1988).
Hutchinson et al. Mutagenesis at a specific position in a DNA sequence. J Biol Chem 253:6551-6560 (1978).
Izumoto et al. Phase II clinical trial of Wilms tumor 1 peptide vaccination for patients with recurrent glioblastoma multiforme. J Neurosurg 108:963-971 (2008).
Janssen letter—Submission under Rule 116 EPC. Submitted by Janssen Biotech to the European Patent Register on Mar. 18, 2016 in connection with their opposition to the EP2155783 patent (6 pages) (2016).
Jones et al. Replacing the complementarity-determining regions in a human antibody with those from a mouse. Nature 321:522-525 (1986).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Laabi et al. The BCMA gene, preferentially expressed during B lymphoid maturation, is bidirectionally transcribed. Nucleic Acids Res 22(7):1147-1154 (1994).
Latchman et al. PD-L2 is a second ligand for PD-1 and inhibits T cell activation. Nat Immunol 2:261-268 (2001).
Le Gall et al. Immunosuppressive properties of anti-CD3 single-chain Fv and diabody. J Immunol Methods 285(1):111-127 (2004).
Li et al. Development of novel tetravalent anti-CD20 antibodies with potent antitumor activity. Cancer Res 68:2400-2408 (2008).
Liu et al. A New Format of Single Chain Tri-specific Antibody with Diminished Molecular Size Efficiently Induces Ovarian Tumor Cell Killing. Biotechnology Letters 27(22):1821-1827 (2005).
Liu et al. MGD011, a CD19 x CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Lowman et al. Monovalent phage display: A method for selecting variant proteins from random libraries. Methods 3:205-216 (1991).
Lu et al. In vitro and in vivo antitumor effect of a trivalent bispecific antibody targeting ErbB2 and CD16. Cancer Biol Ther. 7(11):1744-1750 (2008).
Lutterbuese et al. T cell-engaging BiTE antibodies specific for EGFR potently eliminate KRAS- and BRAF-mutated colorectal cancer cells. PNAS 107:12605-12610 (2007).
MacCallum et al. Antibody-antigen interactions: contact analysis and binding site topography. J Mol Biol. 262(5):732-745 (1996).
Mariuzza et al. The structural basis of antigen-antibody recognition. Annu Rev Biophys Biophys Chem 16:139-159 (1987).
Milone et al. Chimeric receptors containing CD137 signal transduction domains mediate enhanced survival of T cells and increased antileukemic efficacy in vivo. Mol Ther 17(8):1453-1464 (2009).

(56) References Cited

OTHER PUBLICATIONS

Mirsky et al. Antibody-Specific Model of Amino Acid Substitution for Immunological Inferences from Alignments of Antibody Sequences. Mol. Biol. Evol. 32(3):806-819 (2014).
Müller et al. Improved Pharmacokinetics of Recombinant Bispecific Antibody Molecules by Fusion to Human Serum Albumin. J. Biol. Chem. 282(17):12650-60 (2007).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muller et al. Improving the pharmacokinetic properties of biologics by fusion to an anti-HSA shark VNAR domain. MAbs 4(6):673-685 (2012).
Mumtaz et al. Design of liposomes for circumventing the reticuloendothelial cells. Glycobiology 5:505-10 (1991).
Muul et al. Persistence and expression of the adenosine deaminase gene for 12 years and immune reaction to gene transfer components: long-term results of the first clinical gene therapy trial. Blood 101(7):2563-2569 (2003).
Muyldermans. Nanobodies: natural single-domain antibodies. Annu Rev Biochem 82:775-797 (2013).
Nacheva et al. Preventing nondesired RNA-primed RNA extension catalyzed by T7 RNA polymerase. Eur J Biochem 270:1458-1465 (2003).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Needleman et al. A general method applicable to the search for similarities in the amino acid sequence of two proteins. J. Mol. Biol. 48:443-453 (1970).
Nelson et al. Antibody fragments Hope and Hype. mAbs 2(1):77-83 (2010).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Nunez-Prado et al. The coming of age of engineered multivalent antibodies. Drug Discovery Today 20(5):588-594 (2015).
Ohiro et al. A homogeneous and noncompetitive immunoassay based on the enhanced fluorescence resonance energy transfer by leucine zipper interaction. Anal Chem 74(22):5786-5792 (2002).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Padlan. Anatomy of the Antibody Molecule. Mol Immunol 31(3):169-217 (1994).
Padlan, et al., A possible procedure for reducing the immunogenicity of antibody variable domains while preserving their ligand-binding properties. Mol Immunol 28(4-5):489-498 (1991).
Padlan et al. Structure of an antibody-antigen complex: Crystal structure of the HyHEL-10 Fab-lysozyme complex. PNAS USA 86:5938-5942 (1989).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).
PCT/US2016/033644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
PCT/US2017056530 International Search Report and Written Opinion dated Jan. 23, 2018.
PCT/US2017/063121 International Search Report and Written Opinion dated Mar. 26, 2018.
PCT/US2017/063126 International Search Report and Written Opinion dated Apr. 5, 2018.
PCT/US2018/014396 International Search Report and Written Opinion dated Jun. 14, 2018.
PCT/US2018/020185 International Search Report and Written Opinion dated Jun. 15, 2018.
PCT/US2018/020307 International Search Report and Written Opinion dated Aug. 24, 2018.
PCT/US2018/030983 International Search Report and Written Opinion dated Sep. 25, 2018.
PCT/US2018/032418 International Search Report and Written Opinion dated Sep. 24, 2018.
PCT/US2018/032427 International Search Report and Written Opinion dated Sep. 13, 2018.
PCT/US2018/055659 International Search Report and Written Opinion dated Feb. 21, 2019.
PCT/US2018/055682 International Search Report and Written Opinion dated Mar. 1, 2019.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
PCT/US2019/052206 International Search Report and Written Opinion dated Feb. 14, 2020.
PCT/US2019/052270 International Search Report and Written Opinion dated Mar. 5, 2020.
PCT/US2019/053017 International Search Report and Written Opinion dated Jan. 31, 2020.
Pearson et al. Improved Tools for Biological Sequence Comparison. PNAS USA 85:2444-48 (1988).
Pedersen et al. Comparison of surface accessible residues in human and murine immunoglobulin Fv domains. Implication for humanization of murine antibodies. J Mol Biol 235(3):959-973 (1994).
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta. Antibody Engineering. Curr Op Struct Biol 2:593-596 (1992).
Presta et al. Humanization of an antibody directed against IgE. J Immunol 151:2623-2632 (1993).
Ramadoss et al. An Anti-B Cell Maturation Antigen Bispecific Antibody for Multiple Myeloma. J. Ann. Chem. Soc. 137(16):5288-91 (2015).
Riechmann et al. Reshaping human antibodies for therapy. Nature, 332.6162:323-7 (1988).
Riechmann et al. Single domain antibodies: comparison of camel VH and camelised human VH domains. J Immunol Methods 231(1-2):25-38 (1999).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).

(56) References Cited

OTHER PUBLICATIONS

Rosenberg et al. Use of tumor-infiltrating lymphocytes and interleukin-2 in the immunotherapy of patients with metastatic melanoma. A preliminary report. NEJM 319:1676 (1988).
Rosok et al. A Combinatorial Library Strategy for the Rapid Humanization of Anticarcinoma BR96 Fab. J Biol Chem 271:22611-22618 (1996).
Rossolini et al. Use of deoxyinosine-containing primers vs degenerate primers for polymerase chain reaction based on ambiguous sequence information. Mol Cell Probes 8(2):91-98 (1994).
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Running Deer et al. High-level expression of proteins in mammalian cells using transcription regulatory sequences from the Chinese hamster EF-1alpha gene. Biotechnol Prog. 20:880-889 (2004).
Sadelain et al. Targeting tumours with genetically enhanced T lymphocytes. Nat Rev Cancer 3(1):35-45 (2003).
Sadelain et al. The basic principles of chimeric antigen receptor design. Cancer Discov. 3(4):388-98 (2013).
Saerens et al. Identification of a universal VHH framework to graft non-canonical antigen-binding loops of camel single-domain antibodies. J. Mol. Biol. 352(3):597-607 (2005).
Sandhu. A rapid procedure for the humanization of monoclonal antibodies. Gene 150(2):409-410 (1994).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Schmidt et al. Cloning and Characterization of Canine Prostate-Specific Membrane Antigen. The Prostate 73:642-650 (2013).
Schmittgen et al. Expression of prostate specific membrane antigen and three alternatively spliced variants of PSMA in prostate cancer patients. Int J Cancer 107:323-329 (2003).
Sergeeva et al. An anti-PR1/HLA-A2 T-cell receptor-like antibody mediates complement-dependent cytotoxicity against acute myeloid leukemia progenitor cells. Blood 117(16):4262-4272 (2011).
Sims et al. A humanized CD18 antibody can block function without cell destruction. J Immunol. 151:2296-2308 (1993).
Smirnova et al. Identification of new splice variants of the genes BAFF and BCMA. Mol. Immunol. 45 (4):1179-83 (2008).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Spiess et al. Alternative molecular formats and therapeutic applications for bispecific antibodies. Mol. Immunol. 67(2 Pt A):95-106 (2015).
Stepinski et al. Synthesis and properties of mRNAs containing the novel 'anti-reverse' cap analogs 7-methyl(3'0-methyl)GppppG and 7-methyl(e'-deoxy)GppppG. RNA 7:1486-1495 (2001).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Strop. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).
Su et al. PSMA specific single chain antibody-mediated targeted knockdown of Notch1 inhibits human prostate cancer cell proliferation and tumor growth. Cancer Lett. 338 (2): 282-291 (2013).
Tan et al. "Superhumanized" antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Thomas et al. Mesothelin-specific CD8(+) T cell responses provide evidence of in vivo cross- priming by antigen-presenting cells in vaccinated pancreatic cancer patients. J Exp Med 200:297-306 (2004).
Tijink et al. Improved tumor targeting of anti-epidermal growth factor receptor nanobodies through albumin binding: taking advantage of modular Nanobody technology. Mol. Cancer Ther. 7(8):2288-97 (2008).
Tiller et al. Facile Affinity Maturation of Antibody Variable Domains Using Natural Diversity Mutagenesis. Front. Immunol. 8:986 (2017).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 25, 2019.
U.S. Appl. No. 15/600,264 Office Action dated Apr. 26, 2018.
U.S. Appl. No. 15/600,264 Office Action dated Nov. 27, 2018.
U.S. Appl. No. 15/600,264 Office Action dated Oct. 3, 2017.
U.S. Appl. No. 15/600,582 Office Action dated Nov. 16, 2017.
U.S. Appl. No. 15/630,259 Office Action dated Dec. 30, 2019.
U.S. Appl. No. 15/630,259 Office Action dated Sep. 30, 2020.
U.S. Appl. No. 15/704,620 Office Action dated Oct. 26, 2017.
U.S. Appl. No. 15/821,498 Office Action dated Apr. 21, 2020.
U.S. Appl. No. 15/821,498 Office Action dated May 3, 2019.
U.S. Appl. No. 15/821,498 Office Action dated Oct. 26, 2018.
U.S. Appl. No. 15/821,530 Office Action dated Apr. 22, 2020.
U.S. Appl. No. 15/821,530 Office Action dated Apr. 3, 2019.
U.S. Appl. No. 15/821,530 Office Action dated Sep. 25, 2018.
U.S. Appl. No. 15/977,968 Office Action dated Feb. 21, 2019.
U.S. Appl. No. 15/977,988 Office Action dated Aug. 20, 2019.
U.S. Appl. No. 15/977,988 Office Action dated Mar. 26, 2019.
U.S. Appl. No. 15/977,988 Pre-Interview First Office Action dated Jan. 25, 2019.
U.S. Appl. No. 16/159,545 Office Action dated Aug. 6, 2019.
U.S. Appl. No. 16/159,545 Office Action dated Dec. 2, 2019.
U.S. Appl. No. 16/159,554 Office Action dated Jun. 7, 2019.
U.S. Appl. No. 16/159,554 Office Action dated Oct. 1, 2019.
U.S. Appl. No. 16/159,554 Office Action dated Oct. 5, 2020.
U.S. Appl. No. 16/583,070 Office Action dated Mar. 3, 2020.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).

(56) References Cited

OTHER PUBLICATIONS

Van Der Linden et al. Induction of immune responses and molecular cloning of the heavy chain antibody repertoire of Lama glama. J Immunol Methods 240:185-195 (2000).
Vaughan et al. Human antibodies by design. Nature Biotech 16:535-539 (1998).
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal Of Biochemistry 135(4):555-565 (2004).
Willemsen et al. A phage display selected fab fragment with MHC class I-restricted specificity for MAGE-A1 allows for retargeting of primary human T lymphocytes. Gene Ther 8(21):1601-1608 (2001).
Winkler et al. Changing the antigen binding specificity by single point mutations of an anti-p24 (HIV-1) antibody. J Immunol. 165(8):4505-4514 (2000).
Wu et al. Humanization of a murine monoclonal antibody by simultaneous optimization of framework and CDR residues. J.Mol. Biol. 294:151-162 (1999).
Yan et al. Engineering upper hinge improves stability and effector function of a human IgG1. J. Biol. Chem. 287:5891 (2012).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Yoshinaga et al. Ig L-chain shuffling for affinity maturation of phage library-derived human anti-human MCP-1 antibody blocking its chemotactic activity. J Biochem 143(5):593-601 (2008).
Yu et al. Rationalization and design of the complementarity determining region sequences in an antibody-antigen recognition interface. PLoS One 7(3):e33340 (2012).
Zabetakis et al. Contributions of the complementarity determining regions to the thermal stability of a single-domain antibody. PLoS One 8(10):e77678 (2013).
Zare et al. Production of nanobodies against prostate-specific membrane antigen (PSMA) recognizing LnCaP cells. Int. J. Biol. Markers 29(2):e169-e179 (2014).
Zhang et al. New High Affinity Monoclonal Antibodies Recognize Non-Overlapping Epitopes on Mesothelin For Monitoring And Treating Mesothelioma. Sci Rep 5:9928 (2015).
Zhu et al. Combody: one-domain antibody multimer with improved avidity. Immunology and Cell Biology 88(6):667-675 (2010).
Annual Report Pursuant to Section 13 or 15(d) of the Securities Exchange Act of 1934. 2019 22-24 [online]. [Retrieved on Aug. 5, 2021]. Retrieved from website URL:https://www.annualreports.com/HostedData/AnnualReportArchive/h/NASDAQ_HARP_2018.pdf.
Brauchle et al. Characterization of a Novel FLT3 BiTE Molecule for the Treatment of Acute Myeloid Leukemia. Mol Cancer Ther 19:1875-88 (2020).
Glaser et al. Novel antibody hinge regions for efficient production of CH2 domain-deleted antibodies. J. Biol. Chem. 280:41494-503 (2005).
Halaby et al. The immunoglobulin fold family: sequence analysis and 3D structure comparisons. Prot Eng 12(7):563-571 (1999).
Han et al. Masked Chimeric Antigen Receptor for Tumor-Specific Activation. Molecular Therapy 25(1):274-284 (2017).
Hassanzadeh-Ghassabeh et al. Nanobodies and their potential applications. Nanomedicine 8(6):1013-1026 (2013).
Huck et al. Sequence of a human immunoglobulin gamma 3 heavy chain constant region gene: comparison with the other human C gamma genes. Nucl. Acids Res. 14:1779-89 (1986).
Julian et al. Efficient affinity maturation of antibody variable domains requires co-selection of compensatory mutations to maintain thermodynamic stability. Sci Rep 7:45259 (2017).
Škrlec et al. Non-immunoglobulin scaffolds: a focus on their targets. Trends in Biotechnol 33:408-418 (2015).
Krzywinska et al. CD45 Isoform Profile Identifies Natural Killer (NK) Subsets with Differential Activity. PLoS One 11(4):e0150434 (2016).
Leibl et al. Ovarian granulosa cell tumors frequently express EGFR (Her-1), Her-3, and Her-4: An immunohistochemical study. Gynecol Oncol 101(1):18-23 (2006).
Mason et al. CD79a: a novel marker for B-cell neoplasms in routinely processed tissue samples. Blood 86(4):1453-1459 (1995).
PCT/US2020/060184 International Search Report and Written Opinion dated Mar. 4, 2021.
PCT/US2021/018853 International Search Report and Written Opinion dated Jul. 8, 2021.
PCT/US2021/031790 International Search Report and Written Opinion dated Sep. 16. 2021.
Sandler et al. Nondermatologic adverse events associated with anti-EGFR therapy. Oncology (Williston Park) 20(5 Suppl 2):35-40 (2006).
Sheng et al. Novel Transgenic Mouse Model for Studying Human Serum Albumin as a Biomarker of Carcinogenic Exposure. Chem. Res. Toxicol. 29(5):797-809 (2016).
Stehle et al. Albumin-based drug carriers: comparison between serum albumins of different species on pharmacokinetics and tumor uptake of the conjugate. Anticancer Drugs. 10(8):785-90 (1999).
Stirewalt et al. The role of FLT3 in haematopoietic malignancies. Nat Rev Cancer 3:650-665 (2003).
Tan et al. Influence of the hinge region on complement activation, C1q binding, and segmental flexibility in chimeric human immunoglobulins. PNAS USA 87:162-166 (1990).
Thomas. Cetuximab: adverse event profile and recommendations for toxicity management. Clin J Oncol Nurs. 9(3):332-8 (2005).
UniProtKB Accession No. A0A3M1V7M7_9EURY, Ig-like_bact domain-containing protein, Feb. 13, 2019 [online] [Retrieved on Jun. 8, 2021]. Retrieved from the internet <url:<ahref="https://www.uniprotorg/uniprot/A0A3M1V7M7.bct" >https://www.uniprotorg/uniprot/A0A3M1V7M7.bct</url:.<a>.
U.S. Appl. No. 16/159,554 Office Action dated Mar. 16, 2021.
U.S. Appl. No. 16/161,986 Office Action dated Dec. 2, 2021.
Co-pending U.S. Appl. No. 17/933,336, inventors Dubridge; Robert B. et al., filed Sep. 19, 2022.
Co-pending U.S. Appl. No. 18/184,392, inventors Wesche; Holger et al., filed Mar. 10, 2023.
Co-pending U.S. Appl. No. 18/188,037, inventors Dubridge; Robert B. et al., filed Mar. 22, 2023.
U.S. Appl. No. 17/072,370 Office Action dated Jun. 2, 2023.
Allard et al., The ectonucleotidases CD39 and CD73: Novel checkpoint inhibitor targets. Immunol Rev., 276(1):121-144 (2018).
Altenhofer et al., The NOX toolbox: validating the role of NADPH oxidases in physiology and disease. Cell Mol Life Sciences 69(14):2327-2343 (2012).
Austin et al. TriTACs, a Novel Class of T-Cell-Engaging Protein Constructs Designed for the Treatment of Solid Tumors. Mol Cancer Ther 20(1):109-120 (2021).
Ayers et al. IFN-γ-related mRNA profile predicts clinical response to PD-1 blockade. The Journal of Clinical Investigation 127(8):2930-2940 (Aug. 2017).
Balzar et al. Epidermal growth factor-like repeats mediate lateral and reciprocal interactions of Ep-CAM molecules in homophilic adhesions. Mol Cell Biol. 21(7):2570-80 (2001).
Chen et al. Enhancement and destruction of antibody function U by somatic mutation: unequal occurrence is controlled by V gene combinatorial associations. The EMBO Journal 14(12):2784-2794 (1995).
Cheong et al., A patent review of IDO1 inhibitors for cancer. Expert Opin Ther Pat. 28(4):317-330 (2018).
Colman. Effects of amino acid sequence changes on antibody-antigen interactions. Res Immunol 145(1):33-36 (1994).

(56) References Cited

OTHER PUBLICATIONS

Croso et al., Real-time detection of mesothelin in pancreatic cancer cell line supernatant using an acoustic wave immunosensor. Cancer Detect. Prev. 30:180-187 (2006).

Fang et al. Characterization of an anti-human ovarian carcinomaxantihuman CD3 bispecific single-chain antibody with an albumin-original interlinker. Gynecol Oncol 92(1):135-146 (2004).

Galsky et al. Phase I trial of the prostate-specific membrane antigen-directed immunoconjugate MLN2704 in patients with progressive metastatic castration-resistant prostate cancer. J Clin Oncol 26(13):2147-54 (2008).

Gautam et al., Dual Inhibition of NOX2 and Receptor Tyrosine Kinase by BJ-1301 Enhances Anticancer Therapy Efficacy via Suppression of Autocrine-Stimulatory Factors in Lung Cancer. Mol Cancer Ther 16(10):2144-2156 (2017).

Gianni et al., A novel and specific NADPH oxidase-1 (Nox1) small-molecule inhibitor blocks the formation of functional invadopodia in human colon cancer cells. ACS Chem Biol 5(10):981-93 (2010).

Gorshkova et al. Single domain antibodies and bioengineering drugs on their basis: new opportunities for diagnostics and therapy. Medical Immunology (Russia) 18(6):505-520 (2016) (English Abstract).

Harris et al. A bispecific antibody agonist of the IL-2 heterodimeric receptor preferentially promotes in vivo expansion of CD8 and NK cells. Sci Rep. 11(1):10592 (2021).

Henry et al. A prostate-specific membrane antigen-targeted monoclonal antibody-chemotherapeutic conjugate designed for the treatment of prostate cancer. Cancer Res. 64(21):7995-8001 (2004).

Hupe et al. Expression of Prostate-Specific Membrane Antigen (PSMA) on Biopsies Is an Independent Risk Stratifier of Prostate Cancer Patients at Time of Initial Diagnosis. Front Oncol 8:623 (2018).

Jang et al. Human 4-1BB (CD137) signals are mediated by TRAF2 and activate nuclear factor-kappa B. Biochem. Biophys. Res. Commun. 242 (3):613-20 (1998).

Jemaa et al. Co-expression and impact of prostate specific membrane antigen and prostate specific antigen in prostatic pathologies. J Exp Clin Cancer Res 29(1):171 (2010).

Jiang et al. Protritac: A protease cleavable T cell Engager Platform. Scientific Reports 6(Suppl 1):115 Available at https://calidibio.com/wp-content/uploads/2019/10/609-Abstract-_SITC-2018.pdf (2018).

Kakkad et al. Collagen 1 fiber content may predict for recurrence in non-small cell lung cancer. Cancer Research 78(13 Supplement):3691-3691 (2018).

Kauder et al., ALX148 blocks CD47 and enhances innate and adaptive antitumor immunity with a favorable safety profile. PLoS One 13(8):e0201832 (2019).

Kelm et al., Functional groups of sialic acids involved in binding to siglecs (sialoadhesins) deduced from interactions with synthetic analogues. Eur. J. Biochem. 255:663-672 (1998).

Kelm et al., The Sialoadhesins—a family of sialic acid-dependent cellular recognition molecules within the immunoglobulin superfamily. Glycoconj. J. 13:913-926 (1996).

Kim et al., 2077—An oral dual inhibitor of IDO and TDO enhances anti-cancer immunity and synergizes with immune checkpoint blockade. Annals Oncol 29 (suppl_8):viii400-viii441 (2018) (Poster Abstract).

Korenchuk et al. VCaP, a cell-based model system of human prostate cancer. In Vivo. 15(2):163-8 (2001).

Lin et al. ProTriTAC: A Protease-Activatable T Cell Engager Platform that Links Half-Life Extension to Functional Masking Society for Immunotherapy of Cancer (SITC) Annual Meeting. Nov. 2018, Available at https://www.harpoontx.com/file.cfm/43/docs/SITC_2018_ProTriTAC_Poster.pdf.

Loberg et al. Development of the VCaP androgen-independent model of prostate cancer. Urol Oncol 24(2):161-8 (2006).

Lu et al., Characterization of potent and selective iodonium-class inhibitors of NADPH oxidases. Biochem Pharmacol 143:25-38 (2017).

Lv et al. Mesothelin as a biomarker for targeted therapy. Biomark Res 7:18 (2019).

Ma et al. Combination therapy with T cell engager and PD-L1 blockade enhances the antitumor potency of T cells as predicted by a QSP model. J Immunother Cancer. 8(2):e001141 (2020).

Magiera-Mularz et al. Bioactive macrocyclic inhibitors of the PD-1/PD-L1 immune checkpoint Angew. Chem. Int. Ed. 56(44):13732-13735 (2017).

McDevitt et al. An alpha-particle emitting antibody ([213Bi]J591) for radioimmunotherapy of prostate cancer. Cancer Res. 60:6095-6100 (2000).

Monney et al. Th1-specific cell surface protein Tim-3 regulates macrophage activation and severity of an autoimmune disease. Nature 415:536-41 (2002).

Nakae et al. Phenotypic differences between Th1 and Th17 cells and negative regulation of Th1 cell differentiation by IL-17. J Leukoc Biol 81:1258-68 (2007).

Nicolaou et al. Calicheamicin $\Theta'1$ : a rationally designed molecule with extremely potent and selective DNA cleaving properties and apoptosis inducing activity. Angew. Chem. Intl. Ed. Engl., 33:183-186 (1994).

PCT/US2022/019302 International Search Report and Written Opinion dated Jun. 27, 2022.

PCT/US2022/022871 International Search Report and Written Opinion dated Aug. 3, 2022.

PCT/US2022/031916 International Search Report and Written Opinion dated Sep. 29, 2022.

PCT/US2022/031917 International Search Report and Written Opinion dated Dec. 2, 2022.

PCT/US2022/031919 International Search Report and Written Opinion dated Nov. 21, 2022.

PCT/US2022/034856 International Search Report and Written Opinion dated Dec. 8, 2022.

Perrot et al., Blocking Antibodies Targeting the CD39/CD73 Immunosuppressive Pathway Unleash Immune Responses in Combination Cancer Therapies. Cell Reports 8:2411-2425.E9 (2019).

Poczatek et al. Ep-Cam levels in prostatic adenocarcinoma and prostatic intraepithelial neoplasia. J Urol. 162:1462-1464 (1999).

Popoli et al., Effects of SCH 58261, an Adenosine A2A receptor antagonist, on quinpirole-induced turning in 6-Hydroxydopamine-lesioned rats: lack of tolerance after chronic caffeine intake. Neuropsychopharm 22:522-529 (2000).

Schaer et al. Modulation of GITR for cancer immunotherapy. Curr Opin Immunol. 24(2): 217-224 (2012).

Sheridan. IDO inhibitors move center stage in immuno-oncology. Nat Biotechnol 33:321-322 (2015).

Sramkoski et al. A new human prostate carcinoma cell line, 22Rv1. In Vitro Cell Dev Biol Anim 35(7):403-409 (1999).

Stanciu-Herrera et al., Anti-CD19 and anti-CD22 monoclonal antibodies increase the effectiveness of chemotherapy in Pre-B acute lymphoblastic leukemia cell lines . Leuk Res. 32:625-32 (2008).

Stasi et al., Animal models of Parkinson's disease: Effects of two adenosine A2A receptor antagonists ST4206 and ST3932, metabolites of 2-n-Butyl-9-methyl-8-[1,2,3]triazol-2-yl-9H-purin-6-ylamine (ST1535). Europ J Pharmacol 761:353-361 (2015).

Tamura et al. Structural correlates of an anticarcinoma antibody: identification of specificity-determining residues (SDRs) and development of a minimally immunogenic antibody variant by retention of SDRs only. J Immunol. 164(3):1432-41 (2020).

Tang et al., NOX4, a new genetic target for anti-cancer therapy in digestive system cancer. J Dig Dis 19(10):578-585 (2018).

U.S. Appl. No. 16/339,263 Office Action dated Jan. 18, 2023.
U.S. Appl. No. 16/773,843 Office Action dated Aug. 11, 2022.
U.S. Appl. No. 16/802,007 Office Action dated Apr. 14, 2023.
U.S. Appl. No. 16/802,007 Office Action dated Sep. 29, 2022.
U.S. Appl. No. 17/030,118 Office Action dated May 5, 2023.

Wang et al., A Small Molecule Antagonist of PD-1/PD-L1 Interactions Acts as an Immune Checkpoint Inhibitor for NSCLC and Melanoma Immunotherapy. Front. Immunol. 12:654463, 2021.

Wang et al., In vitro characterization of the anti-PD-1 antibody nivolumab, BMS-936558, and in vivo toxicology in non-human primates. Cancer Immunol. Res. 2(9):846-856 (2014).

Watt et al., Homophilic adhesion of human CEACAM1 involves N-terminal domain interactions: structural analysis of the binding site. Blood 98:1469-1479 (2001).

(56) References Cited

OTHER PUBLICATIONS

Weir et al., Colony stimulating factor-1 plays a role in osteoclast formation and function in bone resorption induced by parathyroid hormone and parathyroid hormone-related protein. J Bone Mineral Res 11:1474-1481 (1996).
Ye et al. Androgen and epidermal growth factor down-regulate cyclin-dependent kinase inhibitor p27Kip1 and costimulate proliferation of MDA PCa 2a and MDA PCa 2b prostate cancer cells. Clin Cancer Res 5(8):2171-7 (1999).
PCT/US2022/078178 International Search Report and Written Opinion dated Jul. 18, 2023.

* cited by examiner

DLL3 BINDING PROTEINS AND METHODS OF USE

CROSS-REFERENCE

This application is a continuation of U.S. patent application Ser. No. 16/583,070, filed Sep. 25, 2019, which claims the benefit of U.S. Provisional Application Nos. 62/736,368 filed on Sep. 25, 2018; 62/736,358 filed on Sep. 25, 2018; and 62/877,227 filed Jul. 22, 2019 each of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Sep. 25, 2019, is named 47517-733_201_SL.txt and is 951,519 bytes in size.

BACKGROUND OF THE INVENTION

The selective destruction of an individual cell or a specific cell type is often desirable in a variety of clinical settings. For example, it is a primary goal of cancer therapy to specifically destroy tumor cells, while leaving healthy cells and tissues intact and undamaged. One such method is by inducing an immune response against the tumor, to make immune effector cells such as natural killer (NK) cells or cytotoxic T lymphocytes (CTLs) attack and destroy tumor cells.

SUMMARY OF THE INVENTION

There is still a need for having available further options for the treatment of tumorous diseases related to the overexpression of DLL3, such as neuroendocrine tumors. The present disclosure provides, in certain embodiments, single domain proteins which specifically bind to DLL3 on the surface of tumor target cells and multispecific proteins, such as trispecific proteins containing DLL3 binding domain as described herein. In some embodiments, the present disclosure provides Delta Like Ligand 3 (DLL3) binding proteins, or multispecific proteins as mentioned above, which can be used for diagnosing and treating indications correlated to the expression of DLL3.

One embodiment provides a DLL3 targeting trispecific protein, wherein said protein comprises (a) a first domain (A) which is a single chain variable fragment that specifically binds to a human CD3; (b) a second domain (B) which is a single domain antibody that specifically binds to a human serum albumin protein; and (c) a third domain (C) which is a single domain antibody that specifically binds to a DLL3 protein, wherein the third domain (C) comprises a CDR1 that has the amino acid sequence of SEQ ID No. 874, a CDR2 that has the amino acid sequence of SEQ ID No. 1316, and a CDR3 that has the amino acid sequence of SEQ ID No. 1758.

One embodiment provides a DLL3 targeting trispecific protein, wherein said protein comprises (a) a first domain (A) which is a single chain variable fragment that specifically binds to a human CD3; (b) a second domain (B) which is a single domain antibody that specifically binds to a human serum albumin protein; and (c) a third domain (C) which is a single domain antibody that specifically binds to DLL3, wherein the third domain comprises a CDR1 that has an amino acid sequence selected from the group consisting of SEQ ID Nos. 851, 867, 871, 872, 873, 874, and 1887; a CDR2 that has an amino acid sequence selected from the group consisting of SEQ ID Nos. 1293, 1309, 1313, 1314, 1315, 1316 and 1888; and a CDR3 that has an amino acid sequence selected from the group consisting of SEQ ID Nos. 1735, 1751, 1755, 1756, 1757, 1758, and 1889. In some embodiment, the third domain (C) comprises a sequence that is at least 80% identical to a sequence selected from the group consisting of SEQ ID Nos. 408, 425, 432, 430, 431, and 1886. In some embodiments, the third domain (C) comprises a sequence selected from the group consisting of SEQ ID Nos. 408, 425, 432, 430, 431, and 1886.

In some embodiments, the domains are linked in the order H2N-(A)-(B)—(C)—COOH, H2N-(A)-(C)—(B)—COOH, H2N—(B)-(A)-(C)—COOH, H2N—(B)—(C)-(A)-COOH, H2N—(C)—(B)-(A)-COOH, or H2N—(C)-(A)-(B)—COOH, or by linkers L1 and L2, in the order H2N-(A)-L1-(B)-L2-(C)—COOH, H2N-(A)-L1-(C)-L2-(B)—COOH, H2N—(B)-L1-(A)-L2-(C)—COOH, H2N—(B)-L1-(C)-L2-(A)-COOH, H2N—(C)-L1-(B)-L2-(A)-COOH, or H2N—(C)-L1-(A)-L2-(B)—COOH.

In some embodiments, the domains are linked in the order H2N-(A)-(B)—(C)—COOH or by linkers L1 and L2 in the order of H2N-(A)-L1-(B)-L2-(C)—COOH. In some embodiments, the domains are linked in the order H2N—(C)—(B)-(A)-COOH or by linkers L1 and L2 in the order of H2N—(C)-L1-(B)-L2-(A)-COOH. In some embodiments, the third domain (C) is an affinity matured binding molecule derived from a parental molecule that specifically binds to the DLL3 protein.

In some embodiments, the affinity matured binding DLL3 binding molecule has a binding affinity toward the DLL3 protein that is about 2-fold about 50-fold greater than the binding affinity of the parental molecule toward the DLL3 protein. In some embodiments, the parental molecule comprises the amino acid sequence of SEQ ID No. 68 or SEQ ID No. 75.

In some embodiments, the linkers L1 and L2 are each independently selected from the group consisting of $(GS)_n$ (SEQ ID No.1809), $(GGS)_n$ (SEQ ID No.1810), $(GGGS)_n$ (SEQ ID No.1811), $(GGSG)_n$ (SEQ ID No.1812), $(GGSGG)_n$ (SEQ ID No.1813), or $(GGGGS)_n$ (SEQ ID No.1814), wherein n is 1, 2, 3, 4, 5, 6, 7, 8, 9, or 10. In some embodiments, the linkers L1 and L2 independently comprises the sequence of GGGGSGGGS (SEQ ID No. 1808).

In some embodiments, the second domain (B) comprises an amino acid sequence selected from the group consisting of SEQ ID Nos. 1769-1778. In some embodiments, the first domain (A) comprises an amino acid sequence selected from the group consisting of SEQ ID Nos. 1793-1802 and 1897-1898. In some embodiments, the DLL3 targeting trispecific protein comprises the sequence of SEQ ID No. 1890 or SEQ ID No. 1891. In some embodiments, the ird domain (C) binds to a human DLL3 protein comprising the sequence of SEQ ID No. 1893.

One embodiment provides a DLL3 binding protein comprising a CDR1 that has the amino acid sequence of SEQ ID No. 874, a CDR2 that has the amino acid sequence of SEQ ID No. 1316, and a CDR3 that has the amino acid sequence of SEQ ID No. 1758. In some embodiments, the DLL3 binding protein comprises a sequence that is at least 80% identical to the amino acid sequence of SEQ ID No. 432.

One embodiment provides a DLL3 binding protein comprising a CDR1 that has an amino acid sequence selected from the group consisting of SEQ ID Nos. 851, 867, 871, 872, 873, 874, and 1887; a CDR2 that has an amino acid sequence selected from the group consisting of SEQ ID Nos.

1293, 1309, 1313, 1314, 1315, 1316 and 1888; and a CDR3 that has an amino acid sequence selected from the group consisting of SEQ ID Nos. 1735, 1751, 1755, 1756, 1757, 1758, and 1889. In some embodiments, the DLL3 binding protein comprises a sequence that is at least 80% identical to a sequence selected from the group consisting of SEQ ID Nos. 408, 425, 432, 430, 431, and 1886.

One embodiment provides a method of treating or ameliorating a disease, comprising administering an effective amount of a DLL3 targeting trispecific protein according to any one of the above embodiments.

One embodiment provides a DLL3 targeting trispecific protein, wherein said protein comprises
(a) a first domain (A) which is a single chain variable fragment that specifically binds to a human CD3;
(b) a second domain (B) which is a single domain antibody that specifically binds to a human serum albumin protein; and
(c) a third domain (C) which is a single domain antibody that specifically binds to a DLL3 protein, wherein the third domain (C) comprises a sequence that is at least 80% identical to a sequence selected from the group consisting of SEQ ID Nos. 1-442 and 1886.

In some embodiments, the domains are linked in the order H2N-(A)-(B)—(C)—COOH, H2N-(A)-(C)—(B)—COOH, H2N—(B)-(A)-(C)—COOH, H2N—(B)—(C)-(A)-COOH, H2N—(C)—(B)-(A)-COOH, or H2N—(C)-(A)-(B)—COOH, or by linkers L1 and L2, in the order H2N-(A)-L1-(B)-L2-(C)—COOH, H2N-(A)-L1-(C)-L2-(B)—COOH, H2N—(B)-L1-(A)-L2-(C)—COOH, H2N—(B)-L1-(C)-L2-(A)-COOH, H2N—(C)-L1-(B)-L2-(A)-COOH, or H2N—(C)-L1-(A)-L2-(B)—COOH.

In some embodiments, the third domain (C) is an affinity matured binding molecule derived from a parental molecule that specifically binds to the DLL3 protein. In some embodiments, the affinity matured binding DLL3 binding molecule has a binding affinity toward the DLL3 protein that is about 2-fold about 50-fold greater than the binding affinity of the parental molecule toward the DLL3 protein.

In some embodiments, the third domain (C) comprises a sequence selected from the group consisting of SEQ ID Nos. 1-442 and 1886. In some embodiments, the third domain (C) comprises a sequence that is selected from the group consisting of SEQ ID Nos. 1-52. In some embodiments, the third domain (C) comprises a CDR1, a CDR2, and a CDR3, wherein the CDR1 comprises a sequence selected from the group consisting of SEQ ID Nos. 443-884 and 1887, wherein the CDR2 comprises a sequence selected from the group consisting of SEQ ID Nos. 885-1326 and 1888, and wherein the CDR3 comprises a sequence selected from the group consisting of SEQ ID Nos. 1327-1768 and 1889. In some embodiments, the CDR1 comprises a sequence selected from the group consisting of SEQ ID Nos. 495-528. In some embodiments, the CDR2 comprises a sequence selected from the group consisting of SEQ ID Nos. 937-970. In some embodiments, the CDR3 comprises a sequence selected from the group consisting of SEQ ID Nos. 1379-1412. In some embodiments, the third domain (C) comprises a sequence selected from the group consisting of SEQ ID Nos. 53-86.

In some embodiments, the third domain (C) comprises a CDR1, a CDR2, and a CDR3, and wherein the CDR1 comprises a sequence selected from the group consisting of SEQ ID Nos. 529-809. In some embodiments, the CDR2 comprises a sequence selected from the group consisting of SEQ ID Nos. 971 to 1251. In some embodiments, the CDR3 comprises a sequence selected from the group consisting of SEQ ID Nos. 1379-1412. In some embodiments, the third domain (C) comprises a sequence selected from the group consisting of SEQ ID Nos. 87-367. In some embodiments, the third domain (C) comprises a CDR1, a CDR2, and a CDR3, and wherein the CDR1 comprises a sequence selected from the group consisting of SEQ ID Nos. 810-884. In some embodiments, the CDR2 comprises a sequence selected from the group consisting of SEQ ID Nos. 1252 to 1326. In some embodiments, the CDR3 comprises a sequence selected from the group consisting of SEQ ID Nos. 1692 to 1768. In some embodiments, the third domain (C) comprises a sequence selected from the group consisting of SEQ ID Nos. 368-442. In some embodiments, the first domain (A) comprises a sequence selected from the group consisting of SEQ ID Nos. 1793 to 1807 and 1897-1898.

In some embodiments, the second domain (B) comprises a sequence selected from the group consisting of SEQ ID Nos. 1769-1778. In some embodiments, the linkers L1 and L2 are each independently selected from (GS)$_n$ (SEQ ID No.1809), (GGS)$_n$ (SEQ ID No.1810), (GGGS)$_n$ (SEQ ID No.1811), (GGSG)$_n$ (SEQ ID No.1812), (GGSGG)$_n$ (SEQ ID No.1813), or (GGGGS)$_n$ (SEQ ID No.1814), wherein n is 1, 2, 3, 4, 5, 6, 7, 8, 9, or 10. In some embodiments, the domains are linked in the order H2N-(A)-(B)—(C)—COOH or by linkers L1 and L2 in the order of H2N-(A)-L1-(B)-L2-(C)—COOH. In some embodiments, the linkers L1 and L2 independently comprise the sequence of GGGGSGGGS (SEQ ID No. 1808). In some embodiments, the DLL3 targeting trispecific protein comprises the sequence of SEQ ID No. 1890 or SEQ ID No. 1891.

One embodiment provides a DLL3 targeting trispecific protein, wherein said protein comprises (a) a first domain (A) which is a single chain variable fragment that specifically binds to a human CD3; (b) a second domain (B) which is a single domain antibody that specifically binds to a human serum albumin protein; and (c) a third domain (C) which is a single domain antibody that specifically binds to DLL3, wherein the third domain comprises the sequence of SEQ ID No.68 or SEQ ID No. 75, or is derived from SEQ ID No.68 or SEQ ID No. 75. In some embodiments, the third domain (C) is derived from SEQ ID No. 68 or from SEQ ID No. 75. In some embodiments, the third domain (C) comprises the sequence of SEQ ID No. 68 or the sequence of SEQ ID No. 75.

One embodiment provides a DLL3 binding protein comprising the following formula:

$$f1\text{-}r1\text{-}f2\text{-}r2\text{-}f3\text{-}r3\text{-}f4$$

wherein, r1 is a complementarity determining region 1 (CDR1) and is identical to or comprises one or more amino acid residue substitutions relative to a sequence selected from the group consisting of SEQ ID Nos. 443-884 and 1887; r2 is a CDR2 and is identical to or comprises one or more amino acid residue substitutions relative to a sequence selected from the group consisting of SEQ ID Nos. 885-1326 and 1888; and r3 is a CDR3 and identical to or comprises one or more amino acid residue substitutions relative to a sequence selected from the group consisting of SEQ ID Nos. 1327-1768 and 1889; and wherein f1, f2, f3 and f4 are framework residues. In some embodiments, the CDR1 comprises a sequence selected from the group consisting of SEQ ID Nos. 443-884 and 1887, the CDR2 comprises a sequence selected from the group consisting of SEQ ID Nos. 885-1326 and 1888, and the CDR3 comprises a sequence selected from the group consisting of SEQ ID Nos. 1327-1768 and 1889.

One embodiment provides a DLL3 targeting trispecific protein, wherein said protein comprises (a) a first domain (A) which is a single chain variable fragment that specifically binds to a human CD3; (b) a second domain (B) which is a single domain antibody that specifically binds to a human serum albumin protein; and (c) a third domain (C) which is a single domain antibody that specifically binds to a DLL3 protein.

In some embodiments, the domains are linked in the order H2N-(A)-(B)—(C)—COOH, H2N-(A)-(C)—(B)—COOH, H2N—(B)-(A)-(C)—COOH, H2N—(B)—(C)-(A)-COOH, H2N—(C)—(B)-(A)-COOH, or H2N—(C)-(A)-(B)—COOH, or by linkers L1 and L2, in the order H2N-(A)-L1-(B)-L2-(C)—COOH, H2N-(A)-L1-(C)-L2-(B)—COOH, H2N—(B)-L1-(A)-L2-(C)—COOH, H2N—(B)-L1-(C)-L2-(A)-COOH, H2N—(C)-L1-(B)-L2-(A)-COOH, or H2N—(C)-L1-(A)-L2-(B)—COOH.

In some embodiments, the third domain (C) comprises an affinity matured binding molecule. In some embodiments, the affinity matured binding molecule is derived from a parental molecule that specifically binds to the DLL3 protein. In some embodiments, wherein the affinity matured binding DLL3 binding molecule has a binding affinity toward the DLL3 protein that is about 2-fold about 50-fold greater than the binding affinity of the parental molecule toward the DLL3 protein. In some embodiments, the third domain (C) comprises a sequence that is at least 80% identical to a sequence selected from the group consisting of SEQ ID Nos. 1-442 and 1886. In some embodiments, the third domain (C) comprises a sequence that is at least 80% identical to a sequence selected from the group consisting of SEQ ID Nos. 1-52. In some embodiments, the third domain (C) comprises a CDR1, a CDR2, and a CDR3, wherein the CDR1 comprises a sequence selected from the group consisting of SEQ ID Nos. 443-884 and 1887, wherein the CDR2 comprises a sequence selected from the group consisting of SEQ ID Nos. 885-1326 and 1888, and wherein the CDR3 comprises a sequence selected from the group consisting of SEQ ID Nos. 1327-1768 and 1889. In some embodiments, the CDR1 comprises a sequence selected from the group consisting of SEQ ID Nos. 495-528. In some embodiments, the CDR2 comprises a sequence selected from the group consisting of SEQ ID Nos. 937-970. In some embodiments, the CDR3 comprises a sequence selected from the group consisting of SEQ ID Nos. 1379-1412. In some embodiments, the third domain (C) comprises a sequence that is at least 80% identical to a sequence selected from the group consisting of SEQ ID Nos. 53-86. In some embodiments, the CDR1 comprises a sequence selected from the group consisting of SEQ ID Nos. 529-809. In some embodiments, the CDR2 comprises a sequence selected from the group consisting of SEQ ID Nos. 971 to 1251. In some embodiments, the CDR3 comprises a sequence selected from the group consisting of SEQ ID Nos. 1379-1412. In some embodiments, the third domain (C) comprises a sequence that is at least 80% identical to a sequence selected from the group consisting of SEQ ID Nos. 87-367. In some embodiments, the CDR1 comprises a sequence selected from the group consisting of SEQ ID Nos. 810-884. In some embodiments, the CDR2 comprises a sequence selected from the group consisting of SEQ ID Nos. 1252 to 1326. In some embodiments, the CDR3 comprises a sequence selected from the group consisting of SEQ ID Nos. 1692 to 1768. In some embodiments, The DLL3 targeting trispecific protein of claim 1, wherein the third domain (C) comprises a sequence that is at least 80% identical to a sequence selected from the group consisting of SEQ ID Nos. 368-442.

One embodiment provides a DLL3 targeting trispecific protein, wherein said protein comprises (a) a first domain (A) which is a single chain variable fragment that specifically binds to a human CD3; (b) a second domain (B) which is a single domain antibody that specifically binds to a human serum albumin protein; and (c) a third domain (C) which is a single domain antibody that specifically binds to DLL3, wherein the third domain comprises the sequence of SEQ ID No.68 or SEQ ID No. 75, or is derived from SEQ ID No.68 or SEQ ID No. 75.

In some embodiments, the third domain (C) is derived from SEQ ID No. 75. In some embodiments, the third domain comprises a CDR1, a CDR2, and a CDR3, wherein the CDR1 comprises the following sequence: $X_1X_2X_3X_4X_5X_6X_7SX_8A$, the CDR2 comprises the following sequence: $GJ_1SJ_2J_3GJ_4J_5J_6YJ_7JSVKG$ (SEQ ID No. 1894), and the CDR3 comprises the following sequence: $Z_1Z_2Z_3Z_4Z_5Z_6Z_7Z_8Z_9$.

In some embodiments:
$X_1$ is A, D, E, F, G, H, K, L, M, N, Q, R, S, V, W, or Y;
$X_2$ is D, E, H, K, M, P, R, S, T, or Y;
$X_3$ is A, D, G, H, K, N, P, Q, R, S, T, V, or Y;
$X_4$ is K, S, or V;
$X_5$ is A, F, G, H, K, L, M, N, Q, R, S, T, V, W, or Y;
$X_6$ is D, F, H, I, K, L, M, N, Q, R, S, V, or Y;
$X_7$ is L, or M; and
$X_8$ is I, L, M, S, T, or V.

In some embodiments:
$J_1$ is I, or V;
$J_2$ is A, D, E, G, H, I, K, L, N, P, Q, R, S, T, V, or Y;
$J_3$ is A, D, E, G, H, N, R, or T;
$J_4$ is H, P, R, or S;
$J_5$ is A, H, I, K, M, N, Q, R, T, or V;
$J_6$ is A, D, G, H, I, L, M, N, S, T, V, or Y;
$J_7$ is A, F, I, L, M, R, S, T, V, or Y;
$J_8$ is A, D, E, G, H, K, L, N, R, S, or V;

In some embodiments:
$Z_1$ is L, or Y;
$Z_2$ is D, E, G, H, K, N, Q, R, S, T, V, or Y;
$Z_3$ is Q, or W;
$Z_4$ is A, D, E, G, H, I, K, L, M, P, R, S, T, or V;
$Z_5$ is A, D, E, G, N, R, S, T, or Y;
$Z_6$ is A, P, R, or S;
$Z_7$ is A, D, F, G, H, L, M, N, Q, R, S, T, V, or Y;
$Z_8$ is A, G, I, K, P, Q, R, S, or T; and
$Z_9$ is F, H, or Y.

In some embodiments, the linkers L1 and L2 are each independently selected from $(GS)_n$ (SEQ ID No.1809), $(GGS)_n$ (SEQ ID No.1810), $(GGGS)_n$ (SEQ ID No.1811), $(GGSG)_n$ (SEQ ID No.1812), $(GGSGG)_n$ (SEQ ID No.1813), or $(GGGGS)_n$ (SEQ ID No.1814), wherein n is 1, 2, 3, 4, 5, 6, 7, 8, 9, or 10, or GGGGSGGGS (SEQ ID No. 1808). In some embodiments, the domains are linked in the order H2N-(A)-(B)—(C)—COOH or by linkers L1 and L2 in the order of H2N-(A)-L1-(B)-L2-(C)—COOH.

One embodiment provides a DLL3 binding protein comprising the following formula:

$$f1\text{-}r1\text{-}f2\text{-}r2\text{-}f3\text{-}r3\text{-}f4$$

wherein, r1 is a complementarity determining region 1 (CDR1) and is identical to or comprises one or more amino acid residue substitutions relative to a sequence selected from the group consisting of SEQ ID Nos. 443-884 and 1887; r2 is a CDR2 and is identical to or comprises one or more amino acid residue substitutions relative to a sequence selected from the group consisting of SEQ ID Nos. 885-1326 and 1888; and r3 is a CDR3 and identical to or comprises one or more amino acid residue substitutions relative to a sequence selected from the group consisting of SEQ ID Nos. 1327-1768 and 1889; and wherein f1, f2, f3 and f4 are framework residues.

One embodiment provides a method for the treatment or amelioration of a proliferative disease, or a tumorous disease, comprising the administration of the DLL3 targeting trispecific protein according to this disclosure, to a subject in need thereof.

One embodiment provides a DLL3 targeting trispecific protein, wherein said protein comprises (a) a first domain (A) which specifically binds to human CD3; (b) a second domain (B) which is a half-life extension domain; and (c) a third domain (C) which specifically binds to a DLL3 protein. In some embodiments, the domains are linked in the order H2N-(A)-(B)—(C)—COOH, H2N-(A)-(C)—(B)—COOH, H2N—(B)-(A)-(C)—COOH, H2N—(B)—(C)-(A)-COOH, H2N—(C)—(B)-(A)-COOH, or H2N—(C)-(A)-(B)—COOH. In some embodiments, the third domain (C) comprises an affinity matured binding molecule. In some embodiments, the affinity matured binding molecule is derived from a parental molecule that specifically binds to the DLL3 protein. In some embodiments, the affinity matured binding molecule is derived from the parental molecule that specifically binds to DLL3, after a round of affinity maturation. In some embodiments, the round of affinity maturation comprises panning a phage display library against the DLL3 protein. In some embodiments, the phage display library is generated by mutating one or more residues of the parental molecule. In some embodiments, the phage display library expresses one or more molecules derived from the parental molecule. In some embodiments, affinity matured binding molecule is selected from the one or more molecules derived from the parental molecule. In some embodiments, the affinity matured DLL3 binding molecule has a greater binding affinity toward the DLL3 protein than a binding affinity of the parental molecule toward the DLL3 protein. In some embodiments, the affinity matured binding DLL3 binding molecule has a binding affinity toward the DLL3 protein that is about 2-fold about 50-fold greater than the binding affinity of the parental molecule toward the DLL3 protein. In some embodiments, the affinity matured binding DLL3 binding molecule has a binding affinity toward the DLL3 protein that is about 3-fold greater than the binding affinity of the parental molecule toward the DLL3 protein. In some embodiments, the third domain (C) comprises a sequence that is at least about 75% identical to a sequence selected from the group consisting of SEQ ID Nos. 1-442 and 1886. In some embodiments, the third domain (C) comprises a sequence that is at least about 75% identical to a sequence selected from the group consisting of SEQ ID Nos. 1-52. In some embodiments, the third domain (C) comprises a CDR1, a CDR2, and a CDR3.

In some embodiments, the CDR1 comprises a sequence selected from the group consisting of SEQ ID Nos. 443-884 and 1887, or one or more amino acid substitutions relative to a sequence selected from the group consisting of SEQ ID Nos. 443-884 and 1887. In some embodiments, the CDR2 comprises a sequence selected from the group consisting of SEQ ID Nos. 885-1326 and 1888, or one or more amino acid substitutions relative to a sequence selected from the group consisting of SEQ ID Nos. 885-1326 and 1888. In some embodiments, the CDR3 comprises a sequence selected from the group consisting of SEQ ID Nos. 1327-1768 and 1889, or one or more substitutions relative to a sequence selected from SEQ ID Nos. 1327-1768 and 1889. In some embodiments, the CDR1 comprises a sequence selected from the group consisting of SEQ ID Nos. 495-528, or one or more amino acid substitutions relative to a sequence selected from the group consisting of SEQ ID Nos.495-528. In some embodiments, the CDR2 comprises a sequence selected from the group consisting of SEQ ID Nos. 937-970, or one or more amino acid substitutions relative to a sequence selected from the group consisting of SEQ ID Nos. 937-970. In some embodiments, the CDR3 comprises a sequence selected from the group consisting of SEQ ID Nos. 1379-1412, or one or more amino acid substitutions relative to a sequence selected from the group consisting of SEQ ID Nos. 1379 to 1412.

In some embodiments, the third domain (C) comprises a sequence that is at least about 80% identical to a sequence selected from the group consisting of SEQ ID Nos. 53-86. In some embodiments, the CDR1 comprises a sequence selected from the group consisting of SEQ ID Nos. 529-809, or more amino acid substitutions relative to a sequence selected from the group consisting of SEQ ID Nos. 529-809. In some embodiments, the CDR2 comprises a sequence that has one or more amino acid substitutions relative to a sequence selected from the group consisting of SEQ ID Nos. 971 to 1251. In some embodiments, the CDR3 comprises a sequence selected from the group consisting of SEQ ID Nos. 1379-1412, or one or more amino acid substitutions relative to a sequence selected from the group consisting of SEQ ID Nos. 1379 to 1412. In some embodiments, the third domain (C) comprises a sequence that is at least about 75% identical to a sequence selected from the group consisting of SEQ ID Nos. 87-367. In some embodiments, the CDR1 comprises a sequence selected from the group consisting of SEQ ID Nos. 810-884, or one or more amino acid substitutions relative to a sequence selected from the group consisting of SEQ ID Nos. 810 to 884. In some embodiments, the CDR2 comprises a sequence selected from the group consisting of SEQ ID Nos. 1252 to 1326, or one or more amino acid substitutions relative to a sequence selected from the group consisting of SEQ ID Nos. 1252 to 1326. In some embodiments, the CDR3 comprises a sequence selected from the group consisting of SEQ ID Nos. 1692 to 1768, or one or more amino acid substitutions relative to a sequence selected from the group consisting of SEQ ID Nos. 1692 to 1768. In some embodiments, the third domain (C) comprises a sequence that is at least about 75% identical to a sequence selected from the group consisting of SEQ ID Nos. 368-442.

One embodiment provides a DLL3 targeting trispecific protein, wherein said protein comprises (a) a first domain (A) which specifically binds to human CD3; (b) a second domain (B) which is a half-life extension domain; and (c) a third domain (C) which specifically binds to DLL3, wherein the third domain comprises the sequence of SEQ ID No.68 or is derived from SEQ ID No.68. In some embodiments, the third domain (C) is derived from SEQ ID No.68. In some embodiments, SEQ ID No.68 comprises a CDR1, a CDR2, and a CDR3. In some embodiments, the CDR1 comprises the following sequence: $GX_1X_2X_3X_4X_5NX_6X_7X_8$. In some embodiments, the CDR2 comprises the following sequence: $GJ_1SJ_2J_3J_4J_5J_6J_7J_8J_9J_{10}SJ_{11}KJ_{12}$ (SEQ ID No. 1895).

In some embodiments, the CDR3 comprises the following sequence:
$Z_1Z_2Z_3Z_4Z_5Z_6Z_7Z_8Z_9Z_{10}Z_{11}$. In some embodiments:
$X_1$ is A, E, F, G, I, K, L, N, Q, R, S, T, V, or Y;
$X_2$ is A, G, I, K, P, R, S, T, or V;
$X_3$ is A, D, F, K, L, N, P, Q, R, S, T, or Y;

$X_4$ is A, D, F, H, I, K, L, M, N, P, R, S, T, V, or Y;
$X_5$ is F, I, K, L, M, N, R, S, T, or V;
$X_6$ is A, or G;
$X_7$ is F, I, L, M, T, V, or Y; and
$X_8$ is A, or G.
In some embodiments:
$J_1$ is I, or V;
$J_2$ is A, K, P, R, or S;
$J_3$ is D, or N;
$J_4$ is D, E, G, K, N, Q, R, S, T, or Y;
$J_5$ is S, or T;
$J_6$ is A, E, F, H, I, K, L, N, Q, R, S, T, V, or Y;
$J_7$ is A, I, L, M, V, or Y;
$J_8$ is D, F, H, I, L, N, S, T, V, or Y;
$J_9$ is A, D, E, F, G, I, K, L, N, Q, R, S, T, V, or Y;
$J_{10}$ is A, D, E, G, K, Q, S, or V;
$J_{11}$ is A, or V; and
$J_{12}$ is G, or V.
In some embodiments:
$Z_1$ is F, or Y;
$Z_2$ is G, H, I, K, N, R, S, or T;
$Z_3$ is A, F, H, I, K, L, M, N, P, Q, R, S, T, or Y;
$Z_4$ is A, E, F, G, H, I, K, L, M, N, Q, R, S, T, V, or Y;
$Z_5$ is A, C, D, E, G, H, I, K, L, N, P, Q, R, S, T, W, or Y;
$Z_6$ is G, K, L, R, or T;
$Z_7$ is A, G, H, L, Q, R, S, T, V, or Y;
$Z_8$ is A, D, E, G, H, P, Q, S, T, W, or Y;
$Z_9$ is A, G, I, K, L, M, N, Q, R, S, T, V, or Y;
$Z_{10}$ is A, G, K, P, R, S, T, or V; and
$Z_{11}$ is A, F, S, or Y.

One embodiment provides a DLL3 targeting trispecific protein, wherein said protein comprises (a) a first domain (A) which specifically binds to human CD3; (b) a second domain (B) which is a half-life extension domain; and (c) a third domain (C) which specifically binds to DLL3, wherein the third domain comprises the sequence of SEQ ID No.75 or is derived from SEQ ID No.75. In some embodiments, SEQ ID No.75 comprises a CDR1, a CDR2, and a CDR3, wherein the CDR1 comprises the following sequence: $X_1X_2X_3X_4X_5X_6X_7SX_8A$, the CDR2 comprises the following sequence: $GJ_1SJ_2J_3GJ_4J_5J_6YJ_7JSVKG$ (SEQ ID No. 1894), and the CDR3 comprises the following sequence: $Z_1Z_2Z_3Z_4Z_5Z_6Z_7Z_8Z_9$.

In some embodiments:
$X_1$ is A, D, E, F, G, H, K, L, M, N, Q, R, S, V, W, or Y;
$X_2$ is D, E, H, K, M, P, R, S, T, or Y;
$X_3$ is A, D, G, H, K, N, P, Q, R, S, T, V, or Y;
$X_4$ is K, S, or V;
$X_5$ is A, F, G, H, K, L, M, N, Q, R, S, T, V, W, or Y;
$X_6$ is D, F, H, I, K, L, M, N, Q, R, S, V, or Y;
$X_7$ is L, or M; and
$X_8$ is I, L, M, S, T, or V.
In some embodiments:
$J_1$ is I, or V;
$J_2$ is A, D, E, G, H, I, K, L, N, P, Q, R, S, T, V, or Y;
$J_3$ is A, D, E, G, H, N, R, or T;
$J_4$ is H, P, R, or S;
$J_5$ is A, H, I, K, M, N, Q, R, T, or V;
$J_6$ is A, D, G, H, I, L, M, N, S, T, V, or Y;
$J_7$ is A, F, I, L, M, R, S, T, V, or Y;
$J_8$ is A, D, E, G, H, K, L, N, R, S, or V;
In some embodiments:
$Z_1$ is L, or Y;
$Z_2$ is D, E, G, H, K, N, Q, R, S, T, V, or Y;
$Z_3$ is Q, or W;
$Z_4$ is A, D, E, G, H, I, K, L, M, P, R, S, T, or V;
$Z_5$ is A, D, E, G, N, R, S, T, or Y;
$Z_6$ is A, P, R, or S;
$Z_7$ is A, D, F, G, H, L, M, N, Q, R, S, T, V, or Y;
$Z_8$ is A, G, I, K, P, Q, R, S, or T; and
$Z_9$ is F, H, or Y.

In some embodiments, the third domain (C) comprises a humanized antibody or an antigen binding fragment thereof. In some embodiments, the third domain (C) comprises a single domain antibody, a VHH domain, a scFv, a VH domain, a VL domain, a Fab, a Fab', a non-Ig domain, a ligand, a knottin, or a small molecule entity that specifically binds to DLL3. In some embodiments, the third domain (C) comprises the single domain antibody. In some embodiments, the second domain (B) binds a bulk serum protein. In some embodiments, the second domain (B) comprises a single domain antibody, a VHH domain, a scFv, a VH domain, a VL domain, a Fab, a Fab', a non-Ig domain, a ligand, a knottin, or a small molecule entity that specifically binds to the bulk serum protein. In some embodiments, the second domain (B) comprises the single domain antibody that specifically binds to the bulk serum protein. In some embodiments, the bulk serum protein comprises albumin, transferrin, IgG1, IgG2, IgG4, IgG3, IgA monomer, Factor XIII, Fibrinogen, IgE, pentameric IgM, or Igκ free light chain. In some embodiments, the bulk serum protein comprises the albumin. In some embodiments, the second domain (B) comprises a sequence that is at least about 75% identical to a sequence selected from the group consisting of SEQ ID Nos. 1769-1778. In some embodiments, the second domain (B) comprises a sequence that is at least about 75% identical to SEQ ID No.1774.

In some embodiments, the first domain (A) comprises a single domain antibody, a VHH domain, a scFv, a VH domain, a VL domain, a Fab, a Fab', a non-Ig domain, a ligand, a knottin, or a small molecule entity that specifically binds to CD3. In some embodiments, the first domain (A) comprises a sequence selected from the group consisting of SEQ ID Nos. 1793-1807. In some embodiments, the third domain (C) comprises the following formula:

$$f1\text{-}r1\text{-}f2\text{-}r2\text{-}f3\text{-}r3\text{-}f4$$

wherein, r1 is identical to or comprises one or more amino acid residue substitutions relative to a sequence selected from the group consisting of SEQ ID Nos. 443-884 and 1887; r2 is identical to or comprises one or more amino acid residue substitutions relative to a sequence selected from the group consisting of SEQ ID Nos. 885-1326 and 1888; and r3 is identical to or comprises one or more amino acid residue substitutions relative to a sequence selected from the group consisting of SEQ ID Nos. 1327-1768 and 1889; and wherein f1, f2, f3 and f4 are framework residues. In some embodiments, the third domain (C) comprises a sequence that is at least 75% identical to a sequence selected from the group consisting of SEQ ID Nos. 1-442 and 1886. In some embodiments, the domains C and B are connected by linker L1 and domains B and A are connected by linker L2. In some embodiments, the linkers L1 and L2 are each independently selected from (GS). (SEQ ID No.1809), $(GGS)_n$ (SEQ ID No.1810), $(GGGS)_n$ (SEQ ID No.1811), $(GGSG)_n$ (SEQ ID No.1812), $(GGSGG)_n$ (SEQ ID No.1813), or $(GGGGS)_n$ (SEQ ID No.1814), wherein n is 1, 2, 3, 4, 5, 6, 7, 8, 9, or 10. In some embodiments, the linkers L1 and L2 are each independently $(GGGGS)_4$ (SEQ ID No.1817) or $(GGGGS)_3$ (SEQ ID No.1818). In some embodiments, the protein binds to DLL3 with a binding affinity (Kd) of about 0.1 nM to about 50 nM. In some embodiments, the protein binds to human DLL3, cynomolgus DLL3, or both human and cynomolgus DLL3. In some embodiments, the protein is less than about 80 kDa. In some embodiments, the protein is about 50 to about 75 kDa. In some embodiments, the protein is less than about 60 kDa. In some embodiments, the protein has an elimination half-time of at least about 50 hours. In some embodiments, the protein has an elimination half-time of at least about 100 hours. In some embodiments, the protein has increased tissue penetration as compared to an IgG to the same DLL3. In some embodiments, the domains are linked in the order H2N-(A)-(B)—(C)—COOH.

One embodiment provides a pharmaceutical composition comprising (i) the DLL3 targeting trispecific protein according to any one of above embodiments or a DLL3 binding protein according to this disclosure, and (ii) a pharmaceutically acceptable carrier. One embodiment provides a method for preparing a DLL3 targeting trispecific binding protein according to any one of above embodiments, the method comprising: i) providing a DLL3 protein or a fragment thereof, ii) exposing a recombinant library of DLL3 binding proteins to the DLL3 protein or a fragment thereof; iii) selecting from the library a DLL3 binding protein which specifically binds to said oligomer or derivative thereof, and (iv) preparing the DLL3 targeting trispecific protein using the DLL3 binding protein identified in step (iii). In some embodiments, the recombinant library of DLL3 binding proteins is exposed to the DLL3 protein in vitro by screening the recombinant library with said DLL3 protein. In some embodiments, the recombinant library is expressed on the surface of a bacteriophage. In some embodiments, the recombinant library is expressed on the surface of yeast cells. In some embodiments, the recombinant library is expressed on the surface of bacterial cells. In some embodiments, the recombinant library is expressed as RNA-protein fusions. In some embodiments, the recombinant library is an scFv library or an Fab library. In some embodiments, the recombinant antibody library is a single domain library.

One embodiment provides a process for the production of a DLL3 targeting trispecific protein according to any one of above embodiments, said process comprising culturing a host transformed or transfected with a vector comprising a nucleic acid sequence encoding the DLL3 trispecific protein according to any one of above embodiments under conditions allowing the expression of the DLL3 targeting trispecific protein and recovering and purifying the produced protein from the culture.

One embodiment provides a DLL3 binding protein comprising the following formula:

$$f1\text{-}r1\text{-}f2\text{-}r2\text{-}f3\text{-}r3\text{-}f4$$

wherein, r1 is a complementarity determining region 1 (CDR1) and is identical to or comprises one or more amino acid residue substitutions relative to a sequence selected from the group consisting of SEQ ID Nos. 443-884 and 1887; r2 is a CDR2 and is identical to or comprises one or more amino acid residue substitutions relative to a sequence selected from the group consisting of SEQ ID Nos. 885-1326 and 1888; and r3 is a CDR3 and identical to or comprises one or more amino acid residue substitutions relative to a sequence selected from the group consisting of SEQ ID Nos. 1327-1768 and 1889; and wherein f1, f2, f3 and f4 are framework residues. In some embodiments, the DLL3 binding protein comprises a sequence that is at least about 75% identical to a sequence selected from the group consisting of SEQ ID Nos. 1-442 and 1886. In some embodiments, the DLL3 binding protein comprises a sequence that is at least about 75% identical to a sequence selected from the group consisting of SEQ ID Nos. 1-52. In some embodiments, the DLL3 binding protein comprises a sequence that is at least about 75% identical to a sequence selected from the group consisting of SEQ ID Nos. 53-86. In some embodiments, the DLL3 binding protein comprises a sequence that is at least about 75% identical to a sequence selected from the group consisting of SEQ ID Nos. 87-367. In some embodiments, the DLL3 binding protein comprises a sequence that is at least about 75% identical to a sequence selected from the group consisting of SEQ ID Nos. 368-442. One embodiment provides a DLL3 binding protein that is derived from a parental DLL3 binding protein comprising the sequence of SEQ ID No. 68. One embodiment provides a DLL3 binding protein that is derived from a parental DLL3 binding protein comprising the sequence of SEQ ID No. 75 or comprises the sequence of SEQ ID No. 75.

One embodiment provides a method for preparing a DLL3 binding protein according to this disclosure, the method comprising: i) providing a DLL3 protein or a fragment thereof,
ii) exposing a recombinant library of DLL3 binding proteins to the DLL3 protein or a fragment thereof; iii) selecting from the library a DLL3 binding protein which specifically binds to said oligomer or derivative thereof. In some embodiments, the recombinant library of DLL3 binding proteins is exposed to the DLL3 protein in vitro by screening the recombinant library with said DLL3 protein. In some embodiments, the recombinant library is expressed on the surface of a bacteriophage. In some embodiments, the recombinant library is expressed on the surface of yeast cells. In some embodiments, the recombinant library is expressed on the surface of bacterial cells. In some embodiments, the recombinant library is expressed as RNA-protein fusions. In some embodiments, the recombinant library is an scFv library or an Fab library. In some embodiments, the recombinant antibody library is a single domain library.

One embodiment provides a process for the production of a DLL3 binding protein according to this disclosure, said process comprising culturing a host transformed or transfected with a vector comprising a nucleic acid sequence encoding the DLL3 binding protein according to this disclosure under conditions allowing the expression of the DLL3 binding protein and recovering and purifying the produced protein from the culture.

One embodiment provides a method for the treatment or amelioration of a proliferative disease, or a tumorous disease, comprising the administration of the DLL3 targeting trispecific protein according to any one of above embodiments, a DLL3 binding protein according to this disclosure, or a pharmaceutical composition as provided herein, to a subject in need thereof. In some embodiments, the subject is human. In some embodiments, the method further comprises administration of an agent in combination with the DLL3 targeting trispecific protein according to any one of above embodiments, the DLL3 binding protein according to this disclosure, or the pharmaceutical composition as provided herein. In some embodiments, the DLL3 targeting trispecific protein or the DLL3 binding protein selectively binds to tumor cells expressing DLL3. In some embodiments, the DLL3 targeting trispecific protein mediates T cell killing of tumor cells expressing DLL3. In some embodiments, the tumorous disease comprises a solid tumor disease. In some embodiments, the solid tumor disease comprises lung cancer, gastric cancer, ovarian cancer, or triple negative breast cancer. In some embodiments, in the solid tumor disease is metastatic.

One embodiment provides a method for the treatment or amelioration of a proliferative disease, or a tumorous disease, comprising administration of a DLL3 targeting trispecific protein comprising a DLL3 binding domain comprising sequence selected from the group consisting of SEQ ID Nos. 1-442 and 1886, or a DLL3 binding protein comprising a sequence selected from the group consisting of SEQ ID Nos. 1-442 and 1886. In some embodiments, the DLL3 targeting trispecific protein or the DLL3 binding protein selectively binds to tumor cells expressing DLL3. In some embodiments, the DLL3 targeting trispecific protein directs T cell killing of tumor cells expressing DLL3. In some embodiments, the tumorous disease comprises a solid tumor disease. In some embodiments, the solid tumor disease comprises lung cancer, gastric cancer, ovarian cancer, or triple negative breast cancer. In some embodiments, the solid tumor disease is metastatic.

One embodiment provides a method for the treatment or amelioration of a proliferative disease, or a tumorous disease, comprising administration of a DLL3 binding domain comprising a sequence as set forth in SEQ ID No. 68 or 75 or a DLL3 binding protein comprising a sequence as set forth in SEQ ID No. 68 or 75. In some embodiments, the DLL3 targeting trispecific protein or the DLL3 binding protein at a dose of up to 10 mg/kg. In some embodiments, the protein is administered at least once a week. In some embodiments, the protein is administered twice per week. In some embodiments, the protein is administered every other week. In some embodiments, the protein is administered every three weeks.

In one embodiment is provided a DLL3 binding protein comprising an amino acid sequence as set forth in SEQ ID No. 1890 or SEQ ID No. 1891.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 18:
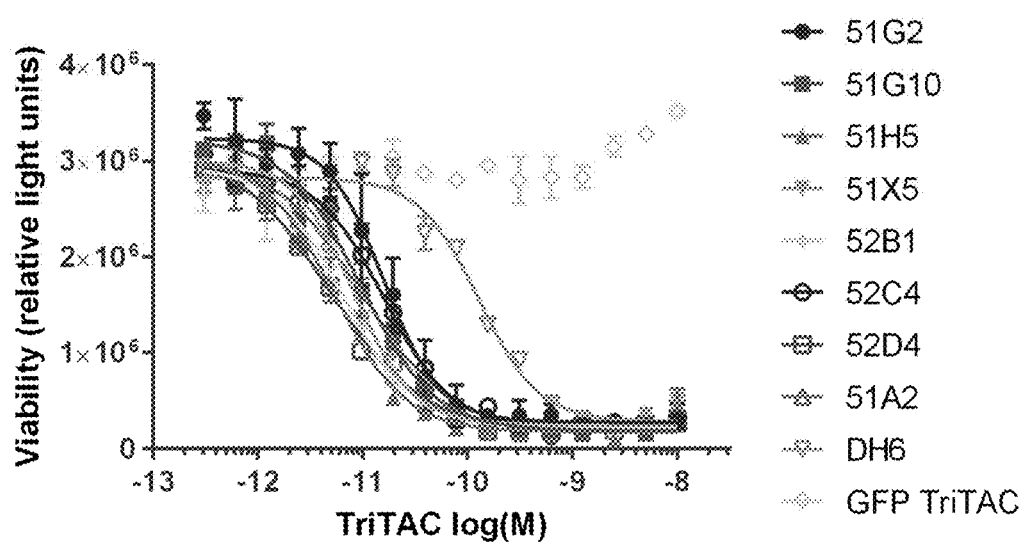

FIG. 18 illustrates results of a TDCC assay on DMS-53 cells, using exemplary purified affinity matured CHO expressed DLL3 targeting trispecific proteins containing exemplary DLL3 binding domains of this disclosure 51G2, 51G10, 51H5, 51X5, 52B1, 52C4, 52D4, 51A2, and parental DLL3 binder domain DH6, and a control trispecific protein.

Figure 19:
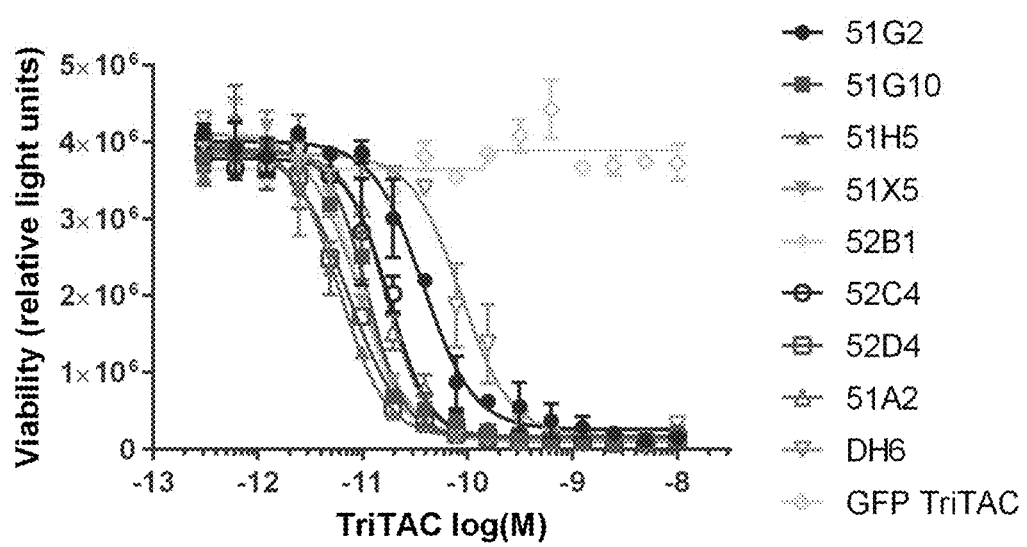

FIG. 19 illustrates results of a TDCC assay on DMS-153 cells, using exemplary purified affinity matured CHO expressed DLL3 targeting trispecific proteins of this disclosure, containing exemplary DLL3 binding domains of this disclosure 51G2, 51G10, 51H5, 51X5, 52B1, 52C4, 52D4, 51A2, and parental DLL3 binder domain DH6, and a control binding trispecific protein that targets GFP.

Figure 20:
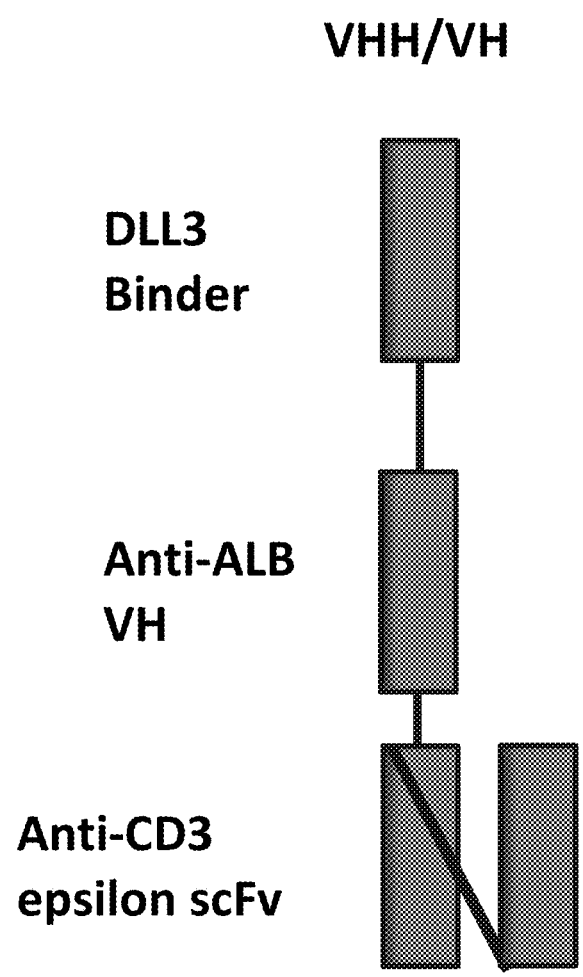

FIG. 20 provides a schematic illustration of a DLL3 targeting trispecific protein containing an exemplary DLL3 binding protein of this disclosure (DLL3 binder), a CD3 binding domain (anti-CD3 epsilon scFv), and an albumin binding (anti-ALB) domain, in an anti-DLL3: anti-ALB: anti-CD3 orientation (TAC orientation).

Figure 21:
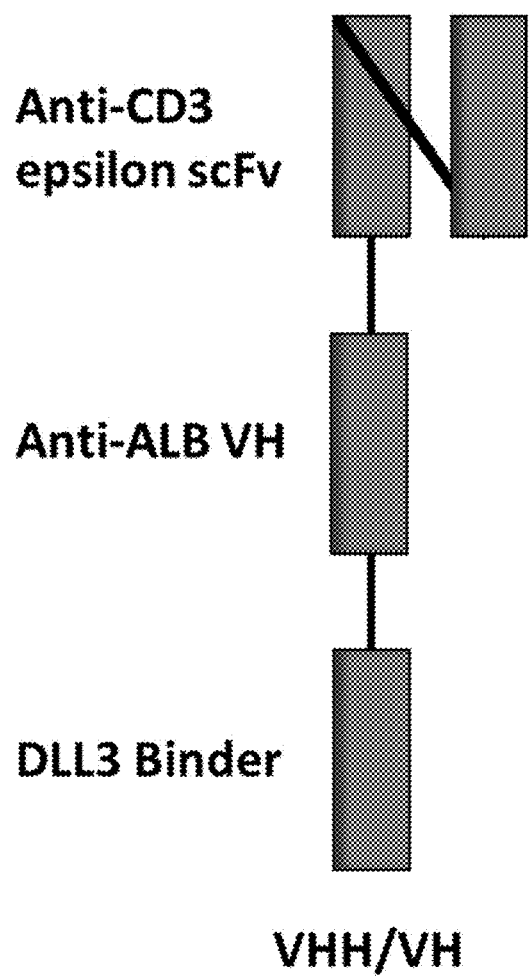

FIG. 21 provides a schematic illustration of a DLL3 targeting trispecific protein containing an exemplary DLL3 binding protein of this disclosure (DLL3 binder), a CD3 binding domain (anti-CD3 epsilon scFv), and an albumin binding (anti-ALB) domain, in an anti-CD3: anti-ALB: anti-DLL3 orientation (CAT orientation).

Figure 22:
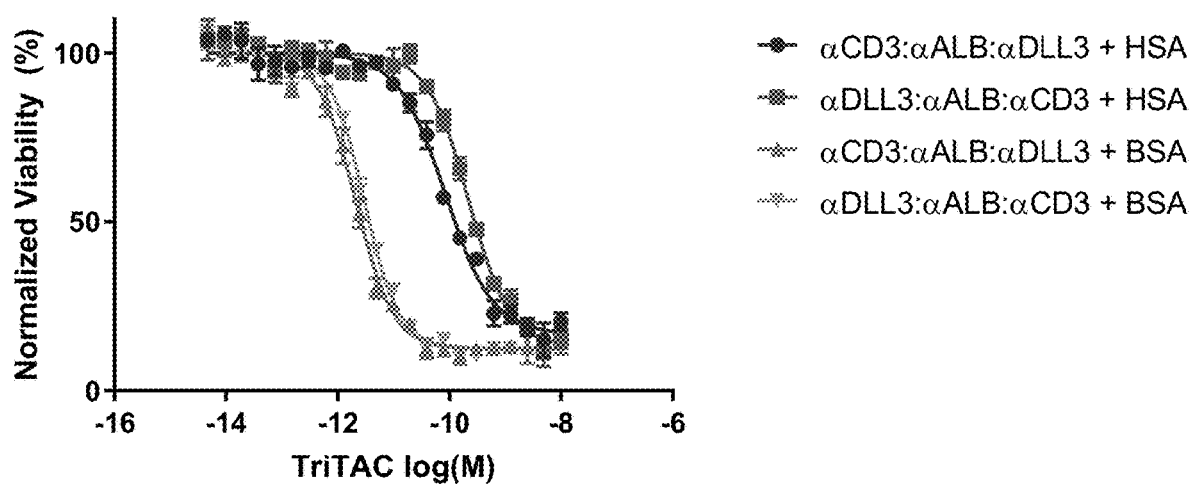

FIG. 22 illustrates results of a T cell dependent cellular cytotoxicity (TDCC) assay on NCI-H2171 cells, using exemplary DLL3 trispecific proteins containing a DLL3 binding domain of this disclosure, 52D04, in an anti-CD3:anti-ALB:anti-DLL3 (CAT) configuration or in an anti-DLL3:anti-ALB:anti-CD3 (TAC) configuration, tested in the presence of human serum albumin (HSA) or bovine serum albumin (BSA).

Figure 23:
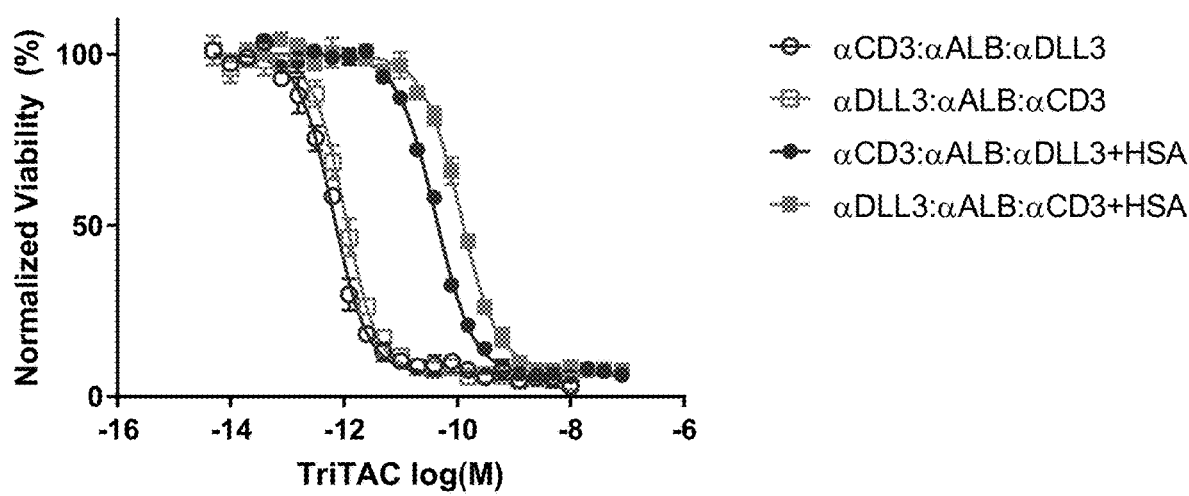

FIG. 23 illustrates results of a T cell dependent cellular cytotoxicity (TDCC) assay on DMS-79 cells, using exemplary DLL3 targeting trispecific proteins containing a DLL3 binding domain of this disclosure, 52D04, in an anti-CD3:anti-ALB:anti-DLL3 (CAT) configuration or in an anti-DLL3:anti-ALB:anti-CD3 (TAC) configuration, tested in the presence or absence of human serum albumin (HSA).

Figure 24:
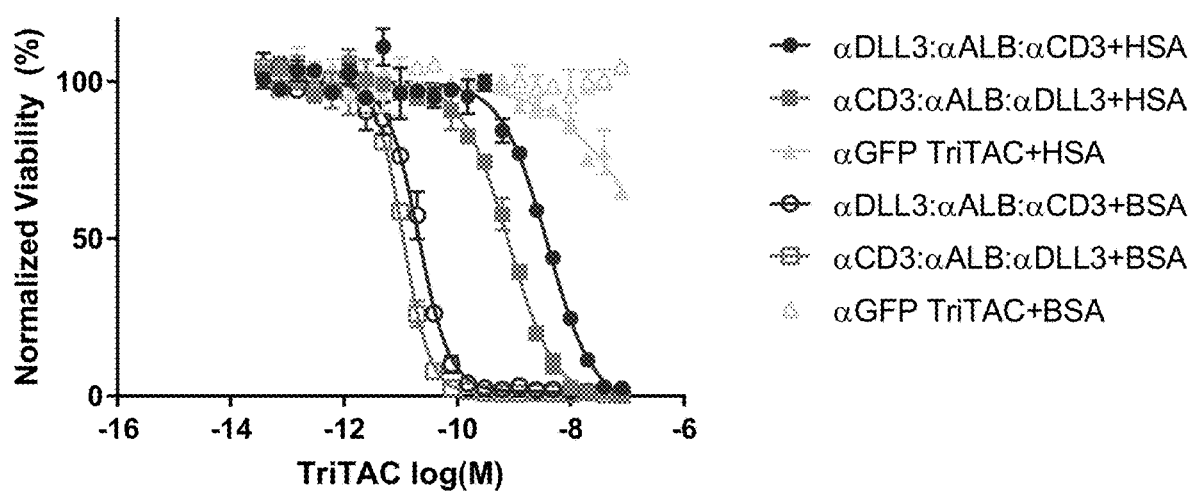

FIG. 24 illustrates results of a T cell dependent cellular cytotoxicity (TDCC) assay on SHP77 cells, using exemplary DLL3 trispecific proteins containing a DLL3 binding domain of this disclosure, 52D04, in an anti-CD3:anti-ALB:anti-DLL3 (CAT) configuration or in an anti-DLL3:anti-ALB:anti-CD3 (TAC) configuration, tested in the presence of human serum albumin (HSA) or bovine serum albumin (BSA).

Figure 25:
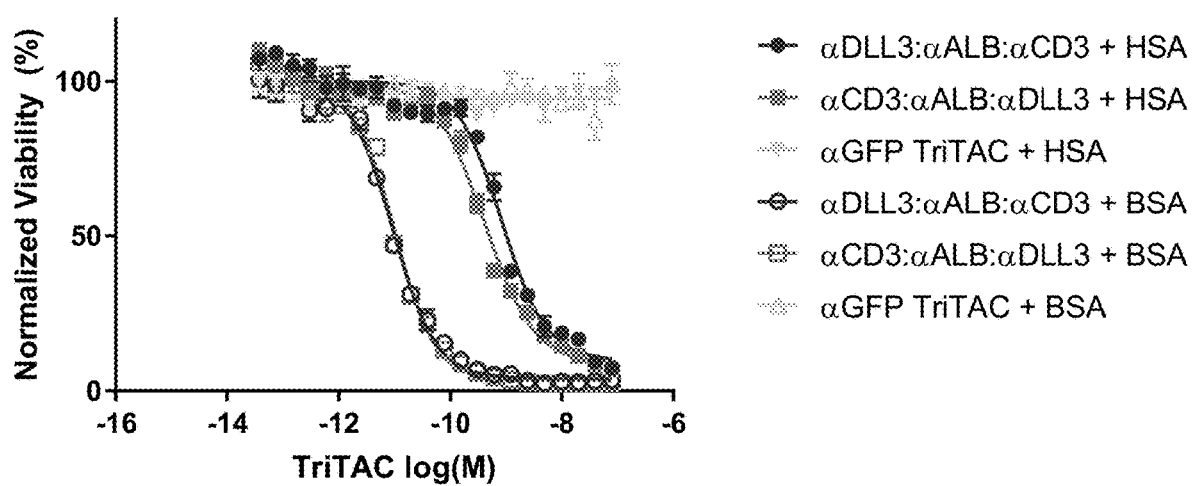

FIG. 25 illustrates results of a T cell dependent cellular cytotoxicity (TDCC) assay on WM2664 cells, using exemplary DLL3 trispecific proteins containing a DLL3 binding domain of this disclosure, 52D04, in an anti-CD3:anti-ALB:anti-DLL3 (CAT) configuration or in an anti-DLL3:anti-ALB:anti-CD3 (TAC) configuration, tested in the presence of human serum albumin (HSA) or bovine serum albumin (BSA).

Figure 26:
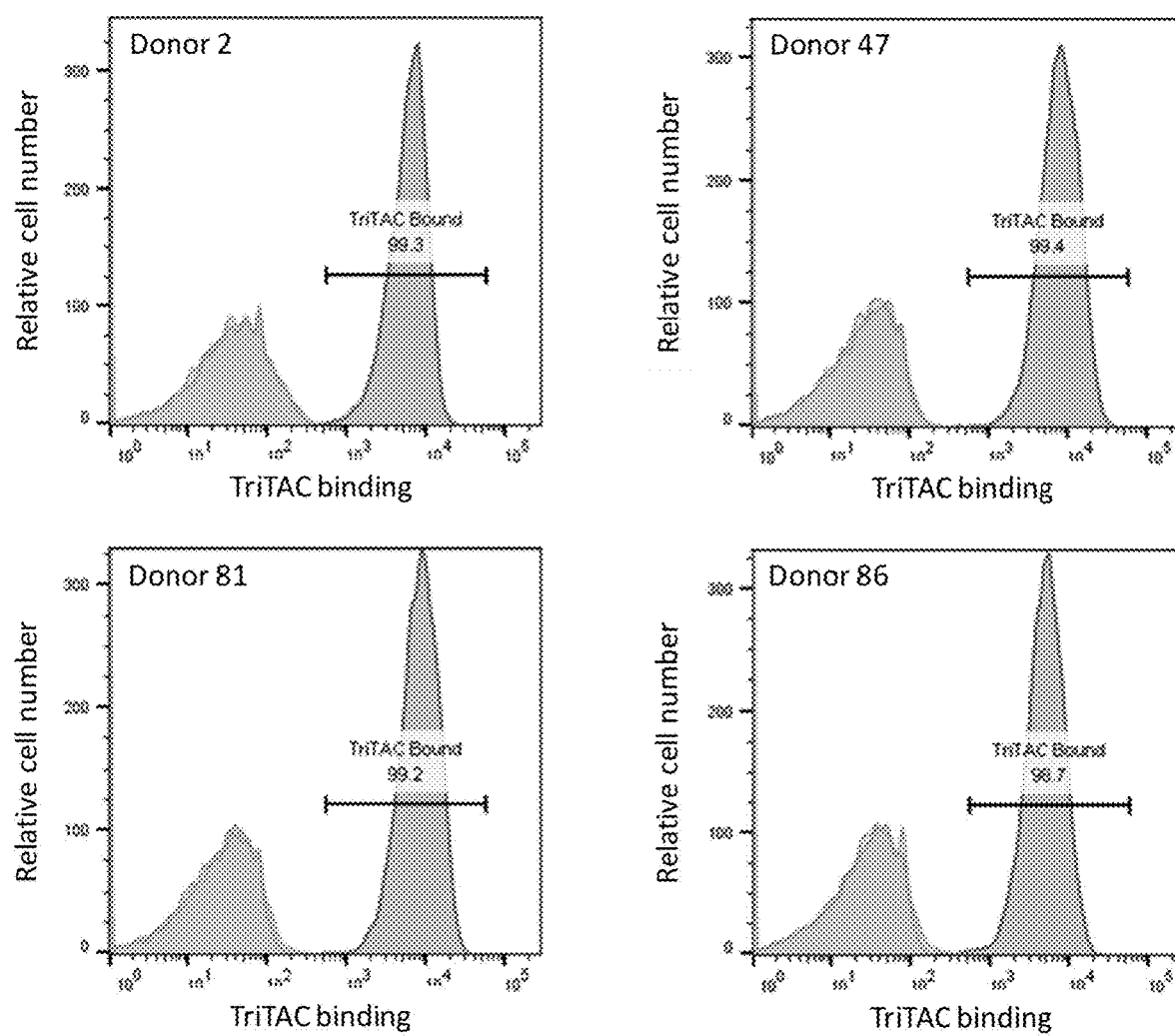

FIG. 26 depicts binding of an exemplary DLL3 targeting trispecific proteins containing DLL3 binding domain of this disclosure, 52D04, in an anti-DLL3:anti-ALB:anti-CD3 (TAC) configuration to human T cells from four different donors as compared to that of a controls with secondary antibody alone or cells without any antibody or trispecific molecule.

Figure 27:
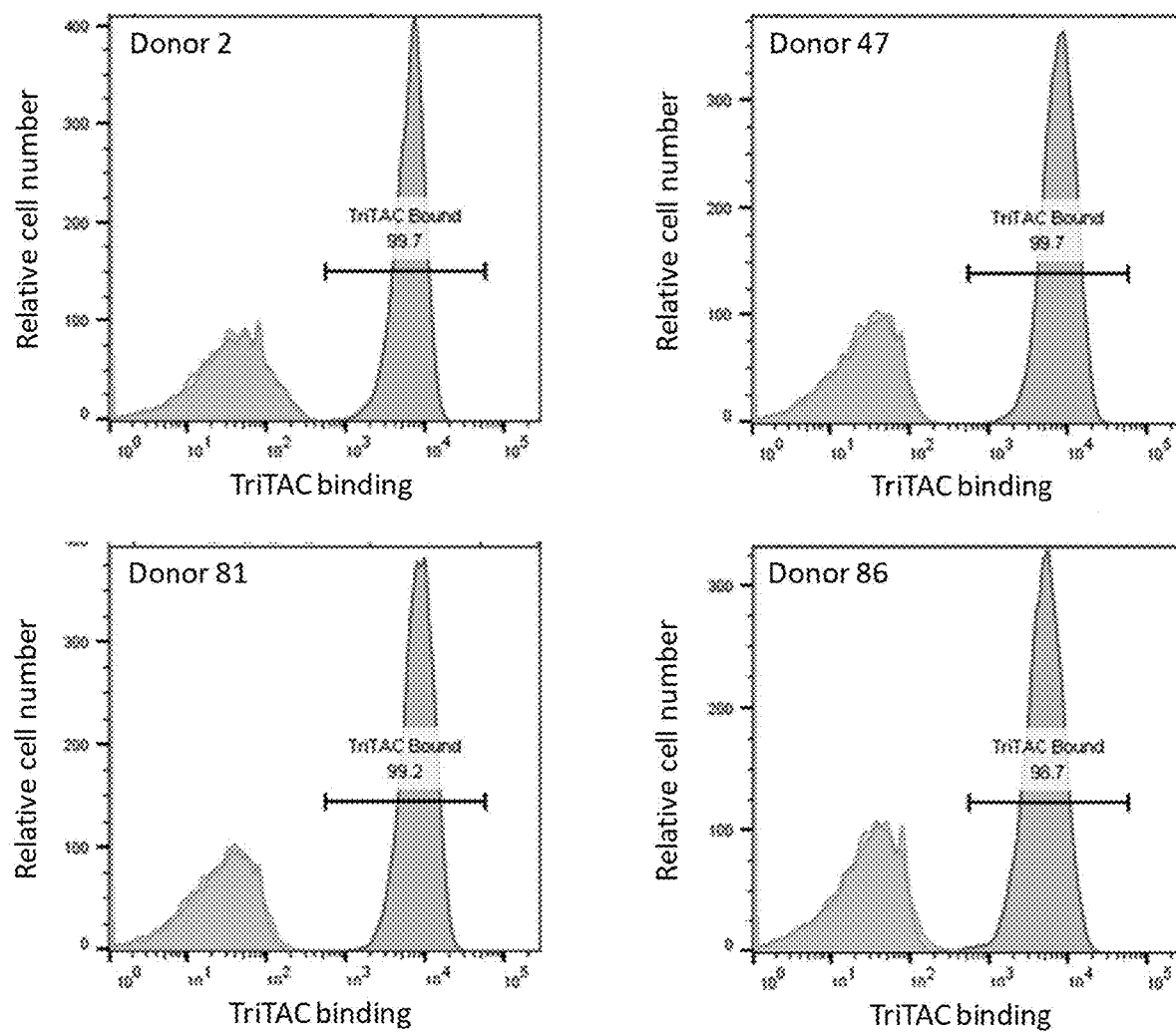

FIG. 27 depicts binding of an exemplary DLL3 targeting trispecific proteins containing DLL3 binding domain of this disclosure, 52D04, in an anti-CD3:anti-ALB:anti-DLL3 (CAT) configuration to human T cells from four different donors as compared to that of a controls with secondary antibody alone or cells without any antibody or trispecific molecule.

Figure 28:
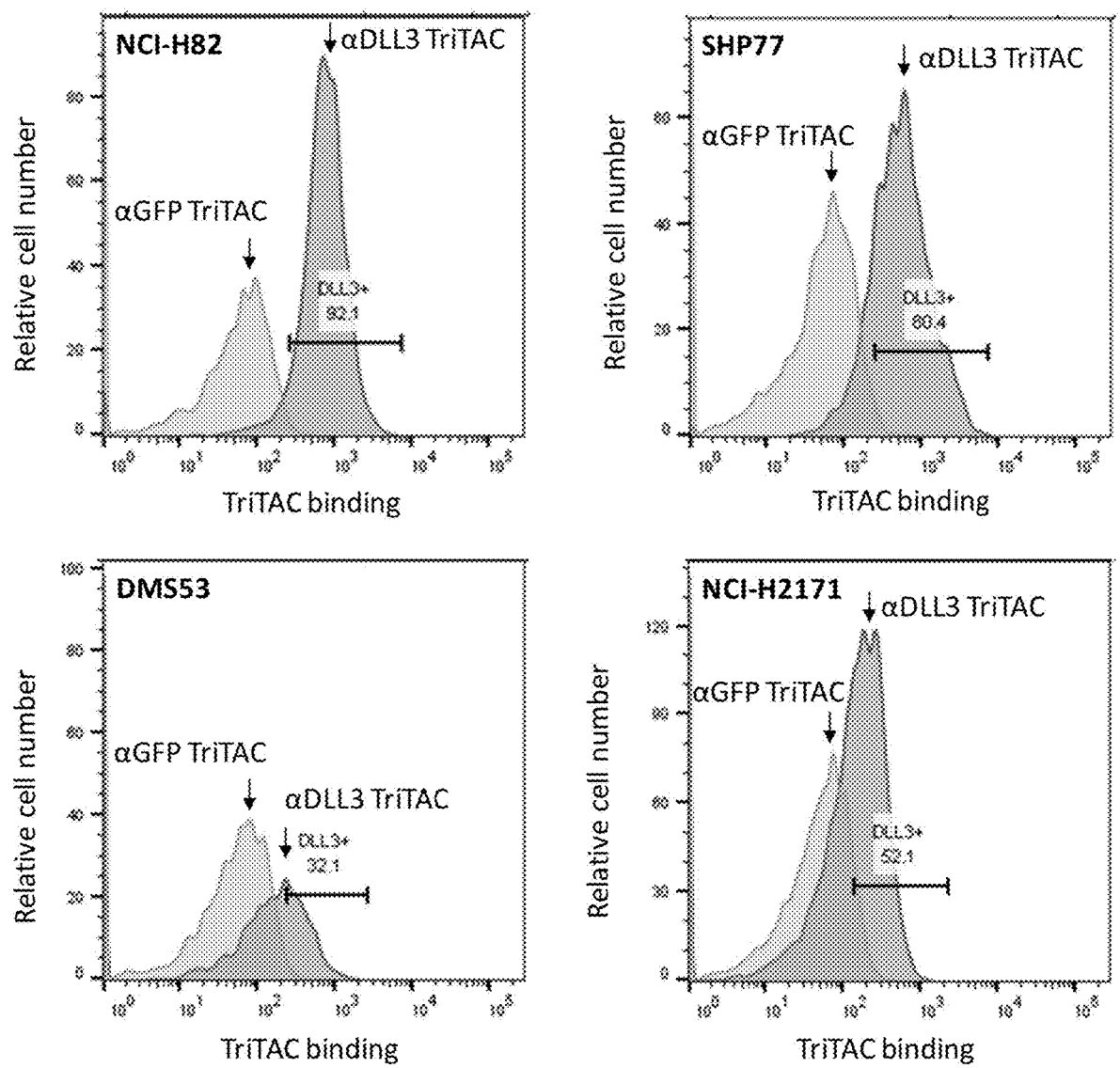

FIG. 28 depicts binding of an exemplary DLL3 targeting trispecific proteins containing DLL3 binding domain of this disclosure, 52D04, in an anti-DLL3:anti-ALB:anti-CD3 (TAC) configuration to human DLL3 expressing cell lines NCI-H82 (top left), SHP77 (top right), DMS53 (bottom left) or NCI-H2171 (bottom right) compared to a trispecific molecules with an GFP binding domain.

Figure 29:
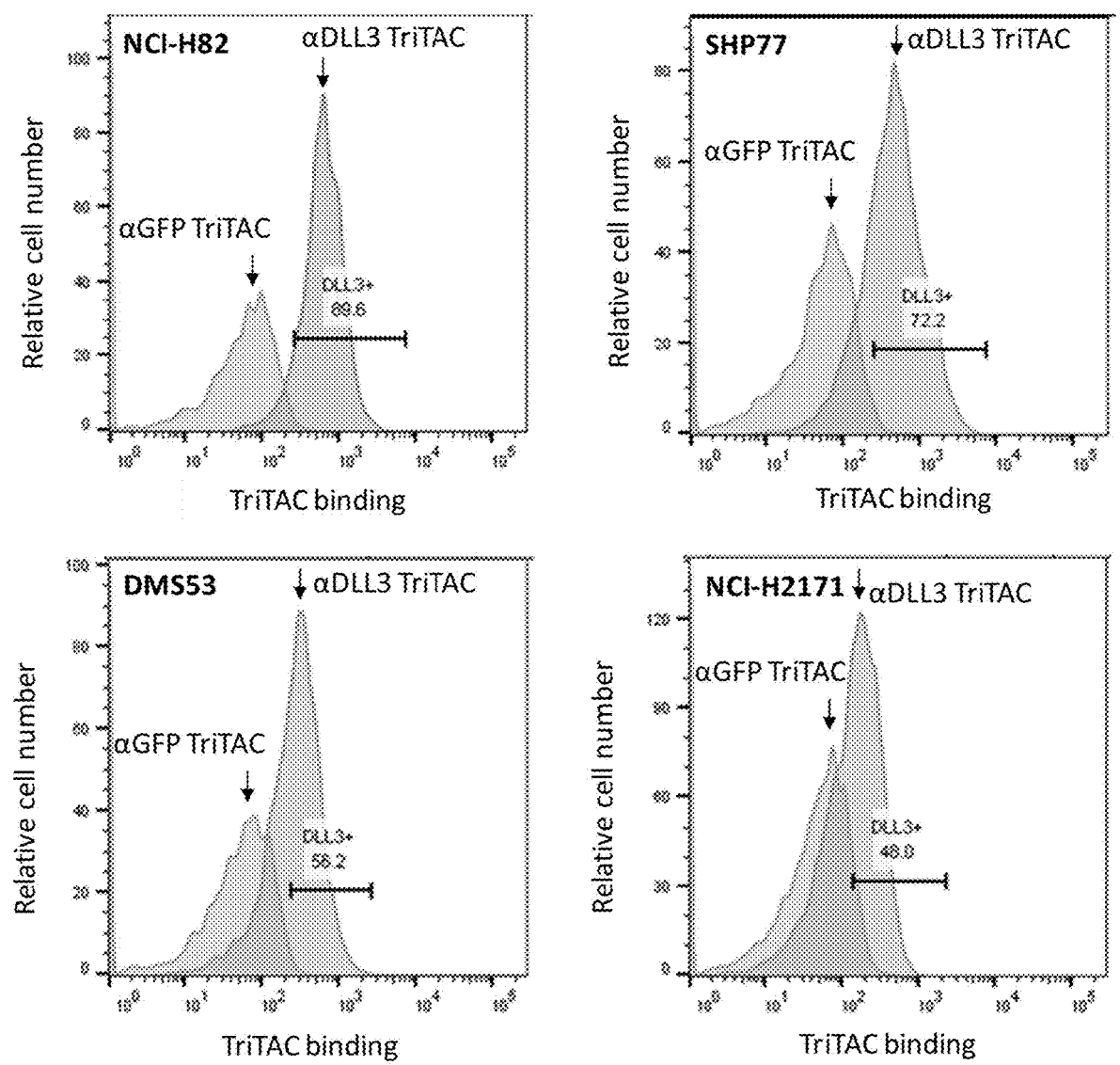

FIG. 29 depicts binding of an exemplary DLL3 targeting trispecific proteins containing DLL3 binding domain of this disclosure, 52D04, in an anti-CD3:anti-ALB:anti-DLL3 (CAT) configuration to human DLL3 expressing cell lines NCI-H82 (top left), SHP77 (top right), DMS53 (bottom left) or NCI-H2171 (bottom right) compared to a trispecific molecules with an GFP binding domain.

Figure 30:
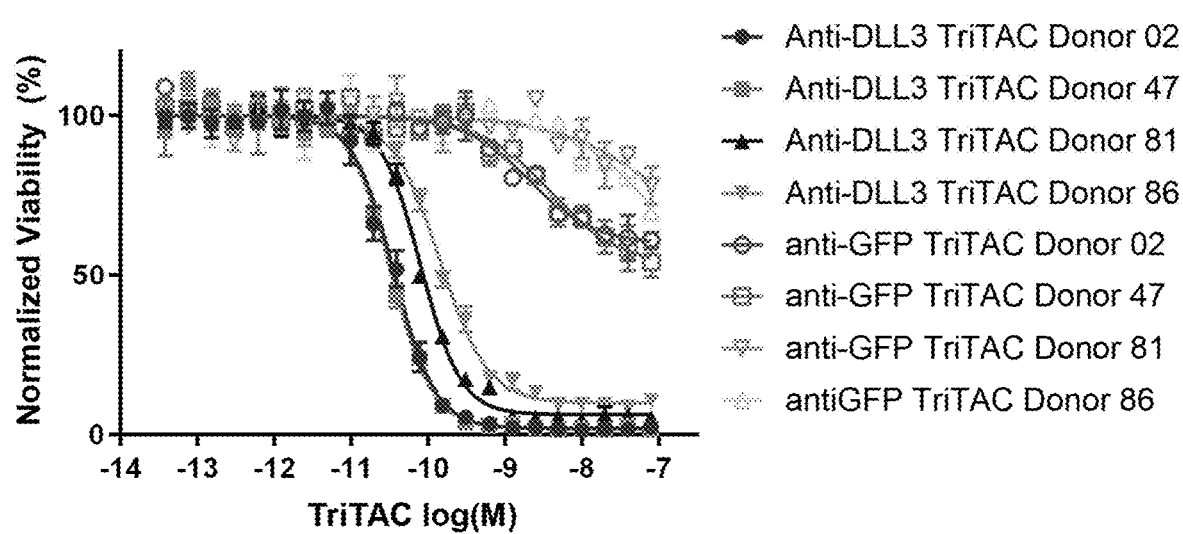

FIG. 30 illustrates the results of a TDCC assay on NCI-H82 cells, using exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA), using T cells from four different donors.

Figure 31:
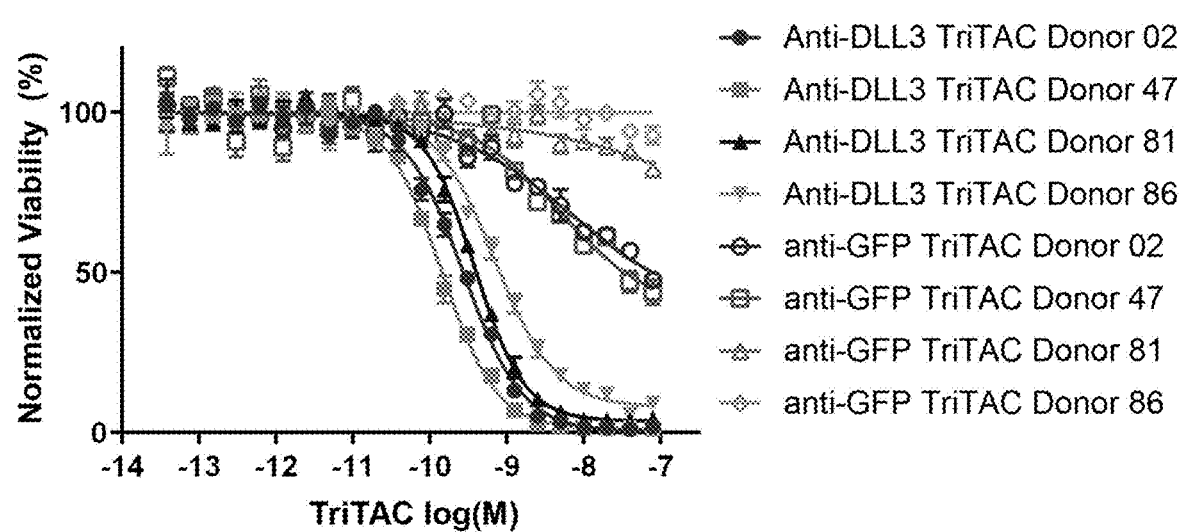

FIG. 31 illustrates the results of a TDCC assay on SHP77 cells, using exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA), using T cells from four different donors.

Figure 32:
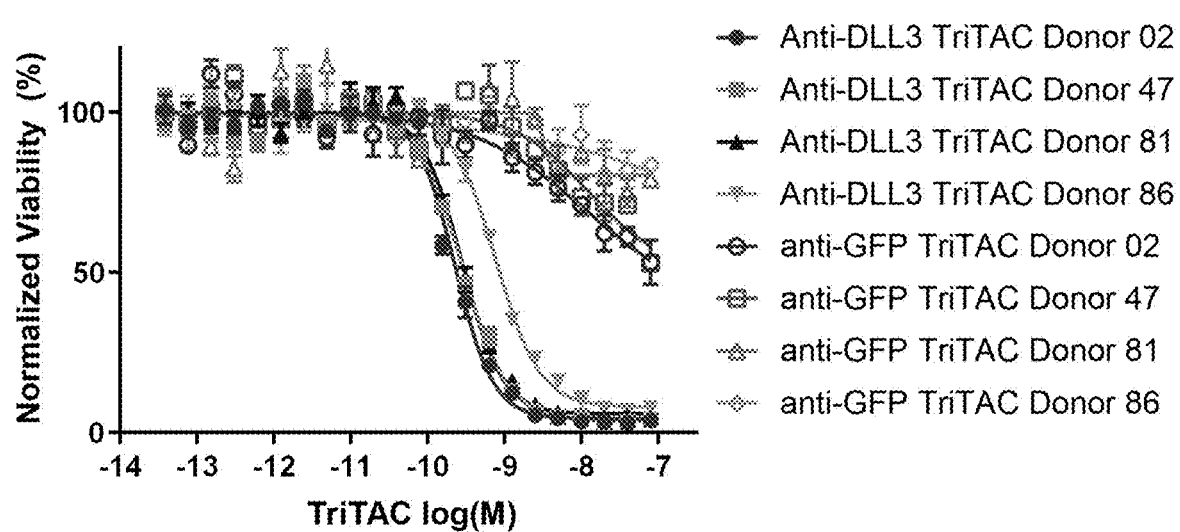

FIG. 32 illustrates the results of a TDCC assay on DMS53 cells, using exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA), using T cells from four different donors.

Figure 33:
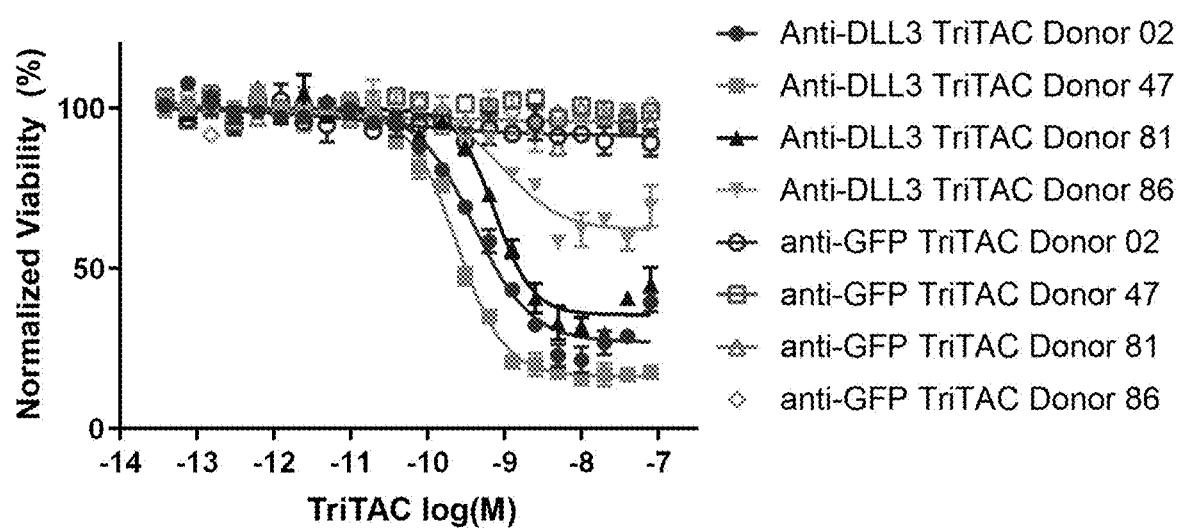

FIG. 33 illustrates the results of a TDCC assay on NCI-H2171 cells, using exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA), using T cells from four different donors.

Figure 34:
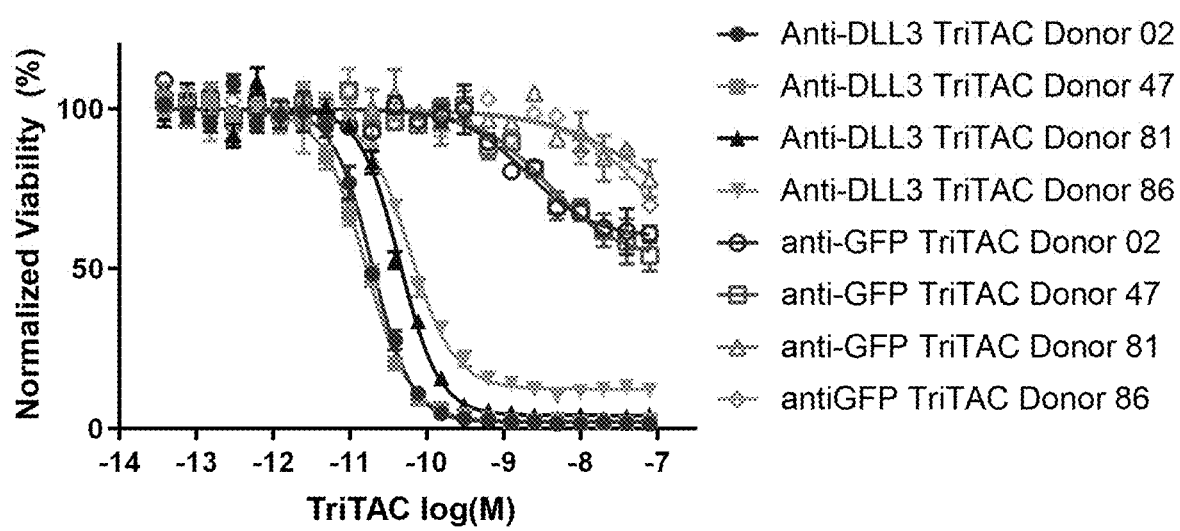

FIG. 34 illustrates the results of a TDCC assay on NCI-H82 cells, using exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA), using T cells from four different donors.

Figure 35:
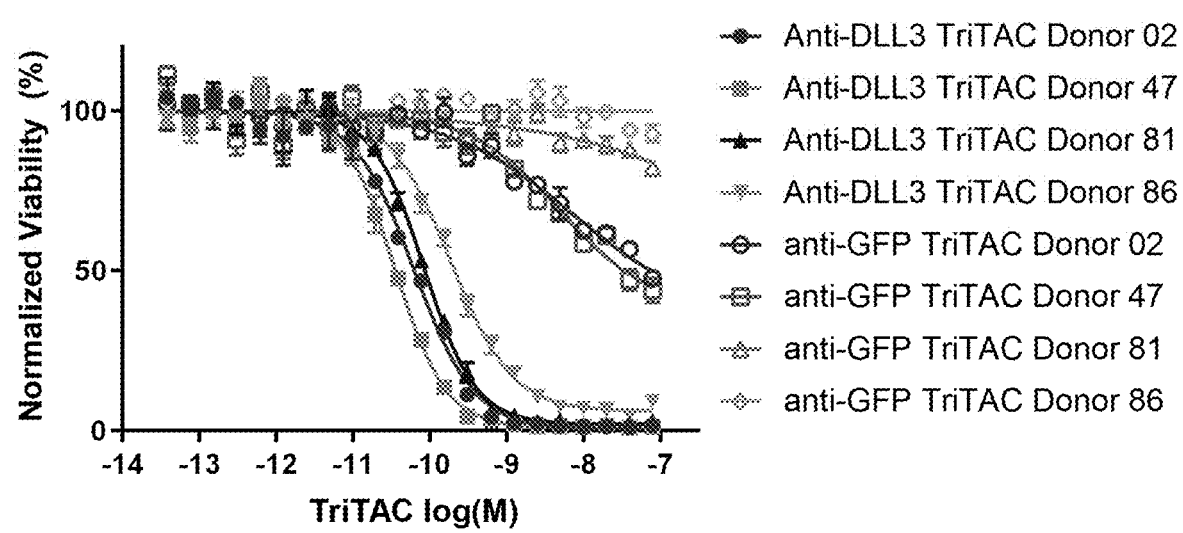

FIG. 35 illustrates the results of a TDCC assay on SHP77 cells, using exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA), using T cells from four different donors.

Figure 36:
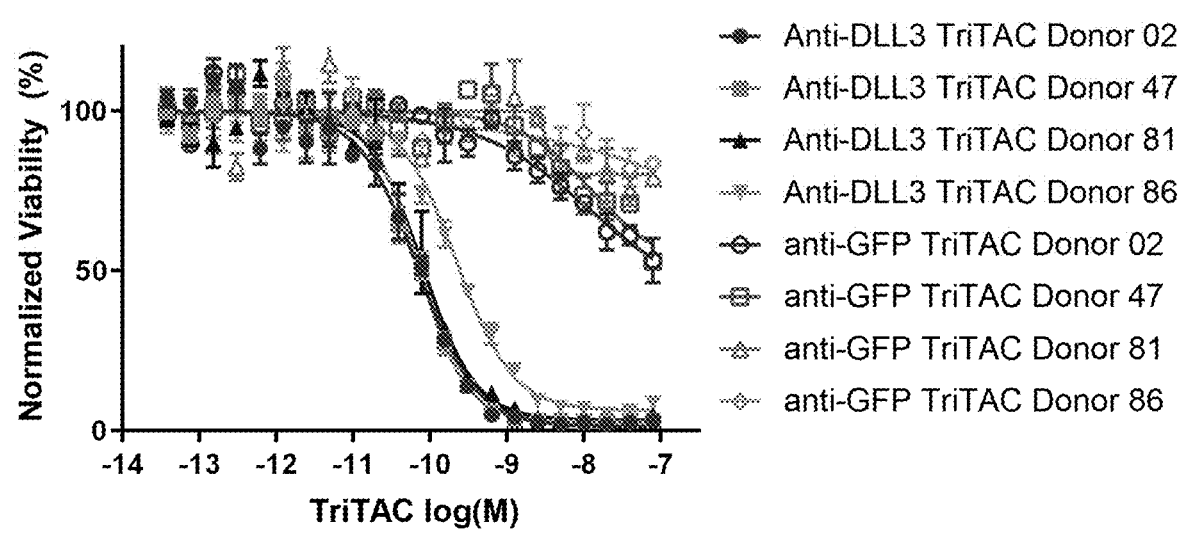

FIG. 36 illustrates the results of a TDCC assay on DMS53 cells, using exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA), using T cells from four different donors.

Figure 37:
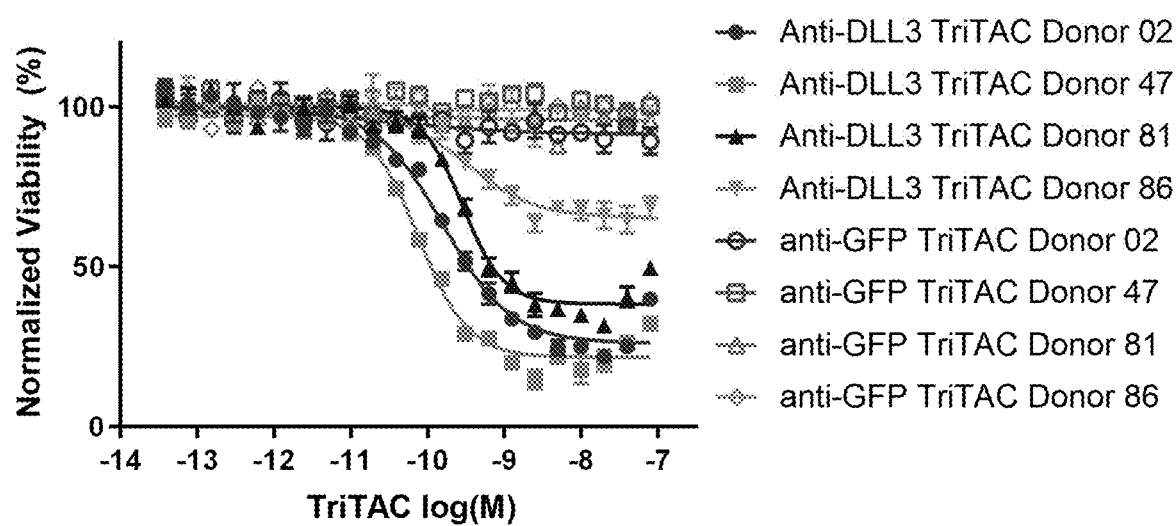

FIG. 37 illustrates the results of a TDCC assay on NCI-H2171 cells, using exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA), using T cells from four different donors.

Figure 38:
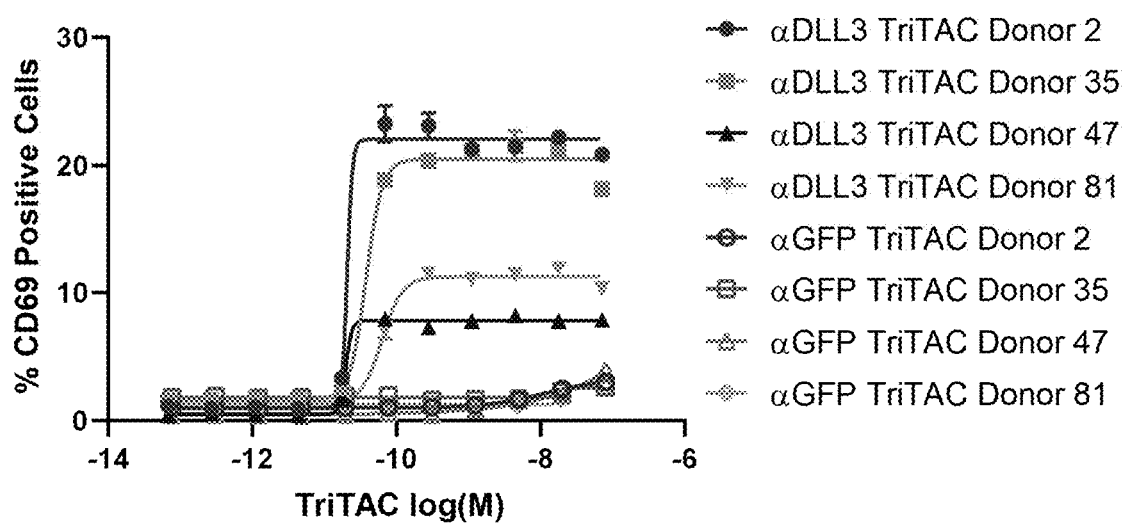

FIG. 38 illustrates the results of a flow cytometry measurements of CD69 expression on T cells co-cultured with NCI-H82 cells with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA), using T cells from four different donors.

Figure 39:
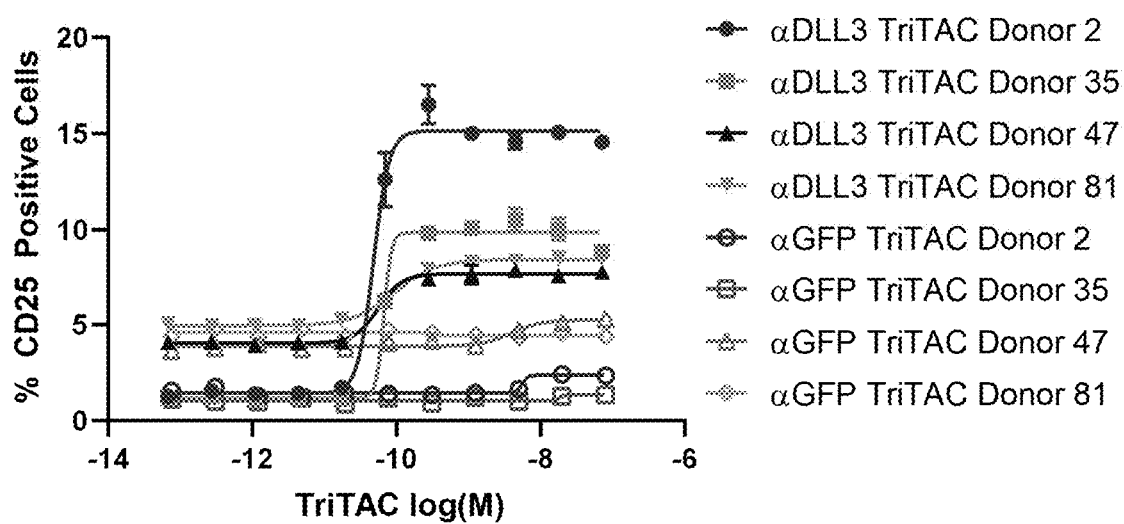

FIG. 39 illustrates the results of a flow cytometry measurements of CD25 expression on T cells co-cultured with NCI-H82 cells with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA), using T cells from four different donors.

Figure 40:
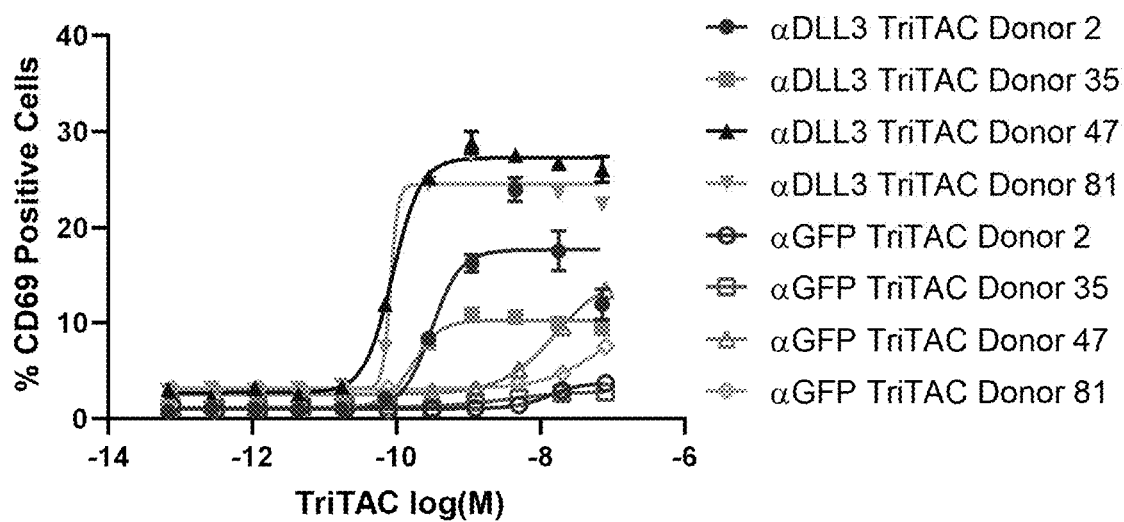

FIG. 40 illustrates the results of a flow cytometry measurements of CD69 expression on T cells co-cultured with DMS53 cells with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA, using T cells from four different donors.

Figure 41:
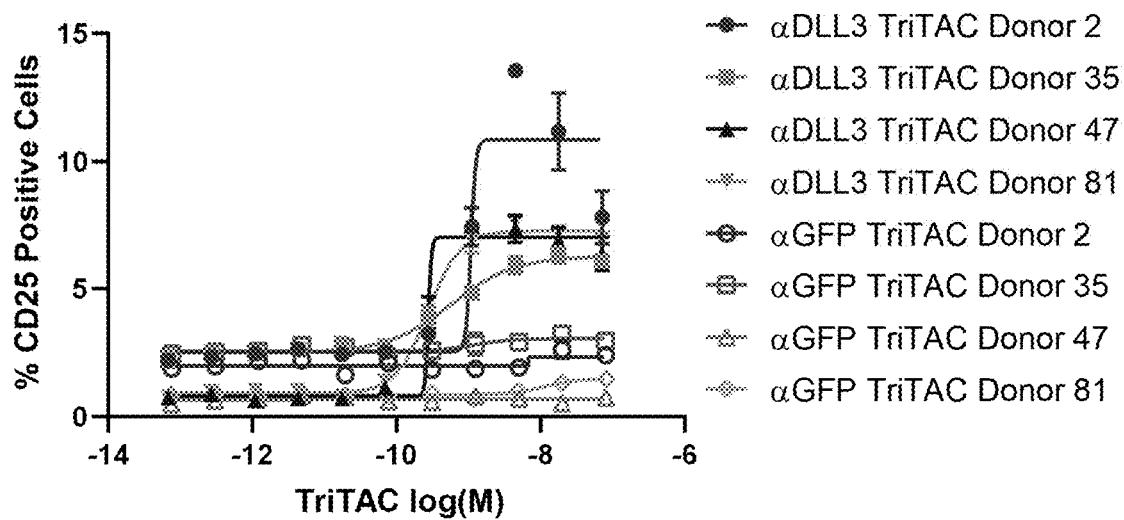

FIG. 41 illustrates the results of a flow cytometry measurements of CD25 expression on T cells co-cultured with DMS53 cells with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA).

Figure 42:
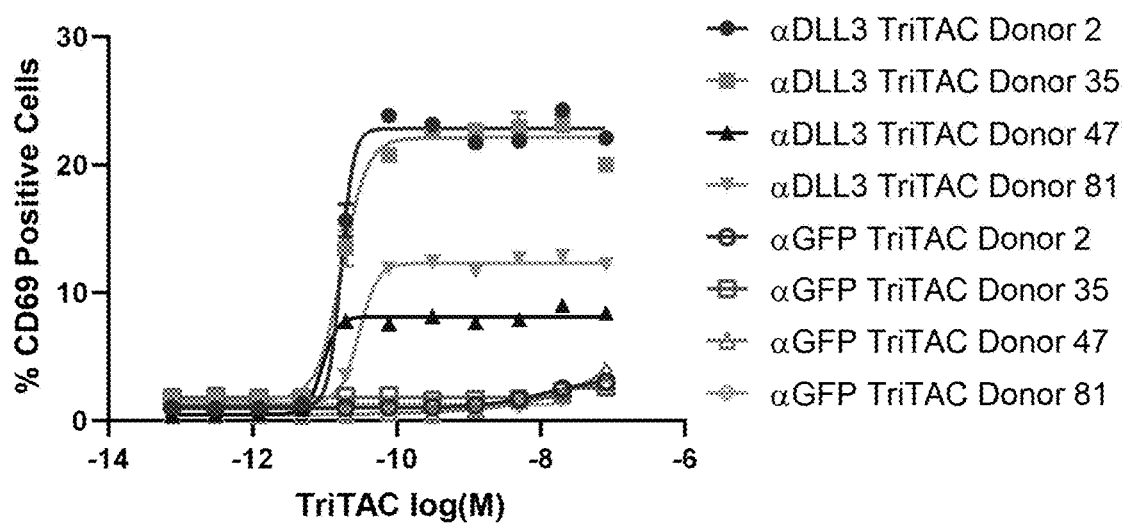

FIG. 42 illustrates the results of a flow cytometry measurements of CD69 expression on T cells co-cultured with NCI-H82 cells with a titration of an exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA), using T cells from four different donors.

Figure 43:
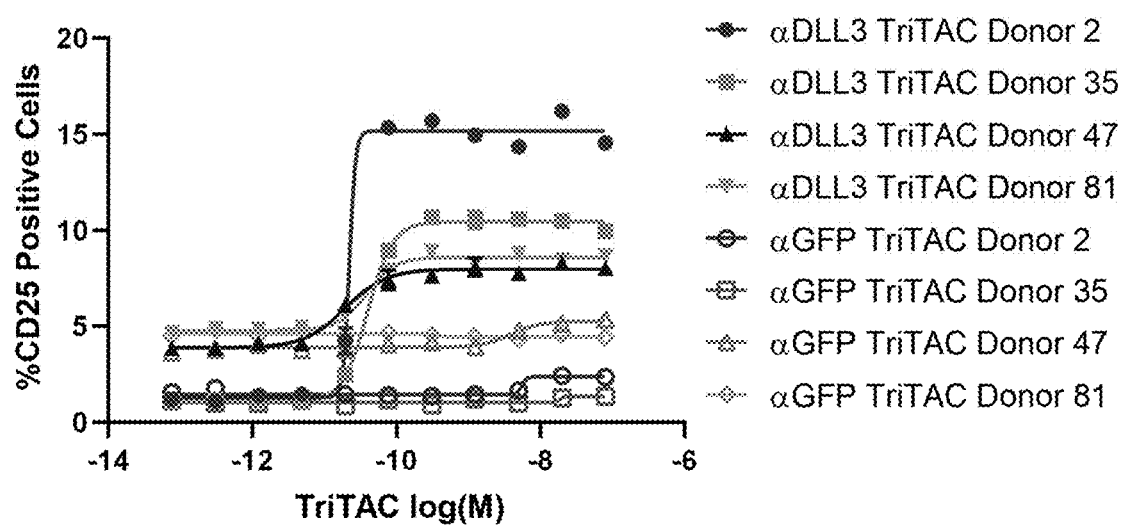

FIG. 43 illustrates the results of a flow cytometry measurements of CD25 expression on T cells co-cultured with NCI-H82 cells with a titration of an exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA), using T cells from four different donors.

Figure 44:
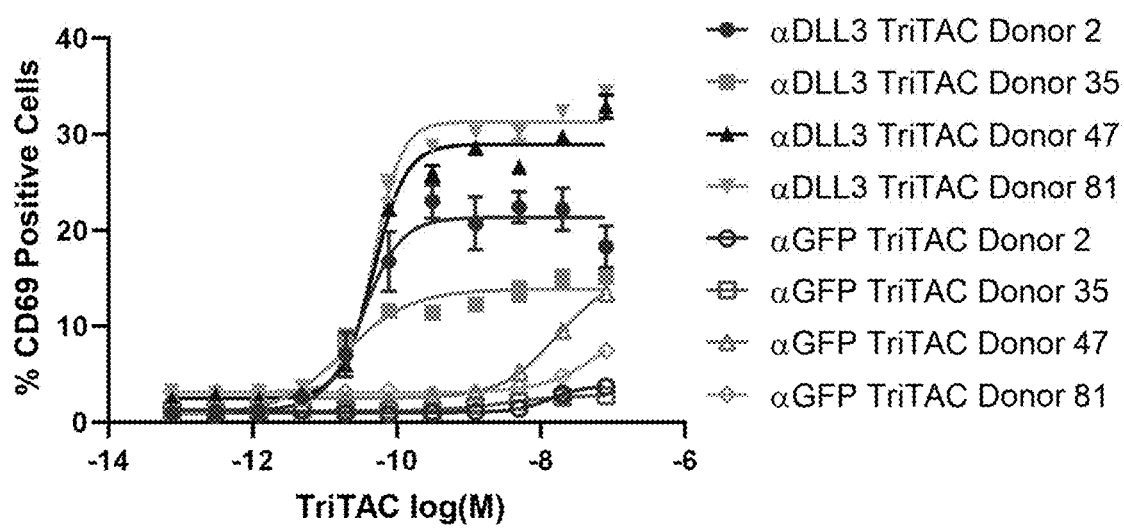

FIG. 44 illustrates the results of a flow cytometry measurements of CD69 expression on T cells co-cultured with DMS53 cells with a titration of an exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA), using T cells from four different donors.

Figure 45:
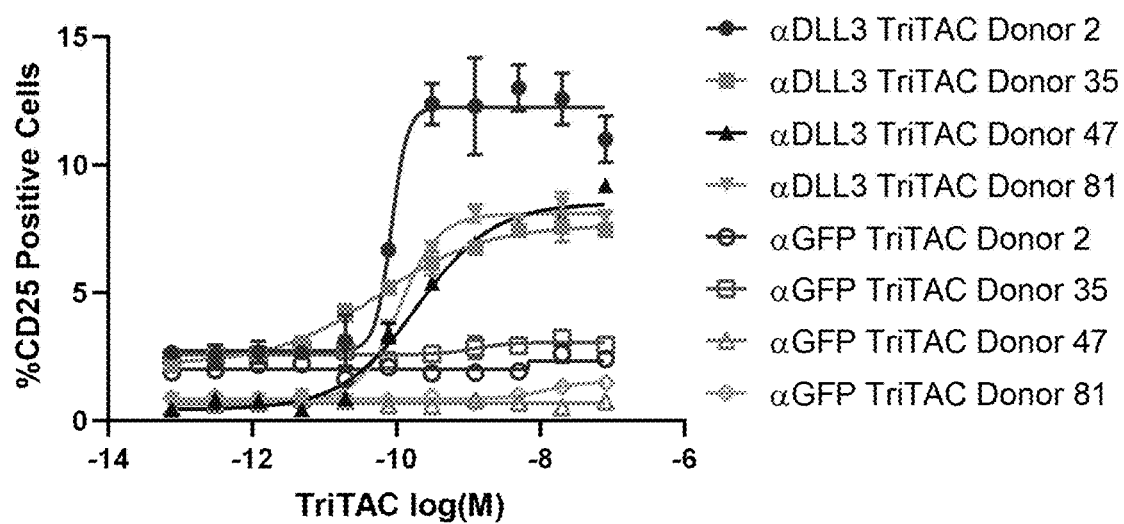

FIG. 45 illustrates the results of a flow cytometry measurements of CD25 expression on T cells co-cultured with DMS53 cells with a titration of an exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA).

Figure 46:
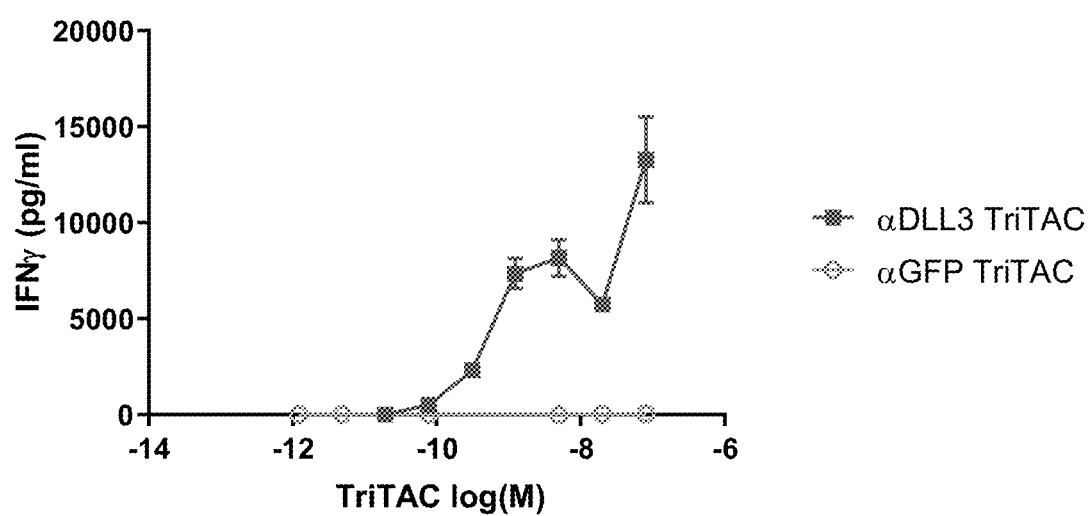

FIG. 46 illustrates the results of IFNγ measurements in conditioned media from co-cultures of T cells and NCI-H82 cells incubated with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA).

Figure 47:
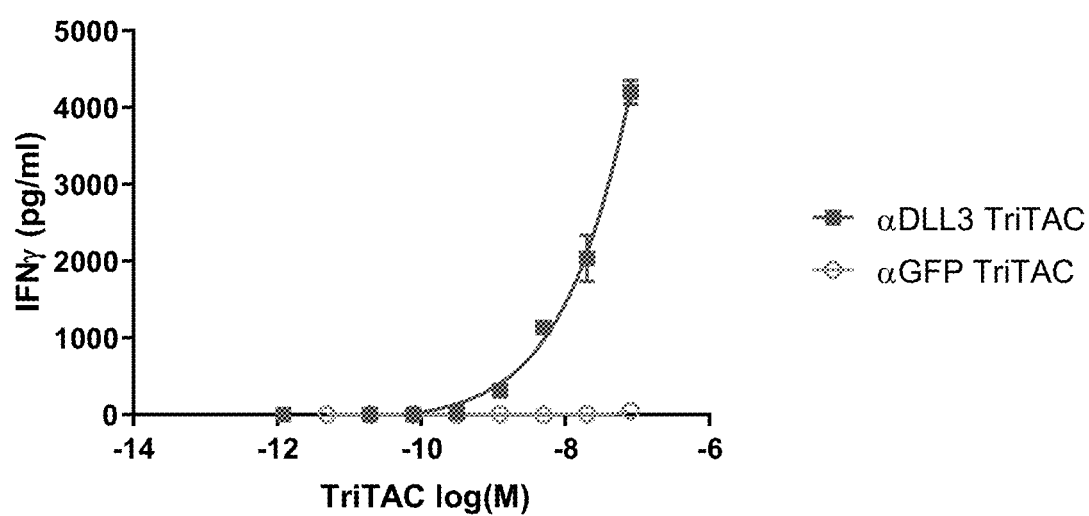

FIG. 47 illustrates the results of IFNγ measurements in conditioned media from co-cultures of T cells and SHP77 cells incubated with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA).

Figure 48:
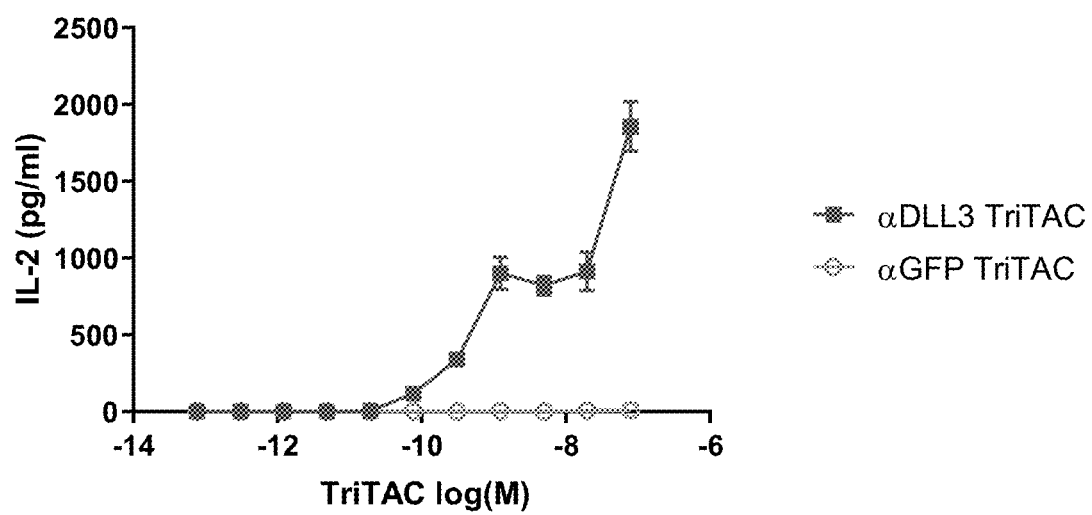

FIG. 48 illustrates the results of IL-2 measurements in conditioned media from co-cultures of T cells and NCI-H82 cells incubated with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA).

Figure 49:
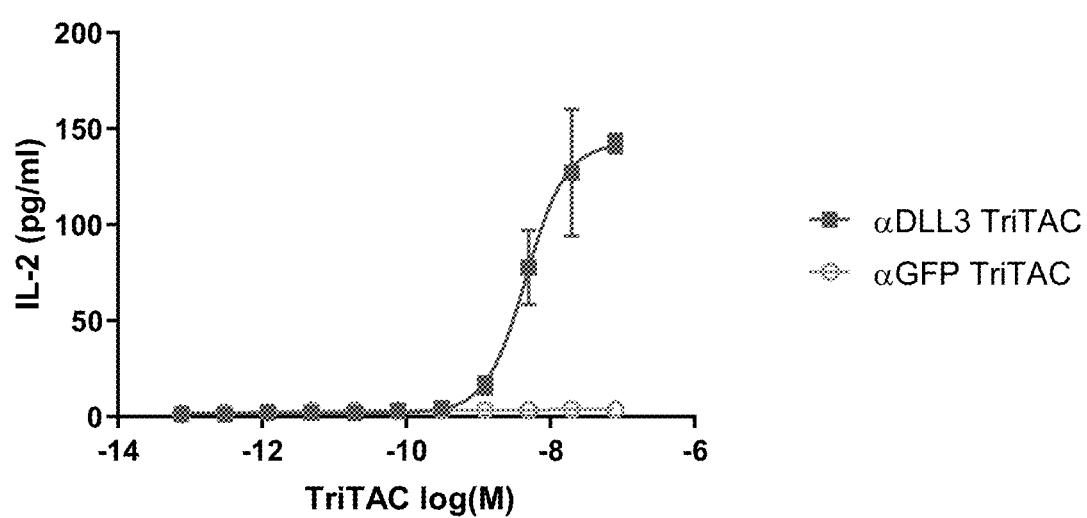

FIG. 49 illustrates the results of IL-2 measurements in conditioned media from co-cultures of T cells and SHP77 cells incubated with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA).

Figure 50:
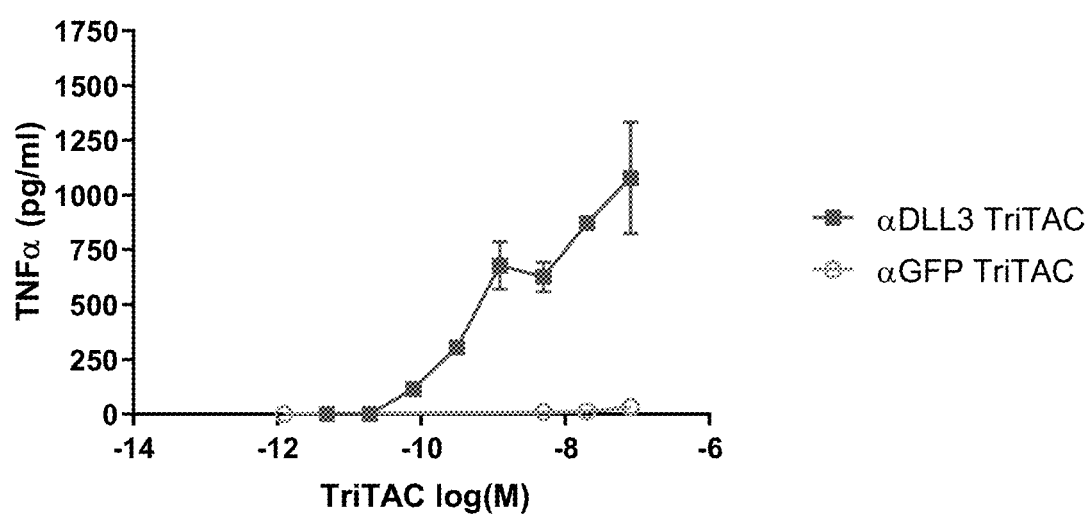

FIG. 50 illustrates the results of TNFα measurements in conditioned media from co-cultures of T cells and NCI-H82 cells incubated with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA).

Figure 51:
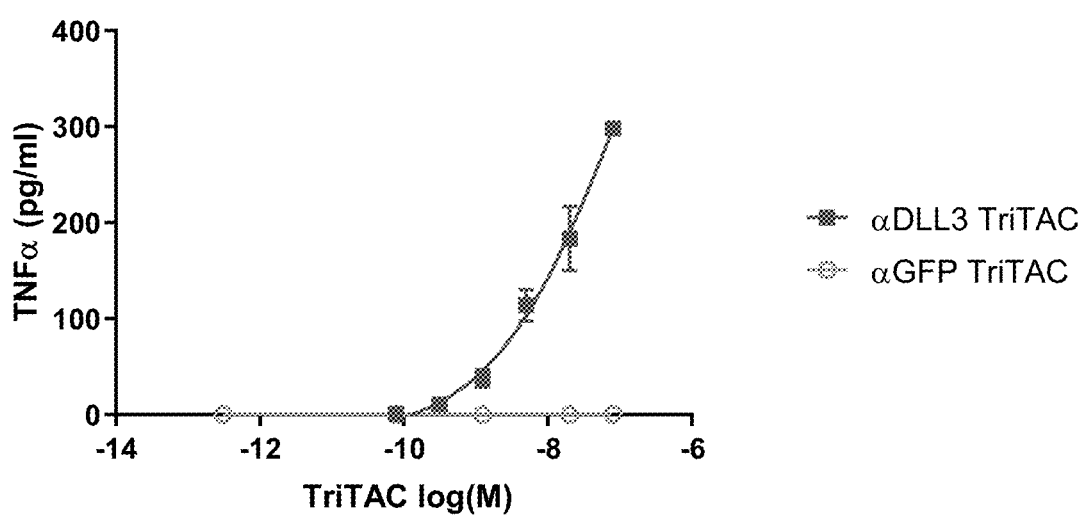

FIG. 51 illustrates the results of TNFα measurements in conditioned media from co-cultures of T cells and SHP77 cells incubated with a titration of an exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA).

Figure 52:
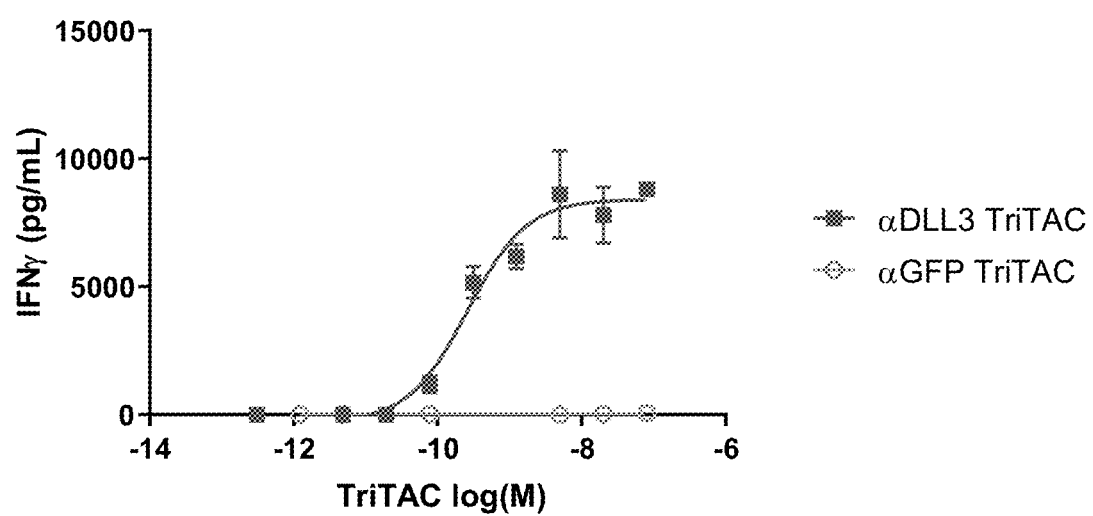

FIG. 52 illustrates the results of IFNγ measurements in conditioned media from co-cultures of T cells and NCI-H82 cells incubated with a titration of an exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA).

Figure 53:
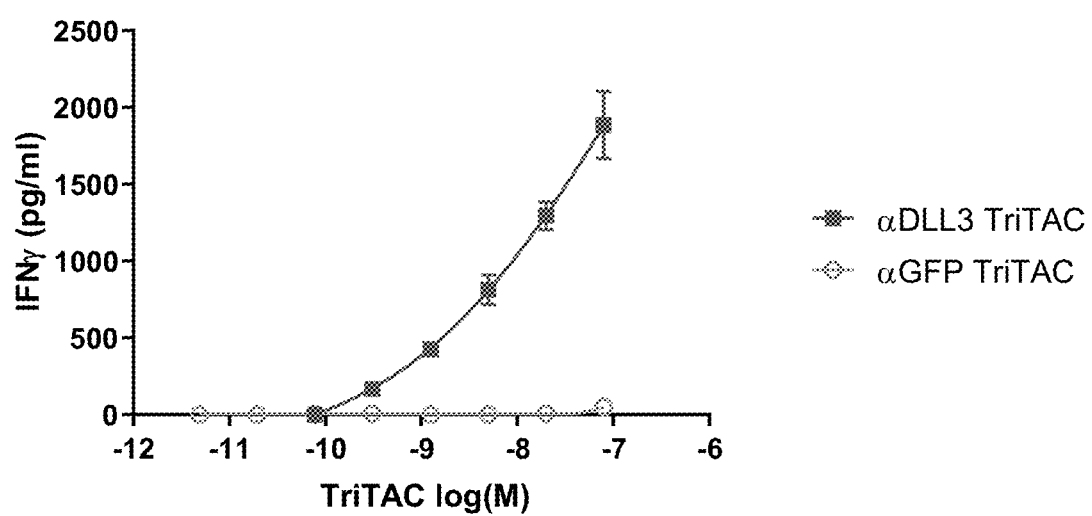

FIG. 53 illustrates the results of IFNγ measurements in conditioned media from co-cultures of T cells and SHP77 cells incubated with a titration of an exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA).

Figure 54:
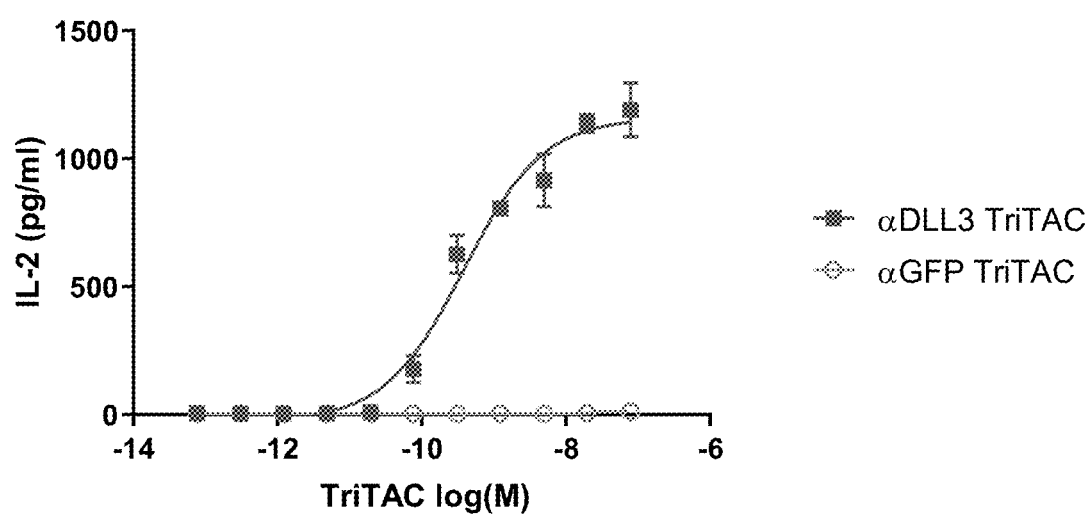

FIG. 54 illustrates the results of IL-2 measurements in conditioned media from co-cultures of T cells and NCI-H82 cells incubated with a titration of an exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA).

Figure 55:
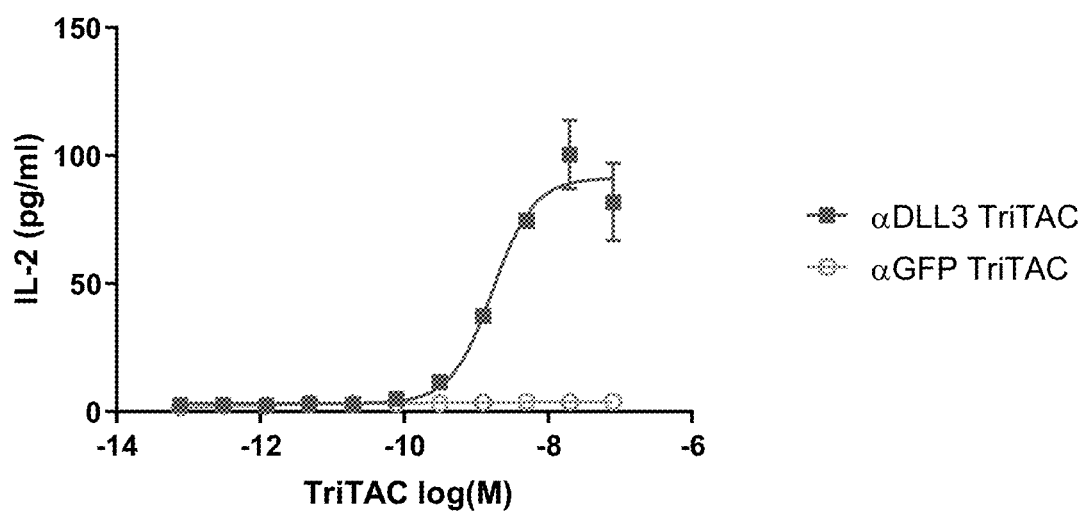

FIG. 55 illustrates the results of IL-2 measurements in conditioned media from co-cultures of T cells and SHP77 cells incubated with a titration of an exemplary DLL3 targeting trispecific proteins containing DLL3 binding domain of this disclosure, 52D04, in an anti-CD3:anti-ALB: anti-DLL3 (CAT) configuration, tested in the presence of human serum albumin (HSA).

Figure 56:
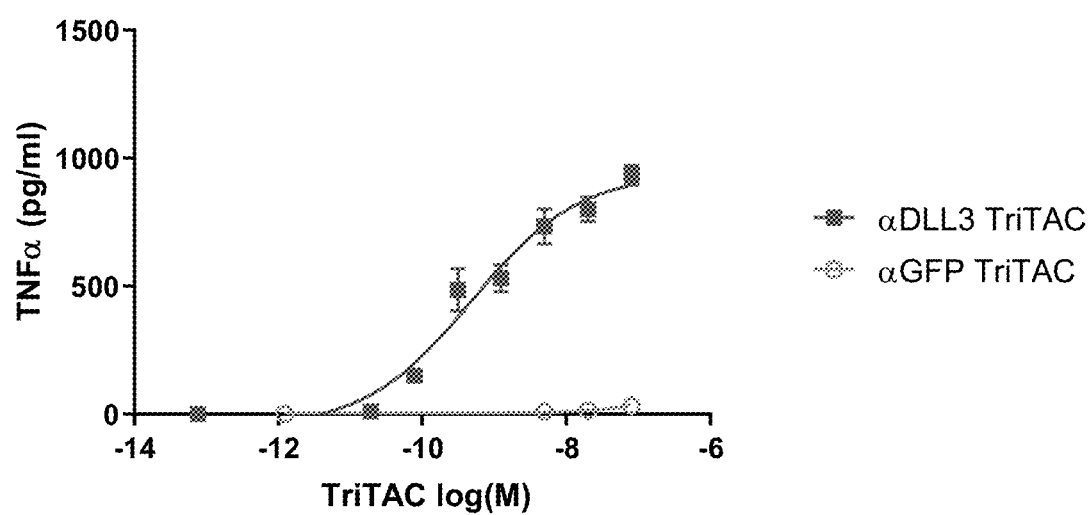

FIG. 56 illustrates the results of TNFα measurements in conditioned media from co-cultures of T cells and NCI-H82 cells incubated with a titration of an exemplary DLL3 targeting trispecific proteins containing DLL3 binding domain of this disclosure, 52D04, in an anti-CD3:anti-ALB: anti-DLL3 (CAT) configuration, tested in the presence of human serum albumin (HSA).

Figure 57:
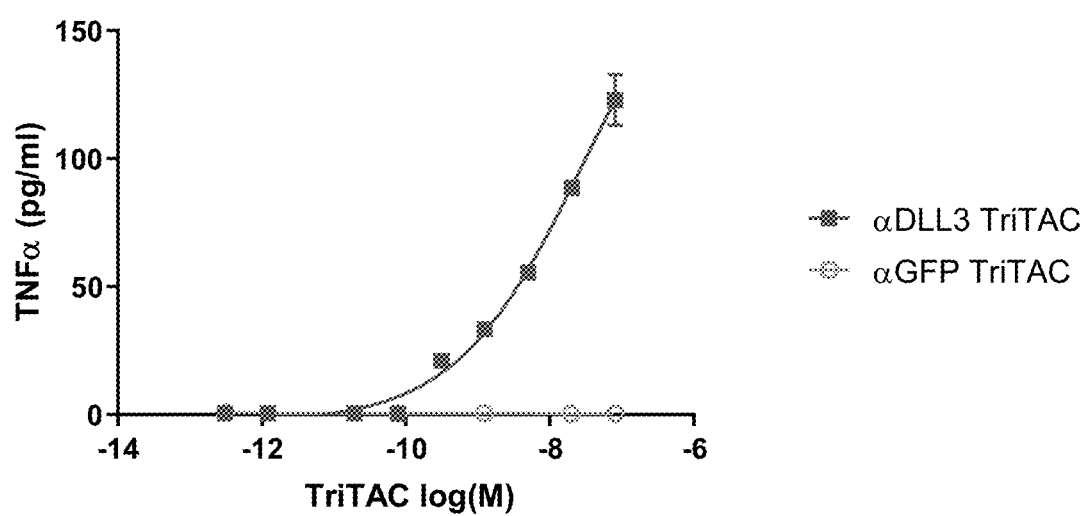

FIG. 57 illustrates the results of TNFα measurements in conditioned media from co-cultures of T cells and SHP77 cells incubated with a titration of an exemplary DLL3 targeting trispecific proteins containing DLL3 binding domain of this disclosure, 52D04, in an anti-CD3:anti-ALB: anti-DLL3 (CAT) configuration, tested in the presence of human serum albumin (HSA).

Figure 58:
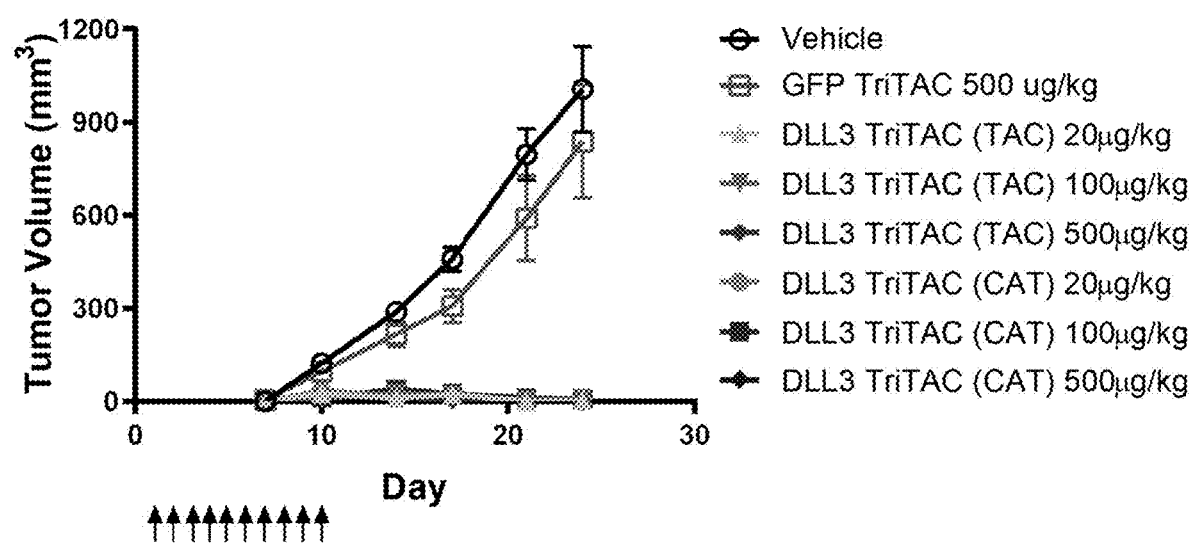

FIG. 58 depicts that an exemplary DLL3 targeting trispecific proteins containing DLL3 binding domain of this disclosure, 52D04, in an anti-DLL3:anti-ALB:anti-CD3 (TAC) configuration or an anti-CD3:anti-ALB:anti-DLL3 (CAT) configuration, was able to inhibit tumor growth in mice injected with a mixture of human T cells and NCI-H82 small cell lung cancer cells at dosages 20 μg/kg, 100 μg/kg or 500 μg/kg.

Figure 59:
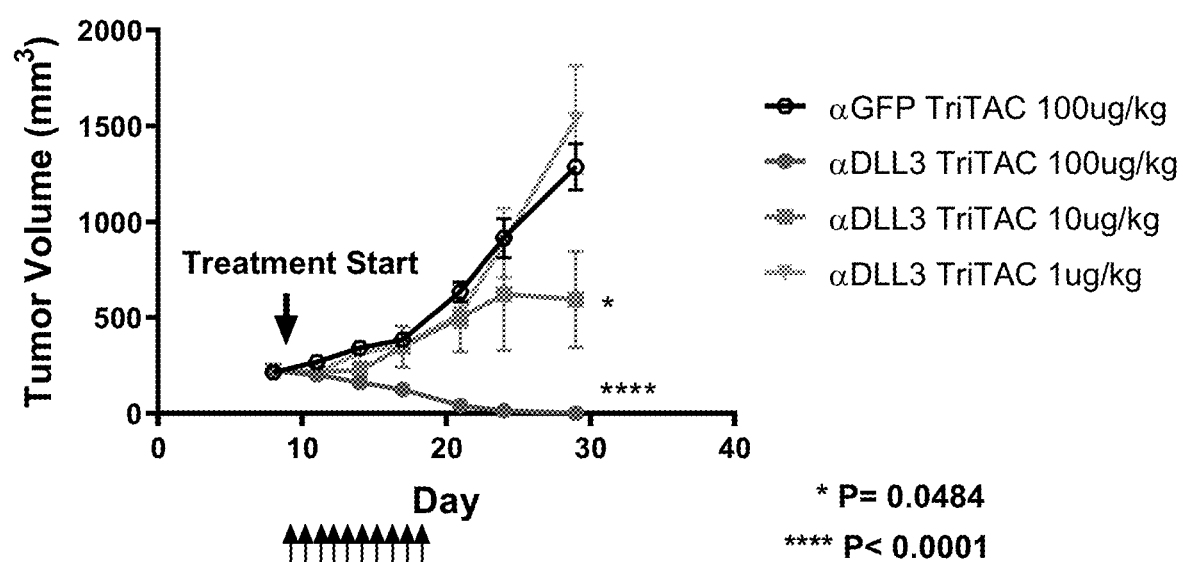

FIG. 59 depicts that an exemplary DLL3 targeting trispecific proteins containing DLL3 binding domain of this disclosure, 52D04, in an anti-CD3:anti-ALB:anti-DLL3 (CAT) configuration, was able to eliminate NCI-H82 xenograft tumors growth in mice injected with human T cells at dosages of 10 μg/kg and 100 μg/kg.

Figure 60:
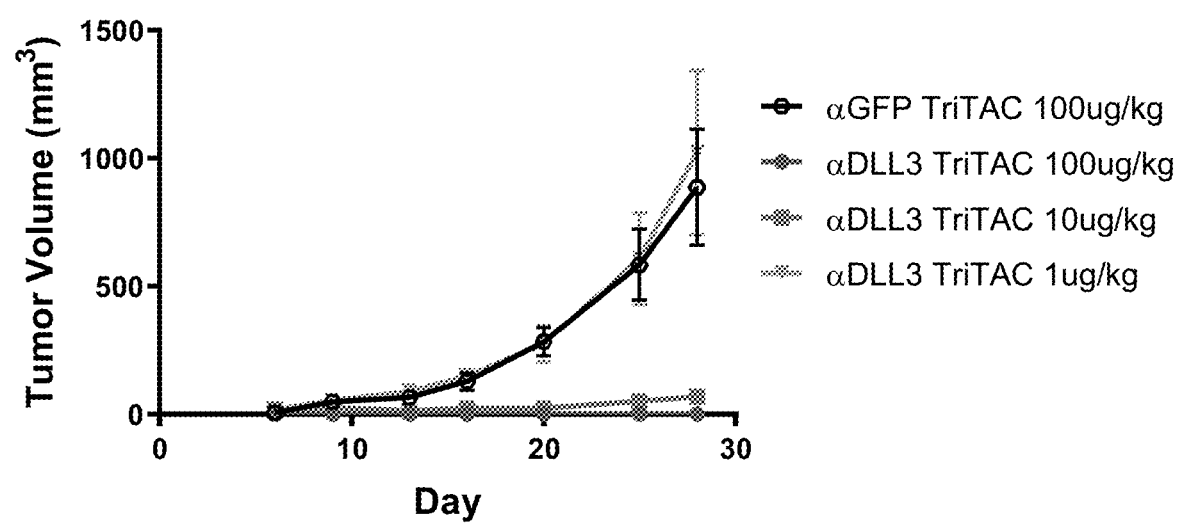

FIG. 60 depicts that an exemplary DLL3 targeting trispecific proteins containing DLL3 binding domain of this disclosure, 52D04, in an anti-CD3:anti-ALB:anti-DLL3 (CAT) configuration, was able to inhibit tumor growth in mice injected with a mixture of human T cells and SHP77 small cell lung cancer cells at dosages 10 μg/kg and 100 μg/kg.

Figure 61:
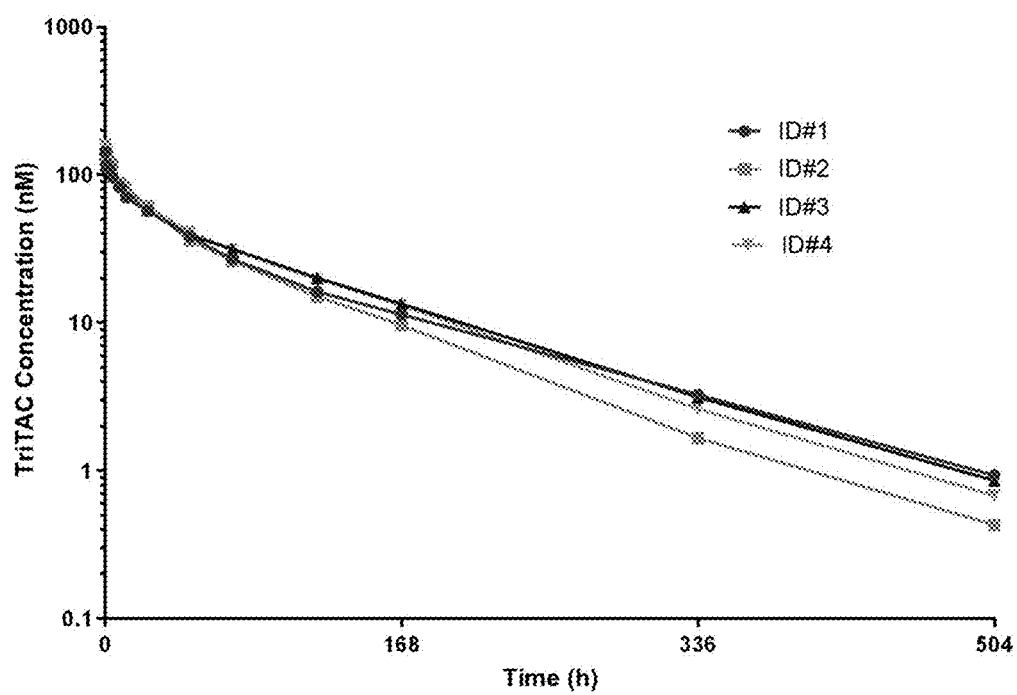

FIG. 61 depicts pharmacokinetic profile of exemplary DLL3 targeting trispecific proteins containing DLL3 binding domain of this disclosure, 52D04, in an anti-CD3:anti-ALB:anti-DLL3 (CAT) configuration (ID numbers 1 and 2) or an anti-DLL3:anti-ALB:anti-CD3 (TAC) configuration (ID numbers 3 and 4). Serum levels of the DLL3 targeting trispecific proteins at various time points following injection into cynomolgus monkeys, at 0.3 mg/kg, are shown in the plot.

Figure 62:
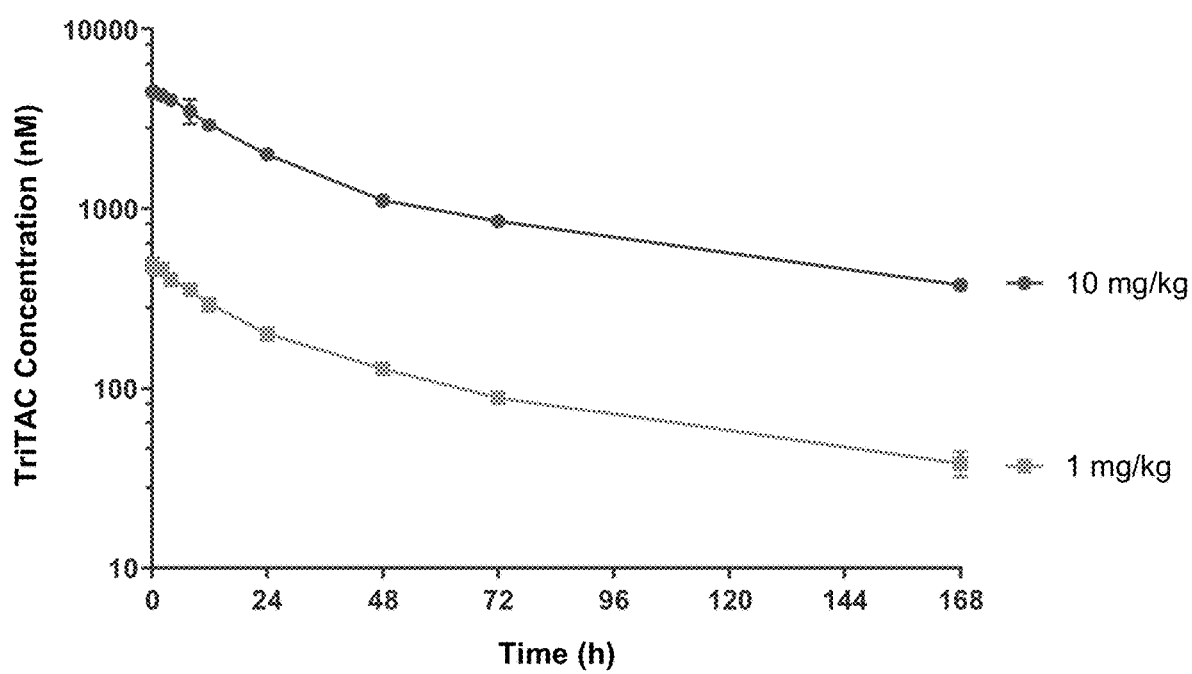

FIG. 62 depicts pharmacokinetic profile of an exemplary DLL3 targeting trispecific proteins containing DLL3 binding domain of this disclosure, 52D04, in an anti-CD3:anti-ALB:anti-DLL3 (CAT) configuration, at various time points following injection into cynomolgus monkeys, at 1 mg/kg or 10 mg/kg, are shown in the plot.

Figure 63:
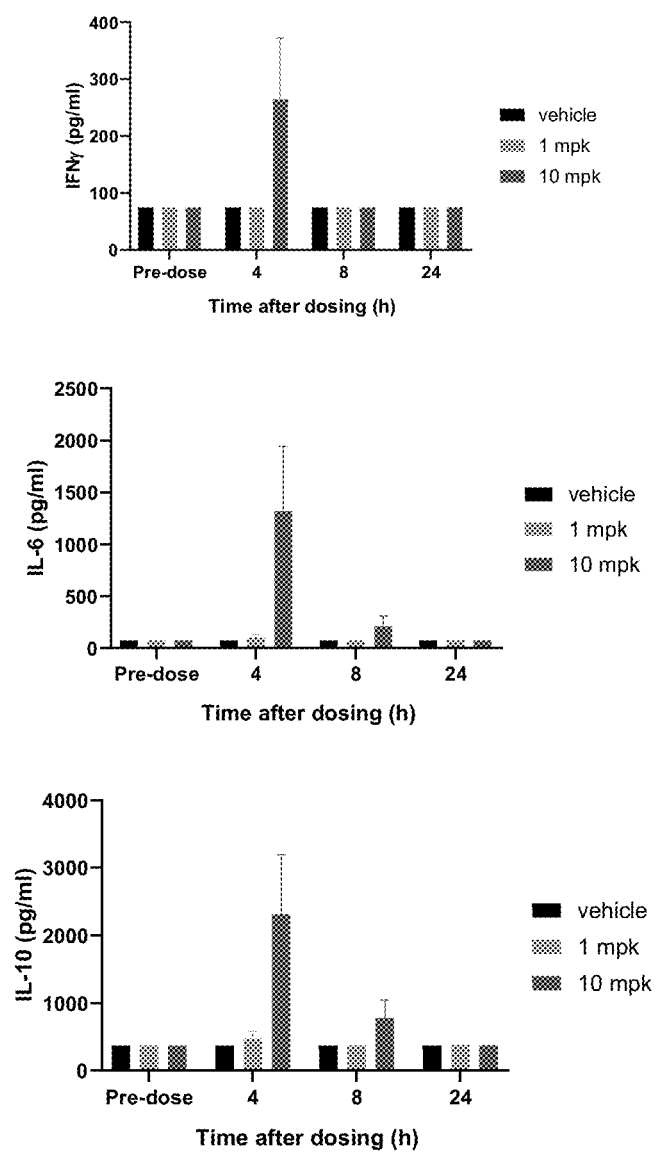

FIG. 63 depicts transient cytokine increase after first dosing of an exemplary DLL3 binding TriTAC molecule of this disclosure at 1 mg/kg and 10 mg/kg or a vehicle control. The top panel shows transient increase of IFNγ, the second panel shows transient increase of IL-6, and third panel show transient increase in IL-10.

Figure 64:
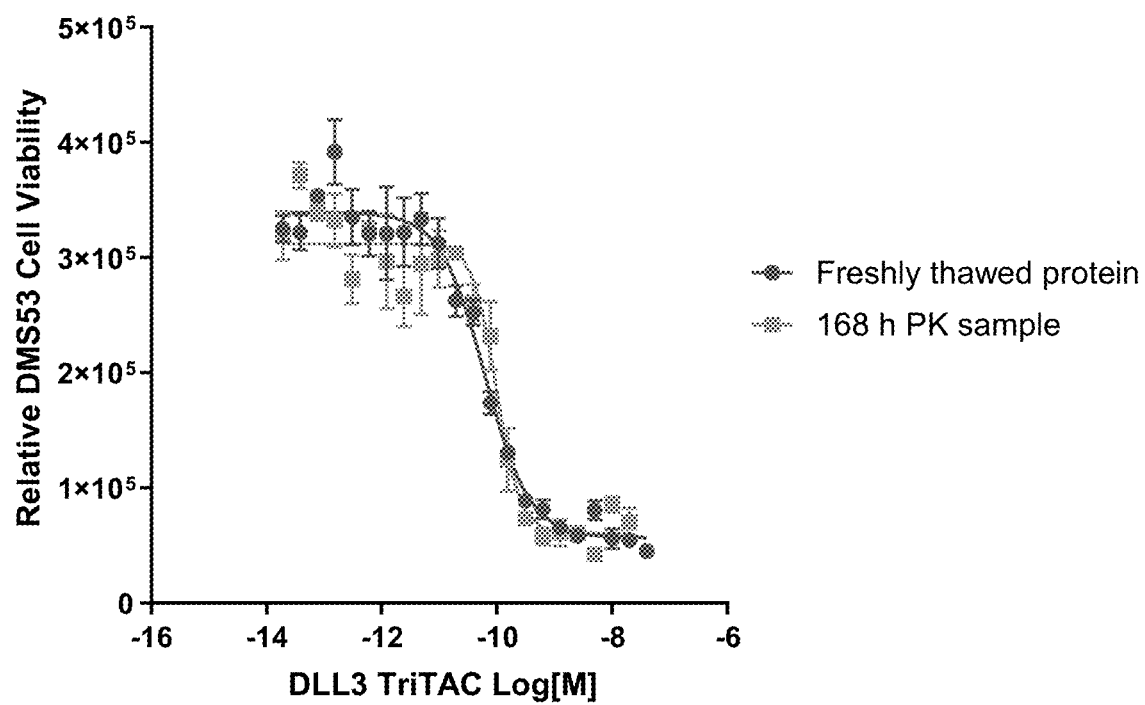

FIG. 64 illustrates the results of a TDCC assay on DMS53 cells, using exemplary DLL3 targeting trispecific proteins containing DLL3 binding domain of this disclosure, 52D04, in an anti-CD3:anti-ALB:anti-DLL3 (CAT) configuration, using freshly thawed protein, or using protein present in a serum sample from a cynomolgus monkey collected 168 h after dosing with 10 mg/kg DLL3 targeting trispecific protein, measured in the presence of 8.4% cynomolgus monkey serum.

DETAILED DESCRIPTION OF THE INVENTION

Figure 1:
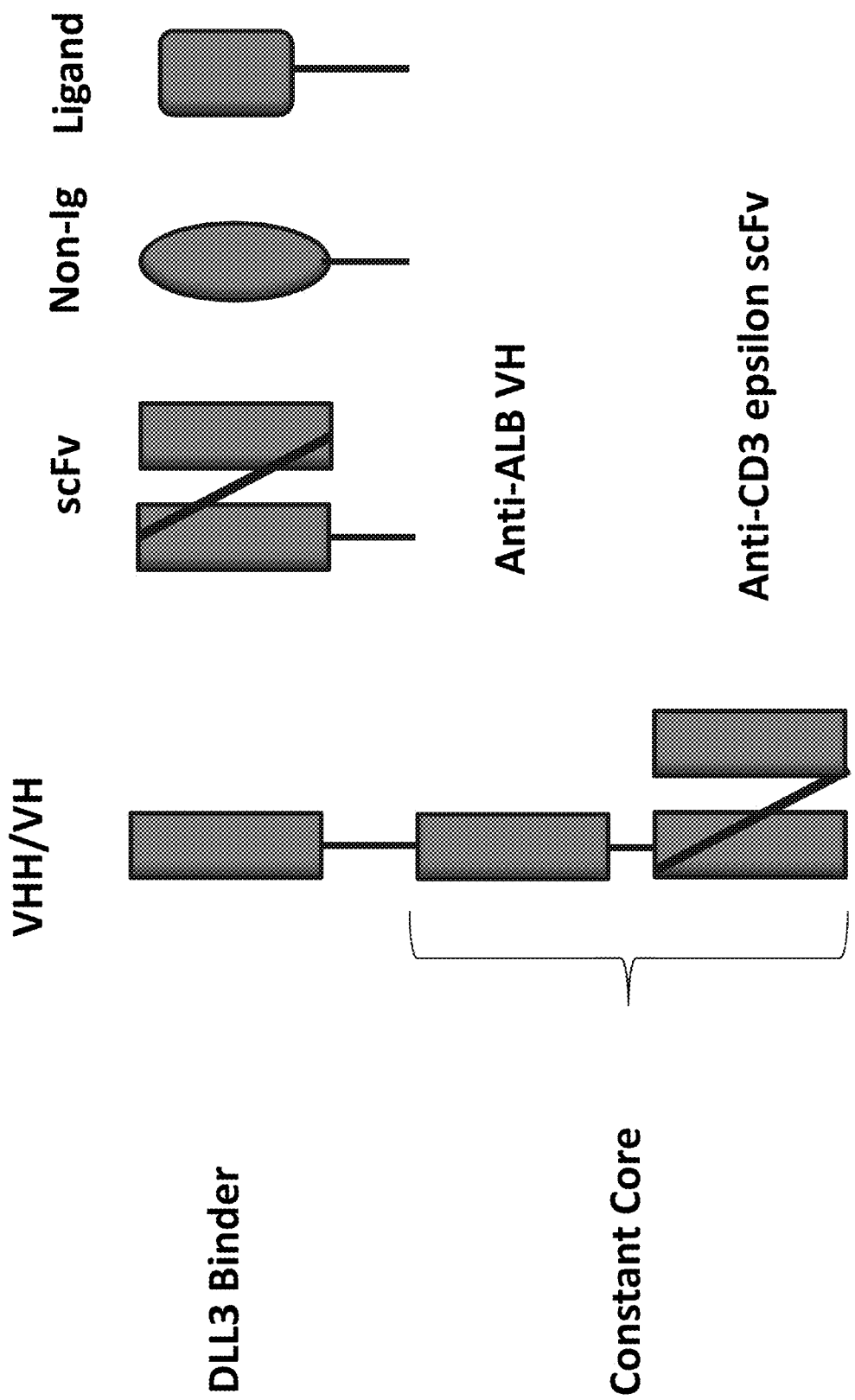
FIG. 1 illustrates the various domains of an exemplary DLL3 targeting trispecific protein of this disclosure.

Described herein, in some embodiments, are proteins that specifically bind delta-like ligand 3 (DLL3) and multispecific (e.g., trispecific) containing the same, pharmaceutical compositions thereof, as well as nucleic acids, recombinant expression vectors and host cells for making such proteins thereof. Also provided are methods of using at least one of the disclosed DLL3 binding proteins, or DLL3 targeting trispecific proteins containing the same, in the prevention, and/or treatment of diseases, conditions and disorders. The DLL3 targeting trispecific proteins are capable of specifically binding to DLL3 as well as CD3 and have a half-life extension domain, such as a domain that is capable of specifically binding to human albumin (ALB). FIG. 1 depicts one non-limiting example of a trispecific DLL3-binding protein. In some embodiments, the DLL3 targeting trispecific protein comprises an antibody, such as a trispecific antibody.

Certain Definitions

An "antibody" typically refers to a Y-shaped tetrameric protein comprising two heavy (H) and two light (L) polypeptide chains held together by covalent disulfide bonds and non-covalent interactions. Human light chains comprise a variable domain (VL) and a constant domain (CL) wherein the constant domain may be readily classified as kappa or lambda based on amino acid sequence and gene loci. Each heavy chain comprises one variable domain (VH) and a constant region, which in the case of IgG, IgA, and IgD, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (generally from about 10 to about 60 amino acids in IgG). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues. There are two types of native disulfide bridges or bonds in immunoglobulin molecules: interchain and intra-chain disulfide bonds. The location and number of interchain disulfide bonds vary according to the immunoglobulin class and species. Interchain disulfide bonds are located on the surface of the immunoglobulin, are accessible to solvent and are usually relatively easily reduced. In the human IgG1 isotype there are four interchain disulfide bonds, one from each heavy chain to the light chain and two between the heavy chains. The interchain disulfide bonds are not required for chain association. As is well known the cysteine rich IgG1 hinge region of the heavy chain has generally been held to consist of three parts: an upper hinge, a core hinge, and a lower hinge. Those skilled in the art will appreciate that that the IgG1 hinge region contain the cysteines in the heavy chain that comprise the interchain disulfide bonds (two heavy/heavy, two heavy/light), which provide structural flexibility that facilitates Fab movements. The interchain disulfide bond between the light and heavy chain of IgG1 are formed between C214 of the kappa or lambda light chain and C220 in the upper hinge region of the heavy chain. The interchain disulfide bonds between the heavy chains are at positions C226 and C229 (all numbered per the EU index according to Kabat, et al., infra.)

As used herein the term "antibody" includes polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof, immunospecific antibody fragments such as Fd, Fab, F(ab')2, F(ab') fragments, single-chain fragments (e.g., ScFv and ScFvFc), disulfide-linked Fvs (sdFv), a Fd fragment consisting of the VH and CH1 domains, linear antibodies, single domain antibodies such as sdAb (VH, VL, or VHH domains); and derivatives thereof including Fc fusions and other modifications, and any other immunoreactive molecule so long as it comprises a domain having a binding site for preferential association or binding with a DLL3 protein. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter alpha, delta, epsilon, gamma, and mu, respectively. Light chains of the antibodies from any vertebrate species can be assigned to one of two clearly distinct types, called kappa (kappa) and lambda (lambda), based on the amino acid sequences of their constant domains.

In some embodiments, the DLL3 binding domain of the DLL3 targeting trispecific proteins of this disclosure comprise a heavy chain only antibody, such as a VH or a VHH domain. In some cases, the DLL3 binding proteins comprise a heavy chain only antibody that is an engineered human VH domain. In some examples, the engineered human VH domain is produced by panning of phage display libraries. In some embodiments, the DLL3 binding domain of the DLL3 targeting trispecific proteins of this disclosure comprise a VHH. The term "VHH," as used herein, refers to single chain antibody binding domain devoid of light chain. In some cases, a VHH is derived from an antibody of the type that can be found in Camelidae or cartilaginous fish which are naturally devoid of light chains or to a synthetic and non-immunized VHH which can be constructed accordingly. Each heavy chain comprises a variable region encoded by V-, D- and J exons. A VHH, in some cases, is a natural VHH, such as a Camelid-derived VHH, or a recombinant protein comprising a heavy chain variable domain. In some embodiments, the VHH is derived from a species selected from the group consisting of camels, llamas, vicugnas, guanacos, and cartilaginous fish (such as, but not limited to, sharks). In another embodiment, the VHH is derived from an alpaca (such as, but not limited to, a Huacaya Alpaca or a Suri alpaca).

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain (VL) and the heavy-chain (VH) variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. ScFv fragments (for single chain fragment variable), which in some cases are obtained by genetic engineering, associates in a single polypeptide chain, the VH and the VL region of an antibody, separated by a peptide linker.

In some embodiments of this disclosure, the DLL3 binding domain, such as the DLL3 binding domain of the DLL3 targeting trispecific proteins comprise a single domain antibody, such as heavy chain only antibodies, such as VH or VHH domains, and comprise three CDRs. Such heavy chain only antibodies, in some embodiments, bind DLL3 as a monomer with no dependency on dimerisation with a VL (light chain variable) region for optimal binding affinity. In some embodiments of this disclosure, the CD3 binding domain of the DLL3 targeting trispecific proteins comprises an scFv. In some embodiments of this disclosure, the albumin binding domain of the DLL3 targeting trispecific proteins comprise a heavy chain only antibody, such as a single domain antibody comprising a VH domain or a VHH domain.

The assignment of amino acids to each domain, framework region and CDR is, in some embodiments, in accordance with one of the numbering schemes provided by Kabat et al. (1991) Sequences of Proteins of Immunological Interest (5th Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) Handbook of Therapeutic Antibodies, 3rd Ed., Wily-VCH Verlag GmbH and Co or AbM (Oxford Molecular/MSI Pharmacopia) unless otherwise noted. It is not intended that CDRs of the present disclosure necessarily correspond to the Kabat numbering convention. In some embodiments of this disclosure, the DLL3 binding proteins comprise single domain antibodies, such as heavy chain only antibodies, such as VH or VHH domains, and comprise three CDRs. Such heavy chain only antibodies, in some embodiments, bind DLL3 as a monomer with no dependency on dimerisation with a VL (light chain variable) region for optimal binding affinity.

"Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer softwares such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

As used herein, "elimination half-time" is used in its ordinary sense, as is described in Goodman and Gillman's The Pharmaceutical Basis of Therapeutics 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, t½ the time required for 50% completion of the process. The units of these two constants are time-1 and time, respectively. A first-order rate constant and the half-time of the reaction are simply related (k×t½=0.693) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

As used herein, the term "binding affinity" refers to the affinity of the proteins described in the disclosure to their binding targets, and is expressed numerically using "Kd" values. If two or more proteins are indicated to have comparable binding affinities towards their binding targets, then the Kd values for binding of the respective proteins towards their binding targets, are within ±2-fold of each other. If two or more proteins are indicated to have comparable binding affinities towards single binding target, then the Kd values for binding of the respective proteins towards said single binding target, are within ±2-fold of each other. If a protein is indicated to bind two or more targets with comparable binding affinities, then the Kd values for binding of said protein to the two or more targets are within ±2-fold of each other. In general, a higher Kd value corresponds to a weaker binding. In some embodiments, the "Kd" is measured by a radiolabeled antigen binding assay (RIA) or surface plasmon resonance assays using a BIAcore™_2000 or a BIAcore™-3000 (BIAcore, Inc., Piscataway, N.J.). In certain embodiments, an "on-rate" or "rate of association" or "association rate" or "kon" and an "off-rate" or "rate of dissociation" or "dissociation rate" or "koff" are also determined with the surface plasmon resonance technique using a BIAcore™-2000 or a BIAcore™-3000 (BIAcore, Inc., Piscataway, N.J.). In additional embodiments, the "Kd", "kon", and "koff" are measured using the OCTET® Systems (Pall Life Sciences). In an exemplary method for measuring binding affinity using the OCTET® Systems, the ligand, e.g., biotinylated human or cynomolgus DLL3, is immobilized on the OCTET® streptavidin capillary sensor tip surface which streptavidin tips are then activated according to manufacturer's instructions using about 20-50 µg/ml human or cynomolgus DLL3 protein. A solution of PBS/Casein is also introduced as a blocking agent. For association kinetic measurements, DLL3 binding protein variants are introduced at a concentration ranging from about 10 ng/mL to about 100 µg/mL, about 50 ng/mL to about 5 µg/mL, or about 2 ng/mL to about 20 µg/mL. In some embodiments, the DLL3 binding single domain proteins are used at a concentration ranging from about 2 ng/mL to about 20 µg/mL. Complete dissociation is observed in case of the negative control, assay buffer without the binding proteins. The kinetic parameters of the binding reactions are then determined using an appropriate tool, e.g., ForteBio software.

One embodiment provides a DLL3 binding protein (also referred to herein as an DLL3 binding domain, such as the DLL3 binding domain of a DLL3 trispecific antibody of this disclosure) that comprises a single domain antibody, comprising a CDR1 sequence comprising a sequence selected from the group consisting of SEQ ID Nos. 443-884 and 1887, a CDR2 sequence comprising a sequence selected from the group consisting of SEQ ID Nos. 885-1326 and 1888, and a CDR3 sequence comprising a sequence selected from the group consisting of SEQ ID Nos. 1327-1768 and 1889. It is contemplated that in some embodiments the DLL3 binding protein of this disclosure is fairly small and no more than 25 kD, no more than 20 kDa, no more than 15 kDa, or no more than 10 kDa in some embodiments. In certain instances, the EGFR binding is 5 kDa or less if it is a peptide or a small molecule entity.

In one aspect, the DLL3 targeting trispecific protein (also referred to herein as a DLL3 binding trispecific protein, a DLL3 trispecific protein, or a DLL3 TriTAC™) comprises (a) a first domain (A) which specifically binds to human CD3; (b) a second domain (B) which is a half-life extension domain; and (c) a third domain (C) which specifically binds to DLL3. The three domains in DLL3 targeting trispecific proteins are arranged in any order. Thus, it is contemplated that the domain order of the DLL3 targeting trispecific proteins are:

$H_2N$-(A)-(B)—(C)—COOH,
$H_2N$-(A)-(C)—(B)—COOH,
$H_2N$—(B)-(A)-(C)—COOH,
$H_2N$—(B)—(C)-(A)-COOH,
$H_2N$—(C)—(B)-(A)-COOH, or
$H_2N$—(C)-(A)-(B)—COOH.

In some embodiments, the DLL3 targeting trispecific proteins have a domain order of $H_2N$-(A)-(B)—(C)—COOH. In some embodiments, the DLL3 targeting trispecific proteins have a domain order of $H_2N$-(A)-(C)—(B)—

COOH. In some embodiments, the DLL3 targeting trispecific proteins have a domain order of H$_2$N—(B)-(A)-(C)—COOH. In some embodiments, the DLL3 targeting trispecific proteins have a domain order of H$_2$N—(B)—(C)-(A)-COOH. In some embodiments, the DLL3 targeting trispecific proteins have a domain order of H$_2$N—(C)—(B)-(A)-COOH. In some embodiments, the DLL3 targeting trispecific proteins have a domain order of H$_2$N—(C)-(A)-(B)—COOH.

In some embodiments, the DLL3 targeting trispecific proteins have the HSA (also referred to herein as ALB) binding domain as the middle domain, such that the domain order is H$_2$N-(A)-(B)—(C)—COOH or H$_2$N—(C)—(B)-(A)-COOH. It is contemplated that in such embodiments where the HSA binding domain as the middle domain, the CD3 and DLL3 binding domains are afforded additional flexibility to bind to their respective targets.

In some embodiments, the trispecific binding protein comprises a third domain that specifically binds DLL3, which third domain is in some cases a DLL3 binding single domain antibody, which binds to DLL3 with equivalent or better affinity as that of a reference DLL3 binding parental molecule. The third domain in some embodiments comprises an affinity matured DLL3 binding molecule (e.g., an affinity matured DLL3 binding single domain antibody), and is derived from the DLL3 binding parental molecule, comprising one or more amino acid mutations (e.g., a stabilizing mutation, a destabilizing mutation) with respect to the DLL3 binding parental molecule. In some embodiments, the affinity matured DLL3 binding molecule has superior stability with respect to selected destabilizing agents, as that of a reference DLL3 binding parental molecule. In some embodiments, the affinity matured DLL3 binding molecule is identified in a process comprising panning of one or more pre-candidate DLL3 binding molecules derived from one or more DLL3 binding parental molecule, expressed in a phage display library, against a DLL3 protein, such as a human DLL3 protein. The pre-candidate DLL3 binding molecule comprises, in some embodiments, amino acid substitutions in the variable regions, CDRs, or framework residues, relative to a parental molecule.

As used herein, "Phage display" refers to a technique by which variant polypeptides are displayed as fusion proteins to at least a portion of a coat protein on the surface of phage, filamentous phage, particles. A utility of phage display lies in the fact that large libraries of randomized protein variants can be rapidly and efficiently selected for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, Curr. Opin. Struct. Biol, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that selection is on the basis of intrinsic ligand affinity, and phagemid vectors are used, which simplify DNA manipulations. Lowman and Wells, Methods: A companion to Methods in Enzymology, 3:205-0216 (1991).

In some embodiments, the panning comprises using varying binding times and concentrations to identify DLL3 binding molecules with increased or decreased on-rates, from pre-candidate DLL3 binding molecules. In some embodiments, the panning comprises using varying wash times to identify DLL3 binding molecules with increased or decreased off-rates, from pre-candidate DLL3 molecules. In some embodiments, the panning comprises using both varying binding times and varying wash times. In some embodiments, one or more stabilizing mutations are combined to increase the stability of the affinity matured DLL3 binding molecule, for example, by shuffling to create a second-stage combinatorial library from such mutants and conducting a second round of panning followed by a binding selection.

In some embodiments, the affinity matured DLL3 binding molecule comprises an equivalent or better affinity to a DLL3 protein (such as human DLL3 protein) as that of a DLL3 binding parental molecule, but that has reduced cross reactivity, or in some embodiments, increased cross reactivity, with selected substances, such as ligands, proteins, antigens, or the like, other than the DLL3 epitope for which the DLL3 binding parental molecule is specific, or is designed to be specific for. In regard to the latter, an affinity matured DLL3 binding molecule, in some embodiments, is more successfully tested in animal models if the affinity matured DLL3 binding molecule is reacted with both human DLL3 and the corresponding target of the animal model, mouse DLL3 or cynomolgus DLL3. In some embodiments, the parental DLL3 binding molecule binds to human DLL3 with an affinity of about 10 nM or less, and to cynomolgus DLL3 with an affinity of about 15 nM or less. In some embodiments, the affinity matured DLL3 binding molecule, identified after one round of panning, binds to human DLL3 with an affinity of about 5 nM or less, and to cynomolgus DLL3 with an affinity of about 7.5 nM or less. In some embodiments, the affinity matured DLL3 binding molecule, identified after two rounds of panning, binds to human DLL3 with an affinity of about 2.5 nM or less, and to cynomolgus DLL3 with an affinity of about 3.5 nM or less.

In some embodiments, domain A, domain B, and domain C of the trispecific binding protein of this disclosure, are independently antigen-specific binding domain polypeptides that specifically bind to targets, such as targets on diseased cells, or targets on other cells that support the diseased state, such as targets on stromal cells that support tumor growth or targets on immune cells that support disease-mediated immunosuppression. In some examples, the antigen-specific binding domains include antibodies, heavy chain only antibodies, including single chain antibodies, Fabs, Fv, T-cell receptor binding domains, ligand binding domains, receptor binding domains, domain antibodies, single domain antibodies, minibodies, nanobodies, peptibodies, or various other antibody mimics (such as affimers, affitins, alphabodies, atrimers, CTLA4-based molecules, adnectins, anticalins, Kunitz domain-based proteins, avimers, knottins, fynomers, darpins, affibodies, affilins, monobodies and armadillo repeat protein-based proteins).

In some embodiments, the DLL3 targeting trispecific proteins described herein comprise a DLL binding polypeptide having a sequence selected from the group consisting of SEQ ID Nos. 1-442 and 1886, subsequences thereof, and variants thereof. In some embodiments, the trispecific antigen binding protein comprises a DLL3 binding polypeptide (i.e., the third domain (C)) having at least 70%-95% or more homology to a sequence selected from SEQ ID Nos. 1-442 and 1886, subsequences thereof, and variants thereof. In some embodiments, the trispecific antigen binding protein comprises a DLL3 binding polypeptide (i.e., the third domain (C)) having at least 70%, 75%, 80%, 85%, 90%, 95%, 96%, 97%, 98%, 99%, or more homology to a sequence selected from the group consisting of SEQ ID Nos. 1-442 and 1886, subsequences thereof, and variants thereof. In some embodiments, the trispecific antigen binding protein comprises a DLL3 binding polypeptide (i.e., the third domain (C)) having at least 70%-95% or more identity to a sequence selected from SEQ ID Nos. 1-442 and 1886, subsequences thereof, and variants thereof. In some embodiments, the trispecific antigen binding protein comprises a DLL3 binding polypeptide (i.e., the third domain (C)) having at least 70%, 75%, 80%, 85%, 90%, 91%, 92%, 93%, 94%, 95%, 96%, 97%, 98%, 99% or more identity to a sequence selected from the group consisting of SEQ ID Nos. 1-442 and 1886, subsequences thereof, and variants thereof.

The DLL3 targeting trispecific proteins described herein are designed to allow specific targeting of cells expressing DLL3 by recruiting cytotoxic T cells. In some embodiments, this improves efficacy compared to ADCC (antibody dependent cell-mediated cytotoxicity), which is using full length antibodies directed to a sole antigen and is not capable of directly recruiting cytotoxic T cells. In contrast, by engaging CD3 molecules expressed specifically on these cells, the DLL3 targeting trispecific proteins can crosslink cytotoxic T cells with cells expressing DLL3 in a highly specific fashion, thereby directing the cytotoxic potential of the T cell towards the target cell. The DLL3 targeting trispecific proteins described herein engage cytotoxic T cells via binding to the surface-expressed CD3 proteins, which form part of the TCR. Simultaneous binding of several DLL3 trispecific antigen-binding protein to CD3 and to DLL3 expressed on the surface of particular cells causes T cell activation and mediates the subsequent lysis of the particular DLL3 expressing cell. Thus, DLL3 targeting trispecific proteins are contemplated to display strong, specific and efficient target cell killing. In some embodiments, the DLL3 targeting trispecific proteins described herein stimulate target cell killing by cytotoxic T cells to eliminate pathogenic cells (e.g., tumor cells expressing DLL3). In some of such embodiments, cells are eliminated selectively, thereby reducing the potential for toxic side effects.

The DLL3 targeting trispecific proteins described herein confer further therapeutic advantages over traditional monoclonal antibodies and other smaller bispecific molecules. Generally, the effectiveness of recombinant protein pharmaceuticals depends heavily on the intrinsic pharmacokinetics of the protein itself. One such benefit here is that the DLL3 targeting trispecific proteins described herein have extended pharmacokinetic elimination half-time due to having a half-life extension domain such as a domain that specifically binds to a serum albumin protein (e.g., a human serum albumin protein, HSA). In this respect, the DLL3 targeting trispecific proteins described herein have an extended serum elimination half-time of about two, three, about five, about seven, about 10, about 12, or about 14 days in some embodiments. This contrasts to other binding proteins such as BiTE or DART molecules which have relatively much shorter elimination half-times. For example, the BiTE CD19×CD3 bispecific scFv-scFv fusion molecule requires continuous intravenous infusion (i.v.) drug delivery due to its short elimination half-time. The longer intrinsic half-times of the DLL3 targeting trispecific proteins solve this issue thereby allowing for increased therapeutic potential such as low-dose pharmaceutical formulations, decreased periodic administration and/or novel pharmaceutical compositions.

The DLL3 targeting trispecific proteins described herein also have an optimal size for enhanced tissue penetration and tissue distribution. Larger sizes limit or prevent penetration or distribution of the protein in the target tissues. The DLL3 targeting trispecific proteins described herein avoid this by having a small size that allows enhanced tissue penetration and distribution. Accordingly, the DLL3 targeting trispecific proteins described herein, in some embodiments have a size of about 50 kDa to about 80 kDa, about 50 kDa to about 75 kDa, about 50 kDa to about 70 kDa, or about 50 kDa to about 65 kDa. In some embodiments, the size of the DLL3 targeting trispecific protein is smaller than about 60 kDa. Thus, the size of the DLL3 targeting trispecific proteins is advantageous over IgG antibodies which are about 150 kDa and the BiTE and DART diabody molecules which are about 55 kDa but are not half-life extended and therefore cleared quickly through the kidney.

In further embodiments, the DLL3 targeting trispecific proteins described herein have an optimal size for enhanced tissue penetration and distribution. In these embodiments, the DLL3 targeting trispecific proteins are constructed to be as small as possible, while retaining specificity toward its targets. Accordingly, in these embodiments, the DLL3 targeting trispecific proteins described herein have a size of about 20 kDa to about 40 kDa or about 25 kDa to about 35 kDa to about 40 kDa, to about 45 kDa, to about 50 kDa, to about 55 kDa, to about 60 kDa, to about 65 kDa. In some embodiments, the DLL3 targeting trispecific proteins described herein have a size of about 50 kDa, 49, kDa, 48 kDa, 47 kDa, 46 kDa, 45 kDa, 44 kDa, 43 kDa, 42 kDa, 41 kDa, 40 kDa, about 39 kDa, about 38 kDa, about 37 kDa, about 36 kDa, about 35 kDa, about 34 kDa, about 33 kDa, about 32 kDa, about 31 kDa, about 30 kDa, about 29 kDa, about 28 kDa, about 27 kDa, about 26 kDa, about 25 kDa, about 24 kDa, about 23 kDa, about 22 kDa, about 21 kDa, or about 20 kDa. An exemplary approach to the small size is through the use of single domain antibody (sdAb) fragments for each of the domains. For example, a particular DLL3 trispecific antigen-binding protein has an anti-CD3 sdAb, anti-ALB sdAb and an sdAb for DLL3. This reduces the size of the exemplary DLL3 trispecific antigen-binding protein to under 60 kDa. Thus in some embodiments, the domains of the DLL3 targeting trispecific proteins are all single domain antibody (sdAb) fragments. It is contemplated that in some embodiments the DLL3 binding protein is fairly small and no more than 25 kDa, no more than 20 kDa, no more than 15 kDa, or no more than 10 kDa in some embodiments. In certain instances, the DLL3 binding protein is 5 kDa or less if it is a peptide or small molecule entity.

In other embodiments, the DLL3 targeting trispecific proteins described herein comprise small molecule entity (SME) binders for ALB, DLL3, CD3, or all. SME binders are small molecules averaging about 500 to 2000 Da in size and are attached to the DLL3 targeting trispecific proteins by known methods, such as sortase ligation or conjugation. In these instances, one of the domains of DLL3 trispecific antigen-binding protein is a sortase recognition sequence, LPETG (SEQ ID No: 1896). To attach a SME binder to DLL3 trispecific antigen-binding protein with a sortase recognition sequence, the protein is incubated with a sortase and a SME binder whereby the sortase attaches the SME binder to the recognition sequence. In yet other embodiments, the domain which binds to DLL3 of DLL3 targeting trispecific proteins described herein comprise a knottin peptide for binding DLL3. Knottins are disulfide-stabilized peptides with a cysteine knot scaffold and have average sizes about 3.5 kDa. Knottins have been contemplated for binding to certain tumor molecules such as DLL3. In further embodiments, the third domain which binds to DLL3 of DLL3 targeting trispecific proteins described herein comprise a natural DLL3 ligand.

Another feature of the DLL3 targeting trispecific proteins described herein is that they are of a single-polypeptide design with flexible linkage of their domains. This allows for facile production and manufacturing of the DLL3 targeting trispecific proteins as they can be encoded by single cDNA molecule to be easily incorporated into a vector. Further, because the DLL3 targeting trispecific proteins described herein are a monomeric single polypeptide chain, there are no chain pairing issues or a requirement for dimerization. It is contemplated that the DLL3 targeting trispecific proteins described herein have a reduced tendency to aggregate unlike other reported molecules such as bispecific proteins with Fc-gamma immunoglobulin domains.

In the DLL3 targeting trispecific proteins described herein, the domains are, in some embodiments, linked by internal linkers L1 and L2, where L1 links the first and second domain of the DLL3 targeting trispecific proteins and L2 links the second and third domains of the DLL3 targeting trispecific proteins. Linkers L1 and L2 have an optimized length and/or amino acid composition. In some embodiments, linkers L1 and L2 are the same length and amino acid composition. In other embodiments, L1 and L2 are different. In certain embodiments, internal linkers L1 and/or L2 are "short," i.e., consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, internal linkers L1 and/or L2 are "long," i.e., consist of 15, 20 or 25 amino acid residues. In some embodiments, these internal linkers consist of about 3 to about 15, for example 8, 9 or 10 contiguous amino acid residues. Regarding the amino acid composition of the internal linkers L1 and L2, peptides are selected with properties that confer flexibility to the DLL3 targeting trispecific proteins, do not interfere with the binding domains as well as resist cleavage from proteases. For example, glycine and serine residues generally provide protease resistance. Examples of internal linkers suitable for linking the domains in the DLL3 targeting trispecific proteins include but are not limited to $(GS)_n$ (SEQ ID No. 1809), $(GGS)_n$ (SEQ ID No. 1810), $(GGGS)_n$ (SEQ ID No. 1811), $(GGSG)_n$ (SEQ ID No. 1812), $(GGSGG)_n$ (SEQ ID No. 1813), $(GGGGS)_n$ (SEQ ID No. 1814), $(GGGGG)_n$ (SEQ ID No. 1815), or $(GGG)_n$ (SEQ ID No. 1816), wherein n is 1, 2, 3, 4, 5, 6, 7, 8, 9, or 10. In one embodiment, internal linker L1 and/or L2 is $(GGGGS)_4$ (SEQ ID No. 1817) or $(GGGGS)_3$ (SEQ ID No. 1818). In another embodiment, internal linker L1 and/or L2 is GGGGSGGGS (SEQ ID No. 1808).

In some cases, the domains within the DLL3 targeting trispecific protein are conjugated using an enzymatic site-specific conjugation method which involves the use of a mammalian or bacterial transglutaminase enzyme. Microbial transglutaminases (mTGs) are versatile tools in modern research and biotechnology. The availability of large quantities of relatively pure enzymes, ease of use, and lack of regulation by calcium and guanosine-5'-triphosphate (GTP) has propelled mTG to be the main cross-linking enzyme used in both the food industry and biotechnology. Currently, mTGs are used in many applications to attach proteins and peptides to small molecules, polymers, surfaces, DNA, as well as to other proteins. See, Pavel Strp, Veracity of microbial transglutaminase, Bioconjugate Chem. 25, 5, 855-862).

In some examples are provided DLL3 targeting trispecific protein wherein one of the domains comprises an acceptor glutamine in a constant region, which can then be conjugated to another domain via a lysine-based linker (e.g., any primary amine chain which is a substrate for TGase, comprising an alkylamine, oxoamine) wherein the conjugation occurs exclusively on one or more acceptor glutamine residues present in the targeting moiety outside of the antigen combining site (e.g., outside a variable region, in a constant region). Conjugation thus does not occur on a glutamine, an at least partly surface exposed glutamine, within the variable region. The trispecific protein, in some examples, is formed by reacting one of the domains with a lysine-based linker in the presence of a TGase.

In some embodiments, where one or more domains within the DLL3 targeting trispecific binding protein are directly joined, a hybrid vector is made where the DNA encoding the directly joined domains are themselves directly ligated to each other. In some embodiments, where linkers are used, a hybrid vector is made where the DNA encoding a first domain out of the three domains is ligated to the DNA encoding one end of a first linker moiety and the DNA encoding a second domain out of the three domains is ligated to the other end of the first linker moiety; further, the DNA encoding the second domain out of the three domains is linked to one end of a second linker moiety and the DNA encoding a third domain out of the three domains is linked to the other end of the second linker moiety, wherein the first domain, the second domain, and the third domain are distinct and wherein the first domain, the second domain, and the third domain are independently selected from domain A, domain B, and domain C. Such ligation is performed, for example, either in series, or as a three way ligation.

CD3 Binding Domain

The specificity of the response of T cells is mediated by the recognition of antigen (displayed in context of a major histocompatibility complex, MHC) by the TCR. As part of the TCR, CD3 is a protein complex that includes a CD3γ (gamma) chain, a CD3δ (delta) chain, and two CD3ε (epsilon) chains which are present on the cell surface. CD3 associates with the α (alpha) and β (beta) chains of the TCR as well as CD3 ζ (zeta) altogether to comprise the complete TCR. Clustering of CD3 on T cells, such as by immobilized anti-CD3 antibodies leads to T cell activation similar to the engagement of the T cell receptor but independent of its clone-typical specificity.

In one aspect, the DLL3 targeting trispecific proteins described herein comprise a domain which specifically binds to CD3. In one aspect, the DLL3 targeting trispecific proteins described herein comprise a domain which specifically binds to human CD3. In some embodiments, the DLL3 targeting trispecific proteins described herein comprise a domain which specifically binds to CD37. In some embodiments, the DLL3 targeting trispecific proteins described herein comprise a domain which specifically binds to CD36. In some embodiments, the DLL3 targeting trispecific proteins described herein comprise a domain which specifically binds to CD3.

In further embodiments, the DLL3 targeting trispecific proteins described herein comprise a domain which specifically binds to the TCR. In certain instances, the DLL3 targeting trispecific proteins described herein comprise a domain which specifically binds the a chain of the TCR. In certain instances, the DLL3 targeting trispecific proteins described herein comprise a domain which specifically binds the β chain of the TCR.

In certain embodiments, the CD3 binding domain of the DLL3 targeting trispecific proteins described herein exhibit not only potent CD3 binding affinities with human CD3, but show also excellent cross reactivity with the respective cynomolgus monkey CD3 proteins.

In some embodiments, the CD3 binding domain of the DLL3 trispecific antigen-binding protein can be any domain that binds to CD3 including but not limited to domains from a monoclonal antibody, a polyclonal antibody, a recombinant antibody, a human antibody, a humanized antibody. In some instances, it is beneficial for the CD3 binding domain to be derived from the same species in which the DLL3 trispecific antigen-binding protein will ultimately be used in. For example, for use in humans, it may be beneficial for the CD3 binding domain of the DLL3 trispecific antigen-binding protein to comprise human or humanized residues from the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-CD3 binding domain comprises one or more (e.g., all three) light chain complementary determining region 1 (LC CDR1), light chain complementary determining region 2 (LC CDR2), and light chain complementary determining region 3 (LC CDR3) of a humanized or human anti-CD3 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-CD3 binding domain described herein, a humanized or human anti-CD3 binding domain comprising one or more, all three, LC CDRs and one or more, all three, HC CDRs.

In some embodiments, the humanized or human anti-CD3 binding domain comprises a humanized or human light chain variable region specific to CD3 where the light chain variable region specific to CD3 comprises human or non-human light chain CDRs in a human light chain framework region. In certain instances, the light chain framework region is a λ (lambda) light chain framework. In other instances, the light chain framework region is a κ (kappa) light chain framework.

In some embodiments, the humanized or human anti-CD3 binding domain comprises a humanized or human heavy chain variable region specific to CD3 where the heavy chain variable region specific to CD3 comprises human or non-human heavy chain CDRs in a human heavy chain framework region.

In certain instances, the complementary determining regions of the heavy chain and/or the light chain are derived from known anti-CD3 antibodies, such as, for example, muromonab-CD3 (OKT3), otelixizumab (TRX4), teplizumab (MGA031), visilizumab (Nuvion), SP34, TR-66 or X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In one embodiment, the anti-CD3 binding domain is a single chain variable fragment (scFv) comprising a light chain and a heavy chain of an amino acid sequence provided herein. As used herein, "single chain variable fragment" or "scFv" refers to an antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived. In an embodiment, the anti-CD3 binding domain comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In some examples, the anti-CD3 binding domain comprises a sequence selected from SEQ ID Nos. 1793-1807, or a sequence that is at least about 60%, about 70%, about 75%, about 80%, about 85%, about 90%, about 91%, about 92%, about 93%, about 94%, about 95%, about 96%, about 97%, about 98%, about 99%, or about 100% identity to a sequence selected from SEQ ID Nos. 1793-1807. In some examples, the anti-CD3 binding domain comprises three heavy chain CDRs (HC CDR1, HC CDR2, and HC CDR3), and three light chain CDRs. The heavy chain CDR1(HC CDR1) of the CD3 binding domain comprises a sequence selected from SEQ ID Nos. 1820-1831, or a sequence comprising one or more modifications or substitutions in a sequence selected from SEQ ID Nos. 1820-1831, or at least about 80% to about 99%. The heavy chain CDR2 (HC CDR2) of the CD3 binding domain comprises a sequence selected from SEQ ID Nos. 1832-1841, or a sequence comprising one or more modifications or substitutions in a sequence selected from SEQ ID Nos. 1832-1841. The heavy chain CDR3 (HC CDR3) of the CD3 binding domain comprises a sequence selected from SEQ ID Nos. 1842-1853, or a sequence comprising one or more modifications or substitutions in a sequence selected from SEQ ID Nos. 1842-1853. The light chain CDR1 (LC CDR1) of the CD3 binding domain comprises a sequence selected from SEQ ID Nos. 1852-1864, or a sequence comprising one or more modifications or substitutions in a sequence selected from SEQ ID Nos. 1852-1864. The light chain CDR2 (LC CDR2) of the CD3 binding domain comprises a sequence selected from SEQ ID Nos. 1865-1877, or a sequence comprising one or more modifications or substitutions in a sequence selected from SEQ ID Nos. 1865-1877. The light chain CDR3 (LC CDR3) of the CD3 binding domain comprises a sequence selected from SEQ ID Nos. 1878-1884, or a sequence comprising one or more modifications or substitutions in a sequence selected from SEQ ID Nos. 1878-1884. In one embodiment, the humanized or human anti-CD3 binding domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be in any of the following orientations: light chain variable region-scFv linker-heavy chain variable region or heavy chain variable region-scFv linker-light chain variable region.

In some instances, scFvs which bind to CD3 are prepared according to known methods. For example, scFv molecules can be produced by linking VH and VL regions together using flexible polypeptide linkers. The scFv molecules comprise a scFv linker (e.g., a Ser-Gly linker) with an optimized length and/or amino acid composition. Accordingly, in some embodiments, the length of the scFv linker is such that the VH or VL domain can associate intermolecularly with the other variable domain to form the CD3 binding site. In certain embodiments, such scFv linkers are "short", i.e. consist of 0, 1, 2, 3, 4, 5, 6, 7, 8, 9, 10, 11 or 12 amino acid residues. Thus, in certain instances, the scFv linkers consist of about 12 or less amino acid residues. In the case of 0 amino acid residues, the scFv linker is a peptide bond. In some embodiments, these scFv linkers consist of about 3 to about 15, for example 8, 9 or 10 contiguous amino acid residues. Regarding the amino acid composition of the scFv linkers, peptides are selected that confer flexibility, do not interfere with the variable domains as well as allow interchain folding to bring the two variable domains together to form a functional CD3 binding site. For example, scFv linkers comprising glycine and serine residues generally provide protease resistance. In some embodiments, linkers in a scFv comprise glycine and serine residues. The amino acid sequence of the scFv linkers can be optimized, for example, by phage-display methods to improve the CD3 binding and production yield of the scFv. Examples of peptide scFv linkers suitable for linking a variable light domain and a variable heavy domain in a scFv include but are not limited to (GS). (SEQ ID No. 1809), $(GGS)_n$ (SEQ ID No. 1810), $(GGGS)_n$ (SEQ ID No. 1811), $(GGSG)_n$ (SEQ ID No. 1812), $(GGSGG)_n$ (SEQ ID No. 1813), $(GGGGS)_n$ (SEQ ID No. 1814), $(GGGGG)_n$ (SEQ ID No. 1815), or $(GGG)_n$ (SEQ ID No. 1816), wherein n is 1, 2, 3, 4, 5, 6, 7, 8, 9, or 10. In one embodiment, the scFv linker can be $(GGGGS)_4$ (SEQ ID No. 1817) or $(GGGGS)_3$ (SEQ ID No. 1818). In some embodiments, a linker comprises a sequence composed of any combinations of the linkers as set forth in SEQ ID Nos. 1809 to 1818, and the length of such a linker is in some examples up to 15 amino acids, or longer than 15 amino acids. Variation in the linker length may retain or enhance activity, giving rise to superior efficacy in activity studies.

In some embodiments, CD3 binding domain of DLL3 targeting trispecific antigen-binding protein has an affinity to CD3 on CD3 expressing cells with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In some embodiments, the CD3 binding domain of DLL3 targeting trispecific antigen-binding protein has an affinity to CD3ε, γ, or δ with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In further embodiments, CD3 binding domain of DLL3 targeting trispecific antigen-binding protein has low affinity to CD3, i.e., about 100 nM or greater.

The affinity to bind to CD3 can be determined, for example, by the ability of the DLL3 targeting trispecific antigen-binding protein itself or its CD3 binding domain to bind to CD3 coated on an assay plate; displayed on a microbial cell surface; in solution; etc. The binding activity of the DLL3 targeting trispecific antigen-binding protein itself or its CD3 binding domain of the present disclosure to CD3 can be assayed by immobilizing the ligand (e.g., CD3) or the DLL3 targeting trispecific antigen-binding protein itself or its CD3 binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

Half-Life Extension Domain

Contemplated herein are domains which extend the half-life of an antigen-binding domain. Such domains are contemplated to include but are not limited to Albumin binding domains, Fc domains, small molecules, and other half-life extension domains known in the art.

Human albumin (ALB) (molecular mass 67 kDa) is the most abundant protein in plasma, present at about 50 mg/ml (600 μM), and has a half-life of around 20 days in humans. ALB serves to maintain plasma pH, contributes to colloidal blood pressure, functions as carrier of many metabolites and fatty acids, and serves as a major drug transport protein in plasma.

Noncovalent association with albumin extends the elimination half-time of short lived proteins. For example, a recombinant fusion of an albumin binding domain to a Fab fragment resulted in an in vivo clearance of 25- and 58-fold and a half-life extension of 26- and 37-fold when administered intravenously to mice and rabbits respectively as compared to the administration of the Fab fragment alone. In another example, when insulin is acylated with fatty acids to promote association with albumin, a protracted effect was observed when injected subcutaneously in rabbits or pigs. Together, these studies demonstrate a linkage between albumin binding and prolonged action.

In one aspect, the DLL3 targeting trispecific proteins described herein comprise a half-life extension domain, for example a domain which specifically binds to ALB. In some embodiments, the ALB binding domain of the DLL3 targeting trispecific antigen-binding protein can be any domain that binds to ALB including but not limited to domains from a monoclonal antibody, a polyclonal antibody, a recombinant antibody, a human antibody, a humanized antibody. In some embodiments, the ALB binding domain is a single chain variable fragments (scFv), single-domain antibody such as a heavy chain variable domain (VH), a light chain variable domain (VL) and a variable domain (VHH) of camelid derived single domain antibody, peptide, ligand or small molecule entity specific for HSA. In certain embodiments, the ALB binding domain is a single-domain antibody. In other embodiments, the HSA binding domain is a peptide. In further embodiments, the HSA binding domain is a small molecule. It is contemplated that the HSA binding domain of DLL3 trispecific antigen-binding protein is fairly small and no more than 25 kD, no more than 20 kDa, no more than 15 kDa, or no more than 10 kDa in some embodiments. In certain instances, the ALB binding is 5 kDa or less if it is a peptide or small molecule entity.

The half-life extension domain of DLL3 targeting trispecific antigen-binding protein provides for altered pharmacodynamics and pharmacokinetics of the DLL3 targeting trispecific antigen-binding protein itself. As above, the half-life extension domain extends the elimination half-time. The half-life extension domain also alters pharmacodynamic properties including alteration of tissue distribution, penetration, and diffusion of the trispecific antigen-binding protein. In some embodiments, the half-life extension domain provides for improved tissue (including tumor) targeting, tissue distribution, tissue penetration, diffusion within the tissue, and enhanced efficacy as compared with a protein without a half-life extension domain. In one embodiment, therapeutic methods effectively and efficiently utilize a reduced amount of the trispecific antigen-binding protein, resulting in reduced side effects, such as reduced non-tumor cell cytotoxicity.

Further, the binding affinity of the half-life extension domain can be selected so as to target a specific elimination half-time in a particular trispecific antigen-binding protein. Thus, in some embodiments, the half-life extension domain has a high binding affinity. In other embodiments, the half-life extension domain has a medium binding affinity. In yet other embodiments, the half-life extension domain has a low or marginal binding affinity. Exemplary binding affinities include KD concentrations at 10 nM or less (high), between 10 nM and 100 nM (medium), and greater than 100 nM (low). As above, binding affinities to ALB are determined by known methods such as Surface Plasmon Resonance (SPR). In some embodiments, ALB binding domains described herein comprise a single domain antibody.

In some embodiments, the half-life extension domain comprises a sequence selected from SEQ ID Nos. 1769-1778, or a sequence that is at least about 70%, about 75%, about 80%, about 85%, about 90%, about 95%, about 96%, about 97%, about 98%, about 99%, or 100% identical to a sequence selected from SEQ ID Nos. 1769-1778. In some examples, the half-life extension comprises three heavy chain CDRs (HC CDR1, HC CDR2, and HC CDR3), and three light chain CDRs. In some examples, the half-life extension comprises three heavy chain CDRs (HC CDR1, HC CDR2, and HC CDR3), or three light chain CDRs. The heavy chain CDR1(HC CDR1) of the half-life extension domain, in some embodiments, comprises a sequence selected from SEQ ID Nos. 1782-1784, or a sequence comprising one or more modifications or substitutions in a sequence selected from SEQ ID Nos. 1782-1784, or at least about 80% to about 99%. The heavy chain CDR2 (HC CDR2) of the half-life extension domain, in some embodiments, comprises a sequence selected from SEQ ID Nos. 1785-1790, or a sequence comprising one or more modifications or substitutions in a sequence selected from SEQ ID Nos. 1785-1790. The heavy chain CDR3 (HC CDR3) of the CD3 binding domain comprises a sequence selected from SEQ ID Nos. 1791 or 1792, or a sequence comprising one or more modifications or substitutions in a sequence selected from SEQ ID Nos. 1791 or 1792.

DLL3 Binding Domain

DLL3 (also known as Delta-like Ligand 3 or SCDO1) is a member of the Delta-like family of Notch DSL ligands. Representative DLL3 protein orthologs include, but are not limited to, human (Accession Nos. NP_058637 and NP_982353), chimpanzee (Accession No. XP_003316395), mouse (Accession No. NP_031892), and rat (Accession No. NP_446118). In humans, the DLL3 gene consists of 8 exons spanning 9.5 kbp located on chromosome 19q13. Alternate splicing within the last exon gives rise to two processed transcripts, one of 2389 bases (Accession No. NM_016941) and one of 2052 bases (Accession No. NM_203486). The former transcript encodes a 618 amino acid protein (Accession No. NP_058637), whereas the latter encodes a 587 amino acid protein (Accession No. NP_982353). These two protein isoforms of DLL3 share overall 100% identity across their extracellular domains and their transmembrane domains, differing only in that the longer isoform contains an extended cytoplasmic tail containing 32 additional residues at the carboxy terminus of the protein. The extracellular region of the DLL3 protein, comprises six EGF-like domains, the single DSL domain and the N-terminal domain. Generally, the EGF domains are recognized as occurring at about amino acid residues 216-249 (domain 1), 274-310 (domain 2), 312-351 (domain 3), 353-389 (domain 4), 391-427 (domain 5) and 429-465 (domain 6), with the DSL domain at about amino acid residues 176-215 and the N-terminal domain at about amino acid residues 27-175 of hDLL3. Each of the EGF-like domains, the DSL domain and the N-terminal domain comprise part of the DLL3 protein as defined by a distinct amino acid sequence. The EGF-like domains are termed, in some embodiments, as EGF1 to EGF6 with EGF1 being closest to the N-terminal portion of the protein. In general, DSL ligands are composed of a series of structural domains: a unique N-terminal domain, followed by a conserved DSL domain, multiple tandem epidermal growth factor (EGF)-like repeats, a transmembrane domain, and a cytoplasmic domain not highly conserved across ligands but one which contains multiple lysine residues that are potential sites for ubiquitination by unique E3 ubiquitin ligases. The DSL domain is a degenerate EGF-domain that is necessary but not sufficient for interactions with Notch receptors. Additionally, the first two EGF-like repeats of most DSL ligands contain a smaller protein sequence motif known as a DOS domain that co-operatively interacts with the DSL domain when activating Notch signaling.

In some embodiments, the disclosed DLL3 trispecific binding proteins of this disclosure are generated, fabricated, engineered or selected so as to react with a selected domain, motif or epitope within a DLL3 protein. In some embodiments, the DLL3 targeting trispecific protein binds to the DSL domain and, in some embodiments, binds to an epitope comprising G203, R205, P206 within the DSL domain.

The DLL3 binding domain of the DLL3 targeting trispecific proteins of the present disclosure are, in some embodiments, engineered fabricated and/or selected to react with both isoform(s) of DLL3 or a single isoform of the protein or, conversely, comprise a pan-DLL binding domain that reacts or associates with at least one additional DLL family member in addition to DLL3. In some embodiments, the DLL3 binding domain, such as DLL3 binding domain are engineered, fabricated, and/or selected so that they react with domains (or epitopes therein) that are exhibited by DLL3 only or with domains that are at least somewhat conserved across multiple or all DLL family members.

In some embodiments the DLL3 binding domain associates or binds to a specific epitope, portion, motif or domain of DLL3. Both DLL3 isoforms incorporate an identical extracellular region comprising at least an N-terminal domain, a DSL (Delta/Serrate/lag-2) domain and six EGF-like domains (i.e., EGF1-EGF6). Accordingly, in certain embodiments the DLL3 binding domain binds or associate with the N-terminal domain of DLL3 (amino acids 27-175 in the mature protein) while in other embodiments the DLL3 binding domain associates with the DSL domain (amino acids 176-215) or epitope therein. In other aspects of the present disclosure the DLL3 binding domain associates or bind to a specific epitope located in a particular EGF-like domain of DLL3. In some embodiments, the DLL3 binding domain associates or binds to an epitope located in EGF1 (amino acids 216-249), EGF2 (amino acids 274-310), EGF3 (amino acids 312-351), EGF4 (amino acids 353-389), EGF5 (amino acids 391.427) or EGF6 (amino acids 429-465). In some embodiments, each of the aforementioned domains comprises more than one epitope and/or more than one bin. In some embodiments the DLL3 binding domain binds, reacts or associates with the DSL domain or an epitope therein. In other embodiments the DLL3 binding domain binds, reacts or associates with a particular EGF-like domain or an epitope therein. In some embodiments the DLL3 binding domain binds, reacts or associates with the N-terminal domain or an epitope therein.

In some embodiments, the DLL3 binding proteins of this disclosure, such as the DLL3 binding domain of the trispecific proteins of this disclosure binds to the full length DLL3 protein or to a fragment thereof, such as epitope containing fragments within the full length DLL3 protein, as described above. In some cases, the epitope containing fragment comprises antigenic or immunogenic fragments and derivatives thereof of the DLL3 protein. Epitope containing fragments, including antigenic or immunogenic fragments, are, in some embodiments, 12 amino acids or more, 20 amino acids or more, 50 or 100 amino acids or more. The DLL3 fragments, in some embodiments, comprises 95% or more of the length of the full protein, 90% or more, 75% or 50% or 25% or 10% or more of the length of the full protein. In some embodiments, the epitope-containing fragments of DLL3 including antigenic or immunogenic fragments are capable of eliciting a relevant immune response in a patient. Derivatives of DLL3 include, in some embodiments, variants on the sequence in which one or more (e.g., 1-20 such as 15 amino acids, or up to 20% such as up to 10% or 5% or 1% by number of amino acids based on the total length of the protein) deletions, insertions or substitutions have been made to the DLL3 sequence provided in SEQ ID No. 1885 (UniProtKB Accession Q9NYJ7). In some embodiments, substitutions comprise conservative substitutions. Derivatives and variants of DLL3, in some examples, have essentially the same biological function as the DLL3 protein from which they are derived. For instance, derivatives and variants of DLL3 are, in some cases, comparably antigenic or immunogenic to the protein from which they are derived, have either the ligand-binding activity, or the active receptor-complex forming ability, or preferably both, of the protein from which they are derived, and have the same tissue distribution as DLL3.

The design of the DLL3 targeting trispecific proteins described herein allows the binding domain to DLL3 to be flexible in that the binding domain to DLL3 can be any type of binding domain, including but not limited to, domains from a monoclonal antibody, a polyclonal antibody, a recombinant antibody, a human antibody, a humanized antibody. In some embodiments, the binding domain to DLL3 is a single chain variable fragments (scFv), a single-domain antibody such as a heavy chain variable domain (VH), a light chain variable domain (VL) and a variable domain (VHH) of camelid derived single domain antibody. In other embodiments, the binding domain to DLL3 is a non-Ig binding domain, i.e., an antibody mimetic, such as anticalins, affilins, affibody molecules, affimers, affitins, alphabodies, avimers, DARPins, fynomers, kunitz domain peptides, and monobodies. In further embodiments, the binding domain to DLL3 is a ligand or peptide that binds to or associates with DLL3. In yet further embodiments, the binding domain to DLL3 is a knottin. In yet further embodiments, the binding domain to DLL3 is a small molecular entity.

In some embodiments, the DLL3 binding domain binds to a protein comprising the sequence of SEQ ID No. 1885 (UniProtKB Accession Q9NYJ7). In some embodiments, the DLL3 binding domain binds to a protein comprising a truncated sequence compared to SEQ ID No. 1885 (UniProtKB Accession Q9NYJ7). In some embodiments, the DLL3 binding domain binds to a protein comprising the sequence of SEQ ID No. 1892 or SEQ ID No. 1893 (which is the mature extracellular domain of a DLL3 protein). In some embodiments, the DLL3 binding domain binds to a protein comprising amino acids 47-492 of SEQ ID No. 1892. In some embodiments, the DLL3 binding domain recognizes an epitope within amino acids 47-4492 of SEQ ID No. 1892.

In some embodiments, the DLL3 binding domain is an anti-DLL3 antibody or an antibody variant. As used herein, the term "antibody variant" refers to variants and derivatives of an antibody described herein. In certain embodiments, amino acid sequence variants of the anti-DLL3 antibodies described herein are contemplated. For example, in certain embodiments amino acid sequence variants of anti-DLL3 antibodies described herein are contemplated to improve the binding affinity and/or other biological properties of the antibodies. Exemplary method for preparing amino acid variants include, but are not limited to, introducing appropriate modifications into the nucleotide sequence encoding the antibody, or by peptide synthesis. Such modifications include, for example, deletions from, and/or insertions into and/or substitutions of residues within the amino acid sequences of the antibody.

Any combination of deletion, insertion, and substitution can be made to arrive at the final construct, provided that the final construct possesses the desired characteristics, antigen-binding. In certain embodiments, antibody variants having one or more amino acid substitutions are provided. Sites of interest for substitution mutagenesis include the CDRs and framework regions. Examples of such substitutions are described below. Amino acid substitutions may be introduced into an antibody of interest and the products screened for a desired activity, retained/improved antigen binding, decreased immunogenicity, or improved T-cell mediated cytotoxicity (TDCC). Both conservative and non-conservative amino acid substitutions are contemplated for preparing the antibody variants.

In another example of a substitution to create a variant anti-DLL3 antibody, one or more hypervariable region residues of a parent antibody are substituted. In general, variants are then selected based on improvements in desired properties compared to a parent antibody, for example, increased affinity, reduced affinity, reduced immunogenicity, increased pH dependence of binding.

In some embodiments, the DLL3 binding domain of the DLL3 targeting trispecific protein is a single domain antibody such as a heavy chain variable domain (VH), a variable domain (VHH) of a llama derived sdAb, a peptide, a ligand or a small molecule entity specific for DLL3. In some embodiments, the DLL3 binding domain of the DLL3 targeting trispecific protein described herein is any domain that binds to DLL3 including but not limited to domains from a monoclonal antibody, a polyclonal antibody, a recombinant antibody, a human antibody, a humanized antibody. In certain embodiments, the DLL3 binding domain is a single-domain antibody. In other embodiments, the DLL3 binding domain is a peptide. In further embodiments, the DLL3 binding domain is a small molecule.

Generally, it should be noted that the term single domain antibody as used herein in its broadest sense is not limited to a specific biological source or to a specific method of preparation. Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. For example, in some embodiments, the single domain antibodies of the disclosure are obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a species of mammal, such as from a human being, or by expression of a nucleic acid encoding such a camelized VH domain; (5) by "camelisation" of a "domain antibody" or "Dab," or by expression of a nucleic acid encoding such a camelized VH domain; (6) by using synthetic or semi-synthetic techniques for preparing proteins, polypeptides or other amino acid sequences; (7) by preparing a nucleic acid encoding a single domain antibody using techniques for nucleic acid synthesis known in the field, followed by expression of the nucleic acid thus obtained; and/or (8) by any combination of one or more of the foregoing.

In one embodiment, a single domain antibody corresponds to the VHH domains of naturally occurring heavy chain antibodies directed against DLL3. As further described herein, such VHH sequences can generally be generated or obtained by suitably immunizing a species of Llama with DLL3, (i.e., so as to raise an immune response and/or heavy chain antibodies directed against DLL3), by obtaining a suitable biological sample from said Llama (such as a blood sample, serum sample or sample of B-cells), and by generating VHH sequences directed against DLL3, starting from said sample, using any suitable technique known in the field.

In another embodiment, such naturally occurring VHH domains against DLL3, are obtained from naïve libraries of Camelid VHH sequences, for example by screening such a library using DLL3, or at least one part, fragment, antigenic determinant or epitope thereof using one or more screening techniques known in the field. Such libraries and techniques are for example described in WO 99/37681, WO 01/90190, WO 03/025020 and WO 03/035694. Alternatively, improved synthetic or semi-synthetic libraries derived from naïve VHH libraries are used, such as VHH libraries obtained from naïve VHH libraries by techniques such as random mutagenesis and/or CDR shuffling, as for example described in WO 00/43507.

In a further embodiment, yet another technique for obtaining VHH sequences directed against DLL3, involves suitably immunizing a transgenic mammal that is capable of expressing heavy chain antibodies (i.e., so as to raise an immune response and/or heavy chain antibodies directed against DLL3), obtaining a suitable biological sample from said transgenic mammal (such as a blood sample, serum sample or sample of B-cells), and then generating VHH sequences directed against DLL3, starting from said sample, using any suitable technique known in the field. For example, for this purpose, the heavy chain antibody-expressing rats or mice and the further methods and techniques described in WO 02/085945 and in WO 04/049794 can be used.

In some embodiments, an anti-DLL3 single domain antibody of the DLL3 targeting trispecific protein comprises a single domain antibody with an amino acid sequence that corresponds to the amino acid sequence of a naturally occurring VHH domain, but that has been "humanized", i.e., by replacing one or more amino acid residues in the amino acid sequence of said naturally occurring VHH sequence (and in particular in the framework sequences) by one or more of the amino acid residues that occur at the corresponding position(s) in a VH domain from a conventional 4-chain antibody from a human being (e.g., as indicated above). This can be performed in a manner known in the field, which will be clear to the skilled person, for example on the basis of the further description herein. Again, it should be noted that such humanized anti-DLL3 single domain antibodies of the disclosure are obtained in any suitable manner known per se (i.e., as indicated under points (1)-(8) above) and thus are not strictly limited to polypeptides that have been obtained using a polypeptide that comprises a naturally occurring VHH domain as a starting material. In some additional embodiments, a single domain anti-DLL3 antibody, as described herein, comprises a single domain antibody with an amino acid sequence that corresponds to the amino acid sequence of a naturally occurring VH domain, but that has been "camelized," i.e., by replacing one or more amino acid residues in the amino acid sequence of a naturally occurring VH domain from a conventional 4-chain antibody by one or more of the amino acid residues that occur at the corresponding position(s) in a VHH domain of a heavy chain antibody. Such "camelizing" substitutions are preferably inserted at amino acid positions that form and/or are present at the VH-VL interface, and/or at the so-called Camelidae hallmark residues (see for example WO 94/04678 and Davies and Riechmann (1994 and 1996)). Preferably, the VH sequence that is used as a starting material or starting point for generating or designing the camelized single domain is preferably a VH sequence from a mammal, more preferably the VH sequence of a human being, such as a VH3 sequence. However, it should be noted that such camelized anti-DLL3 single domain antibodies of the disclosure, in certain embodiments, are obtained in any suitable manner known in the field (i.e., as indicated under points (1)-(8) above) and thus are not strictly limited to polypeptides that have been obtained using a polypeptide that comprises a naturally occurring VH domain as a starting material. For example, as further described herein, both "humanization" and "camelization" is performed by providing a nucleotide sequence that encodes a naturally occurring VHH domain or VH domain, respectively, and then changing, one or more codons in said nucleotide sequence in such a way that the new nucleotide sequence encodes a "humanized" or "camelized" single domain antibody, respectively. This nucleic acid can then be expressed, so as to provide a desired anti-DLL3 single domain antibody of the disclosure. Alternatively, in other embodiments, based on the amino acid sequence of a naturally occurring VHH domain or VH domain, respectively, the amino acid sequence of the desired humanized or camelized anti-DLL3 single domain antibody of the disclosure, respectively, are designed and then synthesized de novo using known techniques for peptide synthesis. In some embodiments, based on the amino acid sequence or nucleotide sequence of a naturally occurring VHH domain or VH domain, respectively, a nucleotide sequence encoding the desired humanized or camelized anti-DLL3 single domain antibody of the disclosure, respectively, is designed and then synthesized de novo using known techniques for nucleic acid synthesis, after which the nucleic acid thus obtained is expressed in using known expression techniques, so as to provide the desired anti-DLL3 single domain antibody of the disclosure.

Other suitable methods and techniques for obtaining the anti-DLL3 single domain antibody of the disclosure and/or nucleic acids encoding the same, starting from naturally occurring VH sequences or VHH sequences for example comprises combining one or more parts of one or more naturally occurring VH sequences (such as one or more framework (FR) sequences and/or complementarity determining region (CDR) sequences), one or more parts of one or more naturally occurring VHH sequences (such as one or more FR sequences or CDR sequences), and/or one or more synthetic or semi-synthetic sequences, in a suitable manner, so as to provide an anti-DLL3 single domain antibody of the disclosure or a nucleotide sequence or nucleic acid encoding the same.

In some embodiments, the DLL3 binding domain is an anti-DLL3 specific antibody comprising a heavy chain variable complementarity determining region CDR1, a heavy chain variable CDR2, a heavy chain variable CDR3, a light chain variable CDR1, a light chain variable CDR2, and a light chain variable CDR3. In some embodiments, the DLL3 binding domain comprises any domain that binds to DLL3 including but not limited to domains from a monoclonal antibody, a polyclonal antibody, a recombinant antibody, a human antibody, a humanized antibody, or antigen binding fragments such as single domain antibodies (sdAb), Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some embodiments, the DLL3 binding domain is a single domain antibody. In some embodiments, the anti-DLL3 single domain antibody comprises heavy chain variable complementarity determining regions (CDR), CDR1, CDR2, and CDR3.

In some embodiments, the DLL3 binding domain is a polypeptide comprising an amino acid sequence that is comprised of four framework regions/sequences (f1-f4) interrupted by three complementarity determining regions/sequences, as represented by the formula: f1-r1-f2-r2-f3-r3-f4, wherein r1, r2, and r3 are complementarity determining regions CDR1, CDR2, and CDR3, respectively, and f1, f2, f3, and f4 are framework residues. The framework residues of the DLL3 binding protein of the present disclosure comprise, for example, 75, 76, 77, 78, 79, 80, 81, 82, 83, 84, 85, 86, 87, 88, 89, 90, 91, 92, 93, or 94 amino acid residues, and the complementarity determining regions comprise, for example, 24, 25, 26, 27, 28, 29, 30, 31, 32, 33, 34, 35, or 36 amino acid residues. In some embodiments, the DLL3 binding domain comprises an amino acid sequence selected from SEQ ID Nos. 1-442 and 1886. In some embodiments, CDR1 of the DLL3 binding domain comprises a sequence selected from SEQ ID Nos. 443-884 and 1887, or one or more amino acid substitutions relative to a sequence selected from the group consisting of SEQ ID Nos. 443-884 and 1887. In some embodiments, CDR2 comprises a sequence selected from the group consisting of SEQ ID Nos. 885-1326 and 1888, or one or more amino acid substitutions relative to a sequence selected from the group consisting of SEQ ID Nos. 885-1326 and 1888. In some embodiments, the CDR3 comprises a sequence selected from the group consisting of SEQ ID Nos. 1327-1768 and 1889, or one or more substitutions relative to a sequence selected from SEQ ID Nos. 1327-1768 and 1889.

In some embodiments, the CDR1 comprises an amino acid sequence selected from SEQ ID Nos. 443-884 and 1887 or a variant having one, two, three, four, five, six, seven, eight, nine, or ten amino acid substitutions in an amino acid selected from SEQ ID Nos. 443-884 and 1887. In some embodiments, the CDR2 comprises an amino acid sequence selected from SEQ ID Nos. 885-1326 and 1888 or a variant having one, two, three, four, five, six, seven, eight, nine, or ten amino acid substitutions in an amino acid sequence selected from SEQ ID Nos. 885-1326 and 1888. In some embodiments, the CDR3 comprises an amino acid sequence selected from SEQ ID Nos. 1327-1768 and 1889 or a variant having one, two, three, four, five, six, seven, eight, nine, or ten amino acid substitutions in a sequence selected from SEQ ID Nos. 1327-1768 and 1889.

In some embodiments, the CDR1 comprises an amino acid sequence selected from SEQ ID Nos. 495-528 or a variant having one, two, three, four, five, six, seven, eight, nine, or ten amino acid substitutions in an amino acid selected from SEQ ID Nos. 495-528. In some embodiments, the CDR2 comprises an amino acid sequence selected from SEQ ID Nos. 937-970 or a variant having one, two, three, four, five, six, seven, eight, nine, or ten amino acid substitutions in an amino acid sequence selected from SEQ ID Nos. 937-970. In some embodiments, the CDR3 comprises an amino acid sequence selected from SEQ ID Nos. 1379-1412 or a variant having one, two, three, four, five, six, seven, eight, nine, or ten amino acid substitutions in a sequence selected from SEQ ID Nos. 1379-1412.

In some embodiments, the CDR1 comprises an amino acid sequence selected from SEQ ID Nos. 529-809 or a variant having one, two, three, four, five, six, seven, eight, nine, or ten amino acid substitutions in an amino acid selected from SEQ ID Nos. 529-809. In some embodiments, the CDR2 comprises an amino acid sequence selected from SEQ ID Nos. 971 to 1251 or a variant having one, two, three, four, five, six, seven, eight, nine, or ten amino acid substitutions in an amino acid sequence selected from SEQ ID Nos. 971 to 1251. In some embodiments, the CDR3 comprises an amino acid sequence selected from SEQ ID Nos. 1379 to 1412 or a variant having one, two, three, four, five, six, seven, eight, nine, or ten amino acid substitutions in a sequence selected from SEQ ID Nos. 1379-1412.

In some embodiments, the CDR1 comprises an amino acid sequence selected from SEQ ID Nos. 810-884 or a variant having one, two, three, four, five, six, seven, eight, nine, or ten amino acid substitutions in an amino acid selected from SEQ ID Nos. 810-884. In some embodiments, the CDR2 comprises an amino acid sequence selected from SEQ ID Nos. 1252 to 1326 or a variant having one, two, three, four, five, six, seven, eight, nine, or ten amino acid substitutions in an amino acid sequence selected from SEQ ID Nos. 1252 to 1326. In some embodiments, the CDR3 comprises an amino acid sequence selected from SEQ ID Nos. 1692 to 1768 or a variant having one, two, three, four, five, six, seven, eight, nine, or ten amino acid substitutions in a sequence selected from SEQ ID Nos. 1692 to 1768.

In various embodiments, the DLL3 binding domain of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID Nos. 1-442 and 1886. In various embodiments, the DLL3 binding domain of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID Nos. 53-86.

In various embodiments, the DLL3 binding domain of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID Nos. 87-367.

In various embodiments, the DLL3 binding domain of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID No.68, or a sequence derived from SEQ ID No.68.

In various embodiments, the DLL3 binding domain of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID No.75, or a sequence derived from SEQ ID No.75.

In some embodiments, the DLL3 binding domain of the DLL3 targeting trispecific binding protein is cross-reactive with human and cynomolgus DLL3. In some embodiments, the DLL3 binding domain is specific for human DLL3. In certain embodiments, the DLL3 binding domain disclosed herein binds to human DLL3 with a human Kd (hKd). In certain embodiments, the DLL3 binding domain disclosed herein binds to cynomolgus DLL3 with a cynomolgus Kd (cKd). In certain embodiments, the DLL3 binding domain disclosed herein binds to both cynomolgus DLL3 and a human DLL3, with a cyno Kd (cKd) and a human Kd, respectively (hKd). In some embodiments, the DLL3 binding protein binds to human and cynomolgus DLL3 with comparable binding affinities (i.e., hKd and cKd values do not differ by more than 10%). In some embodiments, the hKd and the cKd range from about 0.001 nM to about 500 nM. In some embodiments, the hKd and the cKd range from about 0.001 nM to about 450 nM. In some embodiments, the hKd and the cKd range from about 0.001 nM to about 400 nM. In some embodiments, the hKd and the cKd range from about 0.001 nM to about 350 nM. In some embodiments, the hKd and the cKd range from about 0.001 nM to about 300 nM. In some embodiments, the hKd and the cKd range from about 0.001 nM to about 250 nM. In some embodiments, the hKd and the cKd range from about 0.001 nM to about 200 nM. In some embodiments, the hKd and the cKd range from about 0.001 nM to about 150 nM. In some embodiments, the hKd and the cKd range from about 0.001 nM to about 100 nM. In some embodiments, the hKd and the cKd range from about 0.1 nM to about 90 nM. In some embodiments, the hKd and the cKd range from about 0.2 nM to about 80 nM. In some embodiments, the hKd and the cKd range from about 0.3 nM to about 70 nM. In some embodiments, the hKd and the cKd range from about 0.4 nM to about 50 nM. In some embodiments, the hKd and the cKd range from about 0.5 nM to about 30 nM. In some embodiments, the hKd and the cKd range from about 0.6 nM to about 10 nM. In some embodiments, the hKd and the cKd range from about 0.7 nM to about 8 nM. In some embodiments, the hKd and the cKd range from about 0.8 nM to about 6 nM. In some embodiments, the hKd and the cKd range from about 0.9 nM to about 4 nM. In some embodiments, the hKd and the cKd range from about 1 nM to about 2 nM.

In certain embodiments, the DLL3 binding domains of the present disclosure preferentially bind membrane bound DLL3 over soluble DLL3. Membrane bound DLL3 refers to the presence of DLL3 in or on the cell membrane surface of a cell that expresses DLL3. Soluble DLL3 refers to DLL3 that is no longer on in or on the cell membrane surface of a cell that expresses or expressed DLL3. In certain instances, the soluble DLL3 is present in the blood and/or lymphatic circulation in a subject. In one embodiment, the DLL3 binding proteins bind membrane-bound DLL3 at least 5 fold, 10 fold, 15 fold, 20 fold, 25 fold, 30 fold, 40 fold, 50 fold, 100 fold, 500 fold, or 1000 fold greater than soluble DLL3. In one embodiment, the antigen binding proteins of the present disclosure preferentially bind membrane-bound DLL3 30 fold greater than soluble DLL3. Determining the preferential binding of an antigen binding protein to membrane bound DLL3 over soluble DLL3 can be readily determined using assays well known in the art.

In some embodiments, any of the foregoing DLL3 binding domains (e.g., anti-DLL3 single domain antibodies of SEQ ID Nos. 1-442 and 1886) are affinity peptide tagged for ease of purification. In some embodiments, the affinity peptide tag is six consecutive histidine residues, also referred to as 6×-his (SEQ ID No. 1819).

In some embodiments, any of the foregoing DLL3 binding domains (e.g., anti-DLL3 single domain antibodies of SEQ ID Nos. 1-442 and 1886) are affinity peptide tagged for ease of purification. In some embodiments, the affinity peptide tag is six consecutive histidine residues, also referred to as 6×-his (SEQ ID No. 1819).

Integration into Chimeric Antigen Receptors (CAR)

The DLL3 targeting trispecific antigen binding proteins of the present disclosure can, in certain examples, be incorporated into a chimeric antigen receptor (CAR). An engineered immune effector cell, a T cell or NK cell, can be used to express a CAR that includes an anti-DLL3 targeting trispecific protein containing an anti-DLL3 single domain antibody as described herein. In one embodiment, the CAR including an anti-DLL3 targeting trispecific protein as described herein is connected to a transmembrane domain via a hinge region, and further a costimulatory domain, a functional signaling domain obtained from OX40, CD27, CD28, CD5, ICAM-1, LFA-1 (CD11a/CD18), ICOS (CD278), or 4-1BB. In some embodiments, the CAR further comprises a sequence encoding an intracellular signaling domain, such as 4-1BB and/or CD3 zeta.

Tumor Growth Reduction Properties

In certain embodiments, the DLL3 targeting trispecific proteins of the disclosure reduce the growth of tumor cells in vivo when administered to a subject who has tumor cells that express DLL3. Measurement of the reduction of the growth of tumor cells can be determined by multiple different methodologies well known in the art. Non-limiting examples include direct measurement of tumor dimension, measurement of excised tumor mass and comparison to control subjects, measurement via imaging techniques (e.g., CT or MRI) that may or may not use isotopes or luminescent molecules (e.g. luciferase) for enhanced analysis, and the like.

In specific embodiments, administration of the trispecific proteins of the disclosure results in a reduction of in vivo growth of tumor cells as compared to a control antigen binding agent by at least about 10%, 20%, 30%, 40%, 50%, 60%, 70%, 80%, 90% or 100%, with an about 100% reduction in tumor growth indicating a complete response and disappearance of the tumor. In further embodiments, administration of the trispecific proteins of the disclosure results in a reduction of in vivo growth of tumor cells as compared to a control antigen binding agent by about 50-100%, about 75-100% or about 90-100%. In further embodiments, administration of the trispecific proteins of the disclosure results in a reduction of in vivo growth of tumor cells as compared to a control antigen binding agent by about 50-60%, about 60-70%, about 70-80%, about 80-90%, or about 90-100%.

DLL3 Targeting Trispecific Protein Modifications

The DLL3 targeting trispecific proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in DLL3 targeting trispecific proteins described herein, including the peptide backbone, the amino acid side-chains, and the amino or carboxyl termini. Certain common peptide modifications that are useful for modification of DLL3 targeting trispecific proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

In some embodiments, a derivative of the DLL3 targeting trispecific protein as described herein comprises immunoreactive modulator derivatives and antigen binding molecules comprising one or more modifications.

In some embodiments, the trispecific DLL3 binding molecules of the disclosure are monovalent or multivalent, bivalent, trivalent, etc. As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen).

In some embodiments, the DLL3 targeting trispecific proteins of this disclosure contain inter alia one or more additional amino acid residue substitutions, mutations and/or modifications which result in a compound with preferred characteristics including, but not limited to: altered pharmacokinetics, increased serum half-life, increase binding affinity, reduced immunogenicity, increased production, altered Fc ligand binding to an Fc receptor (FcR), enhanced or reduced "ADCC" (antibody-dependent cell mediated cytotoxicity) or "CDC" (complement-dependent cytotoxicity) activity, altered glycosylation and/or disulfide bonds and modified binding specificity. In some cases these DLL3 targeting trispecific protein variants are advantageously used to enhance the effective anti-neoplastic properties of the disclosed DLL3 targeting trispecific proteins.

In some embodiments, the DLL3 targeting trispecific proteins of the disclosure have half-lives in a mammals, such as in a human, or in a cynomolgus monkey of less than about 5 days, about 5 days, greater than about 5 days, greater than 10 days, greater than about 15 days, greater than about 20 days, greater than about 25 days, greater than about 30 days, greater than about 35 days, greater than about 40 days, greater than about 45 days, greater than about 2 months, greater than about 3 months, greater than about 4 months, or greater than about 5 months. The increased half-life, in some cases, results in a higher serum titer which thus reduces the frequency of the administration of the DLL3 targeting trispecific proteins, reduces the concentration of the antibodies to be administered, or both.

Still other embodiments comprise one or more engineered glycoforms, i.e., a DLL3 targeting trispecific binding protein comprising an altered glycosylation pattern or altered carbohydrate composition that is covalently attached to the protein. Engineered glycoforms are useful, in some cases, for a variety of purposes, including but not limited to enhancing or reducing effector function, increasing the affinity of the trispecific protein for a target or facilitating production of the trispecific protein. In certain embodiments where reduced effector function is desired, the molecule is engineered to express an a glycosylated form. Substitutions that result in elimination of one or more variable region framework glycosylation sites to thereby eliminate glycosylation at that site, are included in some embodiments. Conversely, enhanced effector functions or improved binding is imparted to the Fc containing trispecific proteins of this disclosure by engineering in one or more additional glycosylation sites, in some cases.

The DLL3 targeting trispecific proteins, in some cases, are differentially modified during or after production, by glycosylation, acetylation, phosphorylation, amidation, derivatization by known protecting/blocking groups, proteolytic cleavage, linkage to an antibody molecule or other cellular ligand, etc. Any of numerous chemical modifications are carried out by techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin etc.

Various post-translational modifications also encompassed by the disclosure include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. Moreover, the DLL3 targeting trispecific binding proteins are, in some cases, modified with a detectable label, such as an enzymatic, fluorescent, radioisotopic or affinity label to allow for detection and isolation of the modulator.

Polynucleotides Encoding DLL3 Targeting Trispecific Proteins

Also provided, in some embodiments, are polynucleotide molecules encoding an anti-DLL3 trispecific binding protein described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding the three binding domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. In the embodiments where the DLL3 binding domain is a small molecule, the polynucleotides contain genes encoding the CD3 binding domain and the half-life extension domain. In the embodiments where the half-life extension domain is a small molecule, the polynucleotides contain genes encoding the domains that bind to CD3 and DLL3. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described trispecific antigen-binding protein. Examples of expression vectors for expression in *E. coli* are pSKK (Le Gall et al., J Immunol Methods. (2004) 285(1):111-27) or pcDNA5 (Invitrogen) for expression in mammalian cells.

Thus, the DLL3 targeting trispecific proteins as described herein, in some embodiments, are produced by introducing a vector encoding the protein as described above into a host cell and culturing said host cell under conditions whereby the protein domains are expressed, may be isolated and, optionally, further purified.

Pharmaceutical Compositions

Also provided, in some embodiments, are pharmaceutical compositions comprising an anti-DLL3 trispecific binding protein described herein, a vector comprising the polynucleotide encoding the polypeptide of the DLL3 targeting trispecific proteins or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents. A further embodiment provides one or more of the above described DLL3 targeting trispecific proteins packaged in lyophilized form, or packaged in an aqueous medium.

In some embodiments of the pharmaceutical compositions, the DLL3 targeting trispecific proteins described herein are encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the DLL3 targeting trispecific protein is attached to liposomes. In some instances, the DLL3 targeting trispecific proteins are conjugated to the surface of liposomes. In some instances, the DLL3 trispecific antigen-binding protein are encapsulated within the shell of a liposome. In some instances, the liposome is a cationic liposome.

The DLL3 targeting trispecific proteins described herein are contemplated for use as a medicament. Administration is effected by different ways, by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

In some embodiments, the DLL3 targeting trispecific proteins of this disclosure are administered at a dosage of up to 10 mg/kg at a frequency of once a week. In some cases, the dosage ranges from about 1 ng/kg to about 10 mg/kg. In some embodiments, the dose is from about 1 ng/kg to about 10 ng/kg, about 5 ng/kg to about 15 ng/kg, about 12 ng/kg to about 20 ng/kg, about 18 ng/kg to about 30 ng/kg, about 25 ng/kg to about 50 ng/kg, about 35 ng/kg to about 60 ng/kg, about 45 ng/kg to about 70 ng/kg, about 65 ng/kg to about 85 ng/kg, about 80 ng/kg to about 1 µg/kg, about 0.5 µg/kg to about 5 µg/kg, about 2 µg/kg to about 10 µg/kg, about 7 µg/kg to about 15 µg/kg, about 12 µg/kg to about 25 µg/kg, about 20 µg/kg to about 50 µg/kg, about 35 µg/kg to about 70 µg/kg, about 45 µg/kg to about 80 µg/kg, about 65 µg/kg to about 90 µg/kg, about 85 µg/kg to about 0.1 mg/kg, about 0.095 mg/kg to about 10 mg/kg. In some cases, the dosage is about 0.1 mg/kg to about 0.2 mg/kg; about 0.25 mg/kg to about 0.5 mg/kg, about 0.45 mg/kg to about 1 mg/kg, about 0.75 mg/kg to about 3 mg/kg, about 2.5 mg/kg to about 4 mg/kg, about 3.5 mg/kg to about 5 mg/kg, about 4.5 mg/kg to about 6 mg/kg, about 5.5 mg/kg to about 7 mg/kg, about 6.5 mg/kg to about 8 mg/kg, about 7.5 mg/kg to about 9 mg/kg, or about 8.5 mg/kg to about 10 mg/kg. The frequency of administration, in some embodiments, is about less than daily, every other day, less than once a day, twice a week, weekly, once in 7 days, once in two weeks, once in two weeks, once in three weeks, once in four weeks, or once a month. In some cases, the frequency of administration is weekly. In some cases, the frequency of administration is weekly and the dosage is up to 10 mg/kg. In some cases, duration of administration is from about 1 day to about 4 weeks or longer.

Methods of Treatment

In some embodiments, the DLL3 binding proteins, or DLL3 targeting trispecific proteins of the present disclosure is administered to treat a neoplastic condition. Neoplastic conditions, in some embodiments, are benign or malignant; solid tumors or other blood neoplasia; and, in some embodiments, are selected from the group including, but not limited to: adrenal gland tumors, AIDS-associated cancers, alveolar soft part sarcoma, astrocytic tumors, autonomic ganglia tumors, bladder cancer (squamous cell carcinoma and transitional cell carcinoma), blastocoelic disorders, bone cancer (adamantinoma, aneurismal bone cysts, osteochondroma, osteosarcoma), brain and spinal cord cancers, metastatic brain tumors, breast cancer including triple negative breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, epithelial disorders, Ewing's tumors, extraskeletal myxoid chondrosarcoma, fibrogenesis imperfecta ossium, fibrous dysplasia of the bone, gallbladder and bile duct cancers, gastric cancer, gastrointestinal, gestational trophoblastic disease, germ cell tumors, glandular disorders, head and neck cancers, hypothalamic, intestinal cancer, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), macrophagal disorders, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, stromal disorders, synovial sarcoma, testicular cancer, thymic carcinoma, thymoma, thyroid metastatic cancer, and uterine cancers (carcinoma of the cervix, endometrial carcinoma, and leiomyoma).

In certain embodiments the DLL3 binding proteins, or the DLL3 targeting trispecific proteins of the present disclosure is used as a front line therapy and administered to subjects who have not previously been treated for the cancerous condition. In other embodiments the DLL3 targeting trispecific proteins of the present disclosure are used to treat subjects that have previously been treated (with a DLL3 targeting trispecific protein of this disclosure or with other anti-cancer agent) and have relapsed or determined to be refractory to the previous treatment. In some embodiments the DLL3 targeting trispecific proteins of the present disclosure are used to treat subjects that have recurrent tumors.

In some aspects, the DLL3 binding proteins, or the DLL3 targeting trispecific proteins of the present disclosure are administered to treat a proliferative disorder comprising a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors.

In some embodiments, the DLL3 binding proteins, or the DLL3 targeting trispecific proteins of the present disclosure are administered to a subject suffering from melanoma. In some embodiments, the DLL3 targeting trispecific proteins of the present disclosure are used to diagnose, monitor, treat or prevent melanoma. The term "melanoma," as used herein, includes all types of melanoma including, but not limited to, primary melanoma, malignant melanoma, cutaneous melanoma, extracutaneous melanoma, superficial spreading melanoma, polypoid melanoma, melanocarcinomas, melanoepitheliomas, melanosarcomas, melanoma in situ, nodular malignant melanoma, lentigo maligna melanoma, lentiginous melanoma, lentiginous malignant melanoma, mucosal lentiginous melanoma, mucosal melanoma, acral lentiginous melanoma, soft tissue melanoma, ocular melanoma, invasive melanoma, familial atypical mole and melanoma (FAM-M) syndrome, desmoplastic malignant melanoma or uveal melanoma.

DLL3 is an effective tumor marker that is expressed on a number of different cancers and has been found to be associated with cancer stem cells. Thus, in some embodiments where the DLL3 binding proteins, or the DLL3 targeting trispecific proteins of the disclosure are incorporated in a chimeric antigen receptor expressed on lymphocytes, the resulting "DLL3 sensitized lymphocytes" (e.g., natural killer cells or T cells that immunospecifically recognize a DLL3 determinant) are able to effectively mount an immune response directed to aberrant DLL3 positive cells including cancer stem cells. This ability to effectively eliminate tumorigenic "seed" cells is often critical in reducing the possibility of tumor recurrence or metastasis. In some embodiments, such DLL3 sensitized lymphocytes are used in combination with other therapeutic agents or as part of a maintenance regimen following standard of care treatments.

More generally a chimeric antigen receptor is an artificially constructed hybrid protein or polypeptide containing or comprising an antigen binding domain of an antibody linked to a signaling domain (e.g., T-cell signaling or T-cell activation domains). In some embodiments, CARs comprising the DLL3 targeting trispecific binding protein of the present disclosure have the ability to redirect the specificity and reactivity of sensitized lymphocytes (e.g., T-cells) toward DLL3 positive target cells in a non-MHC-restricted manner by exploiting the antigen-binding properties of antibodies or antigen binding fragments thereof. The non-MHC-restricted antigen recognition gives T-cells expressing DLL3 CARs the ability to recognize tumorigenic DLL3 independent of antigen processing, thus bypassing a major mechanism of tumor escape. Moreover, when expressed in T-cells, CARs advantageously do not dimerize with endogenous T cell receptor (TCR) alpha and beta chains.

In selected aspects the DLL3 binding proteins, or the DLL3 targeting trispecific proteins of the disclosure is incorporated into a chimeric antigen receptor (CAR) and the DLL3 CAR is administered in a CAR based therapy effective at treating lung cancer, including the following subtypes: small cell lung cancer, non-small cell lung cancer (e.g., squamous cell non-small cell lung cancer or squamous cell small cell lung cancer) and large cell neuroendocrine carcinoma (LCNEC).

In some embodiments, the DLL3 binding proteins, or the DLL3 sensitive lymphocytes are administered to patients exhibiting limited stage disease or extensive stage disease. In other embodiments the disclosed DLL3 targeting trispecific antibodies are administered to refractory patients (i.e., those whose disease recurs during or shortly after completing a course of initial therapy); sensitive patients (i.e., those whose relapse is longer than 2-3 months after primary therapy); or patients exhibiting resistance to a platinum based agent (e.g., carboplatin, cisplatin, oxaliplatin) and/or a taxane (e.g., docetaxel, paclitaxel, larotaxel or cabazitaxel). In another embodiment the disclosed DLL3 CAR treatments are effective at treating ovarian cancer, including ovarian-serous carcinoma and ovarian-papillary serous carcinoma.

The disclosed DLL3 binding proteins, or the DLL3 targeting trispecific binding proteins, in some embodiments, are used to prevent, treat or diagnose tumors with neuroendocrine features or phenotypes including neuroendocrine tumors. True or canonical neuroendocrine tumors (NETs) arising from the dispersed endocrine system are relatively rare, with an incidence of 2-5 per 100,000 people, but highly aggressive. Neuroendocrine tumors occur in the kidney, genitourinary tract (bladder, prostate, ovary, cervix, and endometrium), gastrointestinal tract (colon, stomach), thyroid (medullary thyroid cancer), and lung (small cell lung carcinoma and large cell neuroendocrine carcinoma). These tumors may secrete several hormones including serotonin and/or chromogranin A that can cause debilitating symptoms known as carcinoid syndrome. Such tumors can be denoted by positive immunohistochemical markers such as neuron-specific enolase (NSE, also known as gamma enolase, gene symbol=ENO2), CD56 (or NCAM1), chromogranin A (CHGA), and synaptophysin (SYP) or by genes known to exhibit elevated expression such as ASCL1. Traditional chemotherapies have not been particularly effective in treating neuroendocrine tumors and liver metastasis is a common outcome. In some embodiments the disclosed DLL3 targeting trispecific antibodies are advantageously used to treat neuroendocrine tumors, and in some embodiments they are used to treat, prevent or diagnose pseudo neuroendocrine tumors (pNETs) that genotypically or phenotypically mimic, resemble or exhibit common traits with canonical neuroendocrine tumors. Pseudo neuroendocrine tumors or tumors with neuroendocrine features are tumors that arise from cells of the diffuse neuroendocrine system or from cells in which a neuroendocrine differentiation cascade has been aberrantly reactivated during the oncogenic process. Such pNETs commonly share certain phenotypic or biochemical characteristics with traditionally defined neuroendocrine tumors, including the ability to produce subsets of biologically active amines, neurotransmitters, and peptide hormones. Histologically, such tumors (NETs and pNETs) share a common appearance often showing densely connected small cells with minimal cytoplasm of bland cytopathology and round to oval stippled nuclei. In some embodiments of the present disclosure commonly expressed histological markers or genetic markers that are used to define neuroendocrine and pseudo neuroendocrine tumors include, but are not limited to, chromogranin A, CD56, synaptophysin, PGP9.5, ASCL1 and neuron-specific enolase (NSE). Accordingly, in some embodiments, the DLL3 targeting trispecific protein of the disclosure, the DLL3 CAR, or the DLL3 sensitized lymphocytes, or any combination thereof, of the present disclosure, are beneficially used to treat both pseudo neuroendocrine tumors and canonical neuroendocrine tumors, such as to treat neuroendocrine tumors (both NET and pNET) arising in the kidney, genitourinary tract (bladder, prostate, ovary, cervix, and endometrium), gastrointestinal tract (colon, stomach), thyroid (medullary thyroid cancer), and lung (small cell lung carcinoma and large cell neuroendocrine carcinoma). Moreover, in some embodiments, the DLL3 targeting trispecific protein of the disclosure, the DLL3 CAR, or the DLL3 sensitized lymphocytes, or any combination thereof are used to treat tumors expressing one or more markers such as NSE, CD56, synaptophysin, chromogranin A, ASCL1, or PGP9.5 (UCHL1). In some embodiments, the DLL3 targeting trispecific protein of the disclosure, the DLL3 CAR, or the DLL3 sensitized lymphocytes, or any combination thereof are used to treat a subject suffering from a tumor that is NSE+ or CD56+ or PGP9.5+ or ASCL1+ or SYP+ or CHGA+ or any combination thereof.

In another embodiment the DLL3 targeting trispecific protein of the disclosure, the DLL3 CAR, or the DLL3 sensitized lymphocytes, or any combination thereof are used in maintenance therapy to reduce or eliminate the chance of tumor recurrence following the initial presentation of the disease. In some cases, the disorder has been treated and the initial tumor mass eliminated, reduced or otherwise ameliorated so the patient is asymptomatic or in remission. At such time the subject is administered pharmaceutically effective amounts of the disclosed the DLL3 binding proteins, the DLL3 targeting trispecific protein of the disclosure, the DLL3 CAR, or the DLL3 sensitized lymphocytes, or any combination thereof one or more times regardless of if there is little or no indication of disease using standard diagnostic procedures. In some embodiments, the DLL3 targeting trispecific protein of the disclosure, the DLL3 CAR, or the DLL3 sensitized lymphocytes, or any combination thereof is administered on a regular schedule over a period of time, such as weekly, every two weeks, monthly, every six weeks, every two months, every three months every six months or annually, for example, to reduce the potential of disease recurrence. Moreover such treatments are in some embodiments continued for a period of weeks, months, years or even indefinitely depending on the patient response and clinical and diagnostic parameters.

In yet another embodiment the DLL3 binding proteins, the DLL3 targeting trispecific protein of the disclosure, the DLL3 CAR, or the DLL3 sensitized lymphocytes, or any combination thereof are used to prophylactically or as an adjuvant therapy to prevent or reduce the possibility of tumor metastasis following a debulking procedure. As used in the present disclosure a "debulking procedure" is defined broadly and means any procedure, technique or method that eliminates, reduces, treats or ameliorates a tumor or tumor proliferation. Exemplary debulking procedures include, but are not limited to, surgery, radiation treatments (i.e., beam radiation), chemotherapy, immunotherapy or ablation. In some embodiments, at appropriate times, the DLL3 binding proteins, the DLL3 targeting trispecific protein of the disclosure, the DLL3 CAR, or the DLL3 sensitized lymphocytes, or any combination thereof are administered as suggested by clinical, diagnostic or theranostic procedures to reduce tumor metastasis. In some embodiments, the dosing regimen is accompanied by appropriate diagnostic or monitoring techniques that allow it to be modified.

Yet other embodiments of the disclosure comprise administering the DLL3 binding proteins, the DLL3 targeting trispecific protein of the disclosure, the DLL3 CAR, or the DLL3 sensitized lymphocytes, or any combination thereof to subjects that are asymptomatic but at risk of developing a proliferative disorder. That is, in some embodiments, the DLL3 binding proteins, the DLL3 targeting trispecific protein of the disclosure, the DLL3 CAR, or the DLL3 sensitized lymphocytes, or any combination thereof are used in preventative sense and given to patients that have been examined or tested and have one or more noted risk factors (e.g., genomic indications, family history, in vivo or in vitro test results, etc.) but have not developed neoplasia. In such cases those skilled in the art would be able to determine an effective dosing regimen through empirical observation or through accepted clinical practices.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

In some embodiments of the methods described herein, the DLL3 binding proteins, the DLL3 targeting trispecific proteins, or compositions as described herein are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, an anti-DLL3 binding protein, or an anti-DLL3 targeting trispecific protein as described herein is administered in combination with anti-diarrheal agents, antiemetic agents, analgesics, opioids and/or non-steroidal anti-inflammatory agents. In some embodiments, an anti-DLL3 binding protein, or an anti-DLL3 targeting trispecific protein as described herein is administered in combination with anti-cancer agents. Non-limiting examples of anti-cancer agents that can be used in the various embodiments of the disclosure, including pharmaceutical compositions and dosage forms and kits of the disclosure, include: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1 interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; zorubicin hydrochloride. Other examples of anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iodoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In some embodiments, the DLL3 targeting trispecific protein of the present disclosure is used in combination with gemcitabine. In some embodiments, the DLL3 targeting trispecific protein as described herein is administered before, during, or after surgery.

Methods of Detection of DLL3 Expression and Diagnosis of DLL3 Associated Cancer

According to another embodiment of the disclosure, kits for detecting expression of DLL3 in vitro or in vivo are provided. The kits include the foregoing DLL3 binding proteins, DLL3 targeting trispecific proteins (e.g., a trispecific protein containing a labeled anti-DLL3 single domain antibody or antigen binding fragments thereof), and one or more compounds for detecting the label. In some embodiments, the label is selected from the group consisting of a fluorescent label, an enzyme label, a radioactive label, a nuclear magnetic resonance active label, a luminescent label, and a chromophore label.

In some cases, DLL3 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine.

A biological sample is typically obtained from a mammal, such as a human or non-human primate.

In one embodiment, provided is a method of determining if a subject has cancer by contacting a sample from the subject with an anti-DLL3 single domain antibody or an anti-DLL3 trispecific protein as disclosed herein; and detecting binding of the single domain antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with an anti-DLL3 single domain antibody or an anti-DLL3 trispecific protein as disclosed herein; and detecting binding of the antibody to the sample. An increase in binding of the antibody to the sample as compared to binding of the antibody to a control sample confirms the diagnosis of cancer in the subject.

In some examples of the disclosed methods, the DLL3 binding protein, or the DLL3 binding single domain antibody of the trispecific protein is directly labeled. In some examples, the methods further include contacting a second antibody that specifically binds an anti-DLL3 single domain antibody or an anti-DLL3 trispecific protein with the sample; and detecting the binding of the second antibody. An increase in binding of the second antibody to the sample as compared to binding of the second antibody to a control sample detects cancer in the subject or confirms the diagnosis of cancer in the subject. In some cases, the cancer is a neuroendocrine cancer, prostate cancer, lung cancer, stomach cancer, squamous cell carcinoma, pancreatic cancer, cholangiocarcinoma, triple negative breast cancer or ovarian cancer, or any other type of cancer that expresses DLL3. In some examples, the control sample is a sample from a subject without cancer. In particular examples, the sample is a blood or tissue sample.

In some cases, the antibody that binds (for example specifically binds) DLL3 is directly labeled with a detectable label. In another embodiment, the antibody that binds (for example, specifically binds) DLL3 (the first antibody) is unlabeled and a second antibody or other molecule that can bind the antibody that specifically binds DLL3 is labeled. A second antibody is chosen such that it is able to specifically bind the specific species and class of the first antibody. For example, if the first antibody is a llama IgG, then the secondary antibody may be an anti-llama-IgG. Other molecules that can bind to antibodies include, without limitation, Protein A and Protein G, both of which are available commercially. Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include 125I, 131I, 35S or 3H.

In an alternative embodiment, DLL3 can be assayed in a biological sample by a competition immunoassay utilizing DLL3 standards labeled with a detectable substance and an unlabeled antibody that specifically binds DLL3. In this assay, the biological sample, the labeled DLL3 standards and the antibody that specifically bind DLL3 are combined and the amount of labeled DLL3 standard bound to the unlabeled antibody is determined. The amount of DLL3 in the biological sample is inversely proportional to the amount of labeled DLL3 standard bound to the antibody that specifically binds DLL3.

The immunoassays and method disclosed herein can be used for a number of purposes. In one embodiment, the antibody that specifically binds DLL3 may be used to detect the production of DLL3 in cells in cell culture. In another embodiment, the antibody can be used to detect the amount of DLL3 in a biological sample, such as a tissue sample, or a blood or serum sample. In some examples, the DLL3 is cell-surface DLL3. In other examples, the DLL3 is soluble DLL3 (e.g., DLL3 in a cell culture supernatant or soluble DLL3 in a body fluid sample, such as a blood or serum sample).

In one embodiment, a kit is provided for detecting DLL3 in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble DLL3 protein or fragment. Kits for detecting a polypeptide will typically comprise a single domain antibody, according to the present disclosure, that specifically binds DLL3. In some embodiments, an antibody fragment, such as an scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds DLL3. The instructional materials may be written, in an electronic form (such as a computer diskette or compact disk) or may be visual (such as video files), or provided through an electronic network, for example, over the internet, World Wide Web, an intranet, or other network. The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting DLL3 in a biological sample generally includes the steps of contacting the biological sample with an antibody which specifically reacts, under immunologically reactive conditions, to a DLL3 polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radio-immunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the single domain antibodies that bind DLL3, as disclosed herein, can be used in these assays. Thus, the antibodies can be used in a conventional immunoassay, including, without limitation, an ELISA, an RIA, FACS, tissue immunohistochemistry, Western blot or imunoprecipitation.

EXAMPLES

Example 1: Screening of Phage Display Library for Identification of DLL3 Binding Domains Llamas were immunized with purified DLL3 protein expressed in EXPI293™ cells. A phage display library for expression of heavy chain variable antibody domains was constructed from circulating B cells (see van der Linden, de Geus, Stok, Bos, van Wassenaar, Verrips, and Frenken. 2000. J Immunol Methods 240:185-195). Phage clones were screening for binding to DLL3 by expressing the clones in *E. coli*, preparing periplasmic extracts, and screening the clones for DLL3 binding activity by ELISA. Fifty-two unique heavy chain only single domain antibodies were identified that produced a signal in the ELISA screening (SEQ ID Nos. 1 to 52). The CDR1, CDR2, and CDR3 sequences for these heavy variable domains were, respectively, SEQ ID Nos. 443 to 494, SEQ ID Nos.885 to 936, and SEQ ID Nos.1327 to 1378.

Example 2: Humanization of DLL3 Binding Single Domain Antibodies and T Cell Dependent Cellular Cytotoxicity Assay Thirty-four (SEQ ID Nos. 53 to 86) exemplary llama anti-DLL3 heavy chain only single domain antibodies from Example 1 were humanized. The CDR1, CDR2, and CDR3 sequences for the 34 heavy chain only single domain antibodies were, respectively, SEQ ID Nos. 495 to 528, SEQ ID Nos. 937 to 970, and SEQ ID Nos. 1379 to 1412.

The humanized anti-DLL3 sequences were cloned into an expression vector, in an expression construct comprising a signal domain followed by an anti-DLL3 heavy chain only variable domain followed by a GGGGSGGGS linker (SEQ ID No. 1808) followed by anti-human albumin single domain antibody 10G (SEQ ID No. 1774) followed by a GGGGSGGGS linker (SEQ ID No. 1808) followed by anti-human CD3 antibody 2B2 (SEQ ID No.1793) followed by a HHHHHH tag (SEQ ID No. 1819), to generate anti-DLL3 trispecific constructs.

The anti-DLL3 trispecific constructs containing the humanized anti-DLL3 binding sequences were then transfected into EXPI293™ cells. These anti-DLL3 trispecific constructs have an engineered with a protein A binding site, and the amount of anti-DLL3 trispecific construct in the conditioned media from the transfected EXPI293™ cells was quantitated using an Octet instrument with protein A tips. A trispecific protein of similar molecular weight as the anti-DLL3 trispecific proteins was used as a standard.

Using conditioned media containing known concentrations of anti-DLL3 trispecific proteins, the binding affinities of the anti-DLL3 trispecific proteins toward human and cynomolgus monkey DLL3 proteins were measured, using a method where the DLL3 proteins were expressed as human IgG1-Fc fusions and the measurements were carried out using an Octet instrument with anti-human Fc tips. The $K_D$ measurements were made using a single 50 nM concentration of the anti-DLL3 trispecific proteins, which allowed for rank ordering based on potency. The relative affinities, measured as described above, are listed in Table 1. All of the sequences were found to bind human DLL3, with relative affinities ($K_D$) ranging from 0.5 to 42 nM. Some of the sequences were found to bind cynomolgus DLL3 with similar affinities to human DLL3, and the relative affinities for the binding of those sequences to cynomolgus DLL3 are also shown in Table 1.

The conditioned media were also tested in a T-cell dependent cellular cytotoxicity assay (see Nazarian A A, Archibeque I L, Nguyen Y H, Wang P, Sinclair A M, Powers D A. 2015. J Biomol Screen. 20:519-27). In this assay, luciferase labelled DMS-153 cells (small-cell lung carcinoma cell line; ATCC No. ATCC® CRL-2064™) were combined with purified human T cells, from a donor, and a titration of the anti-DLL3 trispecific proteins being tested.

It was hypothesized that if an anti-DLL3 trispecific protein directed T cells to kill the DLL3-expressing DMS-153 cells, then the viability of the DMS-153 cells, as determined by running a luciferase assay at 48 hours after starting the experiment, should decrease.

Figure 2:
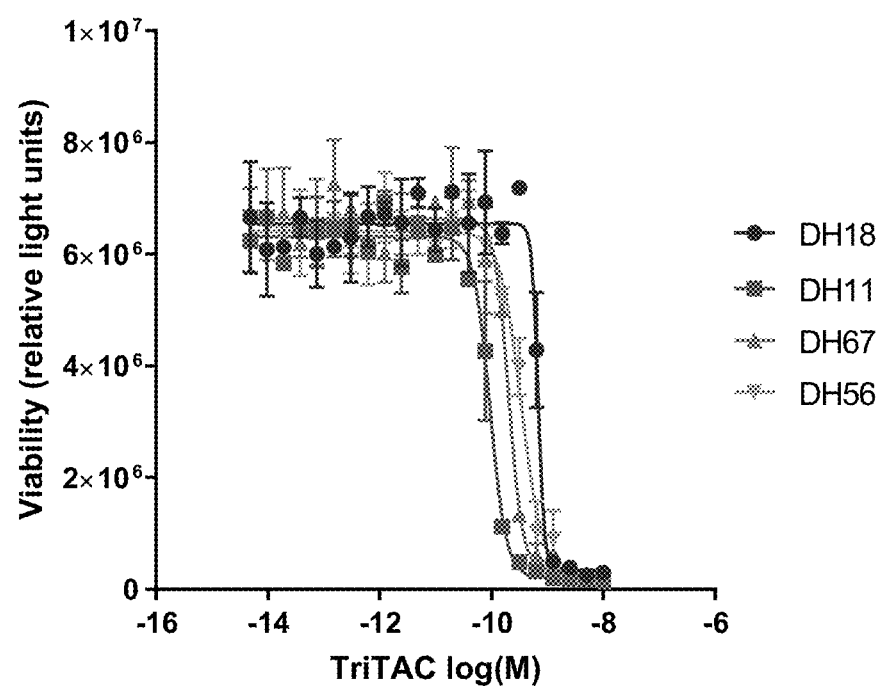
FIG. 2 illustrates results of a T cell dependent cellular cytotoxicity (TDCC) assay on DMS-153 cells, using exemplary DLL3 targeting trispecific proteins containing DLL3 binding domains of this disclosure, DH18, DH11, DH67, and DH56.
Figure 3:
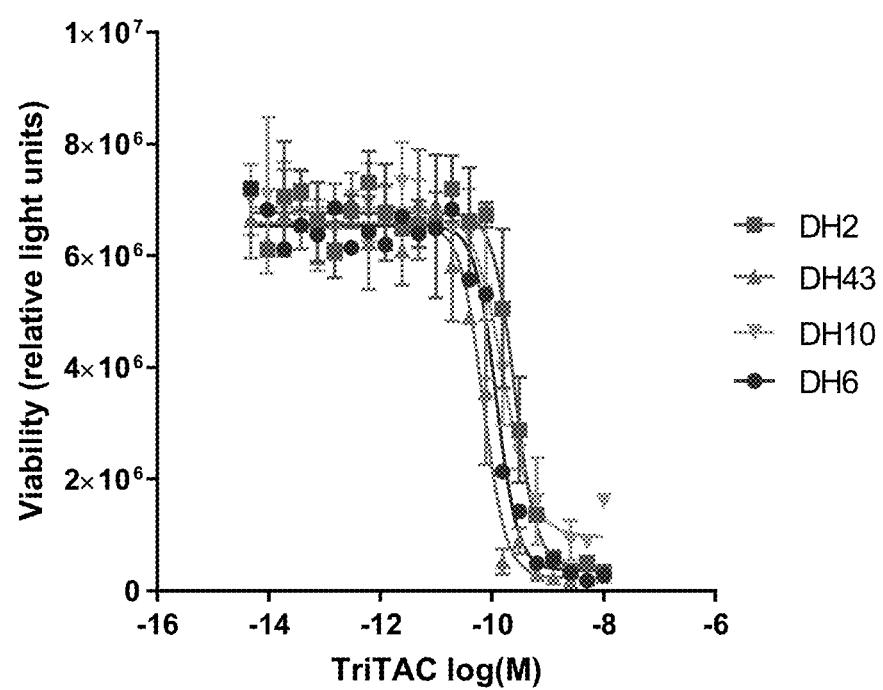
FIG. 3 illustrates results of a TDCC assay on DMS-153 cells, using exemplary DLL3 targeting trispecific proteins containing exemplary DLL3 binding domains of this disclosure DH2, DH43, DH10, and DH6.
Figure 4:
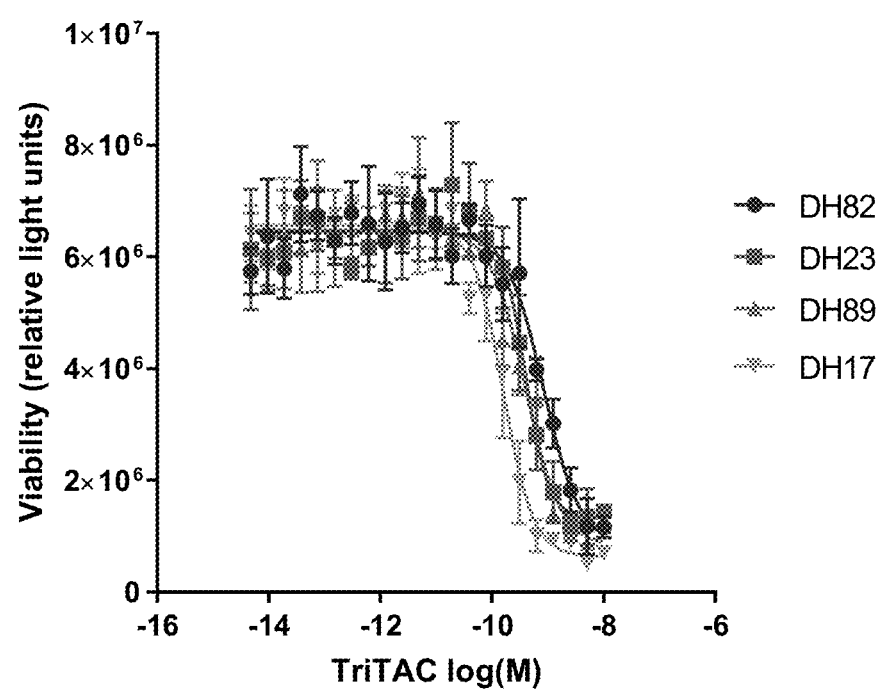
FIG. 4 illustrates results of a TDCC assay on DMS-153 cells, using exemplary DLL3 targeting trispecific proteins containing exemplary DLL3 binding domains of this disclosure DH82, DH23, DH89, and DH17.
Figure 5:
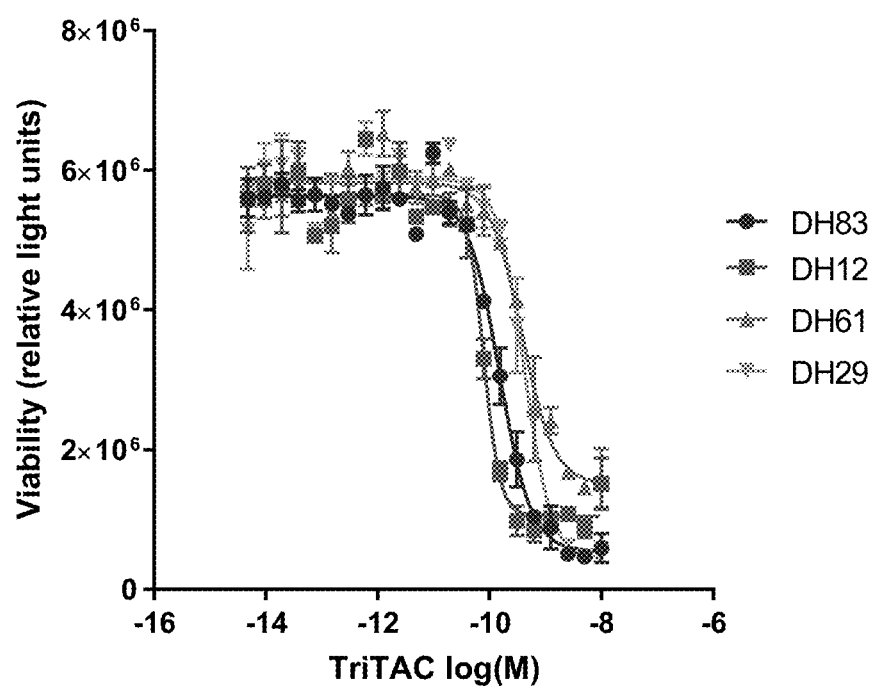
FIG. 5 illustrates results of a TDCC assay on DMS-153 cells, using exemplary DLL3 targeting trispecific proteins containing exemplary DLL3 binding domains of this disclosure DH83, DH12, DH61, and DH29.
Figure 6:
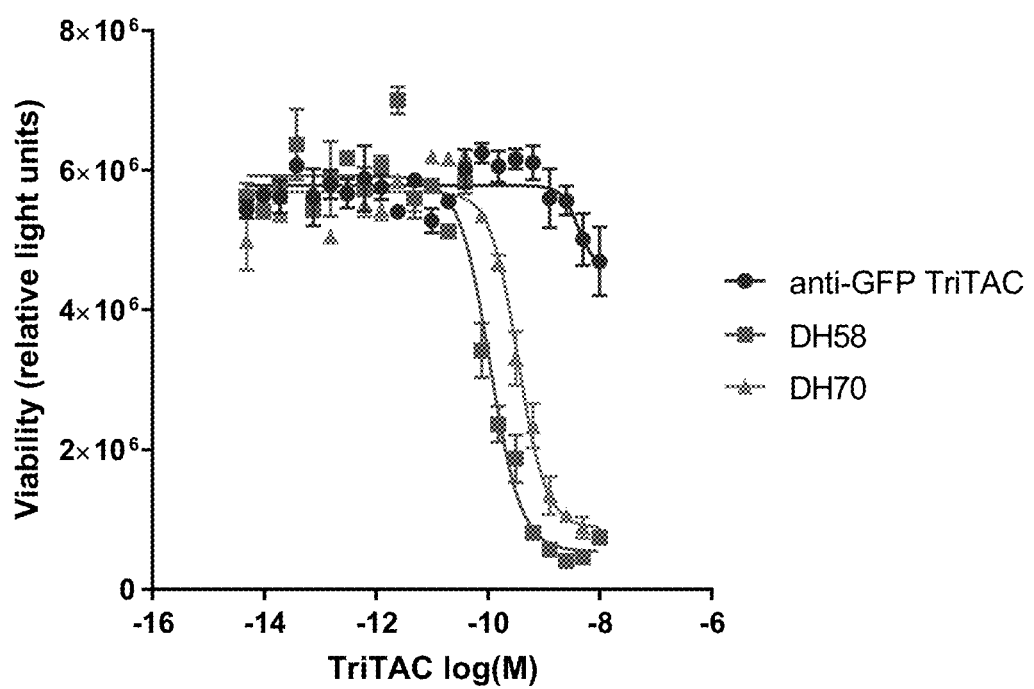
FIG. 6 illustrates results of a TDCC assay on DMS-153 cells, using exemplary DLL3 targeting trispecific proteins containing exemplary DLL3 binding domains of this disclosure DH58, and DH70, and a control trispecific protein.
Figure 7:
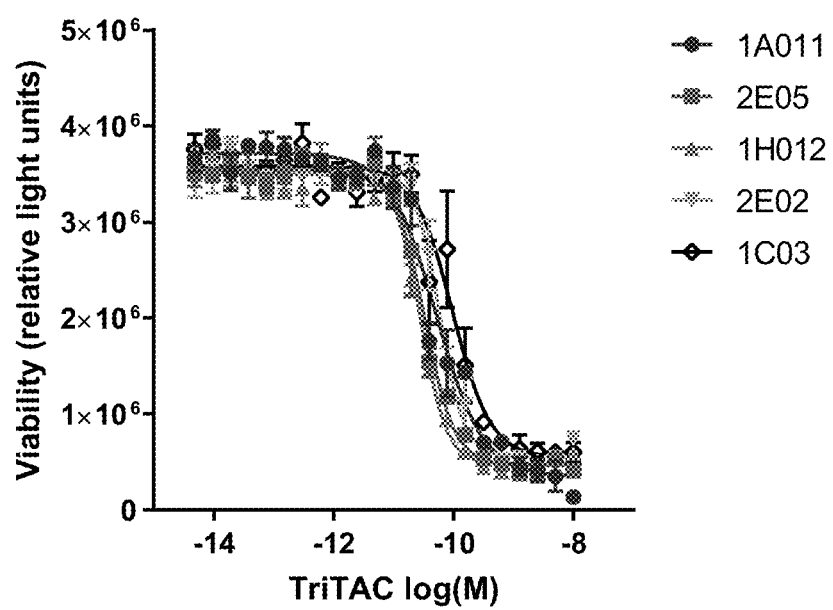
FIG. 7 illustrates results of a TDCC assay on DMS-153 cells, using exemplary affinity matured DLL3 targeting trispecific proteins containing exemplary DLL3 targeting domains of this disclosure 1A011, 2E05, 1H012, 2E02, and 1C03.
Figure 8:
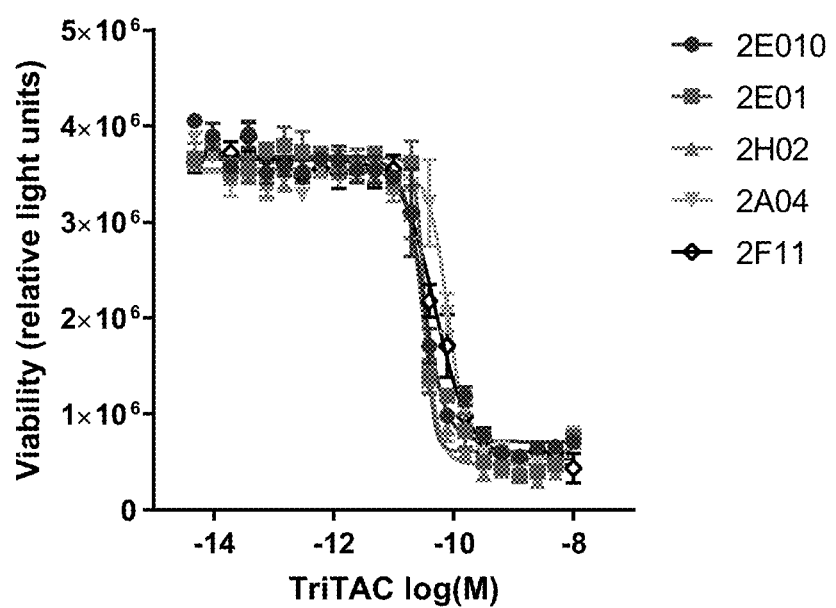
FIG. 8 illustrates results of a TDCC assay on DMS-153 cells, using exemplary affinity matured DLL3 binding trispecific proteins containing exemplary DLL3 targeting domains of this disclosure 2E010, 2E01, 2H02, 2A04, and 2F11.
Figure 9:
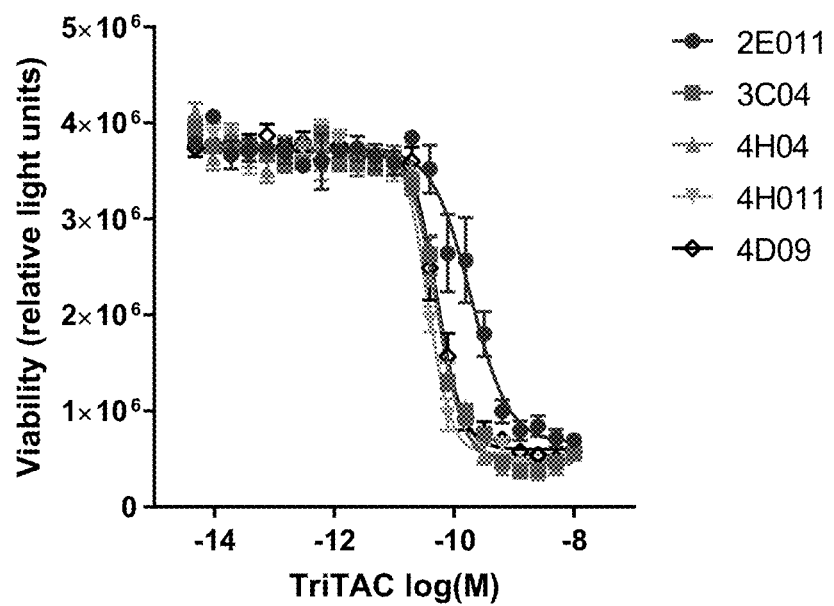
FIG. 9 illustrates results of a TDCC assay on DMS-153 cells, using exemplary affinity matured DLL3 binding trispecific proteins containing exemplary DLL3 targeting domains of this disclosure 2E011, 3C04, 4H04, 4H011, and 4D09.
Figure 10:
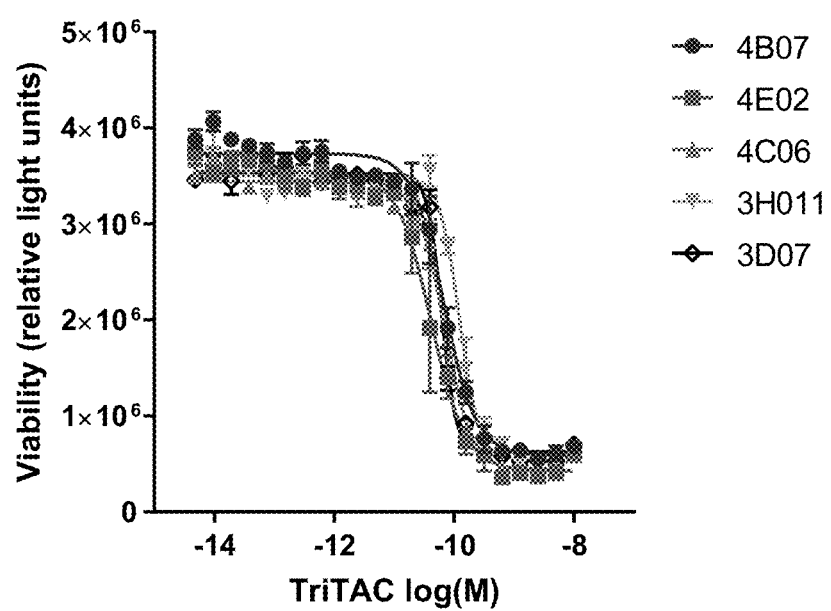
FIG. 10 illustrates results of a TDCC assay on DMS-153 cells, using exemplary affinity matured DLL3 binding trispecific proteins containing exemplary DLL3 targeting domains of this disclosure 4B07, 4E02, 4C06, 3H011, and 3D07.

As illustrated in FIGS. 2-6, which show graphs of representative TDCC data, several exemplary anti-DLL3 trispecific proteins were able to decrease the viability of the DMS-153 cells. FIG. 2 shows results of the TDCC assay for anti-DLL3 trispecific proteins comprising DLL3 binding domains DH18 (SEQ ID No. 59), DH11 (SEQ ID No. 55), DH67 (SEQ ID No. 42), and DH56 (SEQ ID No. 73). FIG. 3 shows results of the TDCC assay for anti-DLL3 trispecific proteins comprising DLL3 binding domains DH2 (SEQ ID No. 60), DH43 (SEQ ID No. 68), DH10 (SEQ ID No. 54), and DH6 (SEQ ID No. 75). FIG. 4 shows results of the TDCC assay for DLL3 trispecific protein comprises DLL3 binding domains DH82 (SEQ ID No. 81), DH23 (SEQ ID No. 62), DH89 (SEQ ID No. 84), and DH17 (SEQ ID No. 58). FIG. 5 shows results of the TDCC assay for DLL3 trispecific protein comprises DLL3 binding domains DH83 (SEQ ID No. 82), DH12 (SEQ ID No. 56), DH61 (SEQ ID No. 76), and DH29 (SEQ ID No. 64). FIG. 6 shows results of the TDCC assay for DLL3 trispecific protein comprises DLL3 binding domains DH58 (SEQ ID No. 74) and DH70 (SEQ ID No. 79). A negative control for the TDCC assays was a trispecific protein targeting GFP instead of DLL3 (as shown in FIG. 6) which did not direct the T cells to kills the DMS-153 cells. $EC_{50}$ values from the TDCC assay are also listed in Table 1. These values ranged from 69 pM to 11 nM.

TABLE 1

Activity of Humanized Anti-DLL3 Trispecific Proteins in DMS-153 TDCC Assays and Their Affinities for Human and Cynomolgus DLL3 Protein. The $K_D$ measurements were made using a single concentration of anti-DLL3 trispecific protein. The TDCC assay was performed using human T cells. n/d indicates binding was not detected.

| DLL3 binder | DMS-153 TDCC EC50 (M) | huDLL3 KD (nM) | cyDLL3 KD (nM) |
|---|---|---|---|
| DH43 | 6.9E−11 | 4.3 | 5.5 |
| DH12 | 7.8E−11 | 1.3 | n/d |
| DH11 | 9.3E−11 | 5.3 | 5.6 |
| DH58 | 1.1E−10 | 3.3 | 27.9 |
| DH6 | 1.2E−10 | 6.1 | 6.8 |
| DH83 | 1.5E−10 | 4.7 | n/d |
| DH10 | 1.6E−10 | 3.9 | 25.0 |

TABLE 1-continued

Activity of Humanized Anti-DLL3 Trispecific Proteins in DMS-153 TDCC Assays and Their Affinities for Human and Cynomolgus DLL3 Protein. The $K_D$ measurements were made using a single concentration of anti-DLL3 trispecific protein. The TDCC assay was performed using human T cells. n/d indicates binding was not detected.

| DLL3 binder | DMS-153 TDCC EC50 (M) | huDLL3 KD (nM) | cyDLL3 KD (nM) |
|---|---|---|---|
| DH17 | 1.6E−10 | 7.0 | n/d |
| DH67 | 2.0E−10 | 8.4 | 8.2 |
| DH2 | 2.6E−10 | 6.5 | 14.6 |
| DH56 | 3.4E−10 | 8.1 | 8.0 |
| DH70 | 3.4E−10 | 16.2 | 86.2 |
| DH61 | 3.8E−10 | 10.6 | 30.8 |
| DH89 | 4.0E−10 | 6.9 | n/d |
| DH23 | 4.0E−10 | 9.9 | n/d |
| DH29 | 4.2E−10 | 5.6 | n/d |
| DH5 | 5.2E−10 | 0.5 | 5.5 |
| DH18 | 6.4E−10 | 1.0 | 5.9 |
| DH45 | 6.9E−10 | 1.9 | 2.8 |
| DH82 | 8.4E−10 | 6.6 | n/d |
| DH80 | 1.0E−09 | 0.8 | 5.5 |
| DH27 | 1.2E−09 | 2.1 | 11.3 |
| DH69 | 1.4E−09 | 1.2 | 7.0 |
| DH92 | 1.7E−09 | 18.0 | 17.5 |
| DH94 | 1.8E−09 | 2.6 | 9.6 |
| DH42 | 1.8E−09 | 4.3 | 11.7 |
| DH1 | 2.0E−09 | 3.5 | 10.7 |
| DH38 | 2.9E−09 | 11.9 | n/d |
| DH51 | 3.8E−09 | 5.1 | 18.2 |
| DH54 | 4.5E−09 | 20.6 | 42.4 |
| DH3 | 6.2E−09 | 41.9 | n/d |
| DH15 | 2.0E−08 | 17.4 | n/d |
| DH22 | 2.8E−08 | 6.8 | 16.4 |
| DH84 | 1.1E−08 | 15.2 | 17.9 |

Example 3: Screening of Phage Display Library for Identification of DLL3 Binding Domains with Higher Binding Affinities, Using Two Humanized DLL3 Single Domain Antibodies from Previous Example Two of the humanized antibody sequences, DH43 (SEQ ID No. 68) and DH6 (SEQ ID No. 75), were used as a starting point for making phage display libraries (following a method as described in WO2016187101A2). The anti-DLL3 sequences from this panning were subsequently cloned into an expression vector, in an expression construct comprising a signal domain followed by an anti-DLL3 heavy chain only variable domain followed by a GGGGSGGGS linker (SEQ ID No. 1808) followed by an anti-human albumin single domain antibody domain followed by a GGGGSGGGS linker (SEQ ID No. 1808) followed by an anti-human CD3 antibody fragment followed by a HHHHHH tag (SEQ ID No. 1819), to generate anti-DLL3 trispecific proteins. These constructs were transfected into EXPI293™ cells, and the expressed anti-DLL3 trispecific proteins were quantitated as described in Example 2. The sequences of the clones identified from the panning are SEQ ID Nos. 87 to 367. Table 2 provides CDR variations obtained in the DH43 DLL3 binder sequences after phage display selection. Three of the clones identified from the panning, SEQ ID Nos. 199 (2E05), 330 (4D09), and 365 (4H011) were engineered to generate variants, where each variant had a single amino acid change from the parental sequence, for example, to remove potential metabolic liabilities of the parental sequence. In particular, the DLL3 binding domains comprising SEQ ID Nos. 227 (2E05-M106Y), 228 (2E05-M106Q) were engineered variants of SEQ ID No. 199 (2E05); SEQ ID No. 366 (4D09-M34L) was an engineered variant of SEQ ID No. 330 (4D09); and SEQ ID No. 367 (4H11-M34L) was an engineered variant of SEQ ID No. 365 (4H011). The CDR1 sequences of these DLL3 binding clones identified by the panning are SEQ ID Nos. 529 to 809, the CDR2 sequences of the clones identified by the panning are SEQ ID Nos. 971 to 1251, and the CDR3 sequences of the clones identified by the panning are SEQ ID Nos. 1413 to 1691.

TABLE 2

Variants in CDR sequences by amino acid position of DH43 and its derivatives

| CDR | Amino acid position | CDR Amino acid Variants |
|---|---|---|
| CDR1 | 26 | G |
| | 27 | A, E, F, G, I, K, L, N, Q, R, S, T, V, Y |
| | 28 | A, G, I, K, P, R, S, T, V |
| | 29 | A, D, F, K, L, N, P, Q, R, S, T, Y |
| | 30 | A, D, F, H, I, K, L, M, N, P, R, S, T, V, Y |
| | 31 | F, I, K, L, M, N, R, S, T, V |
| | 32 | N |
| | 33 | A, G |
| | 34 | F, I, L, M, T, V, Y |
| | 35 | A, G |
| | 36 | W |
| CDR2 | 50 | G |
| | 51 | I, V |
| | 52 | S |
| | 53 | A, K, P, R, S |
| | 54 | D, N |
| | 55 | D, E, G, K, N, Q, R, S, T, Y |
| | 56 | S, T |
| | 57 | A, E, F, H, I, K, L, N, Q, R, S, T, V, Y |
| | 58 | A, I, L, M, V, Y |
| | 59 | D, F, H, I, L, N, S, T, V, Y |
| | 60 | A, D, E, F, G, I, K, L, N, Q, R, S, T, V, Y |
| | 61 | A, D, E, G, K, Q, S, V |
| | 62 | S |
| | 63 | A, V |
| | 64 | K |
| | 65 | G, V |
| CDR3 | 98 | F, Y |
| | 99 | G, H, I, K, N, R, S, T |
| | 100 | A, F, H, I, K, L, M, N, P, Q, R, S, T, Y |
| | 101 | A, E, F, G, H, I, K, L, M, N, Q, R, S, T, V, Y |
| | 102 | A, C, D, E, G, H, I, K, L, N, P, Q, R, S, T, W, Y |
| | 103 | G, K, L, R, T |
| | 104 | A, G, H, L, Q, R, S, T, V, Y |
| | 105 | A, D, E, G, H, P, Q, S, T, W, Y |
| | 106 | A, G, I, K, L, M, N, Q, R, S, T, V, Y |
| | 107 | A, G, K, P, R, S, T, V |
| | 108 | A, F, S, Y |

Using the conditioned medium with known concentrations of the anti-DLL3 trispecific proteins, the binding affinities of the anti-DLL3 trispecific proteins toward human DLL3 protein were measured using a method where biotinylated version of human DLL3 protein were expressed as a human IgG1 fusion protein, and the binding affinity measurement was carried out in an Octet instrument with streptavidin tips. The $K_D$ measurements were made using a single 50 nM concentration of the anti-DLL3 trispecific proteins, which allowed for rank ordering potency. In this experiment, the relative $K_D$ values of the affinity matured clones ranged from 2.3 nM to 64 nM, as listed in Table 3. The parental binders DH43 and DH6, respectively, had $K_D$ values of 7.7±0.6 nM and 9.9±0.3 nM based on four samples of conditioned medium from four transfections.

For select DLL3 binder molecules identified in this round of panning, as well as for the parental DLL3 binders DH43 and DH6, more precise affinity measurements for human DLL3 were made using 60 nM, 20 nM, 6.67 nM, and 2.22 nM concentrations of the anti-DLL3 trispecific proteins. In addition, relative affinity measurements were made using only 60 nM of the anti-DLL3 trispecific proteins. Binding affinities determined from the more precise measurements of certain anti-DLL3 binding molecules are listed in Table 4 [1H012 (SEQ ID No. 162); 1A011 (SEQ ID No. 95); 2E05 (SEQ ID No. 199); 4H011 (SEQ ID No. 365); 3C04 (SEQ ID No. 251); 2E02 (SEQ ID No. 198); 2H02 (SEQ ID No. 221); 3A011(SEQ ID No. 238); 3A02 (SEQ ID No. 230); 4D09 (SEQ ID No. 330); DH43 (SEQ ID No. 68); and DH6(SEQ ID No. 75)]. In this study, the parental binder, DH43, had a $K_D$ value of 8.9 nM, whereas the highest affinity daughter molecule, 1H012 (SEQ ID No. 162), had an affinity of 2.9 nM. Furthermore, 1H012 (SEQ ID No. 162) retained an ability to bind to cynomolgus DLL3 as well. Also in this study, the parental binder, DH6, had a $K_D$ value of 9.0 nM, whereas the highest affinity daughter molecule, 4H011 (SEQ ID No. 365), had an affinity of 3.9 nM. Furthermore, 4H011(SEQ ID No. 365) retained an ability to bind to cynomolgus DLL3 as well.

Figure 11:
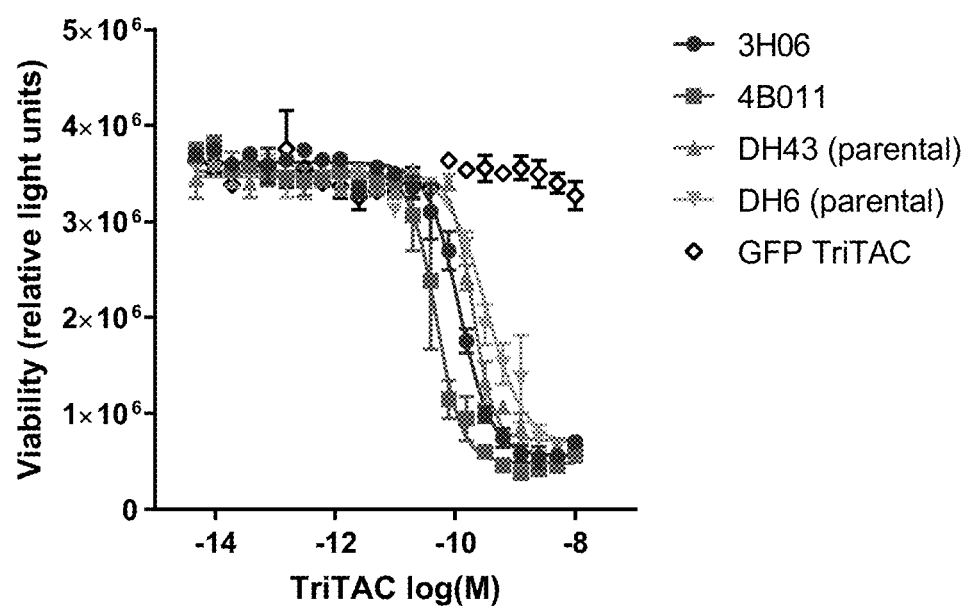
FIG. 11 illustrates results of a TDCC assay on DMS-153 cells, using exemplary affinity matured DLL3 targeting trispecific proteins containing exemplary DLL3 binding domains of this disclosure 3H06, and 4B011, and parental DLL binder domains DH43, DH6, and a control trispecific protein.
Figure 12:
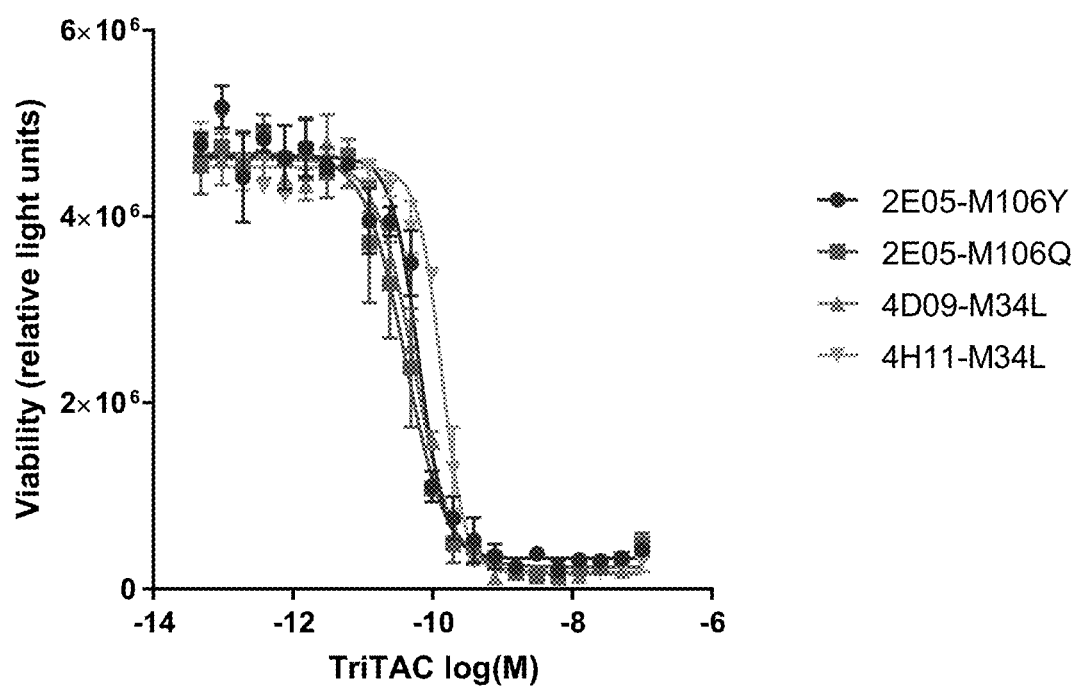
FIG. 12 illustrates results of a TDCC assay on DMS-153 cells, using exemplary purified affinity matured CHO expressed DLL3 binding trispecific proteins containing exemplary DLL3 targeting domains of this disclosure 2E05-M106Y, 2E05-M106Q, 4D09-M34L, and 4H11-M34L.
Figure 13:
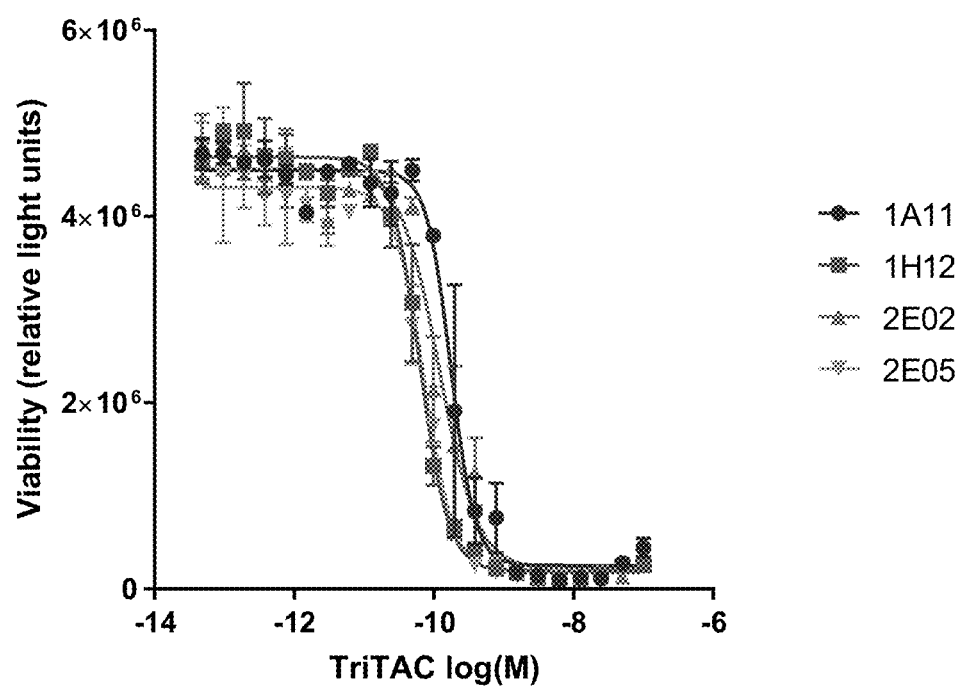
FIG. 13 illustrates results of a TDCC assay on DMS-153 cells, using exemplary purified affinity matured CHO expressed DLL3 targeting trispecific proteins containing exemplary DLL3 binding domains of this disclosure 1A011 (labelled as 1A11 on FIG. 13), 1H012 (labelled as 1H12 on FIG. 13), 2E02, and 2E05.
Figure 14:
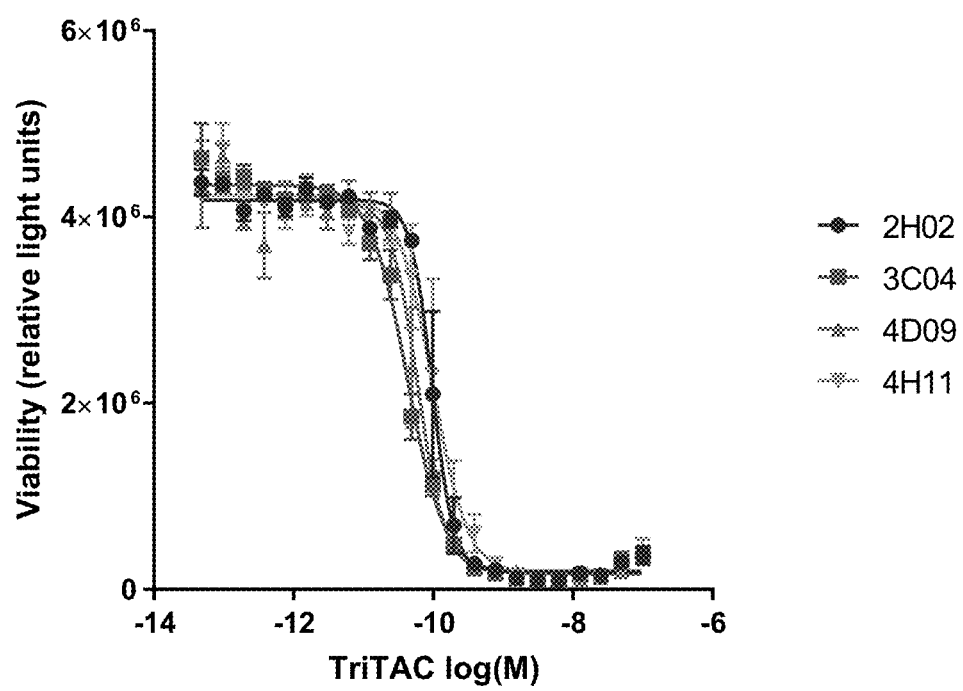
FIG. 14 illustrates results of a TDCC assay on DMS-153 cells, using exemplary purified affinity matured CHO expressed DLL3 targeting trispecific proteins containing exemplary DLL3 binding domains of this disclosure 2H02, 3C04, 4D09, and 4H11.
Figure 15:
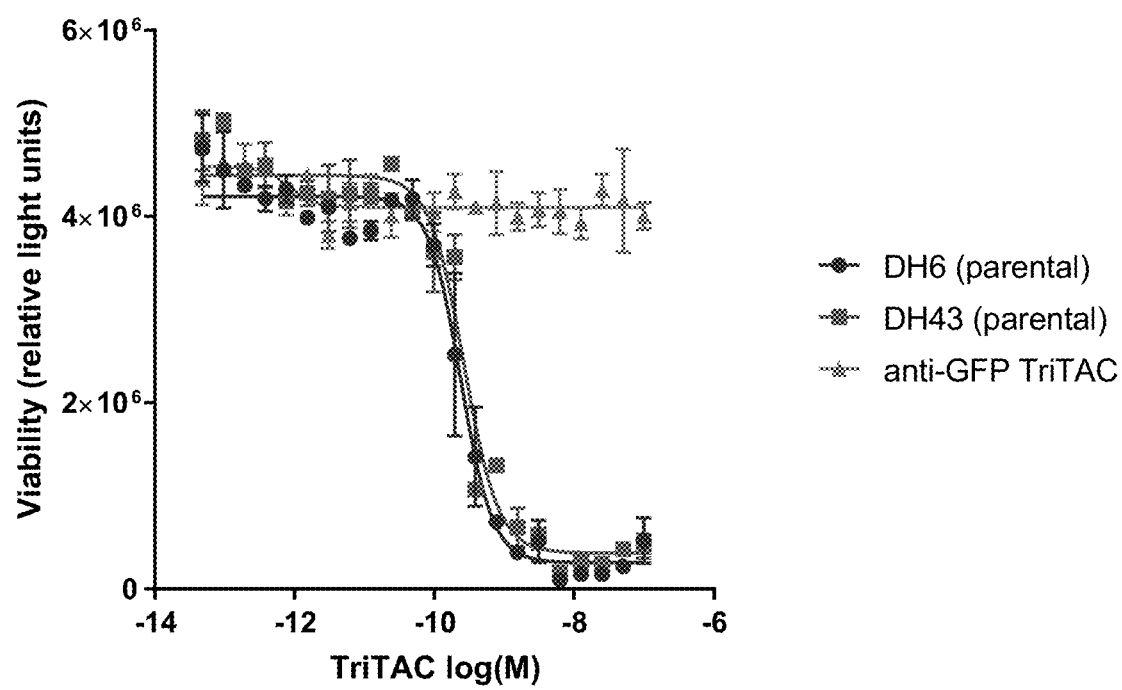
FIG. 15 illustrates results of a TDCC assay on DMS-153 cells, using exemplary purified DLL3 targeting trispecific proteins containing parental exemplary DLL3 binding domains DH43 and DH6, and a control trispecific protein that targets GFP.

Twenty-two DLL3 binder molecules identified in this round of panning were selected for testing in a TDCC assay with DMS-153 cells, using the same protocol as described in Example 2. Exemplary TDCC data are plot as graphs in FIGS. 7-11, and a summary of the $EC_{50}$ values are listed in Table 5. In this experiment, the parental DLL3 molecules, DH43 and DH6, had $EC_{50}$ values of 200 nM and 340 nM, respectively. The most potent daughter molecule of DH43 was 1H012 (SEQ ID No. 162), with an $EC_{50}$ value of 28 nM, demonstrating greater than 7-fold increase in TDCC potency compared to the parental DLL3 binder DH43. The most potent daughter molecule of DH6 was 4H011 (SEQ ID No. 365) with an $EC_{50}$ value of 36 nM, thereby showing greater than 8-fold increase in TDCC potency, compared to the parental DLL3 binder molecule. A control trispecific protein targeting GFP, used as a control, had no activity in this assay (as shown in FIG. 11).

TABLE 3

Relative Affinities of Anti-DLL3 Trispecific Proteins

| Name | $K_D$(M) |
|---|---|
| 4A010 | 2.3E-09 |
| 2E011 | 2.4E-09 |
| 1C010 | 2.5E-09 |
| 3H011 | 2.7E-09 |
| 1E011 | 2.7E-09 |
| 1H012 | 3.5E-09 |
| 4G01 | 3.6E-09 |
| 1A011 | 3.7E-09 |
| 4D01 | 3.7E-09 |
| 4E02 | 3.8E-09 |
| 2E05 | 3.9E-09 |
| 4B011 | 3.9E-09 |
| 1F02 | 4.0E-09 |
| 1A05 | 4.0E-09 |
| 2A011 | 4.0E-09 |
| 2E010 | 4.0E-09 |
| 2C02 | 4.1E-09 |
| 2E01 | 4.1E-09 |
| 2G08 | 4.1E-09 |
| 1C01 | 4.3E-09 |
| 4B07 | 4.3E-09 |
| 1E09 | 4.4E-09 |
| 2H02 | 4.4E-09 |
| 3F010 | 4.4E-09 |
| 1D011 | 4.4E-09 |
| 3C04 | 4.5E-09 |
| 4H011 | 4.5E-09 |

TABLE 3-continued

Relative Affinities of Anti-DLL3 Trispecific Proteins

| Name | $K_D$(M) |
|---|---|
| 4D09 | 4.7E-09 |
| 1A012 | 4.9E-09 |
| 2D012 | 4.9E-09 |
| 3C03 | 4.9E-09 |
| 1F011 | 5.0E-09 |
| 2H011 | 5.0E-09 |
| 1D010 | 5.0E-09 |
| 4C01 | 5.1E-09 |
| 1B01 | 5.2E-09 |
| 1D09 | 5.2E-09 |
| 1E012 | 5.3E-09 |
| 3D011 | 5.3E-09 |
| 1C05 | 5.3E-09 |
| 2H03 | 5.3E-09 |
| 1B09 | 5.4E-09 |
| 4B09 | 5.4E-09 |
| 2D011 | 5.4E-09 |
| 2A04 | 5.6E-09 |
| 1A06 | 5.6E-09 |
| 4A011 | 5.6E-09 |
| 2G03 | 5.6E-09 |
| 2B07 | 5.7E-09 |
| 1B011 | 5.7E-09 |
| 1H01 | 5.7E-09 |
| 1E010 | 5.7E-09 |
| 4F010 | 5.8E-09 |
| 1D01 | 5.8E-09 |
| 1F05 | 5.8E-09 |
| 1D03 | 5.8E-09 |
| 4D011 | 5.8E-09 |
| 1F012 | 5.8E-09 |
| 3C08 | 5.9E-09 |
| 2F03 | 5.9E-09 |
| 4D08 | 5.9E-09 |
| 3D07 | 5.9E-09 |
| 2D07 | 6.0E-09 |
| 2E02 | 6.0E-09 |
| 4C011 | 6.0E-09 |
| 2C08 | 6.1E-09 |
| 1C03 | 6.1E-09 |
| 2H07 | 6.1E-09 |
| 4H04 | 6.1E-09 |
| 1C02 | 6.2E-09 |
| 2C07 | 6.2E-09 |
| 1H011 | 6.2E-09 |
| 1H07 | 6.2E-09 |
| 2D04 | 6.2E-09 |
| 3A09 | 6.3E-09 |
| 2H04 | 6.3E-09 |
| 1F010 | 6.3E-09 |
| 1A03 | 6.3E-09 |
| 2C09 | 6.4E-09 |
| 2H010 | 6.4E-09 |
| 4D05 | 6.5E-09 |
| 2G07 | 6.5E-09 |
| 1A010 | 6.5E-09 |
| 2F09 | 6.5E-09 |
| 2B02 | 6.6E-09 |
| 4C03 | 6.6E-09 |
| 1A09 | 6.6E-09 |
| 2D06 | 6.6E-09 |
| 1G01 | 6.6E-09 |
| 2C06 | 6.7E-09 |
| 4C02 | 6.8E-09 |
| 2C04 | 6.8E-09 |
| 3A011 | 6.8E-09 |
| 1G011 | 6.8E-09 |
| 4C06 | 6.8E-09 |
| 2D03 | 6.8E-09 |
| 1B010 | 6.8E-09 |
| 1D06 | 6.8E-09 |
| 3G010 | 6.9E-09 |
| 4C010 | 7.0E-09 |
| 1E02 | 7.0E-09 |
| 1A01 | 7.0E-09 |
| 4B02 | 7.1E-09 |

TABLE 3-continued

Relative Affinities of Anti-DLL3 Trispecific Proteins

| Name | $K_D(M)$ |
|---|---|
| 1C07 | 7.1E-09 |
| 3F011 | 7.1E-09 |
| 1E07 | 7.1E-09 |
| 4E08 | 7.2E-09 |
| 3B05 | 7.2E-09 |
| 2B012 | 7.3E-09 |
| 3G09 | 7.3E-09 |
| 3B07 | 7.3E-09 |
| 2D010 | 7.3E-09 |
| 2B05 | 7.4E-09 |
| 4D06 | 7.5E-09 |
| 4G011 | 7.5E-09 |
| 4C07 | 7.5E-09 |
| 3F05 | 7.5E-09 |
| 2C010 | 7.6E-09 |
| 2B03 | 7.6E-09 |
| 4G08 | 7.6E-09 |
| 1C011 | 7.6E-09 |
| 2A08 | 7.7E-09 |
| 1A04 | 7.8E-09 |
| 3C09 | 7.8E-09 |
| 2H06 | 7.9E-09 |
| 2G09 | 8.0E-09 |
| 2F07 | 8.0E-09 |
| 1B05 | 8.0E-09 |
| 2A01 | 8.0E-09 |
| 3H06 | 8.0E-09 |
| 1E04 | 8.1E-09 |
| 1C04 | 8.1E-09 |
| 3A02 | 8.1E-09 |
| 2A03 | 8.2E-09 |
| 3G01 | 8.2E-09 |
| 4F011 | 8.2E-09 |
| 2D09 | 8.2E-09 |
| 3C05 | 8.2E-09 |
| 4C05 | 8.3E-09 |
| 1C06 | 8.3E-09 |
| 2D05 | 8.3E-09 |
| 1G07 | 8.3E-09 |
| 1H010 | 8.4E-09 |
| 2E09 | 8.5E-09 |
| 1C012 | 8.5E-09 |
| 1A07 | 8.6E-09 |
| 3H010 | 8.6E-09 |
| 4D04 | 8.6E-09 |
| 1B03 | 8.7E-09 |
| 4F09 | 8.8E-09 |
| 4G09 | 8.8E-09 |
| 3G04 | 8.8E-09 |
| 2A05 | 8.9E-09 |
| 2A06 | 8.9E-09 |
| 1F06 | 8.9E-09 |
| 1B07 | 8.9E-09 |
| 4H08 | 8.9E-09 |
| 4A02 | 9.0E-09 |
| 4F08 | 9.0E-09 |
| 4E010 | 9.0E-09 |
| 3H01 | 9.0E-09 |
| 3B011 | 9.0E-09 |
| 4A09 | 9.0E-09 |
| 4E09 | 9.1E-09 |
| 3C02 | 9.1E-09 |
| 2F01 | 9.2E-09 |
| 3A04 | 9.2E-09 |
| 1D012 | 9.3E-09 |
| 1E08 | 9.4E-09 |
| 4A05 | 9.4E-09 |
| 1F01 | 9.4E-09 |
| 2F02 | 9.6E-09 |
| 1D04 | 9.7E-09 |
| 4G05 | 9.7E-09 |
| 4F04 | 9.8E-09 |
| 4A07 | 9.8E-09 |
| 4G010 | 9.9E-09 |
| 4D010 | 9.9E-09 |
| 3H03 | 9.9E-09 |
| 3F06 | 9.9E-09 |
| 1D08 | 1.0E-08 |
| 2B010 | 1.0E-08 |
| 3B01 | 1.0E-08 |
| 3D01 | 1.0E-08 |
| 4A01 | 1.0E-08 |
| 2B01 | 1.0E-08 |
| 3C06 | 1.0E-08 |
| 1H02 | 1.0E-08 |
| 1G09 | 1.0E-08 |
| 4E06 | 1.0E-08 |
| 2F06 | 1.0E-08 |
| 2A09 | 1.0E-08 |
| 3E09 | 1.0E-08 |
| 1F04 | 1.0E-08 |
| 4B08 | 1.0E-08 |
| 2G04 | 1.1E-08 |
| 4B01 | 1.1E-08 |
| 1B02 | 1.1E-08 |
| 1B04 | 1.1E-08 |
| 2E06 | 1.1E-08 |
| 3E011 | 1.1E-08 |
| 4E01 | 1.1E-08 |
| 3D03 | 1.1E-08 |
| 4E07 | 1.1E-08 |
| 1G04 | 1.1E-08 |
| 3E04 | 1.1E-08 |
| 2B011 | 1.1E-08 |
| 3E02 | 1.2E-08 |
| 3D02 | 1.2E-08 |
| 3A010 | 1.2E-08 |
| 2C01 | 1.2E-08 |
| 3G06 | 1.2E-08 |
| 3B010 | 1.2E-08 |
| 3A03 | 1.2E-08 |
| 3F09 | 1.2E-08 |
| 4B04 | 1.2E-08 |
| 3G08 | 1.2E-08 |
| 3A08 | 1.2E-08 |
| 3B02 | 1.2E-08 |
| 4F03 | 1.2E-08 |
| 1B08 | 1.2E-08 |
| 2G011 | 1.3E-08 |
| 3G07 | 1.3E-08 |
| 4E011 | 1.3E-08 |
| 3H07 | 1.3E-08 |
| 1F07 | 1.3E-08 |
| 4H03 | 1.3E-08 |
| 4A06 | 1.3E-08 |
| 3F03 | 1.3E-08 |
| 3C011 | 1.4E-08 |
| 1D02 | 1.4E-08 |
| 1H06 | 1.4E-08 |
| 2D02 | 1.4E-08 |
| 1E05 | 1.4E-08 |
| 1G05 | 1.4E-08 |
| 3D010 | 1.4E-08 |
| 3F08 | 1.4E-08 |
| 3H09 | 1.4E-08 |
| 3C01 | 1.4E-08 |
| 3A05 | 1.5E-08 |
| 4F02 | 1.5E-08 |
| 4G02 | 1.5E-08 |
| 3B06 | 1.5E-08 |
| 4C08 | 1.6E-08 |
| 3A06 | 1.6E-08 |
| 3D05 | 1.6E-08 |
| 4H09 | 1.6E-08 |
| 4H07 | 1.6E-08 |
| 3A01 | 1.6E-08 |
| 3E01 | 1.6E-08 |
| 4B06 | 1.6E-08 |
| 1H08 | 1.7E-08 |
| 3G011 | 1.7E-08 |
| 3D08 | 1.7E-08 |
| 2E08 | 1.7E-08 |

TABLE 3-continued

Relative Affinities of Anti-DLL3 Trispecific Proteins

| Name | $K_D(M)$ |
|---|---|
| 4H06 | 1.8E-08 |
| 2H08 | 1.8E-08 |
| 4B05 | 1.8E-08 |
| 4G07 | 1.8E-08 |
| 3G02 | 2.0E-08 |
| 3E03 | 2.0E-08 |
| 2F08 | 2.0E-08 |
| 4G03 | 2.0E-08 |
| 3B09 | 2.0E-08 |
| 4H01 | 2.1E-08 |
| 3B04 | 2.4E-08 |
| 4A08 | 2.4E-08 |
| 1C08 | 2.5E-08 |
| 4D03 | 2.6E-08 |
| 1G06 | 2.6E-08 |
| 4D02 | 3.0E-08 |
| 1F08 | 3.1E-08 |
| 3D09 | 3.2E-08 |
| 4A04 | 3.5E-08 |
| 1F09 | 3.5E-08 |
| 4H05 | 6.4E-08 |

TABLE 4

Binding constants for human DLL3 determined using three different concentrations of anti-DLL3 Trispecific proteins and binding constants for cynomolgus DLL3 determine using a single concentration of anti-DLL3 Trispecific proteins

| Name | Human $K_D$ (nM) | Cynomolgus $sK_D$ (nM) |
|---|---|---|
| 1H012 | 2.9 | 4.3 |
| 1A011 | 3.5 | 3.6 |
| 2E05 | 3.5 | 4.8 |
| 4H011 | 3.9 | 5.7 |
| 3C04 | 4.0 | 5.7 |
| 2E02 | 4.4 | 3.4 |
| 2H02 | 4.4 | 5.2 |
| 3A011 | 7.3 | 8.8 |
| 3A02 | 7.8 | 9.5 |
| 4D09 | 8.1 | 8.2 |
| DH43 | 8.9 | 8.5 |
| DH6 | 9.0 | 10 |

TABLE 5

DMS-153 TDCC values of affinity matured anti-DLL3 Trispecific protein in conditioned medium tested in triplicate using human T cells

| Name | $EC_{50}$ (M) |
|---|---|
| 1H012 | 2.8E-11 |
| 2H02 | 3.1E-11 |
| 2E010 | 3.1E-11 |
| 2E05 | 3.3E-11 |
| 2E01 | 3.3E-11 |
| 4H011 | 3.6E-11 |
| 4E02 | 4.1E-11 |
| 4B011 | 4.8E-11 |
| 2F11 | 4.9E-11 |
| 4H04 | 5.1E-11 |
| 1A011 | 5.1E-11 |
| 4D09 | 5.2E-11 |
| 3C04 | 5.2E-11 |
| 2E02 | 5.9E-11 |
| 3D07 | 6.1E-11 |
| 4B07 | 6.7E-11 |
| 4C06 | 6.8E-11 |
| 2A04 | 8.1E-11 |
| 1C03 | 9.6E-11 |
| 3H06 | 1.2E-10 |
| 3H011 | 1.2E-10 |
| 2E011 | 1.9E-10 |
| DH43 | 2.0E-10 |
| DH6 | 3.4E-10 |

Example 4: Cloning of Select DLL3 Binding Molecules from Example 3 into Mammalian Cells Anti-DLL3 trispecific proteins described in Example 3, as well as the parental DLL3 binder molecules were subcloned into a CHO cell expression vector and were stably transfected in CHO cells (see, Running Deer and Allison 2004. Biotechnol. Prog. 20: 880-889). The DLL3 binder molecules were: 2E05-M106Q (SEQ ID No. 228); 2C04 (SEQ ID No. 181); 4D09-M34L (SEQ ID No. 366); 4D09 (SEQ ID No. 330); 2E05-M106Y (SEQ ID No. 227); 1H012 (SEQ ID No.162) (also referred to herein as 1H12); 2E05 (SEQ ID No. 199); 2H02 (SEQ ID No. 221); 4D011 (SEQ ID No. 332) (also referred to herein as 4D11); 2E02 (SEQ ID No. 198); 4H11-M34L (SEQ ID No. 367); 1A011 (SEQ ID No. 95) (also referred to herein as 1A11); DH6 (SEQ ID No. 75); and DH43 (SEQ ID No. 68). The anti-DLL3 trispecific proteins were purified after expression in CHO cells, in conditioned medium from pools of stable clones, using protein A and ion exchange chromatography. The purified proteins were tested in TDCC assay using the same method as described in Example 2. The $EC_{50}$ values from the TDCC assay of the instant example are listed in Table 6, and the graphs of the data are in FIGS. 12-15. The most potent molecule, 2E05-M106Q (SEQ ID No. 228), had an $EC_{50}$ value of 41 nM, which is 6.6 fold more potent than the parental molecule, DH43. The most potent molecule derived from DH6 was 4D09-M34L (SEQ ID No. 366), which had an $EC_{50}$ value of 54 nM and is 4.4 fold more potent than the parental molecule, DH6.

TABLE 6

TDCC Activity of CHO Expressed and Purified Affinity Matured Anti-DLL3 Trispecific Proteins

| Name | $EC_{50}$ (M) |
|---|---|
| 2E05-M106Q | 4.10E-11 |
| 2C04 | 4.30E-11 |
| 4D09-M34L | 5.40E-11 |
| 4D09 | 6.00E-11 |
| 2E05-M106Y | 6.30E-11 |
| 1H12 | 6.30E-11 |
| 2E05 | 7.20E-11 |
| 2H02 | 9.60E-11 |
| 4D11 | 9.80E-11 |
| 2E02 | 1.20E-10 |
| 4H11-M34L | 1.30E-10 |
| 1A11 | 1.70E-10 |
| DH6 | 2.40E-10 |
| DH43 | 2.70E-10 |

Example 5: Affinity Maturation to Obtain Anti-DLL3 Binders of Improved Affinity

To obtain more potent anti-DLL3 binders, a second round of affinity maturation was performed. Phage display libraries were created based on the DH6 (SEQ ID No. 75) and DH58 (SEQ ID No. 74) parental sequences. The sequences for the binders from this round of affinity maturation are provided in SEQ ID Nos. 368 to 442. The CDR1 sequences of DLL3 binders identified in this round of affinity maturation are SEQ ID Nos. 810 to 884, the CDR2 sequences of DLL3 binders identified in this round of affinity maturation are SEQ ID Nos. 1252 to 1326, and the CDR3 sequences of DLL3 binders identified in this round of affinity maturation are SEQ ID Nos. 1692 to 1768. Table 7 provides CDR variations obtained in the DH6 DLL3 binder sequences after phage display selection.

The affinity matured anti-DLL3 sequences identified as above were cloned into an expression vector, in an expression construct comprising a signal domain followed by an anti-DLL3 sequence followed by a GGGGSGGGS linker (SEQ ID No. 1808) followed by anti-human albumin single domain antibody 10G (SEQ ID No. 1774) followed by a GGGGSGGGS linker (SEQ ID No. 1808) followed by anti-human CD3 antibody 2B2 (SEQ ID No.1793) followed by a HHHHHH tag (SEQ ID No. 1819), to generate anti-DLL3 trispecific constructs.

The anti-DLL3 trispecific constructs containing the affinity matured anti-DLL3 binding sequences were then transfected into EXPI293™ cells. These anti-DLL3 trispecific constructs were subsequently engineered with a protein A binding site, and the amount of anti-DLL3 trispecific construct in the conditioned media from the transfected EXPI293™ cells was quantitated using an Octet instrument with protein A tips. A control trispecific protein of similar molecular weight as the anti-DLL3 trispecific proteins was used as a standard.

Using the conditioned medium with known concentrations of the anti-DLL3 trispecific proteins, the relative binding affinities of the anti-DLL3 trispecific proteins toward human DLL3 protein were measured using a method where biotinylated version of human DLL3 protein were expressed as a human IgG1 fusion protein, and the binding affinity measurement was carried out in an Octet instrument with streptavidin tips. The $K_D$ measurements were made using a single 50 nM concentration of anti-DLL3 trispecific protein, which allowed for rank ordering potency. The measured affinities are listed in Table 8. All of the tested sequences were found to bind human DLL3, with $K_D$ values ranging from 0.3 nM to 34 nM.

Figure 16:
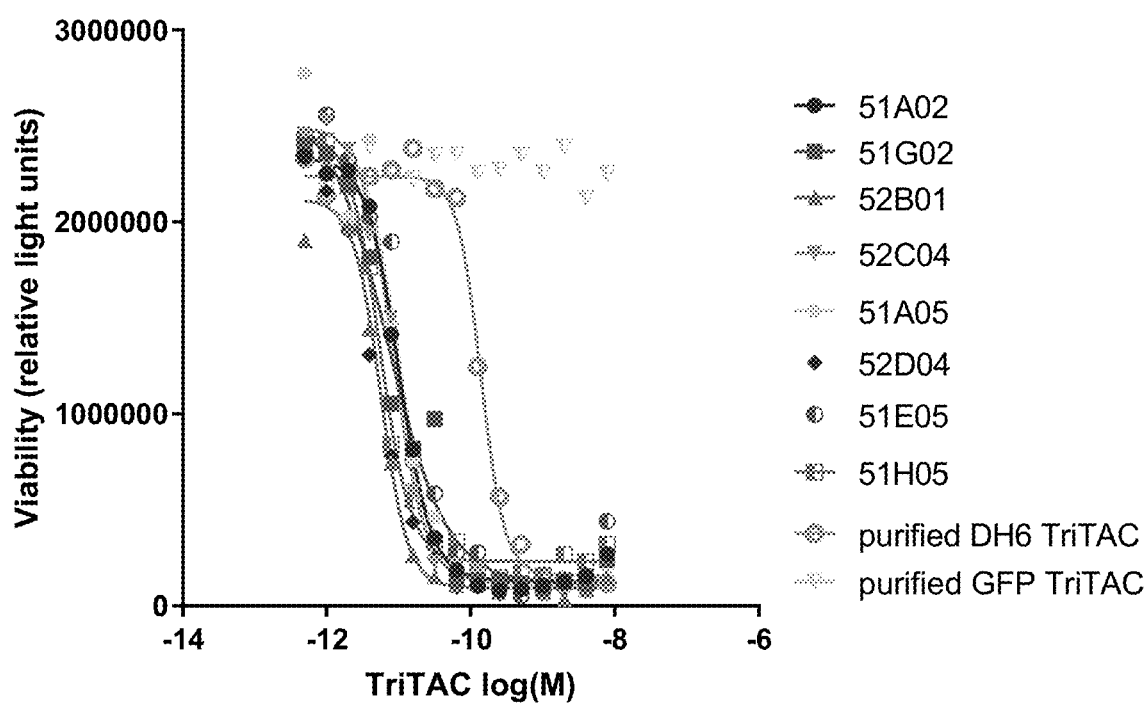
FIG. 16 illustrates results of a TDCC assay DMS-153 cells, using exemplary DLL3 targeting trispecific proteins containing exemplary DLL3 binding domains of this disclosure from second round of affinity maturation.

The conditioned medium was also tested in a T-cell dependent cellular cytotoxicity assay (see Nazarian A A, Archibeque I L, Nguyen Y H, Wang P, Sinclair A M, Powers D A. 2015. J Biomol Screen. 20:519-27). In this assay, luciferase labelled DMS-153 cells were combined with purified human T cells and a titration of anti-DLL3 trispecific proteins. It was hypothesized that if an anti-DLL3 trispecific protein directed T cells to kill the DLL3-expression DMS-153 cells, then the viability of the DMS-153 cells, as determined by running a luciferase assay at 48 hours after starting the experiment, should decrease. FIG. 16 illustrates a graph of representative TDCC data for anti-DLL3 trispecific proteins containing the following DLL3 binding domains: 51A02 (SEQ ID No. 409), 51G02 (SEQ ID No.425), 52B01 (SEQ ID No. 430), 52C04 (SEQ ID No.431), A (SEQ ID No. 411), 52D04 (SEQ ID No. 432), (SEQ ID No. 420), H (SEQ ID No. 429), and for purified DH43 protein (SEQ ID No. 68), and purified DH6 protein (SEQ ID No. 75). $EC_{50}$ values from the TDCC assay are listed in Table 9. The values ranged from 4.2 pM to 1.5 nM. A negative control for the TDCC assays was a trispecific protein targeting GFP (as shown in FIG. 16) which did not direct the T cells to kills the DMS-153 cells.

TABLE 7

Variants in CDR sequences by amino acid position of DH6 and its derivatives

| CDR | Amino acid position | CDR Amino acids |
|---|---|---|
| CDR1 | 26 | A, D, E, F, G, H, K, L, M, N, Q, R, S, V, W, Y |
| | 27 | D, E, H, K, M, P, R, S, T, Y |
| | 28 | A, D, G, H, K, N, P, Q, R, S, T, V, Y |
| | 29 | K, S, V |
| | 30 | A, F, G, H, K, L, M, N, Q, R, S, T, V, W, Y |
| | 31 | D, F, H, I, K, L, M, N, Q, R, S, V, Y |
| | 32 | L, M |
| | 33 | S |
| | 34 | I, L, M, S, T, V |
| | 35 | A |
| CDR2 | 50 | G |
| | 51 | I, V |
| | 52 | S |
| | 53 | A, D, E, G, H, I, K, L, N, P, Q, R, S, T, V, Y |
| | 54 | A, D, E, G, H, N, R, T |
| | 55 | G |
| | 56 | H, P, R, S |
| | 57 | A, H, I, K, M, N, Q, R, T, V |
| | 58 | A, D, G, H, I, L, M, N, S, T, V, Y |
| | 59 | Y |
| | 60 | A, F, I, L, M, R, S, T, V, Y |
| | 61 | A, D, E, G, H, K, L, N, R, S, V |
| | 62 | S |
| | 63 | V |
| | 64 | K |
| | 65 | G |
| CDR3 | 98 | L, Y |
| | 99 | D, E, G, H, K, N, Q, R, S, T, V, Y |
| | 100 | Q, W |
| | 101 | A, D, E, G, H, I, K, L, M, P, R, S, T, V |
| | 102 | A, D, E, G, N, R, S, T, Y |
| | 103 | A, P, R, S |
| | 104 | A, D, F, G, H, L, M, N, Q, R, S, T, V, Y |
| | 105 | A, G, I, K, P, Q, R, S, T |
| | 106 | F, H, Y |

TABLE 8

Binding constants for human DLL3 determined using a single concentration of anti-DLL3 Trispecific proteins

| Name | $K_D$ (nM) |
|---|---|
| 53A05 | 3.1E-10 |
| 53A04 | 4.2E-10 |
| 53C04 | 5.0E-10 |
| 52D04 | 5.0E-10 |
| 53B05 | 6.0E-10 |
| 51G10 | 6.0E-10 |
| 52B01 | 6.1E-10 |
| 51H05 | 6.7E-10 |
| 53B06 | 7.1E-10 |
| 54B05 | 7.6E-10 |
| 52C04 | 8.2E-10 |
| 42C03 | 8.8E-10 |
| 51A01 | 9.2E-10 |
| 51E05 | 9.7E-10 |
| 53A09 | 9.7E-10 |
| 51H04 | 1.0E-09 |
| 42A06 | 1.0E-09 |
| 41H03 | 1.0E-09 |
| 51A05 | 1.1E-09 |
| 42E05 | 1.2E-09 |
| 51A02 | 1.2E-09 |
| 42D08 | 1.3E-09 |
| 51G02 | 1.3E-09 |
| 42B10 | 1.3E-09 |

TABLE 8-continued

Binding constants for human DLL3 determined using a single concentration of anti-DLL3 Trispecific proteins

| Name | $K_D$ (nM) |
|---|---|
| 42G07 | 1.3E-09 |
| 41D01 | 1.4E-09 |
| 51F03 | 1.4E-09 |
| 42D06 | 1.5E-09 |
| 41H04 | 1.5E-09 |
| 51B01 | 1.6E-09 |
| 42C08 | 1.8E-09 |
| 42A03 | 1.9E-09 |
| 42A11 | 2.0E-09 |
| 42H08 | 2.1E-09 |
| 51A03 | 2.2E-09 |
| 42C11 | 2.3E-09 |
| 41C02 | 2.4E-09 |
| 51B11 | 2.4E-09 |
| 51F02 | 2.4E-09 |
| 42H05 | 2.7E-09 |
| 41D02 | 2.7E-09 |
| 42D05 | 2.7E-09 |
| 42E02 | 2.9E-09 |
| 42H11 | 3.1E-09 |
| 42A07 | 3.2E-09 |
| 42C10 | 3.2E-09 |
| 42B06 | 3.2E-09 |
| 42F08 | 3.2E-09 |
| 51D03 | 3.3E-09 |
| 41E02 | 3.4E-09 |
| 42G05 | 3.4E-09 |
| 51E02 | 3.5E-09 |
| 42C01 | 3.6E-09 |
| 42A08 | 3.6E-09 |
| 42E06 | 3.8E-09 |
| 42E07 | 3.9E-09 |
| 41G01 | 4.0E-09 |
| 42E01 | 4.0E-09 |
| 41D03 | 4.8E-09 |
| 41E01 | 5.3E-09 |
| 42D07 | 5.3E-09 |
| 42F01 | 5.5E-09 |
| 42C07 | 6.4E-09 |
| 51F04 | 6.7E-09 |
| 51E03 | 7.2E-09 |
| 51C02 | 7.5E-09 |
| 51D01 | 7.9E-09 |
| 41B11 | 9.9E-09 |
| 51B04 | 1.6E-08 |
| 51F01 | 1.6E-08 |
| 42F10 | 1.7E-08 |
| 51G04 | 2.1E-08 |
| 41F07 | 2.5E-08 |
| 41D07 | 3.4E-08 |

TABLE 9

DMS-153 TDCC values of affinity matured anti-DLL3 Trispecific Proteins in conditioned medium tested in triplicate using human T cells

| Name | TDCC $EC_{50}$ (M) |
|---|---|
| 52D04 | 4.2E-12 |
| 51H05 | 5.3E-12 |
| 52B01 | 5.5E-12 |
| 54B05 | 6.2E-12 |
| 53C04 | 6.2E-12 |
| 51G10 | 6.6E-12 |
| 51G02 | 6.8E-12 |
| 53B06 | 7.7E-12 |
| 52C04 | 8.2E-12 |
| 53A04 | 8.2E-12 |
| 51A02 | 9.5E-12 |
| 51A05 | 9.6E-12 |
| 53A09 | 9.7E-12 |
| 51E05 | 1.1E-11 |
| 51F03 | 1.1E-11 |
| 51H04 | 1.2E-11 |
| 53B05 | 1.2E-11 |
| 53H04 | 1.3E-11 |
| 53A05 | 1.6E-11 |
| 51B01 | 1.8E-11 |
| 42D08 | 1.9E-11 |
| 51A01 | 1.9E-11 |
| 41E02 | 2.1E-11 |
| 41D01 | 2.3E-11 |
| 42C03 | 2.5E-11 |
| 42A03 | 2.5E-11 |
| 42F10 | 2.5E-11 |
| 51B11 | 2.7E-11 |
| 42A07 | 2.8E-11 |
| 42G07 | 2.8E-11 |
| 42A06 | 2.8E-11 |
| 42F08 | 3.1E-11 |
| 42E05 | 3.4E-11 |
| 42C01 | 3.5E-11 |
| 42D05 | 3.6E-11 |
| 41C02 | 3.6E-11 |
| 51D03 | 3.8E-11 |
| 42H05 | 3.8E-11 |
| 51E02 | 3.8E-11 |
| 42C10 | 3.9E-11 |
| 42D06 | 4.0E-11 |
| 42H08 | 4.0E-11 |
| 42A11 | 4.2E-11 |
| 41D02 | 4.4E-11 |
| 42A08 | 4.5E-11 |
| 42E02 | 4.7E-11 |
| 41D03 | 4.8E-11 |
| 41G01 | 5.0E-11 |
| 42C11 | 5.3E-11 |
| 51A03 | 5.4E-11 |
| 42G05 | 5.9E-11 |
| 42B10 | 6.6E-11 |
| 42D07 | 8.5E-11 |
| 42F01 | 8.9E-11 |
| 42C08 | 9.4E-11 |
| 42E07 | 1.0E-10 |
| 42E01 | 1.0E-10 |
| 51C02 | 1.0E-10 |
| 42B06 | 1.1E-10 |
| 41E01 | 1.1E-10 |
| 51F04 | 1.2E-10 |
| 51F02 | 1.2E-10 |
| 42C07 | 1.3E-10 |
| 51D01 | 1.3E-10 |
| 42E06 | 1.8E-10 |
| 51F01 | 5.5E-10 |
| 51E03 | 1.4E-09 |
| 51B04 | 1.5E-09 |

Example 6: Affinity Maturation to Obtain Anti-DLL3 Binders of Improved Affinity

Figure 17:
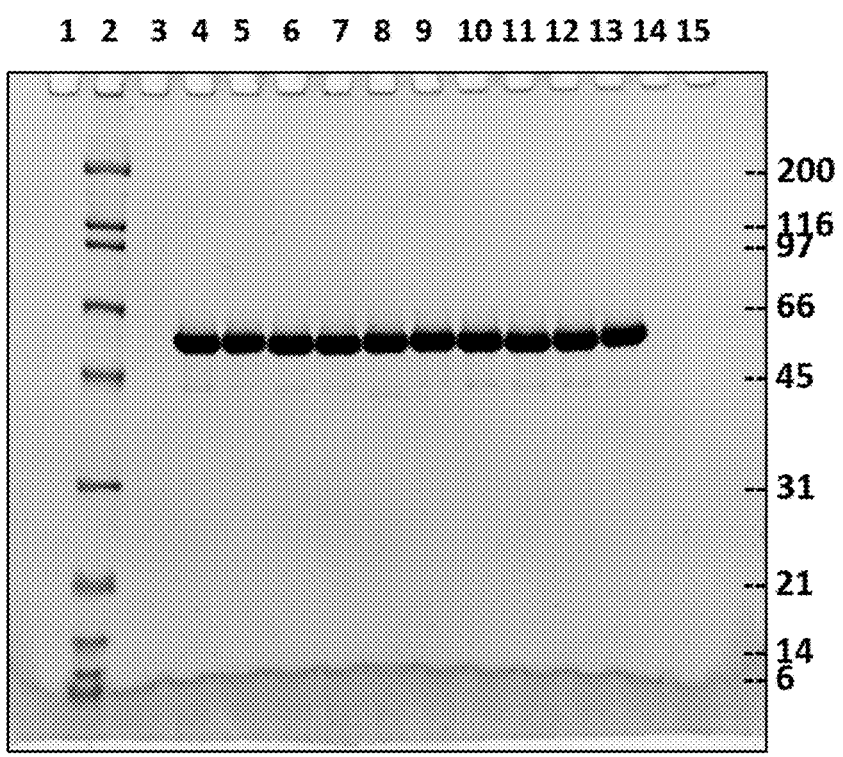
FIG. 17 illustrates an image of a 10-20% TRIS Glycine SDS-PAGE loaded with 2.4 micrograms of non-reduced protein per lane and stained with Coomassie. The lane numbers are indicated by the numbers at the top of the gel image and the migration of molecular weight standards are indicated by the number on the right side of the gel image (in kilodaltons). Gel loading: Lane 1 empty, lane 2 molecular weight standard, lane 3 empty, lane 4 anti-DLL3 trispecific containing DLL3 binding domain 51G2, lane 5 anti-DLL3 trispecific containing DLL3 binding domain 51G10, lane 6 anti-DLL3 trispecific containing DLL3 binding domain 51H5, lane 7 anti-DLL3 trispecific containing DLL3 binding domain 51X5, lane 8 anti-DLL3 trispecific containing DLL3 binding domain 52B1, lane 9 anti-DLL3 trispecific containing DLL3 binding domain 52C4, lane 10 anti-DLL3 trispecific containing DLL3 binding domain 52D4, lane 11 anti-DLL3 trispecific containing DLL3 binding domain 51A2, lane 12 containing DLL3 binding domain anti-DLL3 trispecific 51A5, lane 13 anti-DLL3 trispecific containing DLL3 binding domain 51F3, lane 14 empty, and lane 15 empty.

Certain anti-DLL3 trispecific proteins containing DLL-3 binding sequences that had the most potent TDCC activity in the assay described in Example 5, and an anti-DLL3 trispecific protein containing the parental DLL3 binder DH6, were subcloned into a CHO cell expression vector and were stably transfected in CHO cells (see Running Deer and Allison 2004. Biotechnol. Prog. 20: 880-889). The DLL3 binding sequences were: DH6 (SEQ ID No. 75); 51A2 (SEQ ID No. 408); 51A5 (SEQ ID No. 411); 51F3 (SEQ ID No. 423); 51G2 (SEQ ID No. 425); 51G10 (SEQ ID No. 427); 51H5 (SEQ ID No. 429); 51X5 (SEQ ID No. 1886); 52B1 (SEQ ID No. 430); 52C4 (SEQ ID No. 431); and 52D4 (SEQ ID No. 432). The trispecific proteins were purified into conditioned medium from pools of stable clones using protein A and ion exchange chromatography. An SDS-PAGE image of the purified proteins is provided in FIG. 17.

The affinity measurements for human and cynomolgus DLL3 were made using 60 nM, 20 nM, 6.67 nM, and 2.22 nM concentrations of biotinylated DLL3 targeting trispecific proteins immobilized on Octet streptavidin tips. The affinities determined from the measurements are listed in Table 10. In this experiment, anti-DLL3 trispecific containing DH6, the parental DLL3 binder sequence to the affinity matured DLL3 binder sequences, had $K_D$ values of 13.5 nM for human DLL3 and 11 nM for cynomolgus DLL3. In comparison, the ten anti-DLL3 trispecific proteins containing the affinity matured DLL3 binder molecules tested in this experiment had $K_D$ values ranging from 0.9 to 2.2 nM for human DLL3 and 1.4 to 3.4 nM for cynomolgus DLL3. Thus, the improvements in affinity range from 6.1 to 15 fold for human DLL3 and from 3.2 to 7.9 fold for cynomolgus DLL3.

The purified proteins were tested in TDCC assays, using the same method as described in Example 2 except that two additional DLL3 expressing cell lines were included in the assay, DMS-53 and NCI-H510A. The $EC_{50}$ values from these TDCC assays are listed in Table 11, and the graphs of the DMS-53 and DMS-153 TDCC data are provided, respectively, in FIGS. 18-19. A trispecific molecule targeting GFP had no activity in these assays (as shown in FIGS. 18-19). Compared to the parental molecule DH6, the $EC_{50}$ values improved 2.3 to 12.1 fold in DMS-153 cells, 4.5 to 31.5 fold in NCI-H510A cells, and 8.1 to 26.1 fold in DMS-153 cells.

TABLE 10

Affinities of purified CHO expressed affinity matured anti-DLL3 trispecific proteins for human and cynomolgus DLL3 protein in vitro

| Name | huDLL3 $K_D$ (nM) | cyDLL3 $K_D$ (nM) |
|---|---|---|
| DH6 | 13.5 | 11.0 |
| 51A2 | 1.2 | 2.0 |
| 51A5 | 1.2 | 1.6 |
| 51F3 | 1.4 | 2.0 |
| 51G2 | 2.0 | 3.4 |
| 51G10 | 0.9 | 1.4 |
| 51H5 | 0.9 | 1.6 |
| 51X5 | 1.0 | 1.5 |
| 52B1 | 1.1 | 1.9 |
| 52C4 | 2.2 | 3.0 |
| 52D4 | 0.9 | 1.7 |

TABLE 11

TDCC Activity of purified CHO expressed affinity matured anti-DLL3 trispecific proteins with DMS153, NCI-H510A, and DMS53 cell lines and human T cells

| Name | DMS153 $EC_{50}$ (pM) | NCI-H510A $EC_{50}$ (pM) | DMS53 $EC_{50}$ (pM) |
|---|---|---|---|
| 51A2 | 16.7 | 9.1 | 9.8 |
| 51G2 | 37.7 | 3.7 | 15.9 |
| 51G10 | 11.0 | 2.3 | 9.6 |
| 51H5 | 6.0 | 2.4 | 5.4 |
| 51X5 | 9.0 | 2.8 | 8.3 |
| 52B1 | 9.1 | 1.3 | 6.5 |
| 52C4 | 17.9 | 2.0 | 15.9 |
| 52D4 | 7.2 | 2.5 | 4.9 |

Example 7: T Cell Dependent Cellular Cytotoxicity Assay Using Exemplary DLL3 Targeting Trispecific Proteins Comprising a DLL3 Binding Protein of this Disclosure Several exemplary DLL3 trispecific proteins containing a DLL3 binding domain of this disclosure, 52D04 (SEQ ID NO. 432), were tested in a T cell dependent cellular cytotoxicity (TDCC) assay (see Nazarian A A, Archibeque I L, Nguyen Y H, Wang P, Sinclair A M, Powers D A. 2015. J Biomol Screen. 20:519-27), the results are shown in FIGS. 22-24. The trispecific proteins contained a DLL3 binding domain, an albumin binding domain (anti-ALB), and a CD3 binding domain (anti-CD3), in an anti-DLL3:anti-ALB:anti-CD3 configuration (TAC), as shown in FIG. 20, or in an anti-CD3:anti-ALB:anti-DLL3 (CAT) configuration, as shown in FIG. 21. The TDCC assay was carried out in the presence or absence of 15 mg/ml human serum albumin (HSA). In this assay, luciferase labelled NCI-H2171 (FIG. 22), DMS-79 (FIG. 23), SHP77 (FIG. 24), or WM2664 (FIG. 25) cells were combined with purified human T cells and a titration of the exemplary DLL3 binding trispecific proteins, in the presence or absence of albumin. It was hypothesized that if an DLL3 binding trispecific protein directed T cells to kill the DLL3-expression NCI-H2171, DMS-79, SHP77, or WM2664 cells, then the viability of those cells, as determined by running a luciferase assay at 48 hours after starting the experiment, should decrease. FIG. 22 illustrates a graph of representative TDCC data, using NCI-H2171 cells, for the DLL3 binding trispecific proteins in the TAC or CAT configurations, containing the following DLL3 binding domains. FIG. 23 illustrates a graph of representative TDCC data, using DMS-79 cells, for the DLL3 binding trispecific proteins in the TAC or CAT configurations, containing the following DLL3 binding domains. FIG. 24 illustrates a graph of representative TDCC data, using SHP77 cells, for the DLL3 binding trispecific proteins in the TAC or CAT configurations, containing the following DLL3 binding domains. FIG. 25 illustrates a graph of representative TDCC data, using WM2664 cells, for the DLL3 binding trispecific proteins in the TAC or CAT configurations, containing the following DLL3 binding domains. $EC_{50}$ values from the TDCC assay are listed in Table 12. As shown in the graphs and indicated by the $EC_{50}$ values, in the presence of human serum albumin (HSA) the DLL3 binding trispecific proteins having the CAT orientation (FIG. 21) were more potent in the TDCC assays than the DLL3 binding trispecific proteins having the TAC configuration.

TABLE 12

TDCC Activity of exemplary anti-DLL3 trispecific proteins with NCI-H2171, DMS-79, SHP77, and cell lines and human T cells

| Cell Line | | $EC_{50}$ (pM) no HSA | $EC_{50}$ (pM) with HSA |
|---|---|---|---|
| NCI-H2171 | αDLL3:αALB:αCD3 | 3 | 224 |
| | αCD3:αALB:αDLL3 | 2 | 84 |
| DMS-79 | αDLL3:αALB:αCD3 | 1.1 | 115 |
| | αCD3:αALB:αDLL3 | 0.7 | 41 |
| SHP77 | αDLL3:αALB:αCD3 | 21* | 3953 |
| | αCD3: αALB:αDLL3 | 11* | 821 |
| WM2664 | αDLL3:αALB:αCD3 | 9* | 855 |
| | αCD3:αALB:αDLL3 | 10* | 422 |

* 15 mg/ml bovine serum albumin (BSA) was included in these no HSA assays; the αALB domain did not bind BSA (data not shown)

Example 8: Binding of Exemplary DLL3 Targeting Trispecific Proteins to Human T Cells In a cell binding study, human T cells were incubated in the presence or absence of an exemplary DLL3 targeting trispecific protein (in either anti-DLL3:anti-ALB:anti-CD3 (TAC) configuration (SEQ ID No. 1891; or anti-CD3:anti-ALB:anti-DLL3 (CAT) configuration (SEQ ID No. 1890). The human T cells were further incubated with a secondary antibody (anti-trispecific antibody), which is able to recognize the anti-albumin domain in the exemplary trispecific molecules, conjugated to Alexa Fluor 647. Binding of the anti-trispecific antibody was measured by flow cytometry. Robust binding of anti-trispecific antibody was seen in the presence of the exemplary DLL3 trispecific protein in the anti-DLL3:anti-ALB:anti-CD3 (TAC) configuration (right peaks in the plots in FIG. 26) compared to cells incubated with secondary antibody alone or cells incubated without exemplary trispecific proteins or secondary antibody (left peaks in the plots in FIG. 26). Robust binding of anti-trispecific antibody was also seen in the presence of the exemplary DLL3 trispecific protein in the anti-CD3:anti-ALB:anti-DLL3 (CAT) configuration (right peaks in the plots in FIG. 27) compared to cells incubated with secondary antibody alone or cells incubated without exemplary trispecific proteins or secondary antibody (left peaks in the plots in FIG. 27).

Example 9: Binding of Exemplary DLL3 Targeting Trispecific Proteins to DLL3 Expressing Cancer Cell Lines In another binding study, DLL3 expressing cancer cells [NCI-H82 (lung cancer cell line), SHP77 (lung cancer cell line), DMS53 (lung carcinoma), or NCI-H2171 (lung cancer cell line)] were incubated with exemplary DLL3 targeting trispecific molecules (in CAT or TAC configuration; SEQ ID No. 1890 and SEQ ID No. 1891) or a control trispecific molecule that targets GFP. Following incubation, the cells were washed to remove unbound trispecific molecules and further incubated with a secondary antibody, which is able to recognize the anti-albumin domain in the trispecific molecules, conjugated to Alexa Fluor 647 or FITC. Binding of the exemplary DLL3 targeting trispecific molecules or that of the control trispecific molecules to the cells was measured by flow cytometry. Robust binding of DLL3 targeting trispecific (in TAC configuration) to each cell line was observed (right peaks in the plots in FIG. 28) compared to cells incubated with a control trispecific molecule targeting GFP (left peaks in the plots in FIG. 28). Robust binding of DLL3 targeting trispecific (in CAT configuration) to each cell line was also observed (right peaks in the plots in FIG. 29) compared to cells incubated with a control trispecific molecule targeting GFP (left peaks in the plots in FIG. 29). In control experiments with cell lines that lack DLL3 expression, HCT116 (colon cancer cell line) and NCI-H292 (lung cancer cell line), similar amount of anti-trispecific antibody were bound to cells incubated with the exemplary DLL3 targeting trispecific proteins or GFP-targeting control trispecific molecules (data not shown), indicating the exemplary DLL3-targeting trispecific molecules did not bind to cells lacking DLL3 expression.

Example 10: Ability of Exemplary DLL3 Targeting Trispecific Proteins to Direct T Cell Mediated Killing of DLL3 Expressing Cancer Cell Lines The aim of this study was to assess if exemplary DLL3 targeting trispecific molecules were able to direct T cells to kill the DLL3-expressing cell lines NCI-H82, SHP77, DMS53, and NCI-H2171. The DLL3-expressing cells used in this study were engineered to express luciferase.

For the TDCC assay (T cell dependent cellular cytotoxicity assay) T cells from four healthy donors (donor 2; donor 47; donor 81; donor 86) and the DLL3-expressing cells were mixed and varying amounts of exemplary DLL3 targeting trispecific proteins (in CAT or TAC configurations; SEQ ID No. 1890 and SEQ ID No. 1891) was added to the mixture. The mixture was incubated for 48 hours at 37° C. As a control, parallel experiments were performed using a control trispecific molecule targeting GFP. After 48 hours, the remaining viable DLL3-expressing cells were quantified using a luminescence assay. It was observed that the DLL3-targeting trispecific molecules (in both TAC and CAT configurations) were able to efficiently direct T cells from all four healthy donors to kill all four DLL3 expressing cell lines (see FIGS. 30, 31, 32, and 33 for results using the TAC configuration; see FIGS. 34, 35, 36, and 37 for results using the CAT configuration) whereas the control GFP TriTAC molecule was not able to do that (also shown in FIGS. 30-37). The $EC_{50}$ values are presented in Table 13 and Table 14. Further TDCC assays were carried out with DLL3-targeting TriTAC and cell lines that lack DLL3 expression, NCI-H292 and HCT116. It was observed that the DLL3-targeting TriTAC was not able to direct T cells to kill these two cell lines lack DLL3 expression (data not shown).

TABLE 13

$EC_{50}$ values for TDCC assays performed using exemplary DLL3 targeting trispecific proteins containing DLL3 binding domain of this disclosure, 52D04, in an anti-DLL3:anti-ALB:anti-CD3 (TAC) configuration, tested in the presence of human serum albumin (HSA), using T cells from four different donors.

| Cell Line | $EC_{50}$ (M) | | | |
| --- | --- | --- | --- | --- |
| | Donor 02 | Donor 47 | Donor 81 | Donor 86 |
| NCI-H82 | 3.6E−11 | 3.3E−11 | 8.0E−11 | 1.4E−10 |
| SHP77 | 2.7E−10 | 1.4E−10 | 3.8E−10 | 7.0E−10 |
| DMS53 | 2.3E−10 | 2.8E−10 | 2.8E−10 | 7.7E−10 |
| NCI-2171 | 4.0E−10 | 2.4E−10 | 7.5E−10 | 1.0E−09 |

TABLE 14

EG$_{50}$ values for TDCC assays performed using exemplary DLL3 targeting trispecific proteins containing DLL3 binding domain of this disclosure, 52D04, in an anti-CD3:anti-ALB:anti-DLL3 (CAT) configuration, tested in the presence of human serum albumin (HSA), using T cells from four different donors.

| | EC$_{50}$ (M) | | | |
|---|---|---|---|---|
| Cell Line | Donor 02 | Donor 47 | Donor 81 | Donor 86 |
| NCI-H82 | 2.0E-11 | 1.6E-11 | 4.5E-11 | 5.9E-11 |
| SHP77 | 6.3E-11 | 3.6E-11 | 8.4E-11 | 1.9E-10 |
| DMS53 | 7.0E-11 | 7.2E-11 | 8.0E-11 | 2.2E-10 |
| NCI-2171 | 1.6E-10 | 7.6E-11 | 2.9E-10 | 3.2E-10 |

Example 11: DLL3 Dependent Activation of T Cells by Exemplary DLL3 Targeting Trispecific Proteins In this assay, T cells from 4 different healthy donors (donor 2; donor 35; donor 47; and donor 86) and NCI-H82 or DMS53 cells were incubated with exemplary DLL3 targeting trispecific proteins (in CAT or TAC configurations; SEQ ID No. 1890 and SEQ ID No. 1891) for 48 hours at 37° C. T cells from the same donors were also incubated for 48 hours at 37° C. with a control trispecific molecule, GFP TriTAC, which targets GFP and NCI-H82 or DMS53 cells. After 48 hours, T cells were collected, and CD69 and CD25 expression on the T cells was measured by flow cytometry. Increased CD69 or CD25 expression was detected on T cells from all 4 healthy donors in presence of NCI-H82 or SHP77 cells and DLL3 targeting trispecific molecules but not in presence of the negative control GFP TriTAC, as seen in FIGS. 38-45. A parallel experiment was performed with HCT116 cells, which lack DLL3 expression. No increase CD69 or CD25 expression was observed with DLL3 trispecific molecules tested using HCT116 cells (data not shown).

Example 12: DLL3 Dependent Cytokine Production by T Cells Induced by Exemplary DLL3 Targeting Trispecific Proteins In this assay, T cells from a healthy donor and NCI-H82 or SHP77 cells were incubated with exemplary DLL3 targeting trispecific molecules (in CAT or TAC configuration; SEQ ID No. 1890 and SEQ ID No. 1891) for 48 hours at 37° C. T cells from the same donor were also incubated for 48 hours at 37° C. with a control trispecific molecule, GFP TriTAC, which targets GFP and NCI-H82 or DMS53 cells. After 48 hours, conditioned media were collected, and the amount of various cytokines present in the conditioned media were measured using an electrochemiluminescent assay (Meso Scale Discovery). It was observed that IFNγ, IL-2, and TNFα were secreted into the medium in presence of NCI-H82 or SHP77 cells and DLL3 targeting trispecific molecules but not in presence the control GFP-targeting TriTAC molecule. For the DLL3 targeting trispecific molecule in TAC configuration: IFNγ production is shown in FIGS. 46 and 47; IL-2 production is shown in FIGS. 48 and 49; TNFα production is shown in FIGS. 50 and 51. For the DLL3 targeting trispecific molecule in CAT configuration: IFNγ production is shown in FIGS. 52 and 53; IL-2 production is shown in FIGS. 54 and 55; TNFα production is shown in FIGS. 56 and 57.

Example 13: Inhibition of Growth of NCI-H82 Xenografts by Exemplary DLL3 Targeting Trispecific Proteins For this study, 5×10$^6$ human T cells and 5×10$^6$ NCI-H82 small cell lung cancer cells were injected into mice at day 0. On days 1 to 10, mice were injected daily intraperitoneally (i.p.) with exemplary DLL3 targeting trispecific molecules (in CAT or TAC configurations; SEQ ID No. 1890 and SEQ ID No. 1891) at doses of 20, 100, or 500 μg/kg or negative control GFP-targeting TriTAC at a dose of 500 μg/kg. Tumor volumes were measured after every few days starting at day 7 and ending on day 24. Significant inhibition of tumor growth was observed in the mice injected with the DLL3-targeting trispecific proteins at all doses compared to mice dosed with the GFP-targeting TriTAC dosed at 500 μg/kg, as shown in FIG. 58.

Example 14: Elimination NCI-H82 Xenografts by Exemplary DLL3 Targeting Trispecific Proteins For this study, 5×10$^6$ NCI-H82 small cell lung cancer cells were injected subcutaneously on day 0. Mice were randomized on day 8, and 2×10$^7$ human T cells were injected per mouse. On days 9 to 18, mice were injected daily i.p. with the exemplary DLL3 targeting trispecific molecules (in CAT configuration; SEQ ID No. 1890) at doses of 1, 10, or 100 μg/kg or negative control GFP-targeting TriTAC at a dose of 100 μg/kg. Tumor volumes were measured after every few days starting at day 8 and ending at day 29. Significant inhibition of tumor growth was observed in the mice injected with DLL3 targeting trispecific molecules at doses of 10 and 100 μg/kg compared to mice dosed with the GFP targeting TriTAC dosed at 100 μg/kg, as shown in FIG. 59.

Example 15: Inhibition of Growth of SHP77 Xenografts by Exemplary DLL3 Targeting Trispecific Proteins For this study, 5×10$^6$ human T cells and 1×10$^7$ SHP77 small cell lung cancer cells were injected into mice at day 0. On days 1 to 10, mice were injected daily i.p. with DLL3 targeting trispecific molecules (in CAT configuration; SEQ ID No. 1890) at doses of 1, 10, or 100 μg/kg or negative control GFP-targeting TriTAC at a dose of 100 μg/kg. Tumor volumes were measured after every few days starting at day 6 and ending on day 28. Significant inhibition of tumor growth was observed in the mice injected with DLL3-targeting trispecific molecules at doses of 10 and 100 g/kg compared to mice dosed with the GFP-targeting TriTAC dosed at 100 μg/kg, as shown in FIG. 60.

Example 16: Pharmacokinetic Profile of Exemplary DLL3 Targeting Trispecific Proteins
DLL3-Targeting Trispecific Proteins have a Half-Life of ~3 to ~3.9 Days in Cynomolgus Monkeys when Dosed at 0.3 mg/kg For this study, cynomolgus monkeys were injected with 0.3 mg/kg doses of exemplary DLL3-targeting trispecific molecules (in CAT or TAC configurations; SEQ ID No. 1890 and SEQ ID No. 1891), intravenously, and serum samples were collected at various time points after the injection. Two monkeys were injected for each dose. The amount of DLL3 targeting trispecific molecule in the serum was measured using anti-idiotype antibodies recognizing the trispecific molecule, in an electrochemiluminescent assay. FIG. 61 shows a plot for the serum DLL3 targeting trispecific molecule levels at various time points. The data was then used to calculate the pharmacokinetic properties of the DLL3 targeting trispecific molecules, as provided in Table 15. Human dosing schedule of once or twice a week is contemplated based on the pharmacokinetic data.

TABLE 15

Pharmacokinetics of exemplary DLL3 targeting trispecific molecules

| ID | Half life (h) | AUC 0-inf (h*nM) | CL (L/h/kg) | Vss (l/kg) |
|---|---|---|---|---|
| 1 | 93.1 | 7210 | 0.000832 | 0.0869 |
| 2 | 72.4 | 6690 | 0.000896 | 0.0731 |
| 3 | 82.6 | 7900 | 0.00076 | 0.0767 |
| 4 | 77 | 7890 | 0.00076 | 0.0712 |

DLL3 Targeting Trispecific Protein has a Half-Life of ~2.8 to ~3.3 Days in Cynomolgus Monkeys when Dosed at 1 or 10 mg/kg:

For this study, cynomolgus monkeys were injected with 1 mg/kg or 10 mg/kg dose of exemplary DLL3 targeting trispecific molecules, intravenously, and serum samples were collected at various time points after the injection. Two monkeys were injected for each dose. The amount of DLL3-targeting TriTAC in the serum was measured using anti-idiotype antibodies recognizing the TriTAC molecule, in an electrochemiluminescent assay. FIG. 62 shows a plot for the serum DLL3 targeting trispecific molecule levels at various time points. The data was then used to calculate the pharmacokinetic properties of the TriTAC molecule, as provided in Table 16. The pharmacokinetic data suggest that once or twice weekly dosing in humans.

TABLE 16

Pharmacokinetics of exemplary DLL3 targeting trispecific molecules

| Dose (mg/kg) | Half life (h) | $C_{max}$ (nM) | AUC 0-inf (h*nM) | CL (mL/h/kg) | Vss (l/kg) |
|---|---|---|---|---|---|
| 1 | 67.5 | 493 | 23,800 | 0.79 | 63.8 |
| 10 | 78.6 | 4,492 | 236,500 | 0.80 | 71.9 |

Exemplary DLL3 Targeting Trispecific Proteins were Tolerated in Cynomolgus Monkeys when Given as a Single Dose Up to 10 mg/kg:

A transient increase in serum cytokine levels were observed, mainly at 10 mg/kg dosage of administration of exemplary DLL3 targeting trispecific protein (in CAT configuration) (FIG. 63; IFNγ-FIG. 63 top panel, IL-6 FIG. 63 second panel; IL-10 FIG. 63 third panel). Transient T cell margination and T cell activation were also observed (data not shown). At terminal and recovery euthanasia, no DLL3 trispecific protein-related macroscopic findings or organ weight differences were observed, and at recovery euthanasia, no DLL3 trispecific protein-related microscopic findings were observed.

To demonstrate the DLL3-targeting TriTAC retained cell directed killing activity after being administered to a cyno-molgus monkey, a serum sample form the 10 mg/kg dose group collected at 168 h after dosing was tested in a DMS53 TDCC assay and was compared to DLL3-targeting TriTAC that was freshly thawed. Identical cell DMS53 cell killing was observed with the serum sample and the freshly thawed protein (FIG. 64), indicating the DLL3-targeting TriTAC retains the ability to direct T cells to kill target cells 1 week after being dosed in a cynomolgus monkey.

Example 17: Xenograft Tumor Model

An exemplary anti-DLL3 targeting trispecific protein of this disclosure is evaluated in a xenograft model.

Female immune-deficient NOD/scid mice are sub-lethally irradiated (2 Gy) and subcutaneously inoculated with $1 \times 10^6$ NCI-H28 cells into their right dorsal flank. When tumors reach 100 to 200 mm³, animals are allocated into 3 treatment groups. Groups 2 and 3 (8 animals each) are intraperitoneally injected with $1.5 \times 10^7$ activated human T-cells. Three days later, animals from Group 3 are subsequently treated with a total of 9 intravenous doses of exemplary DLL3 trispecific antigen-binding protein of (such as 1, 10, 50, or 100 µg/kg) (qdx9d). Groups 1 and 2 are only treated with vehicle. Body weight and tumor volume are determined for 30 days.

It is expected that animals treated with the exemplary DLL3 targeting trispecific proteins of the previous examples have a statistically significant delay in tumor growth in comparison to the respective vehicle-treated control group.

Example 18: Proof-of-Concept Clinical Trial Protocol for Administration of an Exemplary DLL3 Trispecific Antigen-Binding Protein (Anti-DLL3 Trispecific Protein) to Neuroendocrine Cancer Patients This is a Phase I/II clinical trial for studying an exemplary DLL3 trispecific antigen-binding protein as a treatment for a Neuroendocrine Cancer.

Study Outcomes:

Primary: Maximum tolerated dose of the exemplary DLL3 targeting trispecific protein Secondary: To determine whether in vitro response of the exemplary DLL3 targeting trispecific proteins are associated with clinical response Phase I The maximum tolerated dose (MTD) will be determined in the phase I section of the trial.
 1.1 The maximum tolerated dose (MTD) will be determined in the phase I section of the trial.
 1.2 Patients who fulfill eligibility criteria will be entered into the trial to evaluate the exemplary DLL3 targeting trispecific protein.
 1.3 The goal is to identify the highest dose of the exemplary anti-DLL3 trispecific protein that can be administered safely without severe or unmanageable side effects in participants. The dose given will depend on the number of participants who have been enrolled in the study prior and how well the dose was tolerated. Not all participants will receive the same dose.

Phase II
 2.1 A subsequent phase II section will be treated at the MTD with a goal of determining if therapy with therapy of the exemplary DLL3 targeting trispecific proteins results in at least a 20% response rate.

Primary Outcome for the Phase II—To determine if therapy with the exemplary DLL3 targeting trispecific protein trispecific protein results in at least 20% of patients achieving a clinical response (blast response, minor response, partial response, or complete response)

Eligibility: Biopsy proven neuroendocrine tumor, which is somatostatin receptor positive as demonstrated on somatostatin receptor PET.

All sites or origin are eligible.

Functional and nonfunctional tumors are allowed.

Not a candidate for surgical debulking.

ECOG performance status 0, 1 or 2

Age >18.

Ability to understand a written informed consent document, and the willingness to sign it.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

| SEQ. ID NO. | name | sequence |
|---|---|---|
| 1 | DL1 | QVQLQESGGGLVQAGGSLRLSCAASGSIFSIASMGWYRQAPGKQRELVAVITSFSSTNYADSVKGRFTISRDNAKNTVYLQMNSLKPEDTGVYYCNARYFERTDWGQGTQVTVSS |
| 2 | DL74 | QVQLQESGGGLVQAGGSLRLSCAAPGSIFSIASMGWYRQAPGKQRELVAVITSFSSTNYADSVKGRFTISRDNAKNTVYLQMNSLKPEDTGVYYCNARYFERTDWGQGTQVTVSS |
| 3 | DL31 | QVQLQESGGGLVQAGGSLRLSCAASGSIFSIASMAWYRQAPGKQRELVAAITSFSSTNYADSVKGRFTISRDNAKNTVYLQMNSLKPEDTGVYYCNARYFERTDWGQGTQVTVSS |
| 4 | DL3 | QVQLQESGGGLVQAGGSLRLSCAASESIFSINVMAWHRQAPGKQRELVARITSGGSTNYADSVKGRFTISRDNAKNTVYLQMNSLKPEDTGVYYCGAYQGLYAYWGQGTQVTVSS |
| 5 | DL80 | QVQLQESGGGLVQAGGSLRLSCVASGSSFSITSMAWYRQAPGKQRDLVAAITSFGSTNYADSVKDRFTISRDNAKNTVYLQMNSLKPEDTAVYYCNGRVFDHVYWGQGTQVTVSS |
| 6 | DL18 | QVQLQESGGGLVQAGGSLKLSCAASSSIFSISSMSWYRQAPGKQRELVAAITTFDYTNYADSVKGRFTISRDNAKNMMYLQMNSLKPEDTAVYLCNARAFGRDYWGQGTQVTVSS |
| 7 | DL94 | QVQLQESGGGLVQAGGSLKLSCAASSSIFSISSMSWYRQAPGKQRELVAAITSFGSTNYADSVKGRFTISRDNAKNMMYLQMNSLKPEDTAVYRCNARTMGRDYWGQGTQVTVSS |
| 8 | DL17 | QVQLQESGGGLVQPGGSLRLSCAASGSTLNIKIMAWHRQAPGKQRELVATLTSGGNTNYADSVKGRFTISRDNAKNTVYLQMNSLQPEDTAVYYCGLWDGVGGAYWGRGTQVTVSS |
| 9 | DL46 | QVQLQESGGGLVQPGGSLRISCAASGSTLNIKIMAWHRQAPGKQRELVATLTSGGNTNYADSVKGRFTISRDNAKNTVYLQMNSLQPEDTAVYYCGLWDGVGGAYWGRGTQVTVSS |
| 10 | DL15 | QVQLQESGGGLVQAGGSLRLSCAASGSTFNIKTMAWHRQAPGNQRELVATLTSGGNTNYADSVKGRFTISRDNAKNTVYLQMNSLKPEDTAVYYCGLWNGVGGAYWGRGTQVTVSS |
| 11 | DL26 | QVQLQDGGGLVQPGGSLRLSCAASGSTFNIKLMAWHRQAPGNQRELVATLTSGGNTNYADSVKGRFTISRDNASNIVYLQMNSLKPEDTAVYYCGLWDGVGGAYWGRGTQVTVSS |
| 12 | DL83 | QVQLQESGGGLVQAGGSLRLSCAASGSTFNEKIMAWHRQAPGKQRELVASLTSEGLTNYRDSVKGRFTISRDNAKNTVYLQMNNLKPEDTAVYYCGLWDGVGGAYWGRGTQVTVSS |
| 13 | DL5 | QVQLQESGGGLVQPGGSLRLSCAASGEMESSYSMSWYRQAPGKQRELVAAITTWGSTNYADSVKGRFTISRDNAKNTVWLQMNSLEPEDTAVYFCNARSWNNYWGQGTQVTVSS |
| 14 | DL22 | QVQLQESGGGLVQVGGSLRLSCAASGEMESSYSMSWYRQAPGKQRELVAAITSYGSTNYADSVKGRFTISRDNAKNTVWLQMNSLKPEDTAVYFCNARSWNNYWGQGTQVTVSS |
| 15 | DL85 | QVQLQESGGGLVQPGGSLRLSCAASGETFSSHSMSWYRQAPGKQRELVAAITTYGSTNYIDSVKGRFTISRDNTKNTVYLQMNSLKPEDTAVYFCNARSWNNYWGQGTQVTVSS |
| 16 | DL69 | QVQLQESGGGLVQAGGSLRLSCVASGSSFSHNTMGWYRQAPGKQRDLVARITTFGTTNYADSVKGRFTISRDNAKNTVYLQMNSLKPEDTAVYYCNGESFGRIWYNWGQGTQVTVSS |
| 17 | DL27 | QVQLQESGGGLVQAGASLRLTCTASGGRFSYATMGWSRQAPGKQREMVARITSSGFSTNYADSVKGRFTISRDNAKNAVYLQMDSLKPEDTAVYYCNAQHFGTDSWGQGTQVTVSS |
| 18 | DL51 | QVQLQESGGGLVQAGASLRLTCTASGSRFSYATMGWSRQAPGKQRELVARITSSGFSTNYADSVKGRFTISRDNAKNAVYLQMDSLKPEDTAVYYCNAQQFGTDSWGQGTQVTVSS |
| 19 | DL54 | QVQLQESGGGLVQAGGSLRLSCAASGSTFTSNVMGWHRQAPGKQRELVANMHSGGSTNYADSVKGRFTISRDNAKNIVYLQMNNLKIEDTAVYYCRWYGIQRAEGYWGQGTQVTVSS |
| 20 | DL11 | QVQLQESGGGLVVAGGSLRLSCAASGSSVSFLSMAWYRQAPGKKRELVAGISVDGSTNYADSVKGRFTVSRDNAKNTVYLQMNSLQPEDTAVYYCYAYRWVGRDTYWGQGTQVTVSS |

| | | -continued |
|---|---|---|
| 21 | DL19 | QVQLQESGGGLVVAGGSLRLSCAASGSSVSFLSMAWYRQAPGKKRELVAGISVDGSTNYAD<br>SVKGRFTISRDNAKNTVYLQMNSLQPEDTAVYYCYAYRWVGRDTYWGQGTQVTVSS |
| 22 | DL68 | QVQLQESGGGLVVSGGSLRLSCAASGSSVSFLSMAWYRQAPGKKRELVAGISVDGSTNYAD<br>SVKGRFTISRDNAKNTVYLQMNSLQPEDTAAYYCYAYRWVGRDTYWGQGTQVTVSS |
| 23 | DL14 | QVQLQESGGGLVVAGGSLRLSCAASGSSVSFLSMAWYRQAPGKKRELVAGISVDGSTNYAD<br>SVKGRFTISRDNAENTVYLQMNSLQPEDTAVYYCYAYRWEGRDTYWGQGTQVTVSS |
| 24 | DL67 | QVQLQESGGGLVVAGGSLRLSCAASGSSVSFLSMAWYRQAPGKKRELVAGISVDGSTNYAD<br>SVKGRFTISRDNAENTVYLQMNSLQPEDTAVYYCYAYRWEGRNTYWGQGTQVTVSS |
| 25 | DL56 | QVQLQESGGGLVQPGGSLRLSCAASGSSVSFLSMAWYRQAPGKKRELVAGISTDGSTNYVD<br>SVKGRFTISRDNAKNTVYLQMNSLQPEDTAVYYCYAYRWVGRYTYWGQGTQVTVSS |
| 26 | DL13 | QVQLQESGGGLVVAGGSLRLSCAASGSSVSFLSMAWYRQAPGKKRELVAGISTDGTTNYVD<br>SVKDRFTISRDNAKNTVYLQMNSLQPEDTAAYYCYAYRWVGRDTYWGQGTQVTVSS |
| 27 | DL77 | QVQLQESGGGLVVAGGSLRLSCAASGSSVSELSIAWYRQAPGKKRELVAGISTDGTTNYVD<br>SVKDRFTISRDNAKNTVYLQMNSLQPEDTAAYYCYAYRWVGRDTYWGQGTQVTVSS |
| 28 | DL79 | QVQLQESGGGLVQAGGSLTLSCAASGSSVSFLSMAWYRQAPGKKRELVAGISTDGTTNYVD<br>SVKDRFTISRDNAKNTVYLQMNSLQPEDTAAYYCYAYRWVGRDTYWGQGTQVTVSS |
| 29 | DL20 | QVQLQESGGGLVQAGGSLRLSCAASGSSVSFLSMAWYRQAPGKKRELVAGISTDGSTNYAD<br>SVKGRFTISEGNAKNTVDLQMNSLQPEDTAVYYCYAYRWVDRYTYWGQGTQVTVSS |
| 30 | DL41 | QVQLQESGGGLVVAGGSLRLSCAASGSSVSFLSMAWYRQAPGKKRELVAGISTDGSTNYAD<br>SVKGRFTISEDNAKNTVDLQMNSLQPEDTAVYYCYAYRWIDRYTYWGQGTQVTVSS |
| 31 | DL59 | QVQLQESGGGLVQPGGSLRLSCAASGSSVSFLSMAWYRQAPGKKRELVAGISTDGSTNYAD<br>SVKGRFTISEDNAKNTVDLQMNSLQPEDTAVYYCYAYRWVDRYTYWGQGTQVTVSS |
| 32 | DL16 | QVQLQESGGGLVVAGGSLRLSCAASGSSVSFLSMAWYRQAPGKKRELVAGISSDGSTNYVD<br>SVKGRFTISRDNAKNIVFLQMNSLQPQDTAVYYCYAYRWVGRDTYWGQGTQVTVSS |
| 33 | DL6 | QVQLQESGGGLVVAGGSLRLSCAASGSSVSFLSMAWYRQAPGKKRELVAGISADGSTDYID<br>SVKGRFTISRDSANNTMYLQMNSLQPEDTAVYYCYAYRWTTRYTYWGQGTQVTVSS |
| 34 | DL84 | QVQLQESGGGLVQPGGSLRLSCAASGETLDYYAIGWYRQAPGKKRELVAGISSDGSTHYVD<br>SVKGRFAISRDNAENTVYLQMNDLQPDDTAVYYCYAYRWVGGYTYWGQGTQVTVSS |
| 35 | DL2 | QVQLQESGGGLVQAGGSLRLSCVASGSTSSINAMGWYRRAPGKQRELVAGISSDGSKNYAD<br>SVKGRFTISRDNAKNTVYLQMNSLKPEDTAVYYCYYFRTVAASSMQYWGQGTQVTVSS |
| 36 | DL43 | QVQLQESGGGLVQAGGSLRLSCVASGSTSSINAMGWYRRAPGKQRELVAGISSDGSKVYAD<br>SVKGRFTISRDNAKNTVYLQMNSLKPEDTAVFYCYYFRTVSGSSMRYWGQGTQVTVSS |
| 37 | DL92 | QVQLQESGGGLVQAGGSLRLSCAASGITSSVYSMGWYRQAPGKQRELVAGSSSDGSTHYVD<br>SVRGRFTISRDNAKNTVYLQMSSLKPEDTAVYYCYANRGFAGAPSYWGQGTQVTVSS |
| 38 | DL10 | QVQLQESGGGLVQAGGSLRLSCAASGRTSMFNSMGWHRQAPGKQRELVAIIRSGGSSNYAD<br>TVKGRFTISRDNTKNTVYLQMNDLKPEDTAVYYCFYYFQSSYWGQGTQVTVSS |
| 39 | DL82 | QVQLQESGGGLVQAGGSLRLSCAASGRTSMVNSMGWHRQAPGKQRELVALITSGGSSNYAD<br>TVKGRFTISRDNTKNTVYLQMNDLKPEDTAVYYCFYYFQSSYWGQGTQVTVSS |
| 40 | DL23 | QVQLQESGGGLVQAGGSLRLSCAASGSVSMFNSMGWHRQPPGKQRELVAIITSGGSSNYAD<br>TVKGRFTISRDNTKNTVYLQMNDLKPEDTAVYYCFYYFQSSYWGQGTQVTVSS |
| 41 | DL42 | QVQLQESGGGLVQAGGSLRLSCTASGSIFSIAVMGWYRQVPGKRREWVATIFDGSYTNYAD<br>SVKGRFTISRDNARNKVYLQMNNLKPEDTAVYYCQTHWTQGSVPKESWGQGTQVTVSS |
| 42 | DL45 | QVQLQESGGGLVQAGGSLRLSCVASSGIFSDMSMVWYRQAPGKQRELVASITTFGSTNYAD<br>PVKGRFTISRDNAKNTVYLQMNSLKPEDTAVYYCSGRSYSSDYWGRGTQVTVSS |
| 43 | DL58 | QVQLQESGGGLVQAGGSLRLSCVASGSISSIIVMGWSRQAPGKQRESVATITRDGTRNYAD<br>SLKGRFTISRDNAKNTSYLQINSLKPEDTAVYSCYARYGDINYWGKGTQVTVSS |
| 44 | DL70 | QVQLQESGGGLVQAGGSLRLSCVASGSISSIIVMGWSRQAPGKQRESLATISRGGTRTYAD<br>SVKGRFTISRDNAKNTSYLQMNSLKPEDTAVYSCYARYGDINYWGKGTQVTVSS |
| 45 | DL89 | QVQLQESGGGLVQAGGSLRLSCVASGSIFTTNSMGWHRQGPGKQRELVALIGSAGSTKYAD<br>SVKGRFTISRDNAKNTVSLQMDSLKPEDTAVYYCFYYDSRSYWGQGTQVTVSS |
| 46 | DL38 | QVQLQESGGGMVQPGGSLRLSCAASGSREISTMGWHRQAPGKQRELAARITSGGITKYADS<br>VKGRFTISRDNAKKTVYLQMNSLKSEDTAVYYCFAYDNINAYWGQGTQVTVSS |

| | | -continued |
|---|---|---|
| 47 | DL52 | QVQLQESGGGWVQAGGSLRLSCAASGSREISTMGWHRQAPGKQRELAARITSGGITKYADS VKGRFTISRDNAKKTVYLQMNSLKSEDTAVYYCFAYDNINAYWGQGTQVTVSS |
| 48 | DL64 | QVQLQESGGGWVQAGGSLRLSCTASGSREISTMGWHRQAPGKQRELAARITSGGITKYADS VKGRFTISRDNAKKTVYLQMDSLKSEDTAVYYCFAYDNINAYWGQGTQVTVSS |
| 49 | DL33 | QVQLQESGGGSVQAGRSLGLSCAASGSREISTMGWHRQAPGKQRELAARITSGGITKYADS VKGRFTISRDNAKKTVYLQMNSLKSEDTAVYYCFAYDNINAYWGQGTQVTVSS |
| 50 | DL12 | QVQLQESGGGLVQAGGSLRLSCTASGSIFRGAAMYWHRQAPGKQRELVAAITTSGNTSYAD SVKGRFTISRDNAKNTMYLQIISLKPEDTAVYYCAFWIAGKAYWGQGTQVTVSS |
| 51 | DL29 | QVQLQESGGGLVQPGGSLRLSCAASGSISSFNEMSWHRQAPGKERELAGVITRGGATNYAD SVKGRFTISRDNVKNTVYLQMNGLKPEDTAVYYCHGRSQLGSTWGQGTQVTVSS |
| 52 | DL61 | QVQLQESGGGLVQAGGSLRLSCLASGTIETASTMGWHRQPPGKQRELVASIAGDGRTNYAE STEGRETISRDDAKNTMYLQMNSLKPEDTAVYYCYAYYLDTYAYWGQGTQVTVSS |
| 53 | DH1 | EVQLVESGGGLVQPGGSLTLSCAASGSIFSIASMGWYRQAPGKQRELVAVITSFSSTNYAD SVKGRFTISRDNAKNSVYLQMNSLRAEDTAVYYCNARYFERTDWGQGTLVTVSS |
| 54 | DH10 | EVQLVESGGGLVQPGGSLTLSCAASGRTSMFNSMGWHRQAPGKQRELVAIIRSGGSSNYAD TVKGRFTISRDNAKNSVYLQMNSLRAEDTAVYYCFYYFQSSYWGQGTLVTVSS |
| 55 | DH11 | EVQLVESGGGLVQPGGSLTLSCAASGSSVSFLSMAWYRQAPGKKRELVAGISVDGSTNYAD SVKGRFTISRDNAKNSVYLQMNSLRAEDTAVYYCYAYRWVGRDTYWGQGTLVTVSS |
| 56 | DH12 | EVQLVESGGGLVQPGGSLTLSCTASGSIFRGAAMYWHRQAPGKQRELVAAITTSGNTSYAD SVKGRFTISRDNAKNSMYLQMNSLRAEDTAVYYCAFWIAGKAYWGQGTLVTVSS |
| 57 | DH15 | EVQLVESGGGLVQPGGSLTLSCAASGSTFNIKTMAWHRQAPGNQRELVATLTSGGNTNYAD SVKGRFTISRDNAKNSVYLQMNSLRAEDTAVYYCGLWNGVGGAYWGQGTLVTVSS |
| 58 | DH17 | EVQLVESGGGLVQPGGSLTLSCAASGSTLNIKIMAWHRQAPGKQRELVATLTSGGNTNYAD SVKGRFTISRDNAKNSVYLQMNSLRAEDTAVYYCGLWDGVGGAYWGQGTLVTVSS |
| 59 | DH18 | EVQLVESGGGLVQPGGSLTLSCAASSSIFSISSMSWYRQAPGKQRELVAAITTFDYTNYAD SVKGRFTISRDNAKNSMYLQMNSLRAEDTAVYYCNARAFGRDYWGQGTLVTVSS |
| 60 | DH2 | EVQLVESGGGLVQPGGSLTLSCVASGSTSSINAMGWYRRAPGKQRELVAGISSDGSKNYAD SVKGRFTISRDNAKNSVYLQMNSLRAEDTAVYYCYYFRTVAASSMQYWGQGTLVTVSS |
| 61 | DH22 | EVQLVESGGGLVQPGGSLTLSCAASGEMESSYSMSWYRQAPGKQRELVAAITSYGSTNYAD SVKGRFTISRDNAKNSVYLQMNSLRAEDTAVYYCNARSWNNYWGQGTLVTVSS |
| 62 | DH23 | EVQLVESGGGLVQPGGSLTLSCAASGSVSMFNSMGWHRQPPGKQRELVAIITSGGSSNYAD TVKGRFTISRDNAKNSVYLQMNSLRAEDTAVYYCFYYFQSSYWGQGTLVTVSS |
| 63 | DH27 | EVQLVESGGGLVQPGGSLTLSCTASGGRFSYATMGWSRQAPGKQREMVARITSSGFSTNYA DSVKGRFTISRDNAKNSVYLQMNSLRAEDTAVYYCNAQHFGTDSWGQGTLVTVSS |
| 64 | DH29 | EVQLVESGGGLVQPGGSLTLSCAASGSISSFNEMSWHRQAPGKERELAGVITRGGATNYAD SVKGRFTISRDNAKNSVYLQMNSLRAEDTAVYYCHGRSQLGSTWGQGTLVTVSS |
| 65 | DH3 | EVQLVESGGGLVQPGGSLTLSCAASESIFSINVMAWHRQAPGKQRELVARITSGGSTNYAD SVKGRFTISRDNAKNSVYLQMNSLRAEDTAVYYCGAYQGLYAYWGQGTLVTVSS |
| 66 | DH38 | EVQLVESGGGLVQPGGSLTLSCAASGREISTMGWHRQAPGKQRELAARITSGGITKYADS VKGRFTISRDNAKNSVYLQMNSLRAEDTAVYYCFAYDNINAYWGQGTLVTVSS |
| 67 | DH42 | EVQLVESGGGLVQPGGSLTLSCTASGSIFSIAVMGWYRQVPGKRREWVATIFDGSYTNYAD SVKGRFTISRDNAKNSVYLQMNSLRAEDTAVYYCQTHWTQGSVPKESWGQGTLVTVSS |
| 68 | DH43 | EVQLVESGGGLVQPGGSLTLSCVASGSTSSINAMGWYRRAPGKQRELVAGISSDGSKVYAD SVKGRFTISRDNAKNSVYLQMNSLRAEDTAVYYCYYFRTVSGSSMRYWGQGTLVTVSS |
| 69 | DH45 | EVQLVESGGGLVQPGGSLTLSCVASSGIFSDMSMVWYRQAPGKQRELVASITTFGSTNYAD PVKGRFTISRDNAKNSVYLQMNSLRAEDTAVYYCSGRSYSSDYWGQGTLVTVSS |
| 70 | DH5 | EVQLVESGGGLVQPGGSLTLSCAASGEMESSYSMSWYRQAPGKQRELVAAITTWGSTNYAD SVKGRFTISRDNAKNSVYLQMNSLRAEDTAVYYCNARSWNNYWGQGTLVTVSS |
| 71 | DH51 | EVQLVESGGGLVQPGGSLTLSCTASGSRFSYATMGWSRQAPGKQRELVARITSSGFSTNYA DSVKGRFTISRDNAKNSVYLQMNSLRAEDTAVYYCNAQQFGTDSWGQGTLVTVSS |
| 72 | DH54 | EVQLVESGGGLVQPGGSLTLSCAASGSTFTSNVMGWHRQAPGKQRELVANMHSGGSTNYAD SVKGRFTISRDNAKNSVYLQMNSLRAEDTAVYYCRWYGIQRAEGYWGQGTLVTVSS |

| | | -continued |
|---|---|---|
| 73 | DH56 | EVQLVESGGGLVQPGGSLTLSCAASGSSVSFLSMAWYRQAPGKKRELVAGISTDGSTNYVD SVKGRFTISRDNAKNSVYLQMNSLRAEDTAVYYCYAYRWVGRYTYWGQGTLVTVSS |
| 74 | DH58 | EVQLVESGGGLVQPGGSLTLSCVASGSISSIIVMGWSRQAPGKQRESVATITRDGTRNYAD SLKGRFTISRDNAKNSSYLQMNSLRAEDTAVYYCYARYGDINYWGQGTLVTVSS |
| 75 | DH6 | EVQLVESGGGLVQPGGSLTLSCAASGSSVSFLSMAWYRQAPGKKRELVAGISADGSTDYID SVKGRFTISRDNAKNSVYLQMNSLRAEDTAVYYCYAYRWTTRYTYWGQGTLVTVSS |
| 76 | DH61 | EVQLVESGGGLVQPGGSLTLSCLASGTIETASTMGWHRQPPGKQRELVASIAGDGRTNYAE STEGRETISRDNAKNSMYLQMNSLRAEDTAVYYCYAYYLDTYAYWGQGTLVTVSS |
| 77 | DH67 | EVQLVESGGGLVQPGGSLTLSCAASGSSVSFLSMAWYRQAPGKKRELVAGISVDGSTNYAD SVKGRFTISRDNAKNSVYLQMNSLRAEDTAVYYCYAYRWEGRNTYWGQGTLVTVSS |
| 78 | DH69 | EVQLVESGGGLVQPGGSLTLSCVASGSSFSHNTMGWYRQAPGKRDLVARITTFGTTNYAD SVKGRFTISRDNAKNSVYLQMNSLRAEDTAVYYCNGESFGRIWYNWGQGTLVTVSS |
| 79 | DH70 | EVQLVESGGGLVQPGGSLTLSCVASGSISSIIVMGWSRQAPGKQRESLATISRGGTRTYAD SVKGRFTISRDNAKNSSYLQMNSLRAEDTAVYYCYARYGDINYWGQGTLVTVSS |
| 80 | DH80 | EVQLVESGGGLVQPGGSLTLSCVASGSSFSITSMAWYRQAPGKRDLVAAITSFGSTNYAD SVKDRFTISRDNAKNSVYLQMNSLRAEDTAVYYCNGRVFDHVYWGQGTLVTVSS |
| 81 | DH82 | EVQLVESGGGLVQPGGSLTLSCAASGRTSMVNSMGWHRQAPGKQRELVALITSGGSSNYAD TVKGRFTISRDNAKNSVYLQMNSLRAEDTAVYYCFYYFQSSYWGQGTLVTVSS |
| 82 | DH83 | EVQLVESGGGLVQPGGSLTLSCAASGTFNEKIMAWHRQAPGKQRELVASLTSEGLTNYRD SVKGRFTISRDNAKNSVYLQMNSLRAEDTAVYYCGLWDGVGGAYWGQGTLVTVSS |
| 83 | DH84 | EVQLVESGGGLVQPGGSLTLSCAASGETLDYYAIGWYRQAPGKKRELVAGISSDGSTHYVD SVKGRFTISRDNAKNSVYLQMNSLRAEDTAVYYCYAYRWVGGYTYWGQGTLVTVSS |
| 84 | DH89 | EVQLVESGGGLVQPGGSLTLSCVASGSIFTTNSMGWHRQGPGKQRELVALIGSAGSTKYAD SVKGRFTISRDNAKNSVYLQMNSLRAEDTAVYYCFYYDSRSYWGQGTLVTVSS |
| 85 | DH92 | EVQLVESGGGLVQPGGSLTLSCAASGITSSVYSMGWYRQAPGKQRELVAGSSSDGSTHYVD SVRGRFTISRDNAKNSVYLQMNSLRAEDTAVYYCYANRGFAGAPSYWGQGTLVTVSS |
| 86 | DH94 | EVQLVESGGGLVQPGGSLTLSCAASSIFSISSMSWYRQAPGKQRELVAAITSFGSTNYAD SVKGRFTISRDNAKNSMYLQMNSLRAEDTAVYYCNARTMGRDYWGQGTLVTVSS |
| 87 | 1A01 | EVQLVESGGGLVQPGGSLTLSCVASGETSSINAMGWYRRAPGKQRELVAGISSDGSFVYAD SVKGRFTISRDNAKNSVYLQMNSLRAEDTAVYYCYYFRHVSGSSMRYWGQGTLVTVSS |
| 88 | 1A03 | EVQLVESGGGLVQPGGSLTLSCVASGSTSSINAMAWYRRAPGKQRELVAGISSDGSKVYAD SVKGRFTISRDNAKNSVYLQMNSLRAEDTAVYYCYYFRTVSGSSSRYWGQGTLVTVSS |
| 89 | 1A04 | EVQLVESGGGLVQPGGSLTLSCVASGSTSSINAMGWYRRAPGKQRELVAGISSDGSKVYED SVKGRFTISRDNAKNSVYLQMNSLRAEDTAVYYCYYFRTVSGSSMRYWGQGTLVTVSS |
| 90 | 1A05 | EVQLVESGGGLVQPGGSLTLSCVASGSPSSINAMGWYRRAPGKQRELSAGISSDGSKVYAD SVKGRFTISRDNAKNSVYLQMNSLRAEDTAVYYCYYFRTVRGSSMSYWGQGTLVTVSS |
| 91 | 1A06 | EVQLVESGGGLVQPGGSLTLSCVASGSTSSINAMGWYRRAPGKQRELAAGISSDGSSVYAD SVKGRFTISRDNAKNSVYLQMNSLRAEDTAVYYCYYFRTVSGSSKRYWGQGTLVTVSS |
| 92 | 1A07 | EVQLVESGGGLVQPGGSLTLSCVASGSISSINAMGWYRRAPGKQRELVAGISSDGSKVYAD SVKGRFTISRDNAKNSVYLQMNSLRAEDTAVYYCYYFRMVSGSSMRYWGQGTLVTVSS |
| 93 | 1A09 | EVQLVESGGGLVQPGGSLTLSCVASGSTSSINAMAWYRRAPGKQRELVAGISSDGSKLYAD SVKGRFTISRDNAKNSVYLQMNSLRAEDTAVYYCYYFRTVQGSSMRYWGQGTLVTVSS |
| 94 | 1A010 | EVQLVESGGGLVQPGGSLTLSCVASGSTSSINAYGWYRRAPGKQRELVAGISSDGSKVYAD SVKGRFTISRDNAKNSVYLQMNSLRAEDTAVYYCYYFRTVYGSSMRYWGQGTLVTVSS |
| 95 | 1A011 | EVQLVESGGGLVQPGGSLTLSCVASGSTSSINAIGWYRRAPGKQRELVAGISSDGSKVYID SVKGRFTISRDNAKNSVYLQMNSLRAEDTAVYYCYYFRTVSGSSYRYWGQGTLVTVSS |
| 96 | 1A012 | EVQLVESGGGLVQPGGSLTLSCVASGSTSSINAMAWYRRAPGKQRELVAGISSDGSKVYSD SVKGRFTISRDNAKNSVYLQMNSLRAEDTAVYYCYYFRTVLGSSMRYWGQGTLVTVSS |
| 97 | 1B01 | EVQLVESGGGLVQPGGSLTLSCVASGSTSIINAMGWYRRAPGKQRELAAGISSDGSKVIAD SVKGRFTISRDNAKNSVYLQMNSLRAEDTAVYYCYYFRRVSGSSMRYWGQGTLVTVSS |
| 98 | 1B02 | EVQLVESGGGLVQPGGSLTLSCVASGSTSSINAMGWYRRAPGKQRELVAGISSDGSKIYAD SVKGRFTISRDNAKNSVYLQMNSLRAEDTAVYYCYYFRTVSGSSMRYWGQGTLVTVSS |

| | | -continued |
|---|---|---|
| 99 | 1B03 | EVQLVESGGGLVQPGGSLTLSCVASGKTSSINAMAWYRRAPGKQRELVAGISSDGSKVYTD SVKGRFTISRDNAKNSVYLQMNSLRAEDTAVYYCYYFRTVSGSSARYWGQGTLVTVSS |
| 100 | 1B04 | EVQLVESGGGLVQPGGSLTLSCVASGTTSSINAMGWYRRAPGKQRELVAGISSDGSLVYAD SVKGRFTISRDNAKNSVYLQMNSLRAEDTAVYYCYYFRIVRGSSMRYWGQGTLVTVSS |
| 101 | 1B05 | EVQLVESGGGLVQPGGSLTLSCVASGSTSSINAMAWYRRAPGKQRELVAGISSDGSKVYAD SVKGRFTISRDNAKNSVYLQMNSLRAEDTAVYYCYYYRTVSGSSMRYWGQGTLVTVSS |
| 102 | 1B07 | EVQLVESGGGLVQPGGSLTLSCVASGSGSSINAMGWYRRAPGKQRELVAGISSDGSKVYSD SVKGRFTISRDNAKNSVYLQMNSLRAEDTAVYYCYYFRHVSGSSMRYWGQGTLVTVSS |
| 103 | 1B08 | EVQLVESGGGLVQPGGSLTLSCVASGTTSSINAMGWYRRAPGKQRELVAGISSDGSKVYVD SVKGRFTISRDNAKNSVYLQMNSLRAEDTAVYYCYYFRFVSGSSMRYWGQGTLVTVSS |
| 104 | 1B09 | EVQLVESGGGLVQPGGSLTLSCVASGSTSSINAMAWYRRAPGKQRELVAGISSDGSKVYVD SVKGRFTISRDNAKNSVYLQMNSLRAEDTAVYYCYYFRTVSGSSMRYWGQGTLVTVSS |
| 105 | 1B010 | EVQLVESGGGLVQPGGSLTLSCVASGSTSRINAMGWYRRAPGKQRELVAGISSDGSKVYAD SVKGRFTISRDNAKNSVYLQMNSLRAEDTAVYYCYYFRTKSGSSMRYWGQGTLVTVSS |
| 106 | 1B011 | EVQLVESGGGLVQPGGSLTLSCVASGSTSRINAMGWYRRAPGKQRELVAGISSDGSKVYAD SVKGRFTISRDNAKNSVYLQMNSLRAEDTAVYYCYYFRTVYGSSMRYWGQGTLVTVSS |
| 107 | 1C01 | EVQLVESGGGLVQPGGSLTLSCVASGSTSSINAMGWYRRAPGKQRELVAGISSDGSKVYRD SVKGRFTISRDNAKNSVYLQMNSLRAEDTAVYYCYYFRTVSGSSMGYWGQGTLVTVSS |
| 108 | 1C02 | EVQLVESGGGLVQPGGSLTLSCVASGSTSSINAMAWYRRAPGKQRELVAGISSDGSKVYSD SVKGRFTISRDNAKNSVYLQMNSLRAEDTAVYYCYYFRTVSGSSMRSWGQGTLVTVSS |
| 109 | 1C03 | EVQLVESGGGLVQPGGSLTLSCVASGSTSSINAMAWYRRAPGKQRELVAGISSDNSKVYAD SVKGRFTISRDNAKNSVYLQMNSLRAEDTAVYYCYYFRTVGGSSMRYWGQGTLVTVSS |
| 110 | 1C04 | EVQLVESGGGLVQPGGSLTLSCVASGNTSSINAMAWYRRAPGKQRELVAGISSDGSKVYAD SVKGRFTISRDNAKNSVYLQMNSLRAEDTAVYYCYYFRTVSGSSMRYWGQGTLVTVSS |
| 111 | 1C05 | EVQLVESGGGLVQPGGSLTLSCVASGSTSSINAMAWYRRAPGKQRELVAGISSDGSKVYAD SVKGRFTISRDNAKNSVYLQMNSLRAEDTAVYYCYYFRTVSGSHMRYWGQGTLVTVSS |
| 112 | 1C06 | EVQLVESGGGLVQPGGSLTLSCVASGSTSIINAMGWYRRAPGKQRELVAGISSDGSKVYED SVKGRFTISRDNAKNSVYLQMNSLRAEDTAVYYCYYFRAVSGSSMRYWGQGTLVTVSS |
| 113 | 1C07 | EVQLVESGGGLVQPGGSLTLSCVASGSTSSINAMAWYRRAPGKQRELVAGISSDGSKVYAD SVKGRFTISRDNAKNSVYLQMNSLRAEDTAVYYCYYFRTVSGSSMRYWGQGTLVTVSS |
| 114 | 1C08 | EVQLVESGGGLVQPGGSLTLSCVASGSTSRINAMGWYRRAPGKQRELPAGISSDGSKVYAV SVKGRFTISRDNAKNSVYLQMNSLRAEDTAVYYCYYFRTVSGSPMRYWGQGTLVTVSS |
| 115 | 1C010 | EVQLVESGGGLVQPGGSLTLSCVASGSTSRINAMGWYRRAPGKQRELVAGVSSDGSKVYAD SVKGRFTISRDNAKNSVYLQMNSLRAEDTAVYYCYYFRTVSGSSMSYWGQGTLVTVSS |
| 116 | 1C011 | EVQLVESGGGLVQPGGSLTLSCVASGTTSSINAMGWYRRAPGKQRELVAGISSDGSKVYED SVKGRFTISRDNAKNSVYLQMNSLRAEDTAVYYCYYFRTVSGSSMRYWGQGTLVTVSS |
| 117 | 1C012 | EVQLVESGGGLVQPGGSLTLSCVASGITSSINAMGWYRRAPGKQRELVAGISSDGSKVYAG SVKGRFTISRDNAKNSVYLQMNSLRAEDTAVYYCYYFRTVRGSSMRYWGQGTLVTVSS |
| 118 | 1D01 | EVQLVESGGGLVQPGGSLTLSCVASGSTSDINAMGWYRRAPGKQRELVAGISSDKSKVYAD SVKGRFTISRDNAKNSVYLQMNSLRAEDTAVYYCYYFRTVRGSSMRYWGQGTLVTVSS |
| 119 | 1D02 | EVQLVESGGGLVQPGGSLTLSCVASGSTSSINAMAWYRRAPGKQRELVAGISSNGSKVYAD SVKGRFTISRDNAKNSVYLQMNSLRAEDTAVYYCYYFRQVSGSSMRYWGQGTLVTVSS |
| 120 | 1D03 | EVQLVESGGGLVQPGGSLTLSCVASGSTSSINAIGWYRRAPGKQRELVAGISSDGSKVLAD SVKGRFTISRDNAKNSVYLQMNSLRAEDTAVYYCYYFRIVSGSSMGYWGQGTLVTVSS |
| 121 | 1D04 | EVQLVESGGGLVQPGGSLTLSCVASGSTSSKNAMGWYRRAPGKQRELVAGISSDGSKVYAD SVKGRFTISRDNAKNSVYLQMNSLRAEDTAVYYCYYFRTVSGASMRYWGQGTLVTVSS |
| 122 | 1D06 | EVQLVESGGGLVQPGGSLTLSCVASGSTSSINAMGWYRRAPGKQRELVAGISSDNSKVYAD SVKGRFTISRDNAKNSVYLQMNSLRAEDTAVYYCYYFRTVHGSSMRYWGQGTLVTVSS |
| 123 | 1D08 | EVQLVESGGGLVQPGGSLTLSCVASGLTSSINAMGWYRRAPGKQRELVAGISSDGSKVYAD SVKGRFTISRDNAKNSVYLQMNSLRAEDTAVYYCYYFRMVSGSSMRYWGQGTLVTVSS |
| 124 | 1D09 | EVQLVESGGGLVQPGGSLTLSCVASGSTSSINAMAWYRRAPGKQRELVAGISSDGSKVYTD SVKGRFTISRDNAKNSVYLQMNSLRAEDTAVYYCYYFRTISGSSMRYWGQGTLVTVSS |

| | | |
|---|---|---|
| 125 | 1D010 | EVQLVESGGGLVQPGGSLTLSCVASGSTSSNNAMAWYRRAPGKQRELVAGISSDGSKVYTD<br>SVKGRFTISRDNAKNSVYLQMNSLRAEDTAVYYCYYFRTRSGSSMRYWGQGTLVTVSS |
| 126 | 1D011 | EVQLVESGGGLVQPGGSLTLSCVASGSTSSINAMAWYRRAPGKQRELVAGISSDNSKVYAD<br>SVKGRFTISRDNAKNSVYLQMNSLRAEDTAVYYCYYFRTVSGHSMRYWGQGTLVTVSS |
| 127 | 1D012 | EVQLVESGGGLVQPGGSLTLSCVASGSTSHINAMGWYRRAPGKQRELVAGISSDGSRVYAD<br>SVKGRFTISRDNAKNSVYLQMNSLRAEDTAVYYCYYFRTVSGGSMRYWGQGTLVTVSS |
| 128 | 1E02 | EVQLVESGGGLVQPGGSLTLSCVASGQTSSINAMGWYRRAPGKQRELVAGISSDGSQVYAD<br>SVKGRFTISRDNAKNSVYLQMNSLRAEDTAVYYCYYFRTKSGSSMRYWGQGTLVTVSS |
| 129 | 1E04 | EVQLVESGGGLVQPGGSLTLSCVASGSTSRINGMGWYRRAPGKQRELPAGISSDGSKAYAD<br>SVKGRFTISRDNAKNSVYLQMNSLRAEDTAVYYCYYFRTASGTSMRYWGQGTLVTVSS |
| 130 | 1E05 | EVQLVESGGGLVQPGGSLTLSCVASGSTSVINAMAWYRRAPGKQRELAAGISSDGSKVYAK<br>SAKGRFTISRDNAKNSVYLQMNSLRAEDTAVYYCYYFNTVSGSSMRYWGQGTLVTVSS |
| 131 | 1E07 | EVQLVESGGGLVQPGGSLTLSCVASGSTSSINAMAWYRRAPGKQRELVAGISSDGSKVYND<br>SVKGRFTISRDNAKNSVYLQMNSLRAEDTAVYYCYYFRTVRGSSQRYWGQGTLVTVSS |
| 132 | 1E08 | EVQLVESGGGLVQPGGSLTLSCVASGKTSSINAMGWYRRAPGKQRELVAGISSDGSKVIAD<br>SVKGRFTISRDNAKNSVYLQMNSLRAEDTAVYYCYYFRTVLGSSMRYWGQGTLVTVSS |
| 133 | 1E09 | EVQLVESGGGLVQPGGSLTLSCVASGSTSSINAMAWYRRAPGKQRELVAGISSDGSKVYTD<br>SVKGRFTISRDNAKNSVYLQMNSLRAEDTAVYYCYYFRTRSGSSMRYWGQGTLVTVSS |
| 134 | 1E010 | EVQLVESGGGLVQPGGSLTLSCVASGSVSSINAMGWYRRAPGKQRELVAGISSDGSKVYID<br>SVKGRFTISRDNAKNSVYLQMNSLRAEDTAVYYCYYFRTVSGLSMRYWGQGTLVTVSS |
| 135 | 1E011 | EVQLVESGGGLVQPGGSLTLSCVASGNTSSINAMGWYRRAPGKQRELVAGISSDGSKVYYD<br>SVKGRFTISRDNAKNSVYLQMNSLRAEDTAVYYCYYFRTVRGSSQRYWGQGTLVTVSS |
| 136 | 1E012 | EVQLVESGGGLVQPGGSLTLSCVASGSTSSTNAMGWYRRAPGKQRELVAGISSDGSKVYVD<br>SVKGRFTISRDNAKNSVYLQMNSLRAEDTAVYYCYYFRTVSGSSMVYWGQGTLVTVSS |
| 137 | 1F01 | EVQLVESGGGLVQPGGSLTLSCVASGSTSSINAMGWYRRAPGKQRELVAGISSDGSKVYGD<br>SVKGRFTISRDNAKNSVYLQMNSLRAEDTAVYYCYYFRTVSRSSMRYWGQGTLVTVSS |
| 138 | 1F02 | EVQLVESGGGLVQPGGSLTLSCVASGSTSSINAMAWYRRAPGKQRELAAGISSDQSKVYAD<br>SAKGRFTISRDNAKNSVYLQMNSLRAEDTAVYYCYYFRTVSGSSMSYWGQGTLVTVSS |
| 139 | 1F04 | EVQLVESGGGLVQPGGSLTLSCVASGGTSSINAMGWYRRAPGKQRELVAGISSDGSKVYSD<br>SVKGRFTISRDNAKNSVYLQMNSLRAEDTAVYYCYYFRTVSGSSARYWGQGTLVTVSS |
| 140 | 1F05 | EVQLVESGGGLVQPGGSLTLSCVASGSTRSINAMGWYRRAPGKQRELVAGISSDGSKVYAD<br>SVKGRFTISRDNAKNSVYLQMNSLRAEDTAVYYCYYFHTVSGSSMRYWGQGTLVTVSS |
| 141 | 1F06 | EVQLVESGGGLVQPGGSLTLSCVASGTTSSINAMGWYRRAPGKQRELVAGISSDGSKVIAD<br>SVKGRFTISRDNAKNSVYLQMNSLRAEDTAVYYCYYFRTVLGSSMRYWGQGTLVTVSS |
| 142 | 1F07 | EVQLVESGGGLVQPGGSLTLSCVASGSTSSINAMGWYRRAPGKQRELVAGISSDGSKVDAD<br>SVKGRFTISRDNAKNSVYLQMNSLRAEDTAVYYCYYFRTVSGSSMRYWGQGTLVTVSS |
| 143 | 1F08 | EVQLVESGGGLVQPGGSLTLSCVASGSTSSINAMAWYRRAPGKQRELVAGISSDGSKVYKD<br>SVKGRFTISRDNAKNSVYLQMNSLRAEDTAVYYCYYFRNVSGSSMRYWGQGTLVTVSS |
| 144 | 1F09 | EVQLVESGGGLVQPGGSLTLSCVASGNTSSINAMGWYRRAPGKQRELVAGISSNGSKVYAD<br>SVKGRFTISRDNAKNSVYLQMNSLRAEDTAVYYCYYFRTVTGSSMRYWGQGTLVTVSS |
| 145 | 1F010 | EVQLVESGGGLVQPGGSLTLSCVASGSTRINAMGWYRRAPGKQRELVAGISSDGSKVYKD<br>SVKGRFTISRDNAKNSVYLQMNSLRAEDTAVYYCYYFRTVSGSSMRYWGQGTLVTVSS |
| 146 | 1F011 | EVQLVESGGGLVQPGGSLTLSCVASGSTSSINAIGWYRRAPGKQRELVAGISSDGSKVYAD<br>SVKGRFTISRDNAKNSVYLQMNSLRAEDTAVYYCYYFRTVKGSSMRYWGQGTLVTVSS |
| 147 | 1F012 | EVQLVESGGGLVQPGGSLTLSCVASGLTSSINAMGWYRRAPGKQRELVAGISSDGSKVYQD<br>SVKGRFTISRDNAKNSVYLQMNSLRAEDTAVYYCYYFRTNSGSSMRYWGQGTLVTVSS |
| 148 | 1G01 | EVQLVESGGGLVQPGGSLTLSCVASGSTSSINAMAWYRRAPGKQRELVAGISSDGSKVYAE<br>SVKGRFTISRDNAKNSVYLQMNSLRAEDTAVYYCYYFRTVSGASMRYWGQGTLVTVSS |
| 149 | 1G04 | EVQLVESGGGLVQPGGSLTLSCVASGSTSSTNAMGWYRRAPGKQRELVAGISSDGSKVLAD<br>SVKGRFTISRDNAKNSVYLQMNSLRAEDTAVYYCYYFRTVNLSSMRYWGQGTLVTVSS |
| 150 | 1G05 | EVQLVESGGGLVQPGGSLTLSCVASGSTSSINAIGWYRRAPGKQRELVAGISSDGSKYYAD<br>SVKGRFTISRDNAKNSVYLQMNSLRAEDTAVYYCYYFRTVTGSSMRYWGQGTLVTVSS |

| | | |
|---|---|---|
| 151 | 1G06 | EVQLVESGGGLVQPGGSLTLSCVASGSTSSINAIGWYRRAPGKQRELVAGISSDGSKVYAV SVKGRFTISRDNAKNSVYLQMNSLRAEDTAVYYCYYFRKVSGSSARYWGQGTLVTVSS |
| 152 | 1G07 | EVQLVESGGGLVQPGGSLTLSCVASGSTSSINAMGWYRRAPGKQRELVAGISSDGSKVVAD SVKGRFTISRDNAKNSVYLQMNSLRAEDTAVYYCYYFRTYSGSSMRYWGQGTLVTVSS |
| 153 | 1G09 | EVQLVESGGGLVQPGGSLTLSCVASGSTSSINAMGWYRRAPGKQRELVAGISSDGSKVYAD SVKGRFTISRDNAKNSVYLQMNSLRAEDTAVYYCYYFRTVSKSSMRYWGQGTLVTVSS |
| 154 | 1G011 | EVQLVESGGGLVQPGGSLTLSCVASGSTSSINAMAWYRRAPGKQRELVAGISSDGSKVYAD SVKGRFTISRDNAKNSVYLQMNSLRAEDTAVYYCYYFKTVSGSSMRYWGQGTLVTVSS |
| 155 | 1H01 | EVQLVESGGGLVQPGGSLTLSCVASGSTSSINAMAWYRRAPGKQRELAAGISSDNSKVYAD SVKGRFTISRDNAKNSVYLQMNSLRAEDTAVYYCYYFRTRSGSSMRYWGQGTLVTVSS |
| 156 | 1H02 | EVQLVESGGGLVQPGGSLTLSCVASGSKSSINAMGWYRRAPGKQRELAAGISSDGSKVYAQ SVKGRFTISRDNAKNSVYLQMNSLRAEDTAVYYCYYFRTSSGSSMRYWGQGTLVTVSS |
| 157 | 1H06 | EVQLVESGGGLVQPGGSLTLSCVASGTTSSINAMGWYRRAPGKQRELVAGISSDGSKVYVD SVKGRFTISRDNAKNSVYLQMNSLRAEDTAVYYCYYFRFLSGSSMRYWGQGTLVTVSS |
| 158 | 1H07 | EVQLVESGGGLVQPGGSLTLSCVASGSTSSINAFGWYRRAPGKQRELVAGISSDGSKVYSD SVKGRFTISRDNAKNSVYLQMNSLRAEDTAVYYCYYFRTVSGSSMRYWGQGTLVTVSS |
| 159 | 1H08 | EVQLVESGGGLVQPGGSLTLSCVASGSTFSINAMGWYRRAPGKQRELVAGISSDGSKVLAD SVKGRFTISRDNAKNSVYLQMNSLRAEDTAVYYCYYFRLVSGSSMRYWGQGTLVTVSS |
| 160 | 1H010 | EVQLVESGGGLVQPGGSLTLSCVASGSTRSINAMGWYRRAPGKQRELVAGISSDGSKVYND SVKGRFTISRDNAKNSVYLQMNSLRAEDTAVYYCYYFRTVSGSSMRFWGQGTLVTVSS |
| 161 | 1H011 | EVQLVESGGGLVQPGGSLTLSCVASGSTSSINAIGWYRRAPGKQRELVAGISSDGSKVYND SVKGRFTISRDNAKNSVYLQMNSLRAEDTAVYYCYYFRTQSGSSMRYWGQGTLVTVSS |
| 162 | 1H012 | EVQLVESGGGLVQPGGSLTLSCVASGSTSSINAMGWYRRAPGKQRELVAGISSDGSKVYVD SVKGRFTISRDNAKNSVYLQMNSLRAEDTAVYYCYYFRTVSGSSMPYWGQGTLVTVSS |
| 163 | 2A01 | EVQLVESGGGLVQPGGSLTLSCVASGSTSSINAMGWYRRAPGKQRELVAGISSDGSKVVAD SVKGRFTISRDNAKNSVYLQMNSLRAEDTAVYYCYYFRTLSGSSMRYWGQGTLVTVSS |
| 164 | 2A03 | EVQLVESGGGLVQPGGSLTLSCVASGTTSSINAMGWYRRAPGKQRELVAGISSDGSKVYGD SVKGRFTISRDNAKNSVYLQMNSLRAEDTAVYYCYYFRTVSGSAMRYWGQGTLVTVSS |
| 165 | 2A04 | EVQLVESGGGLVQPGGSLTLSCVASGSTSSINAMAWYRRAPGKQRELVAGISSDGSKVYTD SVKGRFTISRDNAKNSVYLQMNSLRAEDTAVYYCYYFRTTSGSSMRYWGQGTLVTVSS |
| 166 | 2A05 | EVQLVESGGGLVQPGGSLTLSCVASGRTSSINAMGWYRRAPGKQRELVAGISSDGSKVYND SVKGRFTISRDNAKNSVYLQMNSLRAEDTAVYYCYYFRTVSGTSMRYWGQGTLVTVSS |
| 167 | 2A06 | EVQLVESGGGLVQPGGSLTLSCVASGSTSSRNAMGWYRRAPGKQRELVAGISSDGSKVTAD SVKGRFTISRDNAKNSVYLQMNSLRAEDTAVYYCYYFRTRSGSSMRYWGQGTLVTVSS |
| 168 | 2A08 | EVQLVESGGGLVQPGGSLTLSCVASGSTKSINAMGWYRRAPGKQRELVAGISSDGSKVYRD SVKGRFTISRDNAKNSVYLQMNSLRAEDTAVYYCYYFRTSSGSSMRYWGQGTLVTVSS |
| 169 | 2A09 | EVQLVESGGGLVQPGGSLTLSCVASGSTSSRNAMGWYRRAPGKQRELVAGISSNGSKVYSD SVKGRFTISRDNAKNSVYLQMNSLRAEDTAVYYCYYFRTVSGSSMSYWGQGTLVTVSS |
| 170 | 2A011 | EVQLVESGGGLVQPGGSLTLSCVASGSTSSINAIGWYRRAPGKQRELVAGISSDGSKVYSD SVKGRFTISRDNAKNSVYLQMNSLRAEDTAVYYCYYFRPVSGSSMRYWGQGTLVTVSS |
| 171 | 2B01 | EVQLVESGGGLVQPGGSLTLSCVASGSTSLINAMGWYRRAPGKQRELVAGISSDGSKVYAD SVKGRFTISRDNAKNSVYLQMNSLRAEDTAVYYCYYFRHVSGSSMRYWGQGTLVTVSS |
| 172 | 2B02 | EVQLVESGGGLVQPGGSLTLSCVASGSTSSINAMAWYRRAPGKQRELVAGISSDGSKVYAD SVKGRFTISRDNAKNSVYLQMNSLRAEDTAVYYCYYFRTKSGSSMRYWGQGTLVTVSS |
| 173 | 2B03 | EVQLVESGGGLVQPGGSLTLSCVASGSTSSINAMGWYRRAPGKQRELVAGISSDGSLVYAD SVKGRFTISRDNAKNSVYLQMNSLRAEDTAVYYCYYFTTVSGSSMRYWGQGTLVTVSS |
| 174 | 2B05 | EVQLVESGGGLVQPGGSLTLSCVASGTTSSINAMGWYRRAPGKQRELVAGISSDGTKVYAD SVKGRFTISRDNAKNSVYLQMNSLRAEDTAVYYCYYFHTVSGSSMRYWGQGTLVTVSS |
| 175 | 2B07 | EVQLVESGGGLVQPGGSLTLSCVASGSTSSINAFGWYRRAPGKQRELVAGISSDGSKVYAD SVKGRFTISRDNAKNSVYLQMNSLRAEDTAVYYCYYFRTVRGSSMRYWGQGTLVTVSS |
| 176 | 2B010 | EVQLVESGGGLVQPGGSLTLSCVASGSTSSRNAMGWYRRAPGKQRELVAGISSDGSKLYLD SVKGRFTISRDNAKNSVYLQMNSLRAEDTAVYYCYYFRTVLGSSMRYWGQGTLVTVSS |

| | | |
|---|---|---|
| 177 | 2B011 | EVQLVESGGGLVQPGGSLTLSCVASGNTSSINAMGWYRRAPGKQRELVAGISSDGSRVYAD<br>SVKGRFTISRDNAKNSVYLQMNSLRAEDTAVYYCYYFRTVSGSMRSWGQGTLVTVSS |
| 178 | 2B012 | EVQLVESGGGLVQPGGSLTLSCVASGTTSSINAMGWYRRAPGKQRELVAGISSDGSKVYND<br>SVKGRFTISRDNAKNSVYLQMNSLRAEDTAVYYCYYFRTVRGSSMRYWGQGTLVTVSS |
| 179 | 2C01 | EVQLVESGGGLVQPGGSLTLSCVASGSTASINAMGWYRRAPGKQRELVAGISSDGSKVYAD<br>SVKGRFTISRDNAKNSVYLQMNSLRAEDTAVYYCYYFRYVSGSSMRYWGQGTLVTVSS |
| 180 | 2C02 | EVQLVESGGGLVQPGGSLTLSCVASGSTSSINAVGWYRRAPGKQRELVAGISSDGSKVYVD<br>SVKGRFTISRDNAKNSVYLQMNSLRAEDTAVYYCYYFRTVYGSSMRYWGQGTLVTVSS |
| 181 | 2C04 | EVQLVESGGGLVQPGGSLTLSCVASGSTSSRNAMGWYRRAPGKQRELVAGISSDGSKLYAD<br>SVKGRFTISRDNAKNSVYLQMNSLRAEDTAVYYCYYFRTVLGSSMRYWGQGTLVTVSS |
| 182 | 2C06 | EVQLVESGGGLVQPGGSLTLSCVASGSTNSINAMGWYRRAPGKQRELVAGISSDGSKVYKD<br>SVKGRFTISRDNAKNSVYLQMNSLRAEDTAVYYCYYYRTVSGSSMRYWGQGTLVTVSS |
| 183 | 2C07 | EVQLVESGGGLVQPGGSLTLSCVASGSTSSINAMAWYRRAPGKQRELVAGISSDGSKVYAD<br>SVKGRFTISRDNAKNSVYLQMNSLRAEDTAVYYCYYFRSVSGSSMRYWGQGTLVTVSS |
| 184 | 2C08 | EVQLVESGGGLVQPGGSLTLSCVASGSTSRINAMGWYRRAPGKQRELVAGISSDGSKVYQD<br>SVKGRFTISRDNAKNSVYLQMNSLRAEDTAVYYCYYFRRVSGSSMRYWGQGTLVTVSS |
| 185 | 2C09 | EVQLVESGGGLVQPGGSLTLSCVPSGSTSNINAMGWYRRAPGKQRELPAGISSDGTKIYAD<br>SAKVPFTITRDNAKNSVYLQMNSLRAEDTAVYYCYYFRTVSGTSMRYWGQGTLVTVSS |
| 186 | 2C010 | EVQLVESGGGLVQPGGSLTLSCVASGSTSKINAMGWYRRAPGKQRELVAGISSDRSKVYAD<br>SVKGRFTISRDNAKNSVYLQMNSLRAEDTAVYYCYYFRTVAGSSMRYWGQGTLVTVSS |
| 187 | 2D02 | EVQLVESGGGLVQPGGSLTLSCVASGSTSSINALGWYRRAPGKQRELVAGISSDGSLVYAD<br>SVKGRFTISRDNAKNSVYLQMNSLRAEDTAVYYCYYFRIVSGSSMRYWGQGTLVTVSS |
| 188 | 2D03 | EVQLVESGGGLVQPGGSLTLSCVASGKTSSINAMGWYRRAPGKQRELVAGISSDGSKVYAD<br>SVKGRFTISRDNAKNSVYLQMNSLRAEDTAVYYCYYFRTVSGVSMRYWGQGTLVTVSS |
| 189 | 2D04 | EVQLVESGGGLVQPGGSLTLSCVASGSTSSINAVGWYRRAPGKQRELVAGISSDGSKVYRD<br>SVKGRFTISRDNAKNSVYLQMNSLRAEDTAVYYCYYFRTVQGSSMRYWGQGTLVTVSS |
| 190 | 2D05 | EVQLVESGGGLVQPGGSLTLSCVASGSTSRINAMGWYRRAPGKQRELVAGISSDGSKVYAD<br>SVKGRFTISRDNAKNSVYLQMNSLRAEDTAVYYCYYFRTASGSSMRYWGQGTLVTVSS |
| 191 | 2D06 | EVQLVESGGGLVQPGGSLTLSCVASGSTSSINAMGWYRRAPGKQRELVAGISSDGSKVYSD<br>SVKGRFTISRDNAKNSVYLQMNSLRAEDTAVYYCYYFRTVSGSSRYWGQGTLVTVSS |
| 192 | 2D07 | EVQLVESGGGLVQPGGSLTLSCVASGSTSSINAVGWYRRAPGKQRELVAGISSDGTKVYRD<br>SVKGRFTISRDNAKNSVYLQMNSLRAEDTAVYYCYYFRTVQGSSMRYWGQGTLVTVSS |
| 193 | 2D09 | EVQLVESGGGLVQPGGSLTLSCVASGTTSSINAMGWYRRAPGKQRELAAGISSDGSKVYND<br>SVKGRFTISRDNAKNSVYLQMNSLRAEDTAVYYCYYFRTVRGSSMRYWGQGTLVTVSS |
| 194 | 2D010 | EVQLVESGGGLVQPGGSLTLSCVASGSTSSINAMGWYRRAPGKQRELVAGISSDGSKVYAD<br>SVKGRFTISRDNAKNSVYLQMNSLRAEDTAVYYCYYFRTKSGSSMRYWGQGTLVTVSS |
| 195 | 2D011 | EVQLVESGGGLVQPGGSLTLSCVASGTTSSINAMGWYRRAPGKQRELVAGISSDGSKVYAD<br>SVKGRFTISRDNAKNSVYLQMNSLRAEDTAVYYCYYFRTVWGSSMRYWGQGTLVTVSS |
| 196 | 2D012 | EVQLVESGGGLVQPGGSLTLSCVASGKTSSINAMGWYRRAPGKQRELVAGISSDGSKVYTD<br>SVKGRFTISRDNAKNSVYLQMNSLRAEDTAVYYCYYFRTRSGSSMRYWGQGTLVTVSS |
| 197 | 2E01 | EVQLVESGGGLVQPGGSLTLSCVASGSTSSINAMGWYRRAPFKQGELPAGISPDGTKAYAD<br>SAKVRFTISRDNAKNSVYLQMNSLRAEDTAVYYCYYHTVCGTSMGYWGQGTLVTVSS |
| 198 | 2E02 | EVQLVESGGGLVQPGGSLTLSCVASGSTSAINAMGWYRRAPGKQRELVAGISSDGSKVYVD<br>SVKGRFTISRDNAKNSVYLQMNSLRAEDTAVYYCYYFRTVSGSSQRYWGQGTLVTVSS |
| 199 | 2E05 | EVQLVESGGGLVQPGGSLTLSCVASGSPSSINAYGWYRRAPGKQRELVAGISSDGSKVYSD<br>SVKGRFTISRDNAKNSVYLQMNSLRAEDTAVYYCYYFRTVSGSSMSYWGQGTLVTVSS |
| 200 | 2E06 | EVQLVESGGGLVQPGGSLTLSCVASGSTSSINAMGWYRRAPGKQRELVAGISSDGSKVYAS<br>SVKGRFTISRDNAKNSVYLQMNSLRAEDTAVYYCYYFRTVRGSSMRYWGQGTLVTVSS |
| 201 | 2E08 | EVQLVESGGGLVQPGGSLTLSCVASGSRSSINAMGWYRRAPGKQRELVAGISADGSKVYAD<br>SVKGRFTISRDNAKNSVYLQMNSLRAEDTAVYYCYYFRTQSGSSMRYWGQGTLVTVSS |
| 202 | 2E09 | EVQLVESGGGLVQPGGSLTLSCVASGSVSSINAMGWYRRAPGKQRELVAGISSDGSKVYAS<br>SAKGRFTISRDNAKNSVYLQMNSLRAEDTAVYYCYYFRTLSGSSMRYWGQGTLVTVSS |

| 203 | 2E010 | EVQLVESGGGLVQPGGSLTLSCVASGSTSSINAMAWYRRAPGKQRELVAGISSDGSKVYAD
SVKGRFTISRDNAKNSVYLQMNSLRAEDTAVYYCYYFHTVSGSSMRYWGQGTLVTVSS |
| --- | --- | --- |
| 204 | 2E011 | EVQLVESGGGLVQPGGSLTLSCVASGSTSSINAIGWYRRAPGKQRELVAGISSDGSSVYAD
SVKGRFTISRDNAKNSVYLQMNSLRAEDTAVYYCYYFRRVSGSSMRYWGQGTLVTVSS |
| 205 | 2F01 | EVQLVESGGGLVQPGGSLTLSCVASGSTSSINAMGWYRRAPGKQRELVAGISSDGSKVYSD
SVKGRFTISRDNAKNSVYLQMNSLRAEDTAVYYCYYFRLVSGSSMRYWGQGTLVTVSS |
| 206 | 2F02 | EVQLVESGGGLVQPGGSLTLSCVASGSTSSINAVGWYRRAPGKQRELVAGISSDGSKVYAG
SVKGRFTISRDNAKNSVYLQMNSLRAEDTAVYYCYYFRTVSGSYMRYWGQGTLVTVSS |
| 207 | 2F03 | EVQLVESGGGLVQPGGSLTLSCVASGSTSSINAMAWYRRAPGKQRELAAGISSDNSKVYAD
SVKGRFTISRDNAKNSVYLQMNSLRAEDTAVYYCYYFRTVGGSSMRYWGQGTLVTVSS |
| 208 | 2F06 | EVQLVESGGGLVQPGGSLTLSCVASGSTSSINAYGWYRRAPGKQRELVAGISSDGSAVYAD
SVKGRFTISRDNAKNSVYLQMNSLRAEDTAVYYCYYFRTHSGSSMRYWGQGTLVTVSS |
| 209 | 2F07 | EVQLVESGGGLVQPGGSLTLSCVASGSTSSINAVGWYRRAPGKQRELVAGISSDGSSVYAD
SVKGRFTISRDNAKNSVYLQMNSLRAEDTAVYYCYYFRTVSTSSMRYWGQGTLVTVSS |
| 210 | 2F08 | EVQLVESGGGLVQPGGSLTLSCVASGSKSSINAMGWYRRAPGKQRELPAGISSNGTKVYAD
SAKVRFTISRDNAKNSVYLQMNSLRAEDTAVYYCYYFRTVLGTSMRYWGQGTLVTVSS |
| 211 | 2F09 | EVQLVESGGGLVQPGGSLTLSCVASGSTSSINAMAWYRRAPGKQRELVAGISSDGSKLYAD
SVKGRFTISRDNAKNSVYLQMNSLRAEDTAVYYCYYFRTVSGSSMRYWGQGTLVTVSS |
| 212 | 2F11 | EVQLVESGGGLVQPGGSLTLSCVASGSVSSINAMGWYRRAPGKQRELVAGISSDGSKVYKD
SVKGRFTISRDNAKNSVYLQMNSLRAEDTAVYYCYYFRTVSGSSMGYWGQGTLVTVSS |
| 213 | 2G03 | EVQLVESGGGLVQPGGSLTLSCVASGSTSSINAMGWYRRAPGKQRELVAGISSDGSLVYAD
SVKGRFTISRDNAKNSVYLQMNSLRAEDTAVYYCYYFRTVSGSSMRAWGQGTLVTVSS |
| 214 | 2G04 | EVQLVESGGGLVQPGGSLTLSCVASGSTSSINAMGWYRRAPGKQRELVAGISSDGSLVYAD
SVKGRFTISRDNAKNSVYLQMNSLRAEDTAVYYCYYFRILSGSSMRYWGQGTLVTVSS |
| 215 | 2G07 | EVQLVESGGGLVQPGGSLTLSCVASGSTSSINAMAWYRRAPGKQRELVAGISSDGSKVYAD
SVKGRFTISRDNAKNSVYLQMNSLRAEDTAVYYCYYFRTVQGSSMRYWGQGTLVTVSS |
| 216 | 2G08 | EVQLVESGGGLVQPGGSLTLSCVASGSTSYINAMGWYRRAPGKQRELVAGISSDGSKVYAD
SVKGRFTISRDNAKNSVYLQMNSLRAEDTAVYYCYYFRTVSGQSMGYWGQGTLVTVSS |
| 217 | 2G09 | EVQLVESGGGLVQPGGSLTLSCVASGSTSSINAMGWYRRAPGKQRELVAGVSSDGSKVYAD
SVKGRFTISRDNAKNSVYLQMNSLRAEDTAVYYCYYFRTVSGSSARYWGQGTLVTVSS |
| 218 | 2G011 | EVQLVESGGGLVQPGGSLTLSCVASGSTSSINAMGWYRRAPGKQRELPAGISRDGSKVYAD
SVKGRFTISRDNAKNSVYLQMNSLRAEDTAVYYCYYFRYVSGSSMRYWGQGTLVTVSS |
| 219 | 2H010 | EVQLVESGGGLVQPGGSLTLSCVASGSTSSINAMGWYRRAPGKQRELAAGISSDGSKLYAD
VKGRFTISRDNAKNSVYLQMNSLRAEDTAVYYCYYFRTVSGSSMRYWGQGTLVTVSS |
| 220 | 2H011 | EVQLVESGGGLVQPGGSLTLSCVASGSTSRINAMGWYRRAPGKQRELVAGISSDGSKVYAD
SVKGRFTISRDNAKNSVYLQMNSLRAEDTAVYYCYYFRRVSGSSMRYWGQGTLVTVSS |
| 221 | 2H02 | EVQLVESGGGLVQPGGSLTLSCVASGSTSSINAMAWYRRAPGKQRELAAGISSDGSKVYAD
SVKGRFTISRDNAKNSVYLQMNSLRAEDTAVYYCYYFHTVSGSSMRYWGQGTLVTVSS |
| 222 | 2H03 | EVQLVESGGGLVQPGGSLTLSCVASGSTSSINAMAWYRRAPGKQRELVAGISSDGSKVYAD
SVKGRFTISRDNAKNSVYLQMNSLRAEDTAVYYCYYFRQVSGSSMRYWGQGTLVTVSS |
| 223 | 2H04 | EVQLVESGGGLVQPGGSLTLSCVASGSTSSINAMGWYRRAPGKQRELVAGISSDTSKVYAD
SVKGRFTISRDNAKNSVYLQMNSLRAEDTAVYYCYYFRTVSGSYMRYWGQGTLVTVSS |
| 224 | 2H06 | EVQLVESGGGLVQPGGSLTLSCVASGSTSTINAMGWYRRAPGKQRELVAGISSDGSKVYAD
SVKGRFTISRDNAKNSVYLQMNSLRAEDTAVYYCYYFRTASGSSMRYWGQGTLVTVSS |
| 225 | 2H07 | EVQLVESGGGLVQPGGSLTLSCVASGSTSSINAVGWYRRAPGKQRELVAGISSDGSTVYAD
SVKGRFTISRDNAKNSVYLQMNSLRAEDTAVYYCYYFRTVSGHSMRYWGQGTLVTVSS |
| 226 | 2H08 | EVQLVESGGGLVQPGGSLTLSCVASGSTSSINAMGWYRRAPGKQRELAAGISKDGSKVYAD
SAKGRFTISRDNAKNSVYLQMNSLRAEDTAVYYCYYFRTVSGSSSRYWGQGTLVTVSS |
| 227 | 2E05-M106Y | EVQLVESGGGLVQPGGSLTLSCVASGSPSSINAYGWYRRAPGKQRELVAGISSDGSKVYSD
SVKGRFTISRDNAKNSVYLQMNSLRAEDTAVYYCYYFRTVSGSSYSYWGQGTLVTVSS |
| 228 | 2E05-M106Q | EVQLVESGGGLVQPGGSLTLSCVASGSPSSINAYGWYRRAPGKQRELVAGISSDGSKVYSD
SVKGRFTISRDNAKNSVYLQMNSLRAEDTAVYYCYYFRTVSGSSQSYWGQGTLVTVSS |

|     |       |                                                                                                                                                  |
|-----|-------|--------------------------------------------------------------------------------------------------------------------------------------------------|
| 229 | 3A01  | EVQLVESGGGLVQPGGSLTLSCAASGSSVKFLSMAWYRQAPGKKRELVAGISADGSTDYID SVKGRFTISRDNAKNSVYLQMNSLRAEDTAVYYCYAYRWTRRYTYWGQGTLVTVSS |
| 230 | 3A02  | EVQLVESGGGLVQPGGSLTLSCAASGSSVSFLSLAWYRQAPGKKRELVAGISADGSTAYID SVKGRFTISRDNAKNSVYLQMNSLRAEDTAVYYCYAYRWRTRYTYWGQGTLVTVSS |
| 231 | 3A03  | EVQLVESGGGLVQPGGSLTLSCAASGSRVSFLSMAWYRQAPGKKRELVAGISRDGSTDYID SVKGRFTISRDNAKNSVYLQMNSLRAEDTAVYYCYAYRWTTRRYTYWGQGTLVTVSS |
| 232 | 3A04  | EVQLVESGGGLVQPGGSLTLSCAASGSQVSFLSMAWYRQAPGKKRELVAGISRDGSTDYID SVKGRFTISRDNAKNSVYLQMNSLRAEDTAVYYCYAYRWTTRYIYWGQGTLVTVSS |
| 233 | 3A05  | EVQLVESGGGLVQPGGSLTLSCAASGSSVSFLSMAWYRQAPGKKRELVAGISEAGSTDYID SVKGRFTISRDNAKNSVYLQMNSLRAEDTAVYYCYAYRWRTRYTYWGQGTLVTVSS |
| 234 | 3A06  | EVQLVESGGGLVQPGGSLTLRCAASGSKVSFLSMAWYRQAPGKKRELVAGISADGSTDYVD SVKGRFTISRDNAKNSVYLQMNSLRAEDTAVYYCYAYRWTRRYTYWGQGTLVTVSS |
| 235 | 3A08  | EVQLVESGGGLVQPGGSLTLSCAASGSSVGFLSMAWYRQAPGKKRELVAGISADGSTDYIR SVKGRFTISRDNAKNSVYLQMNSLRAEDTAVYYCYAYRWRTRYTYWGQGTLVTVSS |
| 236 | 3A09  | EVQLVESGGGLVQPGGSLTLSCAASGSSVSFLSMAWYRQAPGKKRELVAGISADGSVDYID SVKGRFTISRDNAKNSVYLQMNSLRAEDTAVYYCYAYRWTTRYIYWGQGTLVTVSS |
| 237 | 3A010 | EVQLVESGGGLVQPGGSLTLSCAASGSRVSFLSMAWYRQAPGKKRELVAGISADGSTLYID SVKGRFTISRDNAKNSVYLQMNSLRAEDTAVYYCYAYRWTTRRTYWGQGTLVTVSS |
| 238 | 3A011 | EVQLVESGGGLVQPGGSLTLSCAASGSSVSFLSLAWYRQAPGKKRELVAGISTDGSTDYID SVKGRFTISRDNAKNSVYLQMNSLRAEDTAVYYCYAYRWRTRYTYWGQGTLVTVSS |
| 239 | 3B01  | EVQLVESGGGLVQPGGSLTLSCAASGSSVSFLSMAWYRQAPGKKRELVAGISGDGSTDYID SVKGRFTISRDNAKNSVYLQMNSLRAEDTAVYYCYAYRWTTRYTYWGQGTLVTVSS |
| 240 | 3B02  | EVQLVESGGGLVQPGGSLTLSCAASGSSVQFLSMAWYRQAPGKKRELVAGISADGSTDYIN SVKGRFTISRDNAKNSVYLQMNSLRAEDTAVYYCYAYRWRTRYTYWGQGTLVTVSS |
| 241 | 3B04  | EVQLVESGGGLVQPGGSLTLSCAASGSNVSFLSMAWYRQAPGKKRELVAGISARGSTDYID SVKGRFTISRDNAKNSVYLQMNSLRAEDTAVYYCYAYHWTTRYTYWGQGTLVTVSS |
| 242 | 3B05  | EVQLVESGGGLVQPGGSLTLSCVASGSSVKFLSMAWYRQAPGKKRELVAGISADGSTTYID SVKGRFTISRDNAKNSVYLQMNSLRAEDTAVYYCYAYRWTTRRTYWGQGTLVTVSS |
| 243 | 3B06  | EVQLVESGGGLVQPGGSLTLSCAASGKSVSFLSMAWYRQAPGKKRELVAGISKDGSTDYID SVKGRFTISRDNAKNSVYLQMNSLRAEDTAVYYCYAYRWTTRYTYWGQGTLVTVSS |
| 244 | 3B07  | EVQLVESGGGLVQPGGSLTLSCAASGSRVSFLSMAWYRQAPGKKRELVAGISADGSTTYID SVKGRFTISRDNAKNSVYLQMNSLRAEDTAVYYCYAYRWTTRYTYWGQGTLVTVSS |
| 245 | 3B09  | EVQLVESGGGLVQPGGSLTLSCAASGSHVSFLSMAWYRQAPGKKRELVAGISANGSTDYID SVKGRFTISRDNAKNSVYLQMNSLRAEDTAVYYCYAYRWTTRYAYWGQGTLVTVSS |
| 246 | 3B010 | EVQLVESGGGLVQPGGSLTLSCAASGSSVSFLSMAWYRQAPGKKRELVAGISRDGSTDYID SVKGRFTISRDNAKNSVYLQMNSLRAEDTAVYYCYAYRWVTRYTYWGQGTLVTVSS |
| 247 | 3B011 | EVQLVESGGGLVQPGGSLTLSCAASGSSVSFLSMAWYRQAPGKKRELVAGISADGSADYID SVKGRFTISRDNAKNSVYLQMNSLRAEDTAVYYCYAYRWVTRYTYWGQGTLVTVSS |
| 248 | 3C01  | EVQLVESGGGLVQPGGSLTLSCAASGSSVRFLSMAWYRQAPGKKRELVAGISAHGSTDYID SVKGRFTISRDNAKNSVYLQMNSLRAEDTAVYYCYAYRWSTRYTYWGQGTLVTVSS |
| 249 | 3C02  | EVQLVESGGGLVQPGGSLTLSCAASGSSVRFLSMAWYRQAPGKKRELVAGISADGSTIYID SVKGRFTISRDNAKNSVYLQMNSLRAEDTAVYYCYAYRWRTRYTYWGQGTLVTVSS |
| 250 | 3C03  | EVQLVESGGGLVQPGGSLTLSCAASGSSVRFLSMAWYRQAPGKKRELVAGISRDGSTVYID SVKGRFTISRDNAKNSVYLQMNSLRAEDTAVYYCYAYRWTTRGTYWGQGTLVTVSS |
| 251 | 3C04  | EVQLVESGGGLVQPGGSLTLSCAASGSHVSFLSMAWYRQAPGKKRELVAGISADGPTDYID SVKGRFTISRDNAKNSVYLQMNSLRAEDTAVYYCYAYRWDTRYTYWGQGTLVTVSS |
| 252 | 3C05  | EVQLVESGGGLVQPGGSLTLSCVASGTSVSFLSMAWYRQAPGKKRELVAGISADGSTTYID SVKGRFTISRDNAKNSVYLQMNSLRAEDTAVYYCYAYRWTTRRTYWGQGTLVTVSS |
| 253 | 3C06  | EVQLVESGGGLVQPGGSLTLSCAASGTSVSFLSIAWYRQAPGKKRELVAGISADGSTDYIA SVKGRFTISRDNAKNSVYLQMNSLRAEDTAVYYCYAYRWRTRYTYWGQGTLVTVSS |
| 254 | 3C08  | EVQLVESGGGLVQPGGSLTLSCAASGSSVKFLSMAWYRQAPGKKRELVAGISLDGSTDYID SVKGRFTISRDNAKNSVYLQMNSLRAEDTAVYYCYAYRWTGRYTYWGQGTLVTVSS |

| 255 | 3C09 | EVQLVESGGGLVQPGGSLTLSCAASGSSVSFLSMAWYRQAPGKKRELVAGISADGSTIYID SVKGRFTISRDNAKNSVYLQMNSLRAEDTAVYYCYAYRWRTRYTYWGQGTLVTVSS |
|---|---|---|
| 256 | 3C011 | EVQLVESGGGLVQPGGSLTLSCAASGSSVRFLSMAWYRQAPGKKRELVAGISAHGSTDYID SVKGRFTISRDNAKNSVYLQMNSLRAEDTAVYYCYAYRWRTRYTYWGQGTLVTVSS |
| 257 | 3D01 | EVQLVESGGGLVQPGGSLTLSCAASGSSVSFLSMAWYRQAPGKKRELVAGISRDGSTDYID SVKGRFTISRDNAKNSVYLQMNSLRAEDTAVYYCYAYRWITRYTYWGQGTLVTVSS |
| 258 | 3D02 | EVQLVESGGGLVQPGGSLTLSCAASGSSVRFLSMAWYRQAPGKKRELVAGISRDGSTDYID SVKGRFTISRDNAKNSVYLQMNSLRAEDTAVYYCYAYRWITRYTYWGQGTLVTVSS |
| 259 | 3D03 | EVQLVESGGGLVQPGGSLTLSCAASGSSVVFLSMAWYRQAPGKKRELVAGISADGSMDYID SVKGRFTISRDNAKNSVYLQMNSLRAEDTAVYYCYAYRWRTRYTYWGQGTLVTVSS |
| 260 | 3D05 | EVQLVESGGGLVQPGGSLTLSCAASGSSVRFLSMAWYRQAPGKKRELVAGISADGSTDYID SVKGRFTISRDNAKNSVYLQMNSLRAEDTAVYYCYAYRWTRRYTYWGQGTLVTVSS |
| 261 | 3D07 | EVQLVESGGGLVQPGGSLTLSCAASGSSVRFLSMAWYRQAPGKKRELVAGISADGSTDYID SVKGRFTISRDNAKNSVYLQMNSLRAEDTAVYYCYAYSWTTRYTYWGQGTLVTVSS |
| 262 | 3D08 | EVQLVESGGGLVQPGGSLTLSCAASGSSVRFLSMAWYRQAPGKKRELVAGISANGSTDYID SVKGRFTISRDNAKNSVYLQMNSLRAEDTAVYYCYAYRWTNRYTYWGQGTLVTVSS |
| 263 | 3D09 | EVQLVESGGGLVQPGGSLTLSCAASGSSVSRLSMAWYRQAPGKKRELVAGISANGSTTYID SVKGRFTISRDNAKNSVYLQMNSLRAEDTAVYYCYAYRWTTRYTYWGQGTLVTVSS |
| 264 | 3D010 | EVQLVESGGGLVQPGGSLTLSCAASGSSKSFLSMAWYRQAPGKKRELVAGISADGSTSYID SVKGRFTISRDNAKNSVYLQMNSLRAEDTAVYYCYAYRWTTRYTYWGQGTLVTVSS |
| 265 | 3D011 | EVQLVESGGGLVQPGGSLTLSCAASGSSVSRLSMAWYRQAPGKKRELVAGISADGSRDYID SVKGRFTISRDNAKNSVYLQMNSLRAEDTAVYYCYAYRWTTRYKYWGQGTLVTVSS |
| 266 | 3E01 | EVQLVESGGGLVQPGGSLTLSCAASGSSVKFLSMAWYRQAPGKKRELVAGISADGSTMYID SVKGRFTISRDNAKNSVYLQMNSLRAEDTAVYYCYAYRWHTRYTYWGQGTLVTVSS |
| 267 | 3E02 | EVQLVESGGGLVQPGGSLTLSCAASGSGVRFLSMAWYRQAPGKKRELVAGISPDGSTDYID SVKGRFTISRDNAKNSVYLQMNSLRAEDTAVYYCYAYRWTRRYTYWGQGTLVTVSS |
| 268 | 3E03 | EVQLVESGGGLVQPGGSLTLSCAASGSSVRFLSMAWYRQAPGKKRELVAGISGDGSTDYID SVKGRFTISRDNAKNSVYLQMNSLRAEDTAVYYCYAYRWMTRYTYWGQGTLVTVSS |
| 269 | 3E04 | EVQLVESGGGLVQPGGSLTLSCAASGSSVHFLSMAWYRQAPGKKRELVAGISRDGSTDYID SVKGRFTISRDNAKNSVYLQMNSLRAEDTAVYYCYAYRWTTRYRYWGQGTLVTVSS |
| 270 | 3E09 | EVQLVESGGGLVQPGGSLTLSCAASGSSVRFLSMAWYRQAPGKKRELVAGISRDGSTDYID SVKGRFTISRDNAKNSVYLQMNSLRAEDTAVYYCYAYRWSTRYTYWGQGTLVTVSS |
| 271 | 3E011 | EVQLVESGGGLVQPGGSLTLSCAASGSKVSFLSMAWYRQAPGKKRELVAGISRDGSTDYID SVKGRFTISRDNAKNSVYLQMNSLRAEDTAVYYCYAYRWTTRYTFWGQGTLVTVSS |
| 272 | 3F03 | EVQLVESGGGLVQPGGSLTLSCAASGSSVSFLSMAWYRQAPGKKRELVAGISADGSTDYID SVKGRFTISRDNAKNSVYLQMNSLRAEDTAVYYCYAYRWRTRYTYWGQGTLVTVSS |
| 273 | 3F05 | EVQLVESGGGLVQPGGSLTLSCAASGSKVSFLSMAWYRQAPGKKRELVAGISTDGSTDYID SVKGRFTISRDNAKNSVYLQMNSLRAEDTAVYYCYAYRWTTRRTYWGQGTLVTVSS |
| 274 | 3F06 | EVQLVESGGGLVQPGGSLTLSCAASGSRVSFLSMAWYRQAPGKKRELVAGISADGSTSYID SVKGRFTISRDNAKNSVYLQMNSLRAEDTAVYYCYAYRWATRYTYWGQGTLVTVSS |
| 275 | 3F08 | EVQLVESGGGLVQPGGSLTLSCAASGSRVSFLSMAWYRQAPGKKRELVAGISADGSTLYID SVKGRFTISRDNAKNSVYLQMNSLRAEDTAVYYCYAYRWHTRYTYWGQGTLVTVSS |
| 276 | 3F09 | EVQLVESGGGLVQPGGSLTLSCAASGSSVRFLSMAWYRQAPGKKRELVAGISRDGSTDYID SVKGRFTISRDNAKNSVYLQMNSLRAEDTAVYYCYAYRWGTRYTYWGQGTLVTVSS |
| 277 | 3F010 | EVQLVESGGGLVQPGGSLTLSCAASYSSVSRLSMAWYRQAPGKKRELVAGISADGSTVYID SVKGRFTISRDNAKNSVYLQMNSLRAEDTAVYYCYAYRWTTRNTYWGQGTLVTVSS |
| 278 | 3F011 | EVQLVESGGGLVQPGGSLTLSCAASGSSVSFLSMAWYRQAPGKKRELVAGISTDGSTDYID SVKGRFTISRDNAKNSVYLQMNSLRAEDTAVYYCYAYRWRTRYTYWGQGTLVTVSS |
| 279 | 3G01 | EVQLVESGGGLVQPGGSLTLSCAASGSSVSFLSMAWYRQAPGKKRELVAGISADGSTLYID SVKGRFTISRDNAKNSVYLQMNSLRAEDTAVYYCYAYRWTTRYAYWGQGTLVTVSS |
| 280 | 3G02 | EVQLVESGGGLVQPGGSLTLSCAASGSSVSFLSMAWYRQAPGKKRELVAGISADGRTDYID SVKGRFTISRDNAKNSVYLQMNSLRAEDTAVYYCYAYRWRTRYTYWGQGTLVTVSS |

| | | |
|---|---|---|
| 281 | 3G04 | EVQLVESGGGLVQPGGSLTLSCVASGTSVSFLSMAWYRQAPGKKRELVAGISADGSTIYID<br>SVKGRFTISRDNAKNSVYLQMNSLRAEDTAVYYCYAYRWTTRRTYWGQGTLVTVSS |
| 282 | 3G06 | EVQLVESGGGLVQPGGSLTLSCAASGSSVKFLSMAWYRQAPGKKRELVAGISADGSTLYID<br>SVKGRFTISRDNAKNSVYLQMNSLRAEDTAVYYCYAYRWTTRRTYWGQGTLVTVSS |
| 283 | 3G07 | EVQLVESGGGLVQPGGSLTLSCAASGSSVSFLSMAWYRQAPGKKRELVAGISRDGSTDYID<br>SVKGRFTISRDNAKNSVYLQMNSLRAEDTAVYYCYAYRWTSRYTYWGQGTLVTVSS |
| 284 | 3G08 | EVQLVESGGGLVQPGGSLTLSCAASGSRVSFLSMAWYRQAPGKKRELVAGISKDGSTDYID<br>SVKGRFTISRDNAKNSVYLQMNSLRAEDTAVYYCYAYRWTTRVTYWGQGTLVTVSS |
| 285 | 3G09 | EVQLVESGGGLVQPGGSLTLSCAASGSSVSVLSMAWYRQAPGKKRELVAGISADGSTDYIG<br>SVKGRFTISRDNAKNSVYLQMNSLRAEDTAVYYCYAYRWTTRTTYWGQGTLVTVSS |
| 286 | 3G010 | EVQLVESGGGLVQPGGSLTLSCAASGSSVSFLSMAWYRQAPGKKRELVAGISVDGSTDYID<br>SVKGRFTISRDNAKNSVYLQMNSLRAEDTAVYYCYAYRWRTRYTYWGQGTLVTVSS |
| 287 | 3G011 | EVQLVESGGGLVQPGGSLTLSCAASGSRVSFLSMAWYRQAPGKKRELVAGISADGSTGYID<br>SVKGRFTISRDNAKNSVYLQMNSLRAEDTAVYYCYAYRWATRYTYWGQGTLVTVSS |
| 288 | 3H01 | EVQLVESGGGLVQPGGSLTLSCVASGSSVKFLSMAWYRQAPGKKRELVAGISGDGSTTYID<br>SVKGRFTISRDNAKNSVYLQMNSLRAEDTAVYYCYAYRWTTRRTYWGQGTLVTVSS |
| 289 | 3H03 | EVQLVESGGGLVQPGGSLTLSCAASGSSVRFLSMAWYRQAPGKKRELVAGISTDGSTDYID<br>SVKGRFTISRDNAKNSVYLQMNSLRAEDTAVYYCYALRWTTRYTYWGQGTLVTVSS |
| 290 | 3H06 | EVQLVESGGGLVQPGGSLTLSCAASGSSVSQLSMAWYRQAPGKKRELVAGISADGSTDYED<br>SVKGRFTISRDNAKNSVYLQMNSLRAEDTAVYYCYAYRWTTRGTYWGQGTLVTVSS |
| 291 | 3H07 | EVQLVESGGGLVQPGGSLTLSCAASGSRVSFLSMAWYRQAPGKKRELVAGISADGSTSYID<br>SVKGRFTISRDNAKNSVYLQMNSLRAEDTAVYYCYAYRWRTRYTYWGQGTLVTVSS |
| 292 | 3H09 | EVQLVESGGGLVQPGGSLTLSCAASKSSVSFLSMAWYRQAPGKKRELVAGISADGSTDYID<br>SVKGRFTISRDNAKNSVYLQMNSLRAEDTAVYYCYAYRWTTRATYWGQGTLVTVSS |
| 293 | 3H010 | EVQLVESGGGLVQPGGSLTLSCAASGSSVSFLSMAWYRQAPGKKRELVAGISADGSTAYID<br>SVKGRFTISRDNAKNSVYLQMNSLRAEDTAVYYCYAYRWTTRRTYWGQGTLVTVSS |
| 294 | 3H011 | EVQLVESGGGLVQPGGSLTLSCAASGSSVKFLSMAWYRQAPGKKRELVAGISADGSTVYID<br>SVKGRFTISRDNAKNSVYLQMNSLRAEDTAVYYCYAYRWPTRYTYWGQGTLVTVSS |
| 295 | 4A01 | EVQLVESGGGLVQPGGSLTLSCAASGSSVRFLSMAWYRQAPGKKRELVAGISQDGSTDYID<br>SVKGRFTISRDNAKNSVYLQMNSLRAEDTAVYYCYAYRWRTRYTYWGQGTLVTVSS |
| 296 | 4A02 | EVQLVESGGGLVQPGGSLTLSCAASGSSVRFLSMAWYRQAPGKKRELVAGISNDGSTDYID<br>SVKGRFTISRDNAKNSVYLQMNSLRAEDTAVYYCYAYRWKTRYTYWGQGTLVTVSS |
| 297 | 4A04 | EVQLVESGGGLVQPGGSLTLSCAASGSRVSFLSMAWYRQAPGKKRELVAGISARGSTDYID<br>SVKGRFTISRDNAKNSVYLQMNSLRAEDTAVYYCYAYRWSTRYTYWGQGTLVTVSS |
| 298 | 4A05 | EVQLVESGGGLVQPGGSLTLSCAASGSSVSFLSLAWYRQAPGKKRELVAGISADGSTDYID<br>SVKGRFTISRDNAKNSVYLQMNSLRAEDTAVYYCYAYRWKTRRTYWGQGTLVTVSS |
| 299 | 4A06 | EVQLVESGGGLVQPGGSLTLSCAASGSSVRFLSMAWYRQAPGKKRELVAGISRDGSTDYID<br>SVKGRFTISRDNAKNSVYLQMNSLRAEDTAVYYCYAYRWTTRRTYWGQGTLVTVSS |
| 300 | 4A07 | EVQLVESGGGLVQPGGSLTLSCAASGSKVSFLSMAWYRQAPGKKRELVAGISADGSTLYID<br>SVKGRFTISRDNAKNSVYLQMNSLRAEDTAVYYCYAYRWTTRYRYWGQGTLVTVSS |
| 301 | 4A08 | EVQLVESGGGLVQPGGSLTLSCAASGSSVSFLSMAWYRQAPGKKRELVAGISADGSTNYID<br>SVKGRFTISRDNAKNSVYLQMNSLRAEDTAVYYCYAYRWRTRYTYWGQGTLVTVSS |
| 302 | 4A010 | EVQLVESGGGLVQPGGSLTLSCAASGSSVRFLSMAWYRQAPGKKRELVAGISADGSTVYID<br>SVKGRFTISRDNAKNSVYLQMNSLRAEDTAVYYCYAYRWTTRYKYWGQGTLVTVSS |
| 303 | 4A011 | EVQLVESGGGLVQPGGSLTLSCAASGSKVSFLSMAWYRQAPGKKRELVAGISADGSTTYID<br>SVKGRFTISRDNAKNSVYLQMNSLRAEDTAVYYCYAYRWKTRYTYWGQGTLVTVSS |
| 304 | 4A09 | EVQLVESGGGLVQPGGSLTLSCAASGSSVKFLSMAWYRQAPGKKRELVAGISADGSTDYIG<br>SVKGRFTISRDNAKNSVYLQMNSLRAEDTAVYYCYAYRWTTRVTYWGQGTLVTVSS |
| 305 | 4B01 | EVQLVESGGGLVQPGGSLTLSCAASGSSVKFLSMAWYRQAPGKKRELVAGISRDGSTDYID<br>SVKGRFTISRDNAKNSVYLQMNSLRAEDTAVYYCYAYRWTTRFTYWGQGTLVTVSS |
| 306 | 4B02 | EVQLVESGGGLVQPGGSLTLSCAASGSRVSFLSMAWYRQAPGKKRELVAGISADGSTTYID<br>SVKGRFTISRDNAKNSVYLQMNSLRAEDTAVYYCYAYRWTTRFTYWGQGTLVTVSS |

-continued

| | | |
|---|---|---|
| 307 | 4B04 | EVQLVESGGGLVQPGGSLTLSCAASGSSVLFLSMAWYRQAPGKKRELVAGVSSDGSTDYID SVKGRFTISRDNAKNSVYLQMNSLRAEDTAVYYCYAYRWRTRYTYWGQGTLVTVSS |
| 308 | 4B05 | EVQLVESGGGLVQPGGSLTLSCAASGSRVSFLSMAWYRQAPGKKRELVAGISADGHTDYID SVKGRFTISRDNAKNSVYLQMNSLRAEDTAVYYCYAYRWTTRYTHWGQGTLVTVSS |
| 309 | 4B06 | EVQLVESGGGLVQPGGSLTLSCAASGSRVSFLSMAWYRQAPGKKRELVAGISADGSTDYED SVKGRFTISRDNAKNSVYLQMNSLRAEDTAVYYCYAYRWTTRRYTYWGQGTLVTVSS |
| 310 | 4B07 | EVQLVESGGGLVQPGGSLTLSCAASGSSVGFLSMAWYRQAPGKKRELVAGISADGSTVYID SVKGRFTISRDNAKNSVYLQMNSLRAEDTAVYYCYAYRWTTRYTYWGQGTLVTVSS |
| 311 | 4B08 | EVQLVESGGGLVQPGGSLTLSCAASGSSVSFMSMAWYRQAPGKKRELVAGISADGSTDYIA SVKGRFTISRDNAKNSVYLQMNSLRAEDTAVYYCYAYRWTTRSTYWGQGTLVTVSS |
| 312 | 4B09 | EVQLVESGGGLVQPGGSLTLSCAASGSSVSFLSMAWYRQAPGKKRELVAGISADGSTDYIS SVKGRFTISRDNAKNSVYLQMNSLRAEDTAVYYCYAYSWTTRYTYWGQGTLVTVSS |
| 313 | 4B011 | EVQLVESGGGLVQPGGSLTLSCAASGSSVTFLSMAWYRQAPGKKRELVAGISADGSTVYID SVKGRFTISRDNAKNSVYLQMNSLRAEDTAVYYCYAYRWTTRGTYWGQGTLVTVSS |
| 314 | 4C01 | EVQLVESGGGLVQPGGSLTLSCAASGSSVRFLSMAWYRQAPGKKRELVAGISADGSTVYID SVKGRFTISRDNAKNSVYLQMNSLRAEDTAVYYCYAYRWKTRYTYWGQGTLVTVSS |
| 315 | 4C02 | EVQLVESGGGLVQPGGSLTLSCAASGSKVSFLSMAWYRQAPGKKRELVAGISADGSTTYID SVKGRFTISRDNAKNSVYLQMNSLRAEDTAVYYCYAYRWTTRFTYWGQGTLVTVSS |
| 316 | 4C03 | EVQLVESGGGLVQPGGSLTLSCAASGSKVSFMSMAWYRQAPGKKRELVAGISVDGSTDYID SVKGRFTISRDNAKNSVYLQMNSLRAEDTAVYYCYAYRWRTRYTYWGQGTLVTVSS |
| 317 | 4C05 | EVQLVESGGGLVQPGGSLTLSCAASGSSVSNLSMAWYRQAPGKKRELVAGISADGSTAYID SVKGRFTISRDNAKNSVYLQMNSLRAEDTAVYYCYAYRWTTRRTYWGQGTLVTVSS |
| 318 | 4C06 | EVQLVESGGGLVQPGGSLTLSCAASNSSVSKLSMAWYRQAPGKKRELVAGISADGSTAYID SVKGRFTISRDNAKNSVYLQMNSLRAEDTAVYYCYAYRWSTRYTYWGQGTLVTVSS |
| 319 | 4C07 | EVQLVESGGGLVQPGGSLTLSCAASGSKVSFLSMAWYRQAPGKKRELVAGISADGSKDYID SVKGRFTISRDNAKNSVYLQMNSLRAEDTAVYYCYAYRWTTRLTYWGQGTLVTVSS |
| 320 | 4C08 | EVQLVESGGGLVQPGGSLTLSCVASGSQVSFLSMAWYRQAPGKKRELVAGISADGSTDYED SVKGRFTISRDNAKNSVYLQMNSLRAEDTAVYYCYAYRWTRRYTYWGQGTLVTVSS |
| 321 | 4C010 | EVQLVESGGGLVQPGGSLTLSCAASGSKVSFMSMAWYRQAPGKKRELVAGISADGSTDYID SVKGRFTISRDNAKNSVYLQMNSLRAEDTAVYYCYAYRWTTRLTYWGQGTLVTVSS |
| 322 | 4C011 | EVQLVESGGGLVQPGGSLTLSCAASGSRVSFLSMAWYRQAPGKKRELVAGISADGSTVYID SVKGRFTISRDNAKNSVYLQMNSLRAEDTAVYYCYAYRWTRRYTYWGQGTLVTVSS |
| 323 | 4D01 | EVQLVESGGGLVQPGGSLTLSCAASGSSVRFLSMAWYRQAPGKKRELVAGISADGSTVYID SVKGRFTISRDNAKNSVYLQMNSLRAEDTAVYYCYAYRWTTRRTYWGQGTLVTVSS |
| 324 | 4D02 | EVQLVESGGGLVQPGGSLTLSCAASGSKVSFLSMAWYRQAPGKKRELVAGISARGSTDYID SVKGRFTISRDNAKNSVYLQMNSLRAEDTAVYYCYAYQWTTRYTYWGQGTLVTVSS |
| 325 | 4D03 | EVQLVESGGGLVQPGGSLTLSCAASGSSVRFLSMAWYRQAPGKKRELVAGISATGSTDYID SVKGRFTISRDNAKNSVYLQMNSLRAEDTAVYYCYAYRWTRRYTYWGQGTLVTVSS |
| 326 | 4D04 | EVQLVESGGGLVQPGGSLTLSCAASGSSVSFLSIAWYRQAPGKKRELVAGISKDGSTDYID SVKGRFTISRDNAKNSVYLQMNSLRAEDTAVYYCYAYRWTTRMTYWGQGTLVTVSS |
| 327 | 4D05 | EVQLVESGGGLVQPGGSLTLSCAASGSSSFLSMAWYRQAPGKKRELVAGISADGSTVYID SVKGRFTISRDNAKNSVYLQMNSLRAEDTAVYYCYAYRWTTRRTYWGQGTLVTVSS |
| 328 | 4D06 | EVQLVESGGGLVQPGGSLTLSCAASGSSVKFLSMAWYRQAPGKKRELVAGISPDGSTDYID SVKGRFTISRDNAKNSVYLQMNSLRAEDTAVYYCYAYRWTTRYRYWGQGTLVTVSS |
| 329 | 4D08 | EVQLVESGGGLVQPGGSLTLSCAASGSSVNFLSMAWYRQAPGKKRELVAGISADGSTHYID SVKGRFTISRDNAKNSVYLQMNSLRAEDTAVYYCYAYRWLTRYTYWGQGTLVTVSS |
| 330 | 4D09 | EVQLVESGGGLVQPGGSLTLSCAASGSSVKFLSMAWYRQAPGKKRELVAGISADGSTDYIL SVKGRFTISRDNAKNSVYLQMNSLRAEDTAVYYCYAYEWTTRYTYWGQGTLVTVSS |
| 331 | 4D010 | EVQLVESGGGLVQPGGSLTLSCAASGSSVSFLSMAWYRQAPGKKRELVAGISADGSTDYIH SVKGRFTISRDNAKNSVYLQMNSLRAEDTAVYYCYAYRWRTRYTYWGQGTLVTVSS |
| 332 | 4D011 | EVQLVESGGGLVQPGGSLTLSCAASGSSVRFLSMAWYRQAPGKKRELVAGISVDGSTDYID SVKGRFTISRDNAKNSVYLQMNSLRAEDTAVYYCYAYRWRTRYTYWGQGTLVTVSS |

| | | -continued |
|---|---|---|
| 333 | 4E01 | EVQLVESGGGLVQPGGSLTLSCAASGSSVSFLSVAWYRQAPGKKRELVAGISRDGSTDYID<br>SVKGRFTISRDNAKNSVYLQMNSLRAEDTAVYYCYAYRWRTRYTYWGQGTLVTVSS |
| 334 | 4E02 | EVQLVESGGGLVQPGGSLTLSCAASGSQVSFLSMAWYRQAPGKKRELVAGISADGSTVYID<br>SVKGRFTISRDNAKNSVYLQMNSLRAEDTAVYYCYAYRWSTRYTYWGQGTLVTVSS |
| 335 | 4E06 | EVQLVESGGGLVQPGGSLTLSCAASGTSVSFLSMAWYRQAPGKKRELVAGISADGSTDYIR<br>SVKGRFTISRDNAKNSVYLQMNSLRAEDTAVYYCYAYRWTTRLTYWGQGTLVTVSS |
| 336 | 4E07 | EVQLVESGGGLVQPGGSLTLSCAASGSRVSFLSMAWYRQAPGKKRELVAGISADGSTMYID<br>SVKGRFTISRDNAKNSVYLQMNSLRAEDTAVYYCYAYRWTTRLTYWGQGTLVTVSS |
| 337 | 4E08 | EVQLVESGGGLVQPGGSLTLSCAASGSSVKFLSMAWYRQAPGKKRELVAGISTDGSTDYID<br>SVKGRFTISRDNAKNSVYLQMNSLRAEDTAVYYCYAYKWTTRYTYWGQGTLVTVSS |
| 338 | 4E09 | EVQLVESGGGLVQPGGSLTLSCAASGSSVSFLSSAWYRQAPGKKRELVAGISADGSTLYID<br>SVKGRFTISRDNAKNSVYLQMNSLRAEDTAVYYCYAYRWTTRSTYWGQGTLVTVSS |
| 339 | 4E010 | EVQLVESGGGLVQPGGSLTLSCAASGSSVKFLSMAWYRQAPGKKRELVAGISADGSTDYID<br>SVKGRFTISRDNAKNSVYLQMNSLRAEDTAVYYCYAYRWRTRYTYWGQGTLVTVSS |
| 340 | 4E011 | EVQLVESGGGLVQPGGSLTLSCAASGSSVSFLSMAWYRQAPGKKRELVAGISATGSTDYID<br>SVKGRFTISRDNAKNSVYLQMNSLRAEDTAVYYCYAYRWSTRYTYWGQGTLVTVSS |
| 341 | 4F02 | EVQLVESGGGLVQPGGSLTLSCAASGSTVSFLSMAWYRQAPGKKRELVAGISHDGSTDYID<br>SVKGRFTISRDNAKNSVYLQMNSLRAEDTAVYYCYAYRWTTRYTYWGQGTLVTVSS |
| 342 | 4F03 | EVQLVESGGGLVQPGGSLTLSCAASGSSVQFLSMAWYRQAPGKKRELVAGISYDGSTDYID<br>SVKGRFTISRDNAKNSVYLQMNSLRAEDTAVYYCYAYRWRTRYTYWGQGTLVTVSS |
| 343 | 4F04 | EVQLVESGGGLVQPGGSLTLSCAASRSSVSFLSMAWYRQAPGKKRELVAGISTDGSTDYID<br>SVKGRFTISRDNAKNSVYLQMNSLRAEDTAVYYCYAYRWLTRYTYWGQGTLVTVSS |
| 344 | 4F08 | EVQLVESGGGLVQPGGSLTLSCAASGSKVSFLSMAWYRQAPGKKRELVAGISADGSTAYID<br>SVKGRFTISRDNAKNSVYLQMNSLRAEDTAVYYCYAYRWRTRYTYWGQGTLVTVSS |
| 345 | 4F09 | EVQLVESGGGLVQPGGSLTLSCAASGSRVSFLSMAWYRQAPGKKRELVAGISADGSTDYIE<br>SVKGRFTISRDNAKNSVYLQMNSLRAEDTAVYYCYAYRWTTRYTYWGQGTLVTVSS |
| 346 | 4F010 | EVQLVESGGGLVQPGGSLTLSCAASGSSVSFLSMAWYRQAPGKKRELVAGISIDGSTDYIK<br>SVKGRFTISRDNAKNSVYLQMNSLRAEDTAVYYCYAYRWTTRYRYWGQGTLVTVSS |
| 347 | 4F011 | EVQLVESGGGLVQPGGSLTLSCAASGSKVSFLSMAWYRQAPGKKRELVAGISADGSKDYID<br>SVKGRFTISRDNAKNSVYLQMNSLRAEDTAVYYCYAYRWTTRYTYWGQGTLVTVSS |
| 348 | 4G01 | EVQLVESGGGLVQPGGSLTLSCAASGSSVRFLSMAWYRQAPGKKRELVAGISADGSTVYID<br>SVKGRFTISRDNAKNSVYLQMNSLRAEDTAVYYCYAYRWPTRYTYWGQGTLVTVSS |
| 349 | 4G02 | EVQLVESGGGLVQPGGSLTLSCAASGSSVKFLSMAWYRQAPGKKRELVAGISRDGSTDYID<br>SVKGRFTISRDNAKNSVYLQMNSLRAEDTAVYYCYAYRWTTRHTYWGQGTLVTVSS |
| 350 | 4G03 | EVQLVESGGGLVQPGGSLTLSCAASGSSVKFLSMAWYRQAPGKKRELVAGISADGSTDYIH<br>SVKGRFTISRDNAKNSVYLQMNSLRAEDTAVYYCYAYRWTRRYTYWGQGTLVTVSS |
| 351 | 4G05 | EVQLVESGGGLVQPGGSLTLSCAASGSSVSILSMAWYRQAPGKKRELVAGISADGSTIYID<br>SVKGRFTISRDNAKNSVYLQMNSLRAEDTAVYYCYAYRWHTRYTYWGQGTLVTVSS |
| 352 | 4G07 | EVQLVESGGGLVQPGGSLTLSCAASGSSVSFLSVAWYRQAPGKKRELVAGISANGSTDYID<br>SVKGRFTISRDNAKNSVYLQMNSLRAEDTAVYYCYAYRWTNRYTYWGQGTLVTVSS |
| 353 | 4G08 | EVQLVESGGGLVQPGGSLTLSCAASGSSVRFLSMAWYRQAPGKKRELVAGISTDGSTDYID<br>SVKGRFTISRDNAKNSVYLQMNSLRAEDTAVYYCYAYRWTTRYRYWGQGTLVTVSS |
| 354 | 4G09 | EVQLVESGGGLVQPGGSLTLSCAASGSRVSFLSMAWYRQAPGKKRELVAGISYDGSTDYID<br>SVKGRFTISRDNAKNSVYLQMNSLRAEDTAVYYCYAYRWTTRRTYWGQGTLVTVSS |
| 355 | 4G010 | EVQLVESGGGLVQPGGSLTLSCAASGHSVSFLSMAWYRQAPGKKRELVAGISADGSTDYIA<br>SVKGRFTISRDNAKNSVYLQMNSLRAEDTAVYYCYAYRWSTRYTYWGQGTLVTVSS |
| 356 | 4G011 | EVQLVESGGGLVQPGGSLTLSCAASGSSVRFLSMAWYRQAPGKKRELVAGISADGSTDYIG<br>SVKGRFTISRDNAKNSVYLQMNSLRAEDTAVYYCYAYRWSTRYTYWGQGTLVTVSS |
| 357 | 4H01 | EVQLVESGGGLVQPGGSLTLSCAASGSSVSFLSMAWYRQAPGKKRELVAGISANGSTDYYD<br>SVKGRFTISRDNAKNSVYLQMNSLRAEDTAVYYCYAYRWRTRYTYWGQGTLVTVSS |
| 358 | 4H03 | EVQLVESGGGLVQPGGSLTLSCAASGSRVSFLSMAWYRQAPGKKRELVAGISADGSTSYID<br>SVKGRFTISRDNAKNSVYLQMNSLRAEDTAVYYCYAYRWTTRYTYWGQGTLVTVSS |

| | | -continued |
|---|---|---|
| 359 | 4H04 | EVQLVESGGGLVQPGGSLTLSCAASGSSVKFLSMAWYRQAPGKKRELVAGVSADGSTDYID SVKGRFTISRDNAKNSVYLQMNSLRAEDTAVYYCYAYEWTTRYTYWGQGTLVTVSS |
| 360 | 4H05 | EVQLVESGGGLVQPGGSLTLSCAASGSSVSRLSMAWYRQAPGKKRELVAGISARGSTDYID SVKGRFTISRDNAKNSVYLQMNSLRAEDTAVYYCYAYRWTTRSTYWGQGTLVTVSS |
| 361 | 4H06 | EVQLVESGGGLVQPGGSLTLSCAASGRSVSFLSMAWYRQAPGKKRELVAGISADGSTIYID SVKGRFTISRDNAKNSVYLQMNSLRAEDTAVYYCYAYRWTTRYTYWGQGTLVTVSS |
| 362 | 4H07 | EVQLVESGGGLVQPGGSLTLSCAASGRSVSFLSMAWYRQAPGKKRELVAGISANGSTDYID SVKGRFTISRDNAKNSVYLQMNSLRAEDTAVYYCYAYRWSTRYTYWGQGTLVTVSS |
| 363 | 4H08 | EVQLVESGGGLVQPGGSLTLSCAASGSSVKFLSMAWYRQAPGKKRELVAGISADGSTDYVD SVKGRFTISRDNAKNSVYLQMNSLRAEDTAVYYCYAYRWSTRYTYWGQGTLVTVSS |
| 364 | 4H09 | EVQLVESGGGLVQPGGSLTLSCAASGSSVSKLSMAWYRQAPGKKRELVAGISADGSTDYRD SVKGRFTISRDNAKNSVYLQMNSLRAEDTAVYYCYAYRWTYRYTYWGQGTLVTVSS |
| 365 | 4H011 | EVQLVESGGGLVQPGGSLTLSCAASGSSVSRLSMAWYRQAPGKKRELVAGISVDGSTDYID SVKGRFTISRDNAKNSVYLQMNSLRAEDTAVYYCYAYRWTTRLTYWGQGTLVTVSS |
| 366 | 4D09-M34L | EVQLVESGGGLVQPGGSLTLSCAASGSSVKFLSLAWYRQAPGKKRELVAGISADGSTDYIL SVKGRFTISRDNAKNSVYLQMNSLRAEDTAVYYCYAYEWTTRYTYWGQGTLVTVSS |
| 367 | 4H11-M34L | EVQLVESGGGLVQPGGSLTLSCAASGSSVSRLSLAWYRQAPGKKRELVAGISVDGSTDYID SVKGRFTISRDNAKNSVYLQMNSLRAEDTAVYYCYAYRWTTRLTYWGQGTLVTVSS |
| 368 | 41B11 | EVQLVESGGGLVQPGGSLTLSCVASGTSSSINAMGWYRRAPGKQRELVAGISSDGSKVFNE SVKGRFTISRDNAKNSVYLQMNSLRAEDTAVYYCYYFRPAAGSPMRYWGQGTLVTVSS |
| 369 | 41C02 | EVQLVESGGGLVQPGGSLTLSCVASGTTSSINAIGWYRRAPGKQRELVAGISSDGSEVYTD SVKGRFTISRDNAKNSVYLQMNSLRAEDTAVYYCYYFRTVDGSPLRYWGQGTLVTVSS |
| 370 | 41D01 | EVQLVESGGGLVQPGGSLTLSCVASGTSSINAMAWYRRAPGKQRELVAGISSDDSNVYYE SVKGRFTISRDNAKNSVYLQMNSLRAEDTAVYYCYYFRTVSGSSKRYWGQGTLVTVSS |
| 371 | 41D02 | EVQLVESGGGLVQPGGSLTLSCVASGQTYRVNAFGWYRRAPGKQRELVAGISSDGSKVYAD SVKGRFTISRDNAKNSVYLQMNSLRAEDTAVYYCYYFSAGSGTEMSYWGQGTLVTVSS |
| 372 | 41D03 | EVQLVESGGGLVQPGGSLTLSCVASGSTSSINAMAWYRRAPGKQRELVAGISSDESTLYVD SVKGRFTISRDNAKNSVYLQMNSLRAEDTAVYYCYYFGSLSGSSTTYWGQGTLVTVSS |
| 373 | 41D07 | EVQLVESGGGLVQPGGSLTLSCVASGSASLTNATGWYRRAPGKQRELVAGISSDDSKVYSD SVKGRFTISRDNAKNSVYLQMNSLRAEDTAVYYCYYFGSVSGSWTRYWGQGTLVTVSS |
| 374 | 41E01 | EVQLVESGGGLVQPGGSLTLSCVASGYPSLNNAMGWYRRAPGKQRELVAGISSDGSQVYGA SVKGRFTISRDNAKNSVYLQMNSLRAEDTAVYYCYYFRLVSGSSMSYWGQGTLVTVSS |
| 375 | 41E02 | EVQLVESGGGLVQPGGSLTLSCVASGSSSTINAIGWYRRAPGKQRELVAGISSDGSKVYAD SVKGRFTISRDNAKNSVYLQMNSLRAEDTAVYYCYYFRTGSGTSKSYWGQGTLVTVSS |
| 376 | 41F07 | EVQLVESGGGLVQPGGSLTLSCVASGSTSYINAMGWYRRAPGKQRELVAGISSDGSNMYAD SVKGRFTISRDNAKNSVYLQMNSLRAEDTAVYYCYYFSNMSGTTRRYWGQGTLVTVSS |
| 377 | 41G01 | EVQLVESGGGLVQPGGSLTLSCVASGTSSVNALGWYRRAPGKQRELVAGISSDGSKVYTD SVKGRFTISRDNAKNSVYLQMNSLRAEDTAVYYCYYFRTVPGSAMGYWGQGTLVTVSS |
| 378 | 42A03 | EVQLVESGGGLVQPGGSLTLSCVASGTSLSNAVGWYRRAPGKQRELVAGISSDGSKVSAE SVKGRFTISRDNAKNSVYLQMNSLRAEDTAVYYCYYFRAESGSSMGYWGQGTLVTVSS |
| 379 | 42A06 | EVQLVESGGGLVQPGGSLTLSCVASGTSSTNAIGWYRRAPGKQRELVAGISSDGSKVYDD SVKGRFTISRDNAKNSVYLQMNSLRAEDTAVYYCYYFRTLYGSSRSYWGQGTLVTVSS |
| 380 | 42A07 | EVQLVESGGGLVQPGGSLTLSCVASGLTSTINAMGWYRRAPGKQRELVAGISSDGSKVYDD SVKGRFTISRDNAKNSVYLQMNSLRAEDTAVYYCYYFSPFSGSDTGYWGQGTLVTVSS |
| 381 | 42A08 | EVQLVESGGGLVQPGGSLTLSCVASGVSPSKNAIGWYRRAPGKQRELVAGISSDGSAVYVG SVKGRFTISRDNAKNSVYLQMNSLRAEDTAVYYCYYFSTFSGSSISYWGQGTLVTVSS |
| 382 | 42A11 | EVQLVESGGGLVQPGGSLTLSCVASGTSSSINAVGWYRRAPGKQRELVAGISSDGSYVYSE SVKGRFTISRDNAKNSVYLQMNSLRAEDTAVYYCYYFRTLAGSEMRYWGQGTLVTVSS |
| 383 | 42B06 | EVQLVESGGGLVQPGGSLTLSCVASGTTMNNAMAWYRRAPGKQRELVAGISSDSSHVYAD SVKGRFTISRDNAKNSVYLQMNSLRAEDTAVYYCYYFRTVSGSGVRYWGQGTLVTVSS |
| 384 | 42B10 | EVQLVESGGGLVQPGGSLTLSCVASGSTSKINAIGWYRRAPGKQRELVAGISSDSSIVYTD SVKGRFTISRDNAKNSVYLQMNSLRAEDTAVYYCYYFRPGAGHSNSYWGQGTLVTVSS |

| | | |
|---|---|---|
| 385 | 42C01 | EVQLVESGGGLVQPGGSLTLSCVASGQTTALNAMGWYRRAPGKQRELVAGISSDGSEVNTD SVKGRFTISRDNAKNSVYLQMNSLRAEDTAVYYCYYFRRASGTAMSYWGQGTLVTVSS |
| 386 | 42C03 | EVQLVESGGGLVQPGGSLTLSCVASGATSSINAIGWYRRAPGKQRELVAGISSDGSKLSSD SVKGRFTISRDNAKNSVYLQMNSLRAEDTAVYYCYYFTSASGTDLSYWGQGTLVTVSS |
| 387 | 42C07 | EVQLVESGGGLVQPGGSLTLSCVASGSTSTINAMGWYRRAPGKQRELVAGISSDNSKVYAD SVKGRFTISRDNAKNSVYLQMNSLRAEDTAVYYCYYFRSANGSSKRYWGQGTLVTVSS |
| 388 | 42C08 | EVQLVESGGGLVQPGGSLTLSCVASGSTSSINAMGWYRRAPGKQRELVAGISSDGSRVYFD SVKGRFTISRDNAKNSVYLQMNSLRAEDTAVYYCYYFKTIAGAGMRYWGQGTLVTVSS |
| 389 | 42C10 | EVQLVESGGGLVQPGGSLTLSCVASGSTSLVNAMGWYRRAPGKQRELVAGISSDGSLVYAE SVKGRFTISRDNAKNSVYLQMNSLRAEDTAVYYCYYFRYGSGSSLSYWGQGTLVTVSS |
| 390 | 42C11 | EVQLVESGGGLVQPGGSLTLSCVASGSTSLNNAIGWYRRAPGKQRELVAGISSDGSVVYVD SVKGRFTISRDNAKNSVYLQMNSLRAEDTAVYYCYYFRTVPGASMKYWGQGTLVTVSS |
| 391 | 42D05 | EVQLVESGGGLVQPGGSLTLSCVASGSTSPVNAMAWYRRAPGKQRELVAGISSDGSKVYVD SVKGRFTISRDNAKNSVYLQMNSLRAEDTAVYYCYYFRTVDGSAISYWGQGTLVTVSS |
| 392 | 42D06 | EVQLVESGGGLVQPGGSLTLSCVASGTTSSMNAIGWYRRAPGKQRELVAGISSDGSKLYDE SVKGRFTISRDNAKNSVYLQMNSLRAEDTAVYYCYYFRTVKGSGGSYWGQGTLVTVSS |
| 393 | 42D07 | EVQLVESGGGLVQPGGSLTLSCVASGETSSINAMAWYRRAPGKQRELVAGISSDYSKLYAD SVKGRFTISRDNAKNSVYLQMNSLRAEDTAVYYCYYFRTVSGSSRGYWGQGTLVTVSS |
| 394 | 42D08 | EVQLVESGGGLVQPGGSLTLSCVASGSTSTINAIGWYRRAPGKQRELVAGISSDSSKVYTE SVKGRFTISRDNAKNSVYLQMNSLRAEDTAVYYCYYFRPGPGSQMAYWGQGTLVTVSS |
| 395 | 42E01 | EVQLVESGGGLVQPGGSLTLSCVASGSTYSMNAMGWYRRAPGKQRELVAGISSDGSQVYVD SVKGRFTISRDNAKNSVYLQMNSLRAEDTAVYYCYYFRTVAGSASGYWGQGTLVTVSS |
| 396 | 42E02 | EVQLVESGGGLVQPGGSLTLSCVASGSPSSINAYGWYRRAPGKQRELVAGISSDGSKVYSD SVKGRFTISRDNAKNSVYLQMNSLRAEDTAVYYCYYFRTVSGSSYSYWGQGTLVTVSS |
| 397 | 42E05 | EVQLVESGGGLVQPGGSLTLSCVASGSTSTINAIGWYRRAPGKQRELVAGISSDGSKVYVD SVKGRFTISRDNAKNSVYLQMNSLRAEDTAVYYCYYFINLKGSSMAYWGQGTLVTVSS |
| 398 | 42E06 | EVQLVESGGGLVQPGGSLTLSCVASGSTSSINAIGWYRRAPGKQRELVAGISSDGSKVYAD SVKGRFTISRDNAKNSVYLQMNSLRAEDTAVYYCYYFRMVTGSYGGYWGQGTLVTVSS |
| 399 | 42E07 | EVQLVESGGGLVQPGGSLTLSCVASGSISSINAMGWYRRAPGKQRELVAGISSDGSSVYAD SVKGRFTISRDNAKNSVYLQMNSLRAEDTAVYYCYYFKSSYGLPMRYWGQGTLVTVSS |
| 400 | 42F01 | EVQLVESGGGLVQPGGSLTLSCVASGSTQVNNAMAWYRRAPGKQRELVAGISSDGSQVYYG SVKGRFTISRDNAKNSVYLQMNSLRAEDTAVYYCYYFKTVSGQSLRYWGQGTLVTVSS |
| 401 | 42F08 | EVQLVESGGGLVQPGGSLTLSCVASGTASFNAMAWYRRAPGKQRELVAGISSDGSKVYTD SVKGRFTISRDNAKNSVYLQMNSLRAEDTAVYYCYYFRTVTGRAARYWGQGTLVTVSS |
| 402 | 42F10 | EVQLVESGGGLVQPGGSLTLSCVASGSPLSINAIGWYRRAPGKQRELVAGISSDGSKVSAD SVKGRFTISRDNAKNSVYLQMNSLRAEDTAVYYCYYFGPAIGASRTYWGQGTLVTVSS |
| 403 | 42G05 | EVQLVESGGGLVQPGGSLTLSCVASGTTFINAIGWYRRAPGKQRELVAGISSDGSKVYED SVKGRFTISRDNAKNSVYLQMNSLRAEDTAVYYCYYFRTVSGAPKSYWGQGTLVTVSS |
| 404 | 42G07 | EVQLVESGGGLVQPGGSLTLSCVASGSTSSINAIGWYRRAPGKQRELVAGISSDRSKVYAD SVKGRFTISRDNAKNSVYLQMNSLRAEDTAVYYCYYFHTVSGSSMSYWGQGTLVTVSS |
| 405 | 42H05 | EVQLVESGGGLVQPGGSLTLSCVASGETDTINAVGWYRRAPGKQRELVAGISSDGSKVYAE SVKGRFTISRDNAKNSVYLQMNSLRAEDTAVYYCYYFRRLEGYSNRYWGQGTLVTVSS |
| 406 | 42H08 | EVQLVESGGGLVQPGGSLTLSCVASGSTSPINAIGWYRRAPGKQRELVAGISSDGSVVTTE SVKGRFTISRDNAKNSVYLQMNSLRAEDTAVYYCYYFRTGSGSSMGYWGQGTLVTVSS |
| 407 | 42H11 | EVQLVESGGGLVQPGGSLTLSCVASGSITSSNAMGWYRRAPGKQRELVAGISSDGSHVHQE SVKGRFTISRDNAKNSVYLQMNSLRAEDTAVYYCYYFTTVTGSSMSYWGQGTLVTVSS |
| 408 | 51A01 | EVQLVESGGGLVQPGGSLTLSCAASRYSVSNLSMAWYRQAPGKKRELVAGISADGSTVYVE SVKGRFTISRDNAKNSVYLQMNSLRAEDTAVYYCAYYWTERRPYWGQGTLVTVSS |
| 409 | 51A02 | EVQLVESGGGLVQPGDSLTLSCAASMSTVSVLSMAWYRQAPGKKRELVAGISSDGSTVYID SVKGRFTISRDNAKNSVYLQMNSLRAEDTAIYYCAYSWDDAHPYWGQGTLVTVSS |
| 410 | 51A03 | EVQLVESGGGLVQPGGSLTLSCAASDSYVSLLSMAWYRQAPGKKRELVAGISVDGSTHYVA SVKGRFTISRDNAKNSVYLQMNSLRAEDTAVYYCAYRWMTRLTYWGQGTLVTVSS |

-continued

| 411 | 51A05 | EVQLVESGGGLVQPGGSLTLSCAASDSAVSVLSIAWYRQAPGKKRELVAGISTDGSKHYID SVKGRFTISRDNAKNSVYLQMNSLRAEDTAVYYCYAYDWADAQPYWGQGTLVTVSS |
| --- | --- | --- |
| 412 | 51B01 | EVQLVESGGGLVQPGGSLTLSCAASHSSVTSLSLAWYRQAPGKKRELVAGISYDGSKYYAE SVKGRFTISRDNAKNSVYLQMNSLRAEDTAVYYCYAYSWTDRLPYWGQGTLVTVSS |
| 413 | 51B04 | EVQLVESGGGLVQPGGSLTLSCAASDSVVKFLSMAWYRQAPGKKRELVAGISANGSRTYME SVKGRFTISRDNAKNSVYLQMNSLRAEDTAVYYCYAYRWATRLPYWGQGTLVTVSS |
| 414 | 51B11 | EVQLVESGGGLVQPGGSLTLSCAASDPSVWNLSMAWYRQAPGKKRELVAGISPDGSTDYVD SVKGRFTISRDNAKNSVYLQMNSLRAEDTAVYYCYAYKWSNRLPYWGQGTLVTVSS |
| 415 | 51C02 | EVQLVESGGGLVQPGGSLTLSCAASGTSVMLLSLAWYRQAPGKKRELVAGISPNGSAVYTE SVKGRFTISRDNAKNSVYLQMNSLRAEDTAVYYCYAYGWKTRQPYWGQGTLVTVSS |
| 416 | 51D01 | EVQLVESGGGLVQPGGSLTLSCAASSSPVSNLSLAWYRQAPGKKRELVAGISPDGSTAYME SVKGRFTISRDNAKNSVYLQMNSLRAEDTAVYYCYAYRWPNRRGYWGQGTLVTVSS |
| 417 | 51D03 | EVQLVESGGGLVQPGGSLTLSCAASWRSVLLLSVAWYRQAPGKKRELVAGISNDGSTDYID SVKGRFTISRDNAKNSVYLQMNSLRAEDTAVYYCYAYDWTTRQRYWGQGTLVTVSS |
| 418 | 51E02 | EVQLVESGGGLVQPGGSLTLSCAASSSSVQYLSMAWYRQAPGKKRELVAGISTDGSAVYFD SVKGRFTISRDNAKNSVYLQMNSLRAEDTAVYYCYAYNWSYAQPYWGQGTLVTVSS |
| 419 | 51E03 | EVQLVESGGGLVQPGGSLTLSCAASGTSVSLLSLAWYRQAPGKKRELVAGISTGGSTHYIE SVKGRFTISRDNAKNSVYLQMNSLRAEDTAVYYCYAYNWTDSLQYWGQGTLVTVSS |
| 420 | 51E05 | EVQLVESGGGLVQPGGSLTLSCAASLSSVSNLSIAWYRQAPGKKRELVAGISTDGSTVYID SVKGRFTISRDNAKNSVYLQMNSLRAEDTAVYYCYAYSWTTSLPYWGQGTLVTVSS |
| 421 | 51F01 | EVQLVESGGGLVQPGGSLTLSCAASMYSVSFLSMAWYRQAPGKKRELVAGISNEGSTYYMD SVKGRFTISRDNAKNSVYLQMNSLRAEDTAVYYCYAYKWRSRSTYWGQGTLVTVSS |
| 422 | 51F02 | EVQLVESGGGLVQPGGSLTLSCAASKSSVSHLSLAWYRQAPGKKRELVAGISADGSHVYTN SVKGRFTISRDNAKNSVYLQMNSLRAEDTAVYYCYAYSQTTRDPYWGQGTLVTVSS |
| 423 | 51F03 | EVQLVESGGGLVQPGGSLTLSCAASYTSVLDLSIAWYRQAPGKKRELVAGISDDGSRYYTD SVKGRFTISRDNAKNSVYLQMNSLRAEDTAVYYCYAYRWTARDTYWGQGTLVTVSS |
| 424 | 51F04 | EVQLVESGGGLVQPGGSLTLSCAASMSDVSFLSMAWYRQAPGKKRELVAGISAEGSTLYME SVKGRFTISRDNAKNSVYLQMNSLRAEDTAVYYCYAYRWTSRLSYWGQGTLVTVSS |
| 425 | 51G02 | EVQLVESGGGLVQPGGSLTLSCAASESSVSFLSSAWYRQAPGKKRELVAGISTDGSTVYID SVKGRFTISRDNAKNSVYLQMNSLRAEDTAVYYCYAYSWTTRSRYWGQGTLVTVSS |
| 426 | 51G04 | EVQLVESGGGLVQPGGSLTLSCAASGDSVSLLSMAWYRQAPGKKRELVAGISANGSTSYID SVKGRFTISRDNAKNSVYLQMNSLRAEDTAVYYCYAYNWTSRYRYWGQGTLVTVSS |
| 427 | 51G10 | EVQLVESGGGLVQPGGSLTLSCAASGDVWYLSLAWYRQAPGKKRELVAGISDDGSRHYIE SVKGRFTISRDNAKNSVYLQMNSLRAEDTAVYYCYAYSWKTRFPYWGQGTLVTVSS |
| 428 | 51H04 | EVQLVESGGGLVQPGGSLTLSCAASKSAVAFLSIAWYRQAPGKKRELVAGISPDGSTVYIE SVKGRFTISRDNAKNSVYLQMNSLRAEDTAVYYCYAYSWTTRYPYWGQGTLVTVSS |
| 429 | 51H05 | EVQLVESGGGLVQPGGSLTLSCAASFSAVAYLSMAWYRQAPGKKRELVAGISDDGSTVYVD SVKGRFTISRDNAKNSVYLQMNSLRAEDTAVYYCYAYEWTNALPYWGQGTLVTVSS |
| 430 | 52B01 | EVQLVESGGGLVQPGGSLTLSCAASVYSVYDLSTAWYRQAPGKKRELVAGISDDGSTVYFD SVKGRFTISRDNAKNSVYLQMNSLRAEDTAVYYCYAYSWITRSPYWGQGTLVTVSS |
| 431 | 52C04 | EVQLVESGGGLVQPGGSLTLSCAASGDSVSFLSMAWYRQAPGKKRELVAGISDEGSTVYIG SVKGRFTISRDNAKNSVYLQMNSLRAEDTAVYYCYAYSWTTRRQYWGQGTLVTVSS |
| 432 | 52D04 | EVQLVESGGGLVQPGGSLTLSCAASSSSVSLLSLAWYRQAPGKKRELVAGISDDGSIVYMD SVKGRFTISRDNAKNSVYLQMNSLRAEDTAVYYCYAYSWITRSPYWGQGTLVTVSS |
| 433 | 53A04 | EVQLVESGGGLVQPGGSLTLSCAASADSVSFLSIAWYRQAPGKKRELVAGISDDGSKHYFD SVKGRFTISRDNAKNSVYLQMNSLRAEDTAVYYCYAYRWEESRQYWGQGTLVTVSS |
| 434 | 53A05 | EVQLVESGGGLVQPGGSLTLSCAASASSVTLLSIAWYRQAPGKKRELVAGISTDGSTDYLH SVKGRFTISRDNAKNSVYLQMNSLRAEDTAVYYCYAYTWTTRLPYWGQGTLVTVTS |
| 435 | 53A09 | EVQLVESGGGLVQPGGSLTLSCAASADSVSFLSIAWYRQAPGKKRELVAGISDDGSKHYFD SVKGRFTISRDNAKNSVYLQMNSLRAEDTAVYYCYAYRWEESRQYWGQGTLVTVSS |
| 436 | 53B05 | EVQLVESGGGLVQPGGSLTLSCAASGTSVWLLSMAWYRQAPGKKRELVAGISYDGSTVYVE SVKGRFTISRDNAKNSVYLQMNSLRAEDTAVYYCYAYSWTTRQPYWGQGTLVTVSS |

-continued

| | | |
|---|---|---|
| 437 | 53B06 | EVQLVESGGGLVQPGGSLTLSCAASGSSVSILSIAWYRQAPGKKRELVAGISDDGSTVYID<br>SVKGRFTISRDNAKNSVYLQMNSLRAEDTAVYYCYAYVWGTRLPYWGQGTLVTVSS |
| 438 | 53C03 | EVQLVESGGGLVQPGGSLTLSCAASGTAVSNLSIAWYRQAPGKKRELVAGISDDGSTVYVD<br>SVKGRFTISRDNAKNSVYLQMNSLRAEDTAVYYCYAYEWTNALPYWGQGTLVTVSS |
| 439 | 53C04 | EVQLVESGGGLVQPGGSLTLSCAASGSAVSMLSLAWYRQAPGKKRELVAGISDDGSQVYID<br>SVKGRFTISRDNAKNSVYLQMNSLRAEDTAVYYCYAYRWEDALTYWGQGTLVTVSS |
| 440 | 53H03 | EVQLVESGGGLVQPGGSLTLSCAASGMTVFFLSMAWYRQAPGKKRELVAGISVDGSTVYSD<br>SVKGRFTISRDNAKNSVYLQMNSLRAEDTAVYYCYAYSWTTRYPYWGQGTLVTVSS |
| 441 | 53H04 | EVQLVESGGGLVQPGGSLTLSCAASQYSVTFLSVAWYRQAPGKKRELVAGISDDGSNVYID<br>SVKGRFTISRDNAKNSVYLQMNSLRAEDTAVYYCYAYSWIDSLRYWGQGTLVTVSS |
| 442 | 54B05 | EVQLVESGGGLVQPGGSLTLSCAASGETVSFLSLAWYRQAPGKKRELVAGISTDGSTVYFV<br>SVKGRFTISRDNAKNSVYLQMNSLRAEDTAVYYCYAYSWTTPRAYWGQGTLVTVSS |

| SEQ ID NO. | name | CDR1 |
|---|---|---|
| 443 | DL1 | GSIFSIASMG |
| 444 | DL74 | GSIFSIASMG |
| 445 | DL31 | GSIFSIASMA |
| 446 | DL3 | ESIFSINVMA |
| 447 | DL80 | GSSFSITSMA |
| 448 | DL18 | SSIFSISSMS |
| 449 | DL94 | SSIFSISSMS |
| 450 | DL17 | GSTLNIKIMA |
| 451 | DL46 | GSTLNIKIMA |
| 452 | DL15 | GSTFNIKTMA |
| 453 | DL26 | GSTFNIKLMA |
| 454 | DL83 | GSTFNFKIMA |
| 455 | DL5 | GFMFSSYSMS |
| 456 | DL22 | GFMFSSYSMS |
| 457 | DL85 | GFTFSSHSMS |
| 458 | DL69 | GSSFSHNTMG |
| 459 | DL27 | GGRFSYATMG |
| 460 | DL51 | GSRFSYATMG |
| 461 | DL54 | GSTFTSNVMG |
| 462 | DL11 | GSSVSFLSMA |
| 463 | DL19 | GSSVSFLSMA |
| 464 | DL68 | GSSVSFLSMA |
| 465 | DL14 | GSSVSFLSMA |
| 466 | DL67 | GSSVSFLSMA |
| 467 | DL56 | GSSVSFLSMA |
| 468 | DL13 | GSSVSFLSMA |
| 469 | DL77 | GSSVSFLSIA |
| 470 | DL79 | GSSVSFLSMA |
| 471 | DL20 | GSSVSFLSMA |

-continued

| 472 | DL41 | GSSVSFLSMA |
| 473 | DL59 | GSSVSFLSMA |
| 474 | DL16 | GSSVSFLSMA |
| 475 | DL6 | GSSVSFLSMA |
| 476 | DL84 | GFTLDYYAIG |
| 477 | DL2 | GSTSSINAMG |
| 478 | DL43 | GSTSSINAMG |
| 479 | DL92 | GITSSVYSMG |
| 480 | DL10 | GRTSMFNSMG |
| 481 | DL82 | GRTSMVNSMG |
| 482 | DL23 | GSVSMFNSMG |
| 483 | DL42 | GSIFSIAVMG |
| 484 | DL45 | SGIFSDMSMV |
| 485 | DL58 | GSISSIIVMG |
| 486 | DL70 | GSISSIIVMG |
| 487 | DL89 | GSIFTTNSMG |
| 488 | DL38 | GSREISTMG |
| 489 | DL52 | GSREISTMG |
| 490 | DL64 | GSREISTMG |
| 491 | DL33 | GSREISTMG |
| 492 | DL12 | GSIFRGAAMY |
| 493 | DL29 | GSISSFNFMS |
| 494 | DL61 | GTIFTASTMG |
| 495 | DH1 | GSIFSIASMG |
| 496 | DH10 | GRTSMFNSMG |
| 497 | DH11 | GSSVSFLSMA |
| 498 | DH12 | GSIFRGAAMY |
| 499 | DH15 | GSTFNIKTMA |
| 500 | DH17 | GSTLNIKIMA |
| 501 | DH18 | SSIFSISSMS |
| 502 | DH2 | GSTSSINAMG |
| 503 | DH22 | GFMFSSYSMS |
| 504 | DH23 | GSVSMFNSMG |
| 505 | DH27 | GGRFSYATMG |
| 506 | DH29 | GSISSFNFMS |
| 507 | DH3 | ESIFSINVMA |
| 508 | DH38 | GSREISTMG |
| 509 | DH42 | GSIFSIAVMG |
| 510 | DH43 | GSTSSINAMG |

| | | |
|---|---|---|
| 511 | DH45 | SGIFSDMSMV |
| 512 | DH5 | GFMFSSYSMS |
| 513 | DH51 | GSRFSYATMG |
| 514 | DH54 | GSTFTSNVMG |
| 515 | DH56 | GSSVSFLSMA |
| 516 | DH58 | GSISSIIVMG |
| 517 | DH6 | GSSVSFLSMA |
| 518 | DH61 | GTIFTASTMG |
| 519 | DH67 | GSSVSFLSMA |
| 520 | DH69 | GSSFSHNTMG |
| 521 | DH70 | GSISSIIVMG |
| 522 | DH80 | GSSFSITSMA |
| 523 | DH82 | GRTSMVNSMG |
| 524 | DH83 | GSTFNFKIMA |
| 525 | DH84 | GFTLDYYAIG |
| 526 | DH89 | GSIFTTNSMG |
| 527 | DH92 | GITSSVYSMG |
| 528 | DH94 | SSIFSISSMS |
| 529 | 1A01 | GFTSSINAMG |
| 530 | 1A03 | GSTSSINAMA |
| 531 | 1A04 | GSTSSINAMG |
| 532 | 1A05 | GSPSSINAMG |
| 533 | 1A06 | GSTSSINAMG |
| 534 | 1A07 | GSISSINAMG |
| 535 | 1A09 | GSTSSINAMA |
| 536 | 1A010 | GSTSSINAYG |
| 537 | 1A011 | GSTSSINAIG |
| 538 | 1A012 | GSTSSINAMA |
| 539 | 1B01 | GSTSIINAMG |
| 540 | 1B02 | GSTSSINAMG |
| 541 | 1B03 | GKTSSINAMA |
| 542 | 1B04 | GTTSSINAMG |
| 543 | 1B05 | GSTSSINAMA |
| 544 | 1B07 | GSGSSINAMG |
| 545 | 1B08 | GTTSSINAMG |
| 546 | 1B09 | GSTSSINAMA |
| 547 | 1B010 | GSTSRINAMG |
| 548 | 1B011 | GSTSRINAMG |
| 549 | 1C01 | GSTSSINAMG |
| 550 | 1C02 | GSTSSINAMA |

| | | |
|---|---|---|
| 551 | 1C03 | GSTSSINAMA |
| 552 | 1C04 | GNTSSINAMA |
| 553 | 1C05 | GSTSSINAMA |
| 554 | 1C06 | GSTSIINAMG |
| 555 | 1C07 | GSTSSINAMA |
| 556 | 1C08 | GSTSRINAMG |
| 557 | 1C010 | GSTSRINAMG |
| 558 | 1C011 | GTTSSINAMG |
| 559 | 1C012 | GITSSINAMG |
| 560 | 1D01 | GSTSDINAMG |
| 561 | 1D02 | GSTSSINAMA |
| 562 | 1D03 | GSTSSINAIG |
| 563 | 1D04 | GSTSSKNAMG |
| 564 | 1D06 | GSTSSINAMG |
| 565 | 1D08 | GLTSSINAMG |
| 566 | 1D09 | GSTSSINAMA |
| 567 | 1D010 | GSTSSNNAMA |
| 568 | 1D011 | GSTSSINAMA |
| 569 | 1D012 | GSTSHINAMG |
| 570 | 1E02 | GQTSSINAMG |
| 571 | 1E04 | GSTSRINGMG |
| 572 | 1E05 | GSTSVINAMA |
| 573 | 1E07 | GSTSSINAMA |
| 574 | 1E08 | GKTSSINAMG |
| 575 | 1E09 | GSTSSINAMA |
| 576 | 1E010 | GSVSSINAMG |
| 577 | 1E011 | GNTSSINAMG |
| 578 | 1E012 | GSTSSTNAMG |
| 579 | 1F01 | GSTSSINAMG |
| 580 | 1F02 | GSTSSINAMA |
| 581 | 1F04 | GGTSSINAMG |
| 582 | 1F05 | GSTRSINAMG |
| 583 | 1F06 | GTTSSINAMG |
| 584 | 1F07 | GSTSSINAMG |
| 585 | 1F08 | GSTSSINAMA |
| 586 | 1F09 | GNTSSINAMG |
| 587 | 1F010 | GSTSRINAMG |
| 588 | 1F011 | GSTSSINAIG |
| 589 | 1F012 | GLTSSINAMG |

| | | -continued |
|---|---|---|
| 590 | 1G01 | GSTSSINAMA |
| 591 | 1G04 | GSTSSTNAMG |
| 592 | 1G05 | GSTSSINAIG |
| 593 | 1G06 | GSTSSINAIG |
| 594 | 1G07 | GSTSSINAMG |
| 595 | 1G09 | GSTSSINAMG |
| 596 | 1G011 | GSTSSINAMA |
| 597 | 1H01 | GSTSSINAMA |
| 598 | 1H02 | GSKSSINAMG |
| 599 | 1H06 | GTTSSINAMG |
| 600 | 1H07 | GSTSSINAFG |
| 601 | 1H08 | GSTFSINAMG |
| 602 | 1H010 | GSTRSINAMG |
| 603 | 1H011 | GSTSSINAIG |
| 604 | 1H012 | GSTSSINAMG |
| 605 | 2A01 | GSTSSINAMG |
| 606 | 2A03 | GTTSSINAMG |
| 607 | 2A04 | GSTSSINAMA |
| 608 | 2A05 | GRTSSINAMG |
| 609 | 2A06 | GSTSSRNAMG |
| 610 | 2A08 | GSTKSINAMG |
| 611 | 2A09 | GSTSSRNAMG |
| 612 | 2A011 | GSTSSINAIG |
| 613 | 2B01 | GSTSLINAMG |
| 614 | 2B02 | GSTSSINAMA |
| 615 | 2B03 | GSTSSINAMG |
| 616 | 2B05 | GTTSSINAMG |
| 617 | 2B07 | GSTSSINAFG |
| 618 | 2B010 | GSTSSRNAMG |
| 619 | 2B011 | GNTSSINAMG |
| 620 | 2B012 | GTTSSINAMG |
| 621 | 2C01 | GSTASINAMG |
| 622 | 2C02 | GSTSSINAVG |
| 623 | 2C04 | GSTSSRNAMG |
| 624 | 2C06 | GSTNSINAMG |
| 625 | 2C07 | GSTSSINAMA |
| 626 | 2C08 | GSTSRINAMG |
| 627 | 2C09 | GSTSNINAMG |
| 628 | 2C010 | GSTSKINAMG |
| 629 | 2D02 | GSTSSINALG |

-continued

| | | |
|---|---|---|
| 630 | 2D03 | GKTSSINAMG |
| 631 | 2D04 | GSTSSINAVG |
| 632 | 2D05 | GSTSRINAMG |
| 633 | 2D06 | GSTSSINAMG |
| 634 | 2D07 | GSTSSINAVG |
| 635 | 2D09 | GTTSSINAMG |
| 636 | 2D010 | GSTSSINAMG |
| 637 | 2D011 | GTTSSINAMG |
| 638 | 2D012 | GKTSSINAMG |
| 639 | 2E01 | GSTSSINAMG |
| 640 | 2E02 | GSTSAINAMG |
| 641 | 2E05 | GSPSSINAYG |
| 642 | 2E06 | GSTSSINAMG |
| 643 | 2E08 | GSRSSINAMG |
| 644 | 2E09 | GSVSSINAMG |
| 645 | 2E010 | GSTSSINAMA |
| 646 | 2E011 | GSTSSINAIG |
| 647 | 2F01 | GSTSSINAMG |
| 648 | 2F02 | GSTSSINAVG |
| 649 | 2F03 | GSTSSINAMA |
| 650 | 2F06 | GSTSSINAYG |
| 651 | 2F07 | GSTSSINAVG |
| 652 | 2F08 | GSKSSINAMG |
| 653 | 2F09 | GSTSSINAMA |
| 654 | 2F11 | GSVSSINAMG |
| 655 | 2G03 | GSTSSINAMG |
| 656 | 2G04 | GSTSSINAMG |
| 657 | 2G07 | GSTSSINAMA |
| 658 | 2G08 | GSTSYINAMG |
| 659 | 2G09 | GSTSSINAMG |
| 660 | 2G011 | GSTSSINAMG |
| 661 | 2H010 | GSTSSINAMG |
| 662 | 2H011 | GSTSRINAMG |
| 663 | 2H02 | GSTSSINAMA |
| 664 | 2H03 | GSTSSINAMA |
| 665 | 2H04 | GSTSSINAMG |
| 666 | 2H06 | GSTSTINAMG |
| 667 | 2H07 | GSTSSINAVG |
| 668 | 2H08 | GSTSSINAMG |

| 669 | 2E05-M106Y | GSPSSINAYG |
| 670 | 2E05-M106Q | GSPSSINAYG |
| 671 | 3A01 | GSSVKFLSMA |
| 672 | 3A02 | GSSVSFLSLA |
| 673 | 3A03 | GSRVSFLSMA |
| 674 | 3A04 | GSQVSFLSMA |
| 675 | 3A05 | GSSVSFLSMA |
| 676 | 3A06 | GSKVSFLSMA |
| 677 | 3A08 | GSSVGFLSMA |
| 678 | 3A09 | GSSVSFLSMA |
| 679 | 3A010 | GSRVSFLSMA |
| 680 | 3A011 | GSSVSFLSLA |
| 681 | 3B01 | GSSVSFLSMA |
| 682 | 3B02 | GSSVQFLSMA |
| 683 | 3B04 | GSNVSFLSMA |
| 684 | 3B05 | GSSVKFLSMA |
| 685 | 3B06 | GKSVSFLSMA |
| 686 | 3B07 | GSRVSFLSMA |
| 687 | 3B09 | GSHVSFLSMA |
| 688 | 3B010 | GSSVSFLSMA |
| 689 | 3B011 | GSSVSFLSMA |
| 690 | 3C01 | GSSVRFLSMA |
| 691 | 3C02 | GSSVRFLSMA |
| 692 | 3C03 | GSSVRFLSMA |
| 693 | 3C04 | GSHVSFLSMA |
| 694 | 3C05 | GTSVSFLSMA |
| 695 | 3C06 | GTSVSFLSIA |
| 696 | 3C08 | GSSVKFLSMA |
| 697 | 3C09 | GSSVSFLSMA |
| 698 | 3C011 | GSSVRFLSMA |
| 699 | 3D01 | GSSVSFLSMA |
| 700 | 3D02 | GSSVRFLSMA |
| 701 | 3D03 | GSSVVFLSMA |
| 702 | 3D05 | GSSVRFLSMA |
| 703 | 3D07 | GSSVRFLSMA |
| 704 | 3D08 | GSSVRFLSMA |
| 705 | 3D09 | GSSVSRLSMA |
| 706 | 3D010 | GSSKSFLSMA |
| 707 | 3D011 | GSSVSRLSMA |

-continued

| | | |
|---|---|---|
| 708 | 3E01 | GSSVKFLSMA |
| 709 | 3E02 | GSGVRFLSMA |
| 710 | 3E03 | GSSVRFLSMA |
| 711 | 3E04 | GSSVHFLSMA |
| 712 | 3E09 | GSSVRFLSMA |
| 713 | 3E011 | GSKVSFLSMA |
| 714 | 3F03 | GSSVSFLSMA |
| 715 | 3F05 | GSKVSFLSMA |
| 716 | 3F06 | GSRVSFLSMA |
| 717 | 3F08 | GSRVSFLSMA |
| 718 | 3F09 | GSSVRFLSMA |
| 719 | 3F010 | YSSVSRLSMA |
| 720 | 3F011 | GSSVSFLSMA |
| 721 | 3G01 | GSSVSFLSMA |
| 722 | 3G02 | GSSVSFLSMA |
| 723 | 3G04 | GTSVSFLSMA |
| 724 | 3G06 | GSSVKFLSMA |
| 725 | 3G07 | GSSVSFLSMA |
| 726 | 3G08 | GSRVSFLSMA |
| 727 | 3G09 | GSSVSVLSMA |
| 728 | 3G010 | GSSVSFLSMA |
| 729 | 3G011 | GSRVSFLSMA |
| 730 | 3H01 | GSSVKFLSMA |
| 731 | 3H03 | GSSVRFLSMA |
| 732 | 3H06 | GSSVSQLSMA |
| 733 | 3H07 | GSRVSFLSMA |
| 734 | 3H09 | KSSVSFLSMA |
| 735 | 3H010 | GSSVSFLSMA |
| 736 | 3H011 | GSSVKFLSMA |
| 737 | 4A01 | GSSVRFLSMA |
| 738 | 4A02 | GSSVRFLSMA |
| 739 | 4A04 | GSRVSFLSMA |
| 740 | 4A05 | GSSVSFLSLA |
| 741 | 4A06 | GSSVRFLSMA |
| 742 | 4A07 | GSKVSFLSMA |
| 743 | 4A08 | GSSVSFLSMA |
| 744 | 4A010 | GSSVRFLSMA |
| 745 | 4A011 | GSKVSFLSMA |
| 746 | 4A09 | GSSVKFLSMA |

| | | |
|---|---|---|
| 747 | 4B01 | GSSVKFLSMA |
| 748 | 4B02 | GSRVSFLSMA |
| 749 | 4B04 | GSSVLFLSMA |
| 750 | 4B05 | GSRVSFLSMA |
| 751 | 4B06 | GSRVSFLSMA |
| 752 | 4B07 | GSSVGFLSMA |
| 753 | 4B08 | GSSVSFMSMA |
| 754 | 4B09 | GSSVSFLSMA |
| 755 | 4B011 | GSSVTFLSMA |
| 756 | 4C01 | GSSVRFLSMA |
| 757 | 4C02 | GSKVSFLSMA |
| 758 | 4C03 | GSKVSFMSMA |
| 759 | 4C05 | GSSVSNLSMA |
| 760 | 4C06 | NSSVSKLSMA |
| 761 | 4C07 | GSKVSFLSMA |
| 762 | 4C08 | GSQVSFLSMA |
| 763 | 4C010 | GSKVSFMSMA |
| 764 | 4C011 | GSRVSFLSMA |
| 765 | 4D01 | GSSVRFLSMA |
| 766 | 4D02 | GSKVSFLSMA |
| 767 | 4D03 | GSSVRFLSMA |
| 768 | 4D04 | GSSVSFLSIA |
| 769 | 4D05 | GSSSSFLSMA |
| 770 | 4D06 | GSSVKFLSMA |
| 771 | 4D08 | GSSVNFLSMA |
| 772 | 4D09 | GSSVKFLSMA |
| 773 | 4D010 | GSSVSFLSMA |
| 774 | 4D011 | GSSVRFLSMA |
| 775 | 4E01 | GSSVSFLSVA |
| 776 | 4E02 | GSQVSFLSMA |
| 777 | 4E06 | GTSVSFLSMA |
| 778 | 4E07 | GSRVSFLSMA |
| 779 | 4E08 | GSSVKFLSMA |
| 780 | 4E09 | GSSVSFLSSA |
| 781 | 4E010 | GSSVKFLSMA |
| 782 | 4E011 | GSSVSFLSMA |
| 783 | 4F02 | GSTVSFLSMA |
| 784 | 4F03 | GSSVQFLSMA |
| 785 | 4F04 | RSSVSFLSMA |
| 786 | 4F08 | GSKVSFLSMA |

| | | |
|---|---|---|
| 787 | 4F09 | GSRVSFLSMA |
| 788 | 4F010 | GSSVSFLSMA |
| 789 | 4F011 | GSKVSFLSMA |
| 790 | 4G01 | GSSVRFLSMA |
| 791 | 4G02 | GSSVKFLSMA |
| 792 | 4G03 | GSSVKFLSMA |
| 793 | 4G05 | GSSVSILSMA |
| 794 | 4G07 | GSSVSFLSVA |
| 795 | 4G08 | GSSVRFLSMA |
| 796 | 4G09 | GSRVSFLSMA |
| 797 | 4G010 | GHSVSFLSMA |
| 798 | 4G011 | GSSVRFLSMA |
| 799 | 4H01 | GSSVSFLSMA |
| 800 | 4H03 | GSRVSFLSMA |
| 801 | 4H04 | GSSVKFLSMA |
| 802 | 4H05 | GSSVSRLSMA |
| 803 | 4H06 | GRSVSFLSMA |
| 804 | 4H07 | GRSVSFLSMA |
| 805 | 4H08 | GSSVKFLSMA |
| 806 | 4H09 | GSSVSKLSMA |
| 807 | 4H011 | GSSVSRLSMA |
| 808 | 4D09-M34L | GSSVKFLSLA |
| 809 | 4H11-M34L | GSSVSRLSLA |
| 810 | 41B11 | GTSSSINAMG |
| 811 | 41C02 | GTTSSINAIG |
| 812 | 41D01 | GSTSSINAMA |
| 813 | 41D02 | GQTYRVNAFG |
| 814 | 41D03 | GSTSSINAMA |
| 815 | 41D07 | GSASLTNATG |
| 816 | 41E01 | GYPSLNNAMG |
| 817 | 41E02 | GSSSTINAIG |
| 818 | 41F07 | GSTSYINAMG |
| 819 | 41G01 | GSTSSVNALG |
| 820 | 42A03 | GSTSLSNAVG |
| 821 | 42A06 | GSTSSTNAIG |
| 822 | 42A07 | GLTSTINAMG |
| 823 | 42A08 | GVSPSKNAIG |
| 824 | 42A11 | GSTSSINAVG |

| | | |
|---|---|---|
| 825 | 42B06 | GSTTMNNAMA |
| 826 | 42B10 | GSTSKINAIG |
| 827 | 42C01 | GQTTALNAMG |
| 828 | 42C03 | GATSSINAIG |
| 829 | 42C07 | GSTSTINAMG |
| 830 | 42C08 | GSTSSINAMG |
| 831 | 42C10 | GSTSLVNAMG |
| 832 | 42C11 | GSTSLNNAIG |
| 833 | 42D05 | GSTSPVNAMA |
| 834 | 42D06 | GTTSSMNAIG |
| 835 | 42D07 | GETSSINAMA |
| 836 | 42D08 | GSTSTINAIG |
| 837 | 42E01 | GSTYSMNAMG |
| 838 | 42E02 | GSPSSINAYG |
| 839 | 42E05 | GSTSTINAIG |
| 840 | 42E06 | GSTSSINAIG |
| 841 | 42E07 | GSISSINAMG |
| 842 | 42F01 | GSTQVNNAMA |
| 843 | 42F08 | GSTASFNAMA |
| 844 | 42F10 | GSPLSINAIG |
| 845 | 42G05 | GSTTFINAIG |
| 846 | 42G07 | GSTSSINAIG |
| 847 | 42H05 | GETDTINAVG |
| 848 | 42H08 | GSTSPINAIG |
| 849 | 42H11 | GSITSSNAMG |
| 850 | 51A01 | RYSVSNLSMA |
| 851 | 51A02 | MSTVSVLSMA |
| 852 | 51A03 | DSYVSLLSMA |
| 853 | 51A05 | DSAVSVLSIA |
| 854 | 51B01 | HSSVTSLSLA |
| 855 | 51B04 | DSVVKFLSMA |
| 856 | 51B11 | DPSVWNLSMA |
| 857 | 51C02 | GTSVMLLSLA |
| 858 | 51D01 | SSPVSNLSLA |
| 859 | 51D03 | WRSVLLLSVA |
| 860 | 51E02 | SSSVQYLSMA |
| 861 | 51E03 | GTSVSLLSLA |
| 862 | 51E05 | LSSVSNLSIA |
| 863 | 51F01 | MYSVSFLSMA |
| 864 | 51F02 | KSSVSHLSLA |

| | | |
|---|---|---|
| 865 | 51F03 | YTSVLDLSIA |
| 866 | 51F04 | MSDVSFLSMA |
| 867 | 51G02 | ESSVSFLSSA |
| 868 | 51G04 | GDSVSLLSMA |
| 869 | 51G10 | GSDVWYLSLA |
| 870 | 51H04 | KSAVAFLSIA |
| 871 | 51H05 | FSAVAYLSMA |
| 872 | 52B01 | VYSVYDLSTA |
| 873 | 52C04 | GDSVSFLSMA |
| 874 | 52D04 | SSSVSLLSLA |
| 875 | 53A04 | ADSVSFLSIA |
| 876 | 53A05 | ASSVTLLSIA |
| 877 | 53A09 | ADSVSFLSIA |
| 878 | 53B05 | GTSVWLLSMA |
| 879 | 53B06 | GSSVSILSIA |
| 880 | 53C03 | GTAVSNLSIA |
| 881 | 53C04 | GSAVSMLSLA |
| 882 | 53H03 | GMTVFFLSMA |
| 883 | 53H04 | QYSVTFLSVA |
| 884 | 54B05 | GETVSFLSLA |

| SEQ. ID NO. | name | CDR2 |
|---|---|---|
| 885 | DL1 | VITSFSSTNYADSVKG |
| 886 | DL74 | VITSFSSTNYADSVKG |
| 887 | DL31 | AITSFSSTNYADSVKG |
| 888 | DL3 | RITSGGSTNYADSVKG |
| 889 | DL80 | AITSFGSTNYADSVKD |
| 890 | DL18 | AITTFDYTNYADSVKG |
| 891 | DL94 | AITSFGSTNYADSVKG |
| 892 | DL17 | TLTSGGNTNYADSVKG |
| 893 | DL46 | TLTSGGNTNYADSVKG |
| 894 | DL15 | TLTSGGNTNYADSVKG |
| 895 | DL26 | TLTSGGNTNYADSVKG |
| 896 | DL83 | SLTSEGLTNYRDSVKG |
| 897 | DL5 | AITTWGSTNYADSVKG |
| 898 | DL22 | AITSYGSTNYADSVKG |
| 899 | DL85 | AITTYGSTNYIDSVKG |
| 900 | DL69 | RITTFGTTNYADSVKG |
| 901 | DL27 | RITSSGFSTNYADSVKG |
| 902 | DL51 | RITSSGFSTNYADSVKG |

| | | |
|---|---|---|
| 903 | DL54 | NMHSGGSTNYADSVKG |
| 904 | DL11 | GISVDGSTNYADSVKG |
| 905 | DL19 | GISVDGSTNYADSVKG |
| 906 | DL68 | GISVDGSTNYADSVKG |
| 907 | DL14 | GISVDGSTNYADSVKG |
| 908 | DL67 | GISVDGSTNYADSVKG |
| 909 | DL56 | GISTDGSTNYVDSVKG |
| 910 | DL13 | GISTDGTTNYVDSVKD |
| 911 | DL77 | GISTDGTTNYVDSVKD |
| 912 | DL79 | GISTDGTTNYVDSVKD |
| 913 | DL20 | GISTDGSTNYADSVKG |
| 914 | DL41 | GISTDGSTNYADSVKG |
| 915 | DL59 | GISTDGSTNYADSVKG |
| 916 | DL16 | GISSDGSTNYVDSVKG |
| 917 | DL6 | GISADGSTDYIDSVKG |
| 918 | DL84 | GISSDGSTHYVDSVKG |
| 919 | DL2 | GISSDGSKNYADSVKG |
| 920 | DL43 | GISSDGSKVYADSVKG |
| 921 | DL92 | GSSSDGSTHYVDSVRG |
| 922 | DL10 | IIRSGGSSNYADTVKG |
| 923 | DL82 | LITSGGSSNYADTVKG |
| 924 | DL23 | IITSGGSSNYADTVKG |
| 925 | DL42 | TIFDGSYTNYADSVKG |
| 926 | DL45 | SITTFGSTNYADPVKG |
| 927 | DL58 | TITRDGTRNYADSLKG |
| 928 | DL70 | TISRGGTRTYADSVKG |
| 929 | DL89 | LIGSAGSTKYADSVKG |
| 930 | DL38 | RITSGGITKYADSVKG |
| 931 | DL52 | RITSGGITKYADSVKG |
| 932 | DL64 | RITSGGITKYADSVKG |
| 933 | DL33 | RITSGGITKYADSVKG |
| 934 | DL12 | AITTSGNTSYADSVKG |
| 935 | DL29 | VITRGGATNYADSVKG |
| 936 | DL61 | SIAGDGRTNYAESTEG |
| 937 | DH1 | VITSFSSTNYADSVKG |
| 938 | DH10 | IIRSGGSSNYADTVKG |
| 939 | DH11 | GISVDGSTNYADSVKG |
| 940 | DH12 | AITTSGNTSYADSVKG |
| 941 | DH15 | TLTSGGNTNYADSVKG |

-continued

| | | |
|---|---|---|
| 942 | DH17 | TLTSGGNTNYADSVKG |
| 943 | DH18 | AITTFDYTNYADSVKG |
| 944 | DH2 | GISSDGSKNYADSVKG |
| 945 | DH22 | AITSYGSTNYADSVKG |
| 946 | DH23 | IITSGGSSNYADTVKG |
| 947 | DH27 | RITSSGFSTNYADSVKG |
| 948 | DH29 | VITRGGATNYADSVKG |
| 949 | DH3 | RITSGGSTNYADSVKG |
| 950 | DH38 | RITSGGITKYADSVKG |
| 951 | DH42 | TIFDGSYTNYADSVKG |
| 952 | DH43 | GISSDGSKVYADSVKG |
| 953 | DH45 | SITTFGSTNYADPVKG |
| 954 | DH5 | AITTWGSTNYADSVKG |
| 955 | DH51 | RITSSGFSTNYADSVKG |
| 956 | DH54 | NMHSGGSTNYADSVKG |
| 957 | DH56 | GISTDGSTNYVDSVKG |
| 958 | DH58 | TITRDGTRNYADSLKG |
| 959 | DH6 | GISADGSTDYIDSVKG |
| 960 | DH61 | SIAGDGRTNYAESTEG |
| 961 | DH67 | GISVDGSTNYADSVKG |
| 962 | DH69 | RITTFGTTNYADSVKG |
| 963 | DH70 | TISRGGTRTYADSVKG |
| 964 | DH80 | AITSFGSTNYADSVKD |
| 965 | DH82 | LITSGGSSNYADTVKG |
| 966 | DH83 | SLTSEGLTNYRDSVKG |
| 967 | DH84 | GISSDGSTHYVDSVKG |
| 968 | DH89 | LIGSAGSTKYADSVKG |
| 969 | DH92 | GSSSDGSTHYVDSVRG |
| 970 | DH94 | AITSFGSTNYADSVKG |
| 971 | 1A01 | GISSDGSFVYADSVKG |
| 972 | 1A03 | GISSDGSKVYADSVKG |
| 973 | 1A04 | GISSDGSKVYEDSVKG |
| 974 | 1A05 | GISSDGSKVYADSVKG |
| 975 | 1A06 | GISSDGSSVYADSVKG |
| 976 | 1A07 | GISSDGSKVYADSVKG |
| 977 | 1A09 | GISSDGSKLYADSVKG |
| 978 | 1A010 | GISSDGSKVYADSVKG |
| 979 | 1A011 | GISSDGSKVYIDSVKG |
| 980 | 1A012 | GISSDGSKVYSDSVKG |
| 981 | 1B01 | GISSDGSKVIADSVKG |

| | | -continued |
|---|---|---|
| 982 | 1B02 | GISSDGSKIYADSVKG |
| 983 | 1B03 | GISSDGSKVYTDSVKG |
| 984 | 1B04 | GISSDGSLVYADSVKG |
| 985 | 1B05 | GISSDGSKVYADSVKG |
| 986 | 1B07 | GISSDGSKVYSDSVKG |
| 987 | 1B08 | GISSDGSKVYVDSVKG |
| 988 | 1B09 | GISSDGSKVYVDSVKG |
| 989 | 1B010 | GISSDGSKVYADSVKG |
| 990 | 1B011 | GISSDGSKVYADSVKG |
| 991 | 1C01 | GISSDGSKVYRDSVKG |
| 992 | 1C02 | GISSDGSKVYSDSVKG |
| 993 | 1C03 | GISSDNSKVYADSVKG |
| 994 | 1C04 | GISSDGSKVYADSVKG |
| 995 | 1C05 | GISSDGSKVYADSVKG |
| 996 | 1C06 | GISSDGSKVYEDSVKG |
| 997 | 1C07 | GISSDGSKVYADSVKG |
| 998 | 1C08 | GISSDGSKVYAVSVKG |
| 999 | 1C010 | GVSSDGSKVYADSVKG |
| 1000 | 1C011 | GISSDGSKVYEDSVKG |
| 1001 | 1C012 | GISSDGSKVYAGSVKG |
| 1002 | 1D01 | GISSDKSKVYADSVKG |
| 1003 | 1D02 | GISSNGSKVYADSVKG |
| 1004 | 1D03 | GISSDGSKVLADSVKG |
| 1005 | 1D04 | GISSDGSKVYADSVKG |
| 1006 | 1D06 | GISSDNSKVYADSVKG |
| 1007 | 1D08 | GISSDGSKVYADSVKG |
| 1008 | 1D09 | GISSDGSKVYTDSVKG |
| 1009 | 1D010 | GISSDGSKVYTDSVKG |
| 1010 | 1D011 | GISSDNSKVYADSVKG |
| 1011 | 1D012 | GISSDGSRVYADSVKG |
| 1012 | 1E02 | GISSDGSQVYADSVKG |
| 1013 | 1E04 | GISSDGSKAYADSVKG |
| 1014 | 1E05 | GISSDGSKVYAKSAKG |
| 1015 | 1E07 | GISSDGSKVYNDSVKG |
| 1016 | 1E08 | GISSDGSKVIADSVKG |
| 1017 | 1E09 | GISSDGSKVYTDSVKG |
| 1018 | 1E010 | GISSDGSKVYIDSVKG |
| 1019 | 1E011 | GISSDGSKVYYDSVKG |
| 1020 | 1E012 | GISSDGSKVYVDSVKG |

-continued

| | | |
|---|---|---|
| 1021 | 1F01 | GISSDGSKVYGDSVKG |
| 1022 | 1F02 | GISSDQSKVYADSAKG |
| 1023 | 1F04 | GISSDGSKVYSDSVKG |
| 1024 | 1F05 | GISSDGSKVYADSVKG |
| 1025 | 1F06 | GISSDGSKVIADSVKG |
| 1026 | 1F07 | GISSDGSKVDADSVKG |
| 1027 | 1F08 | GISSDGSKVYKDSVKG |
| 1028 | 1F09 | GISSNGSKVYADSVKG |
| 1029 | 1F010 | GISSDGSKVYKDSVKG |
| 1030 | 1F011 | GISSDGSKVYADSVKG |
| 1031 | 1F012 | GISSDGSKVYQDSVKG |
| 1032 | 1G01 | GISSDGSKVYAESVKG |
| 1033 | 1G04 | GISSDGSKVLADSVKG |
| 1034 | 1G05 | GISSDGSKYYADSVKG |
| 1035 | 1G06 | GISSDGSKVYAVSVKG |
| 1036 | 1G07 | GISSDGSKVVADSVKG |
| 1037 | 1G09 | GISSDGSKVYADSVKG |
| 1038 | 1G011 | GISSDGSKVYADSVKG |
| 1039 | 1H01 | GISSDNSKVYADSVKG |
| 1040 | 1H02 | GISSDGSKVYAQSVKG |
| 1041 | 1H06 | GISSDGSKVYVDSVKG |
| 1042 | 1H07 | GISSDGSKVYSDSVKG |
| 1043 | 1H08 | GISSDGSKVLADSVKG |
| 1044 | 1H010 | GISSDGSKVYNDSVKG |
| 1045 | 1H011 | GISSDGSKVYNDSVKG |
| 1046 | 1H012 | GISSDGSKVYVDSVKG |
| 1047 | 2A01 | GISSDGSKVVADSVKG |
| 1048 | 2A03 | GISSDGSKVYGDSVKG |
| 1049 | 2A04 | GISSDGSKVYTDSVKG |
| 1050 | 2A05 | GISSDGSKVYNDSVKG |
| 1051 | 2A06 | GISSDGSKVTADSVKG |
| 1052 | 2A08 | GISSDGSKVYRDSVKG |
| 1053 | 2A09 | GISSNGSKVYSDSVKG |
| 1054 | 2A011 | GISSDGSKVYSDSVKG |
| 1055 | 2B01 | GISSDGSKVYADSVKG |
| 1056 | 2B02 | GISSDGSKVYADSVKG |
| 1057 | 2B03 | GISSDGSLVYADSVKG |
| 1058 | 2B05 | GISSDGTKVYADSVKG |
| 1059 | 2B07 | GISSDGSKVYADSVKG |
| 1060 | 2B010 | GISSDGSKLYLDSVKG |

| | | |
|---|---|---|
| 1061 | 2B011 | GISSDGSRVYADSVKG |
| 1062 | 2B012 | GISSDGSKVYNDSVKG |
| 1063 | 2C01 | GISSDGSKVYADSVKG |
| 1064 | 2C02 | GISSDGSKVYVDSVKG |
| 1065 | 2C04 | GISSDGSKLYADSVKG |
| 1066 | 2C06 | GISSDGSKVYKDSVKG |
| 1067 | 2C07 | GISSDGSKVYADSVKG |
| 1068 | 2C08 | GISSDGSKVYQDSVKG |
| 1069 | 2C09 | GISSDGTKIYADSAKV |
| 1070 | 2C010 | GISSDRSKVYADSVKG |
| 1071 | 2D02 | GISSDGSLVYADSVKG |
| 1072 | 2D03 | GISSDGSKVYADSVKG |
| 1073 | 2D04 | GISSDGSKVYRDSVKG |
| 1074 | 2D05 | GISSDGSKVYADSVKG |
| 1075 | 2D06 | GISSDGSKVYSDSVKG |
| 1076 | 2D07 | GISSDGTKVYRDSVKG |
| 1077 | 2D09 | GISSDGSKVYNDSVKG |
| 1078 | 2D010 | GISSDGSKVYADSVKG |
| 1079 | 2D011 | GISSDGSKVYADSVKG |
| 1080 | 2D012 | GISSDGSKVYTDSVKG |
| 1081 | 2E01 | GISPDGTKAYADSAKV |
| 1082 | 2E02 | GISSDGSKVYVDSVKG |
| 1083 | 2E05 | GISSDGSKVYSDSVKG |
| 1084 | 2E06 | GISSDGSKVYASSVKG |
| 1085 | 2E08 | GISADGSKVYADSVKG |
| 1086 | 2E09 | GISSDGSKVYASSAKG |
| 1087 | 2E010 | GISSDGSKVYADSVKG |
| 1088 | 2E011 | GISSDGSSVYADSVKG |
| 1089 | 2F01 | GISSDGSKVYSDSVKG |
| 1090 | 2F02 | GISSDGSKVYAGSVKG |
| 1091 | 2F03 | GISSDNSKVYADSVKG |
| 1092 | 2F06 | GISSDGSAVYADSVKG |
| 1093 | 2F07 | GISSDGSSVYADSVKG |
| 1094 | 2F08 | GISSNGTKVYADSAKV |
| 1095 | 2F09 | GISSDGSKLYADSVKG |
| 1096 | 2F11 | GISSDGSKVYKDSVKG |
| 1097 | 2G03 | GISSDGSLVYADSVKG |
| 1098 | 2G04 | GISSDGSLVYADSVKG |
| 1099 | 2G07 | GISSDGSKVYADSVKG |

-continued

| | | |
|---|---|---|
| 1100 | 2G08 | GISSDGSKVYADSVKG |
| 1101 | 2G09 | GVSSDGSKVYADSVKG |
| 1102 | 2G011 | GISRDGSKVYADSVKG |
| 1103 | 2H010 | GISSDGSKLYADSVKG |
| 1104 | 2H011 | GISSDGSKVYADSVKG |
| 1105 | 2H02 | GISSDGSKVYADSVKG |
| 1106 | 2H03 | GISSDGSKVYADSVKG |
| 1107 | 2H04 | GISSDTSKVYADSVKG |
| 1108 | 2H06 | GISSDGSKVYADSVKG |
| 1109 | 2H07 | GISSDGSTVYADSVKG |
| 1110 | 2H08 | GISKDGSKVYADSAKG |
| 1111 | 2E05-M106Y | GISSDGSKVYSDSVKG |
| 1112 | 2E05-M106Q | GISSDGSKVYSDSVKG |
| 1113 | 3A01 | GISADGSTDYIDSVKG |
| 1114 | 3A02 | GISADGSTAYIDSVKG |
| 1115 | 3A03 | GISRDGSTDYIDSVKG |
| 1116 | 3A04 | GISRDGSTDYIDSVKG |
| 1117 | 3A05 | GISEAGSTDYIDSVKG |
| 1118 | 3A06 | GISADGSTDYVDSVKG |
| 1119 | 3A08 | GISADGSTDYIRSVKG |
| 1120 | 3A09 | GISADGSVDYIDSVKG |
| 1121 | 3A010 | GISADGSTLYIDSVKG |
| 1122 | 3A011 | GISTDGSTDYIDSVKG |
| 1123 | 3B01 | GISGDGSTDYIDSVKG |
| 1124 | 3B02 | GISADGSTDYINSVKG |
| 1125 | 3B04 | GISARGSTDYIDSVKG |
| 1126 | 3B05 | GISADGSTTYIDSVKG |
| 1127 | 3B06 | GISKDGSTDYIDSVKG |
| 1128 | 3B07 | GISADGSTTYIDSVKG |
| 1129 | 3B09 | GISANGSTDYIDSVKG |
| 1130 | 3B010 | GISRDGSTDYIDSVKG |
| 1131 | 3B011 | GISADGSADYIDSVKG |
| 1132 | 3C01 | GISAHGSTDYIDSVKG |
| 1133 | 3C02 | GISADGSTIYIDSVKG |
| 1134 | 3C03 | GISRDGSTVYIDSVKG |
| 1135 | 3C04 | GISADGPTDYIDSVKG |
| 1136 | 3C05 | GISADGSTTYIDSVKG |
| 1137 | 3C06 | GISADGSTDYIASVKG |
| 1138 | 3C08 | GISLDGSTDYIDSVKG |

-continued

| 1139 | 3C09  | GISADGSTIYIDSVKG |
| 1140 | 3C011 | GISAHGSTDYIDSVKG |
| 1141 | 3D01  | GISRDGSTDYIDSVKG |
| 1142 | 3D02  | GISRDGSTDYIDSVKG |
| 1143 | 3D03  | GISADGSMDYIDSVKG |
| 1144 | 3D05  | GISADGSTDYIDSVKG |
| 1145 | 3D07  | GISADGSTDYIDSVKG |
| 1146 | 3D08  | GISANGSTDYIDSVKG |
| 1147 | 3D09  | GISANGSTTYIDSVKG |
| 1148 | 3D010 | GISADGSTSYIDSVKG |
| 1149 | 3D011 | GISADGSRDYIDSVKG |
| 1150 | 3E01  | GISADGSTMYIDSVKG |
| 1151 | 3E02  | GISPDGSTDYIDSVKG |
| 1152 | 3E03  | GISGDGSTDYIDSVKG |
| 1153 | 3E04  | GISRDGSTDYIDSVKG |
| 1154 | 3E09  | GISRDGSTDYIDSVKG |
| 1155 | 3E011 | GISRDGSTDYIDSVKG |
| 1156 | 3F03  | GISADGSTDYIDSVKG |
| 1157 | 3F05  | GISTDGSTDYIDSVKG |
| 1158 | 3F06  | GISADGSTSYIDSVKG |
| 1159 | 3F08  | GISADGSTLYIDSVKG |
| 1160 | 3F09  | GISRDGSTDYIDSVKG |
| 1161 | 3F010 | GISADGSTVYIDSVKG |
| 1162 | 3F011 | GISTDGSTDYIDSVKG |
| 1163 | 3G01  | GISADGSTLYIDSVKG |
| 1164 | 3G02  | GISADGRTDYIDSVKG |
| 1165 | 3G04  | GISADGSTIYIDSVKG |
| 1166 | 3G06  | GISADGSTLYIDSVKG |
| 1167 | 3G07  | GISRDGSTDYIDSVKG |
| 1168 | 3G08  | GISKDGSTDYIDSVKG |
| 1169 | 3G09  | GISADGSTDYIGSVKG |
| 1170 | 3G010 | GISVDGSTDYIDSVKG |
| 1171 | 3G011 | GISADGSTGYIDSVKG |
| 1172 | 3H01  | GISGDGSTTYIDSVKG |
| 1173 | 3H03  | GISTDGSTDYIDSVKG |
| 1174 | 3H06  | GISADGSTDYFDSVKG |
| 1175 | 3H07  | GISADGSTSYIDSVKG |
| 1176 | 3H09  | GISADGSTDYIDSVKG |
| 1177 | 3H010 | GISADGSTAYIDSVKG |

| | | |
|---|---|---|
| 1178 | 3H011 | GISADGSTVYIDSVKG |
| 1179 | 4A01 | GISQDGSTDYIDSVKG |
| 1180 | 4A02 | GISNDGSTDYIDSVKG |
| 1181 | 4A04 | GISARGSTDYIDSVKG |
| 1182 | 4A05 | GISADGSTDYIDSVKG |
| 1183 | 4A06 | GISRDGSTDYIDSVKG |
| 1184 | 4A07 | GISADGSTLYIDSVKG |
| 1185 | 4A08 | GISADGSTNYIDSVKG |
| 1186 | 4A010 | GISADGSTVYIDSVKG |
| 1187 | 4A011 | GISADGSTTYIDSVKG |
| 1188 | 4A09 | GISADGSTDYIGSVKG |
| 1189 | 4B01 | GISRDGSTDYIDSVKG |
| 1190 | 4B02 | GISADGSTTYIDSVKG |
| 1191 | 4B04 | GVSSDGSTDYIDSVKG |
| 1192 | 4B05 | GISADGHTDYIDSVKG |
| 1193 | 4B06 | GISADGSTDYFDSVKG |
| 1194 | 4B07 | GISADGSTVYIDSVKG |
| 1195 | 4B08 | GISADGSTDYIASVKG |
| 1196 | 4B09 | GISADGSTDYISSVKG |
| 1197 | 4B011 | GISADGSTVYIDSVKG |
| 1198 | 4C01 | GISADGSTVYIDSVKG |
| 1199 | 4C02 | GISADGSTTYIDSVKG |
| 1200 | 4C03 | GISVDGSTDYIDSVKG |
| 1201 | 4C05 | GISADGSTAYIDSVKG |
| 1202 | 4C06 | GISADGSTAYIDSVKG |
| 1203 | 4C07 | GISADGSKDYIDSVKG |
| 1204 | 4C08 | GISADGSTDYFDSVKG |
| 1205 | 4C010 | GISADGSTDYIDSVKG |
| 1206 | 4C011 | GISADGSTVYIDSVKG |
| 1207 | 4D01 | GISADGSTVYIDSVKG |
| 1208 | 4D02 | GISARGSTDYIDSVKG |
| 1209 | 4D03 | GISATGSTDYIDSVKG |
| 1210 | 4D04 | GISKDGSTDYIDSVKG |
| 1211 | 4D05 | GISADGSTVYIDSVKG |
| 1212 | 4D06 | GISPDGSTDYIDSVKG |
| 1213 | 4D08 | GISADGSTHYIDSVKG |
| 1214 | 4D09 | GISADGSTDYILSVKG |
| 1215 | 4D010 | GISADGSTDYIHSVKG |
| 1216 | 4D011 | GISVDGSTDYIDSVKG |
| 1217 | 4E01 | GISRDGSTDYIDSVKG |

| | | |
|---|---|---|
| 1218 | 4E02 | GISADGSTVYIDSVKG |
| 1219 | 4E06 | GISADGSTDYIRSVKG |
| 1220 | 4E07 | GISADGSTMYIDSVKG |
| 1221 | 4E08 | GISTDGSTDYIDSVKG |
| 1222 | 4E09 | GISADGSTLYIDSVKG |
| 1223 | 4E010 | GISADGSTDYIDSVKG |
| 1224 | 4E011 | GISATGSTDYIDSVKG |
| 1225 | 4F02 | GISHDGSTDYIDSVKG |
| 1226 | 4F03 | GISYDGSTDYIDSVKG |
| 1227 | 4F04 | GISTDGSTDYIDSVKG |
| 1228 | 4F08 | GISADGSTAYIDSVKG |
| 1229 | 4F09 | GISADGSTDYIESVKG |
| 1230 | 4F010 | GISIDGSTDYIKSVKG |
| 1231 | 4F011 | GISADGSKDYIDSVKG |
| 1232 | 4G01 | GISADGSTVYIDSVKG |
| 1233 | 4G02 | GISRDGSTDYIDSVKG |
| 1234 | 4G03 | GISADGSTDYIHSVKG |
| 1235 | 4G05 | GISADGSTIYIDSVKG |
| 1236 | 4G07 | GISANGSTDYIDSVKG |
| 1237 | 4G08 | GISTDGSTDYIDSVKG |
| 1238 | 4G09 | GISYDGSTDYIDSVKG |
| 1239 | 4G010 | GISADGSTDYIASVKG |
| 1240 | 4G011 | GISADGSTDYIGSVKG |
| 1241 | 4H01 | GISANGSTDYYDSVKG |
| 1242 | 4H03 | GISADGSTSYIDSVKG |
| 1243 | 4H04 | GVSADGSTDYIDSVKG |
| 1244 | 4H05 | GISARGSTDYIDSVKG |
| 1245 | 4H06 | GISADGSTIYIDSVKG |
| 1246 | 4H07 | GISANGSTDYIDSVKG |
| 1247 | 4H08 | GISADGSTDYVDSVKG |
| 1248 | 4H09 | GISADGSTDYRDSVKG |
| 1249 | 4H011 | GISVDGSTDYIDSVKG |
| 1250 | 4D09-M34L | GISADGSTDYILSVKG |
| 1251 | 4H11-M34L | GISVDGSTDYIDSVKG |
| 1252 | 41B11 | GISSDGSKVFNESVKG |
| 1253 | 41C02 | GISSDGSEVYTDSVKG |
| 1254 | 41D01 | GISSDDSNVYYESVKG |
| 1255 | 41D02 | GISSDGSKVYADSVKG |

-continued

| | | |
|---|---|---|
| 1256 | 41D03 | GISSDESTLYVDSVKG |
| 1257 | 41D07 | GISSDDSKVYSDSVKG |
| 1258 | 41E01 | GISSDGSQVYGASVKG |
| 1259 | 41E02 | GISSDGSKVYADSVKG |
| 1260 | 41F07 | GISSDGSNMYADSVKG |
| 1261 | 41G01 | GISSDGSKVYTDSVKG |
| 1262 | 42A03 | GISSDGSKVSAESVKG |
| 1263 | 42A06 | GISSDGSKVYDDSVKG |
| 1264 | 42A07 | GISSDGSKVYDDSVKG |
| 1265 | 42A08 | GISSDGSAVYVGSVKG |
| 1266 | 42A11 | GISSDGSYVYSESVKG |
| 1267 | 42B06 | GISSDSSHVYADSVKG |
| 1268 | 42B10 | GISSDSSIVYTDSVKG |
| 1269 | 42C01 | GISSDGSEVNTDSVKG |
| 1270 | 42C03 | GISSDGSKLSSDSVKG |
| 1271 | 42C07 | GISSDNSKVYADSVKG |
| 1272 | 42C08 | GISSDGSRVYFDSVKG |
| 1273 | 42C10 | GISSDGSLVYAESVKG |
| 1274 | 42C11 | GISSDGSVVYVDSVKG |
| 1275 | 42D05 | GISSDGSKVYVDSVKG |
| 1276 | 42D06 | GISSDGSKLYDESVKG |
| 1277 | 42D07 | GISSDYSKLYADSVKG |
| 1278 | 42D08 | GISSDSSKVYTESVKG |
| 1279 | 42E01 | GISSDGSQVYVDSVKG |
| 1280 | 42E02 | GISSDGSKVYSDSVKG |
| 1281 | 42E05 | GISSDGSKVYVDSVKG |
| 1282 | 42E06 | GISSDGSKVYADSVKG |
| 1283 | 42E07 | GISSDGSSVYADSVKG |
| 1284 | 42F01 | GISSDGSQVYYGSVKG |
| 1285 | 42F08 | GISSDGSKVYTDSVKG |
| 1286 | 42F10 | GISSDGSKVSADSVKG |
| 1287 | 42G05 | GISSDGSKVYEDSVKG |
| 1288 | 42G07 | GISSDRSKVYADSVKG |
| 1289 | 42H05 | GISSDGSKVYAESVKG |
| 1290 | 42H08 | GISSDGSVVTTESVKG |
| 1291 | 42H11 | GISSDGSHVHQESVKG |
| 1292 | 51A01 | GISADGSTVYVESVKG |
| 1293 | 51A02 | GISSDGSTVYIDSVKG |
| 1294 | 51A03 | GISVDGSTHYVASVKG |
| 1295 | 51A05 | GISTDGSKHYIDSVKG |

-continued

| | | |
|---|---|---|
| 1296 | 51B01 | GISYDGSKYYAESVKG |
| 1297 | 51B04 | GISANGSRTYMESVKG |
| 1298 | 51B11 | GISPDGSTDYVDSVKG |
| 1299 | 51C02 | GISPNGSAVYTESVKG |
| 1300 | 51D01 | GISPDGSTAYMESVKG |
| 1301 | 51D03 | GISNDGSTDYIDSVKG |
| 1302 | 51E02 | GISTDGSAVYFDSVKG |
| 1303 | 51E03 | GISTGGSTHYIESVKG |
| 1304 | 51E05 | GISTDGSTVYIDSVKG |
| 1305 | 51E01 | GISNEGSTYYMDSVKG |
| 1306 | 51E02 | GISADGSHVYTNSVKG |
| 1307 | 51E03 | GISDDGSRYYTDSVKG |
| 1308 | 51E04 | GISAEGSTLYMESVKG |
| 1309 | 51G02 | GISTDGSTVYIDSVKG |
| 1310 | 51G04 | GISANGSTSYIDSVKG |
| 1311 | 51G10 | GISDDGSRHYIESVKG |
| 1312 | 51H04 | GISPDGSTVYIESVKG |
| 1313 | 51H05 | GISDDGSTVYVDSVKG |
| 1314 | 52B01 | GISDDGSTVYFDSVKG |
| 1315 | 52C04 | GISDEGSTVYIGSVKG |
| 1316 | 52D04 | GISDDGSIVYMDSVKG |
| 1317 | 53A04 | GISDDGSKHYFDSVKG |
| 1318 | 53A05 | GISTDGSTDYLHSVKG |
| 1319 | 53A09 | GISDDGSKHYFDSVKG |
| 1320 | 53B05 | GISYDGSTVYVESVKG |
| 1321 | 53B06 | GISDDGSTVYIDSVKG |
| 1322 | 53C03 | GISDDGSTVYVDSVKG |
| 1323 | 53C04 | GISDDGSQVYIDSVKG |
| 1324 | 53H03 | GISVDGSTVYSDSVKG |
| 1325 | 53H04 | GISDDGSNVYIDSVKG |
| 1326 | 54B05 | GISTDGSTVYFVSVKG |

| SEQ.ID NO. | name | CDR3 |
|---|---|---|
| 1327 | DL1 | RYFERTD |
| 1328 | DL74 | RYFERTD |
| 1329 | DL31 | RYFERTD |
| 1330 | DL3 | YQGLYAY |
| 1331 | DL80 | RVFDHVY |
| 1332 | DL18 | RAFGRDY |
| 1333 | DL94 | RTMGRDY |

| | | |
|---|---|---|
| 1334 | DL17 | WDGVGGAY |
| 1335 | DL46 | WDGVGGAY |
| 1336 | DL15 | WNGVGGAY |
| 1337 | DL26 | WDGVGGAY |
| 1338 | DL83 | WDGVGGAY |
| 1339 | DL5 | RSWNNY |
| 1340 | DL22 | RSWNNY |
| 1341 | DL85 | RSWNNY |
| 1342 | DL69 | ESFGRIWYN |
| 1343 | DL27 | QHFGTDS |
| 1344 | DL51 | QQFGTDS |
| 1345 | DL54 | YGIQRAEGY |
| 1346 | DL11 | YRWVGRDTY |
| 1347 | DL19 | YRWVGRDTY |
| 1348 | DL68 | YRWVGRDTY |
| 1349 | DL14 | YRWEGRDTY |
| 1350 | DL67 | YRWEGRNTY |
| 1351 | DL56 | YRWVGRYTY |
| 1352 | DL13 | YRWVGRDTY |
| 1353 | DL77 | YRWVGRDTY |
| 1354 | DL79 | YRWVGRDTY |
| 1355 | DL20 | YRWVDRYTY |
| 1356 | DL41 | YRWIDRYTY |
| 1357 | DL59 | YRWVDRYTY |
| 1358 | DL16 | YRWVGRDTY |
| 1359 | DL6 | YRWTTRYTY |
| 1360 | DL84 | YRWVGGYTY |
| 1361 | DL2 | FRTVAASSMQY |
| 1362 | DL43 | FRTVSGSSMRY |
| 1363 | DL92 | NRGFAGAPSY |
| 1364 | DL10 | YFQSSY |
| 1365 | DL82 | YFQSSY |
| 1366 | DL23 | YFQSSY |
| 1367 | DL42 | HWTQGSVPKES |
| 1368 | DL45 | RSYSSDY |
| 1369 | DL58 | RYGDINY |
| 1370 | DL70 | RYGDINY |
| 1371 | DL89 | YDSRSY |
| 1372 | DL38 | YDNINAY |

-continued

| | | |
|---|---|---|
| 1373 | DL52 | YDNINAY |
| 1374 | DL64 | YDNINAY |
| 1375 | DL33 | YDNINAY |
| 1376 | DL12 | WIAGKAY |
| 1377 | DL29 | RSQLGST |
| 1378 | DL61 | YYLDTYAY |
| 1379 | DH1 | RYFERTD |
| 1380 | DH10 | YFQSSY |
| 1381 | DH11 | YRWVGRDTY |
| 1382 | DH12 | WIAGKAY |
| 1383 | DH15 | WNGVGGAY |
| 1384 | DH17 | WDGVGGAY |
| 1385 | DH18 | RAFGRDY |
| 1386 | DH2 | FRTVAASSMQY |
| 1387 | DH22 | RSWNNY |
| 1388 | DH23 | YFQSSY |
| 1389 | DH27 | QHFGTDS |
| 1390 | DH29 | RSQLGST |
| 1391 | DH3 | YQGLYAY |
| 1392 | DH38 | YDNINAY |
| 1393 | DH42 | HWTQGSVPKES |
| 1394 | DH43 | FRTVSGSSMRY |
| 1395 | DH45 | RSYSSDY |
| 1396 | DH5 | RSWNNY |
| 1397 | DH51 | QQFGTDS |
| 1398 | DH54 | YGIQRAEGY |
| 1399 | DH56 | YRWVGRYTY |
| 1400 | DH58 | RYGDINY |
| 1401 | DH6 | YRWTTRYTY |
| 1402 | DH61 | YYLDTYAY |
| 1403 | DH67 | YRWEGRNTY |
| 1404 | DH69 | ESFGRIWYN |
| 1405 | DH70 | RYGDINY |
| 1406 | DH80 | RVFDHVY |
| 1407 | DH82 | YFQSSY |
| 1408 | DH83 | WDGVGGAY |
| 1409 | DH84 | YRWVGGYTY |
| 1410 | DH89 | YDSRSY |
| 1411 | DH92 | NRGFAGAPSY |
| 1412 | DH94 | RTMGRDY |

-continued

| | | |
|---|---|---|
| 1413 | 1A01 | FRHVSGSSMRY |
| 1414 | 1A03 | FRTVSGSSSRY |
| 1415 | 1A04 | FRTVSGSSMRY |
| 1416 | 1A05 | FRTVRGSSMSY |
| 1417 | 1A06 | FRTVSGSSKRY |
| 1418 | 1A07 | FRMVSGSSMRY |
| 1419 | 1A09 | FRTVQGSSMRY |
| 1420 | 1A010 | FRTVYGSSMRY |
| 1421 | 1A011 | FRTVSGSSYRY |
| 1422 | 1A012 | FRTVLGSSMRY |
| 1423 | 1B01 | FRRVSGSSMRY |
| 1424 | 1B02 | FRTVSGSSMRY |
| 1425 | 1B03 | FRTVSGSSARY |
| 1426 | 1B04 | FRIVRGSSMRY |
| 1427 | 1B05 | YRTVSGSSMRY |
| 1428 | 1B07 | FRHVSGSSMRY |
| 1429 | 1B08 | FRFVSGSSMRY |
| 1430 | 1B09 | FRTVSGSSMRY |
| 1431 | 1B010 | FRTKSGSSMRY |
| 1432 | 1B011 | FRTVYGSSMRY |
| 1433 | 1C01 | FRTVSGSSMGY |
| 1434 | 1C02 | FRTVSGSSMRS |
| 1435 | 1C03 | FRTVGGSSMRY |
| 1436 | 1C04 | FRTVSGSSMRY |
| 1437 | 1C05 | FRTVSGSHMRY |
| 1438 | 1C06 | FRAVSGSSMRY |
| 1439 | 1C07 | FRTVSGSSMRY |
| 1440 | 1C08 | FRTVSGSPMRY |
| 1441 | 1C010 | FRTVSGSSMSY |
| 1442 | 1C011 | FRTVSGSSMRY |
| 1443 | 1C012 | FRTVRGSSMRY |
| 1444 | 1D01 | FRTVRGSSMRY |
| 1445 | 1D02 | FRQVSGSSMRY |
| 1446 | 1D03 | FRIVSGSSMGY |
| 1447 | 1D04 | FRTVSGASMRY |
| 1448 | 1D06 | FRTVHGSSMRY |
| 1449 | 1D08 | FRMVSGSSMRY |
| 1450 | 1D09 | FRTISGSSMRY |
| 1451 | 1D010 | FRTRSGSSMRY |

| | | |
|---|---|---|
| 1452 | 1D011 | FRTVSGHSMRY |
| 1453 | 1D012 | FRTVSGGSMRY |
| 1454 | 1E02 | FRTKSGSSMRY |
| 1455 | 1E04 | FRTASGTSMRY |
| 1456 | 1E05 | FNTVSGSSMRY |
| 1457 | 1E07 | FRTVRGSSQRY |
| 1458 | 1E08 | FRTVLGSSMRY |
| 1459 | 1E09 | FRTRSGSSMRY |
| 1460 | 1E010 | FRTVSGLSMRY |
| 1461 | 1E011 | FRTVRGSSQRY |
| 1462 | 1E012 | FRTVSGSSMVY |
| 1463 | 1F01 | FRTVSRSSMRY |
| 1464 | 1F02 | FRTVSGSSMSY |
| 1465 | 1F04 | FRTVSGSSARY |
| 1466 | 1F05 | FHTVSGSSMRY |
| 1467 | 1F06 | FRTVLGSSMRY |
| 1468 | 1F07 | FRTVSGSSMRY |
| 1469 | 1F08 | FRNVSGSSMRY |
| 1470 | 1F09 | FRTVTGSSMRY |
| 1471 | 1F010 | FRTVSGSSMRY |
| 1472 | 1F011 | FRTVKGSSMRY |
| 1473 | 1F012 | FRTNSGSSMRY |
| 1474 | 1G01 | FRTVSGASMRY |
| 1475 | 1G04 | FRTVNLSSMRY |
| 1476 | 1G05 | FRTVTGSSMRY |
| 1477 | 1G06 | FRKVSGSSARY |
| 1478 | 1G07 | FRTYSGSSMRY |
| 1479 | 1G09 | FRTVSKSSMRY |
| 1480 | 1G011 | FKTVSGSSMRY |
| 1481 | 1H01 | FRTRSGSSMRY |
| 1482 | 1H02 | FRTSSGSSMRY |
| 1483 | 1H06 | FRFLSGSSMRY |
| 1484 | 1H07 | FRTVSGSSMRY |
| 1485 | 1H08 | FRLVSGSSMRY |
| 1486 | 1H010 | FRTVSGSSMRF |
| 1487 | 1H011 | FRTQSGSSMRY |
| 1488 | 1H012 | FRTVSGSSMPY |
| 1489 | 2A01 | FRTLSGSSMRY |
| 1490 | 2A03 | FRTVSGSAMRY |
| 1491 | 2A04 | FRTTSGSSMRY |

| | | |
|---|---|---|
| 1492 | 2A05 | FRTVSGTSMRY |
| 1493 | 2A06 | FRTRSGSSMRY |
| 1494 | 2A08 | FRTSSGSSMRY |
| 1495 | 2A09 | FRTVSGSSMSY |
| 1496 | 2A011 | FRPVSGSSMRY |
| 1497 | 2B01 | FRHVSGSSMRY |
| 1498 | 2B02 | FRTKSGSSMRY |
| 1499 | 2B03 | FTTVSGSSMRY |
| 1500 | 2B05 | FHTVSGSSMRY |
| 1501 | 2B07 | FRTVRGSSMRY |
| 1502 | 2B010 | FRTVLGSSMRY |
| 1503 | 2B011 | FRTVSGSSMRS |
| 1504 | 2B012 | FRTVRGSSMRY |
| 1505 | 2C01 | FRYVSGSSMRY |
| 1506 | 2C02 | FRTVYGSSMRY |
| 1507 | 2C04 | FRTVLGSSMRY |
| 1508 | 2C06 | YRTVSGSSMRY |
| 1509 | 2C07 | FRSVSGSSMRY |
| 1510 | 2C08 | FRRVSGSSMRY |
| 1511 | 2C09 | FRTVSGTSMRY |
| 1512 | 2C010 | FRTVAGSSMRY |
| 1513 | 2D02 | FRIVSGSSMRY |
| 1514 | 2D03 | FRTVSGVSMRY |
| 1515 | 2D04 | FRTVQGSSMRY |
| 1516 | 2D05 | FRTASGSSMRY |
| 1517 | 2D06 | FRTVSGSSSRY |
| 1518 | 2D07 | FRTVQGSSMRY |
| 1519 | 2D09 | FRTVRGSSMRY |
| 1520 | 2D010 | FRTKSGSSMRY |
| 1521 | 2D011 | FRTVWGSSMRY |
| 1522 | 2D012 | FRTRSGSSMRY |
| 1523 | 2E01 | FHTVCGTSMGY |
| 1524 | 2E02 | FRTVSGSSQRY |
| 1525 | 2E05 | FRTVSGSSMSY |
| 1526 | 2E06 | FRTVRGSSMRY |
| 1527 | 2E08 | FRTQSGSSMRY |
| 1528 | 2E09 | FRTLSGSSMRY |
| 1529 | 2E010 | FHTVSGSSMRY |
| 1530 | 2E011 | FRRVSGSSMRY |

-continued

| | | |
|---|---|---|
| 1531 | 2F01 | FRLVSGSSMRY |
| 1532 | 2F02 | FRTVSGSYMRY |
| 1533 | 2F03 | FRTVGGSSMRY |
| 1534 | 2F06 | FRTHSGSSMRY |
| 1535 | 2F07 | FRTVSTSSMRY |
| 1536 | 2F08 | FRTVLGTSMRY |
| 1537 | 2F09 | FRTVSGSSMRY |
| 1538 | 2F11 | FRTVSGSSMGY |
| 1539 | 2G03 | FRTVSGSSMRA |
| 1540 | 2G04 | FRILSGSSMRY |
| 1541 | 2G07 | FRTVQGSSMRY |
| 1542 | 2G08 | FRTVSGQSMGY |
| 1543 | 2G09 | FRTVSGSSARY |
| 1544 | 2G011 | FRYVSGSSMRY |
| 1545 | 2H010 | FRTVSGSSMRY |
| 1546 | 2H011 | FRRVSGSSMRY |
| 1547 | 2H02 | FHTVSGSSMRY |
| 1548 | 2H03 | FRQVSGSSMRY |
| 1549 | 2H04 | FRTVSGSYMRY |
| 1550 | 2H06 | FRTASGSSMRY |
| 1551 | 2H07 | FRTVSGHSMRY |
| 1552 | 2H08 | FRTVSGSSSRY |
| 1553 | 2E05-M106Y | FRTVSGSSYSY |
| 1554 | 2E05-M106Q | FRTVSGSSQSY |
| 1555 | 3A01 | YRWTRRYTY |
| 1556 | 3A02 | YRWRTRYTY |
| 1557 | 3A03 | YRWTTRRTY |
| 1558 | 3A04 | YRWTTRYIY |
| 1559 | 3A05 | YRWRTRYTY |
| 1560 | 3A06 | YRWTRRYTY |
| 1561 | 3A08 | YRWRTRYTY |
| 1562 | 3A09 | YRWTTRYIY |
| 1563 | 3A010 | YRWTTRRTY |
| 1564 | 3A011 | YRWRTRYTY |
| 1565 | 3B01 | YRWTTRYTY |
| 1566 | 3B02 | YRWRTRYTY |
| 1567 | 3B04 | YHWTTRYTY |
| 1568 | 3B05 | YRWTTRRTY |
| 1569 | 3B06 | YRWTTRYTY |

| | | |
|---|---|---|
| 1570 | 3B07 | YRWTTRYTY |
| 1571 | 3B09 | YRWTTRYAY |
| 1572 | 3B010 | YRWVTRYTY |
| 1573 | 3B011 | YRWVTRYTY |
| 1574 | 3C01 | YRWSTRYTY |
| 1575 | 3C02 | YRWRTRYTY |
| 1576 | 3C03 | YRWTTRGTY |
| 1577 | 3C04 | YRWDTRYTY |
| 1578 | 3C05 | YRWTTRRTY |
| 1579 | 3C06 | YRWRTRYTY |
| 1580 | 3C08 | YRWTGRYTY |
| 1581 | 3C09 | YRWRTRYTY |
| 1582 | 3C011 | YRWRTRYTY |
| 1583 | 3D01 | YRWITRYTY |
| 1584 | 3D02 | YRWITRYTY |
| 1585 | 3D03 | YRWRTRYTY |
| 1586 | 3D05 | YRWTRRYTY |
| 1587 | 3D07 | YSWTTRYTY |
| 1588 | 3D08 | YRWTNRYTY |
| 1589 | 3D09 | YRWTTRYRY |
| 1590 | 3D010 | YRWTTRYTY |
| 1591 | 3D011 | YRWTTRYKY |
| 1592 | 3E01 | YRWHTRYTY |
| 1593 | 3E02 | YRWTRRYTY |
| 1594 | 3E03 | YRWMTRYTY |
| 1595 | 3E04 | YRWTTRYRY |
| 1596 | 3E09 | YRWSTRYTY |
| 1597 | 3E011 | YRWTTRYTF |
| 1598 | 3F03 | YRWRTRYTY |
| 1599 | 3F05 | YRWTTRRTY |
| 1600 | 3F06 | YRWATRYTY |
| 1601 | 3F08 | YRWHTRYTY |
| 1602 | 3F09 | YRWGTRYTY |
| 1603 | 3F010 | YRWTTRNTY |
| 1604 | 3F011 | YRWRTRYTY |
| 1605 | 3G01 | YRWTTRYAY |
| 1606 | 3G02 | YRWRTRYTY |
| 1607 | 3G04 | YRWTTRRTY |
| 1608 | 3G06 | YRWTTRRTY |

-continued

| | | |
|---|---|---|
| 1609 | 3G07 | YRWTSRYTY |
| 1610 | 3G08 | YRWTTRVTY |
| 1611 | 3G09 | YRWTTRTTY |
| 1612 | 3G010 | YRWRTRYTY |
| 1613 | 3G011 | YRWATRYTY |
| 1614 | 3H01 | YRWTTRRTY |
| 1615 | 3H03 | LRWTTRYTY |
| 1616 | 3H06 | YRWTTRGTY |
| 1617 | 3H07 | YRWRTRYTY |
| 1618 | 3H09 | YRWTTRATY |
| 1619 | 3H010 | YRWTTRRTY |
| 1620 | 3H011 | YRWPTRYTY |
| 1621 | 4A01 | YRWRTRYTY |
| 1622 | 4A02 | YRWKTRYTY |
| 1623 | 4A04 | YRWSTRYTY |
| 1624 | 4A05 | YRWKTRRTY |
| 1625 | 4A06 | YRWTTRRTY |
| 1626 | 4A07 | YRWTTRYRY |
| 1627 | 4A08 | YRWRTRYTY |
| 1628 | 4A010 | YRWTTRYKY |
| 1629 | 4A011 | YRWKTRYTY |
| 1630 | 4A09 | YRWTTRVTY |
| 1631 | 4B01 | YRWTTRFTY |
| 1632 | 4B02 | YRWTTRFTY |
| 1633 | 4B04 | YRWRTRYTY |
| 1634 | 4B05 | YRWTTRYTH |
| 1635 | 4B06 | YRWTRRYTY |
| 1636 | 4B07 | YRWTTRYTY |
| 1637 | 4B08 | YRWTTRSTY |
| 1638 | 4B09 | YSWTTRYTY |
| 1639 | 4B011 | YRWTTRGTY |
| 1640 | 4C01 | YRWKTRYTY |
| 1641 | 4C02 | YRWTTRFTY |
| 1642 | 4C03 | YRWRTRYTY |
| 1643 | 4C05 | YRWTTRRTY |
| 1644 | 4C06 | YRWSTRYTY |
| 1645 | 4C07 | YRWTTRLTY |
| 1646 | 4C08 | YRWTRRYTY |
| 1647 | 4C010 | YRWTTRLTY |
| 1648 | 4C011 | YRWTRRYTY |

| | | |
|---|---|---|
| 1649 | 4D01 | YRWTTRRTY |
| 1650 | 4D02 | YQWTTRYTY |
| 1651 | 4D03 | YRWTRRYTY |
| 1652 | 4D04 | YRWTTRMTY |
| 1653 | 4D05 | YRWTTRRTY |
| 1654 | 4D06 | YRWTTRYRY |
| 1655 | 4D08 | YRWLTRYTY |
| 1656 | 4D09 | YEWTTRYTY |
| 1657 | 4D010 | YRWRTRYTY |
| 1658 | 4D011 | YRWRTRYTY |
| 1659 | 4E01 | YRWRTRYTY |
| 1660 | 4E02 | YRWSTRYTY |
| 1661 | 4E06 | YRWTTRLTY |
| 1662 | 4E07 | YRWTTRLTY |
| 1663 | 4E08 | YKWTTRYTY |
| 1664 | 4E09 | YRWTTRSTY |
| 1665 | 4E010 | YRWRTRYTY |
| 1666 | 4E011 | YRWSTRYTY |
| 1667 | 4F02 | YRWTTRYTY |
| 1668 | 4F03 | YRWRTRYTY |
| 1669 | 4F04 | YRWLTRYTY |
| 1670 | 4F08 | YRWRTRYTY |
| 1671 | 4F09 | YRWTTRYTY |
| 1672 | 4E010 | YRWTTRYRY |
| 1673 | 4E011 | YRWTTRYTY |
| 1674 | 4G01 | YRWPTRYTY |
| 1675 | 4G02 | YRWTTRHTY |
| 1676 | 4G03 | YRWTRRYTY |
| 1677 | 4G05 | YRWHTRYTY |
| 1678 | 4G07 | YRWTNRYTY |
| 1679 | 4G08 | YRWTTRYRY |
| 1680 | 4G09 | YRWTTRRTY |
| 1681 | 4G010 | YRWSTRYTY |
| 1682 | 4G011 | YRWSTRYTY |
| 1683 | 4H01 | YRWRTRYTY |
| 1684 | 4H03 | YRWTTRYTY |
| 1685 | 4H04 | YEWTTRYTY |
| 1686 | 4H05 | YRWTTRSTY |
| 1687 | 4H06 | YRWTTRYTY |

| | | |
|---|---|---|
| 1688 | 4H07 | YRWSTRYTY |
| 1689 | 4H08 | YRWSTRYTY |
| 1690 | 4H09 | YRWTYRYTY |
| 1691 | 4H011 | YRWTTRLTY |
| 1692 | 4D09-M34L | YEWTTRYTY |
| 1693 | 4H11-M34L | YRWTTRLTY |
| 1694 | 41B11 | FRPAAGSPMRY |
| 1695 | 41C02 | FRTVDGSPLRY |
| 1696 | 41D01 | FRTVSGSSKRY |
| 1697 | 41D02 | FSAGSGTEMSY |
| 1698 | 41D03 | FGSLSGSSTTY |
| 1699 | 41D07 | FGSVSGSWTRY |
| 1700 | 41E01 | FRLVSGSSMSY |
| 1701 | 41E02 | FRTGSGTSKSY |
| 1702 | 41F07 | FSNMSGTTRRY |
| 1703 | 41G01 | FRTVPGSAMGY |
| 1704 | 42A03 | FRAESGSSMGY |
| 1705 | 42A06 | FRTLYGSSRSY |
| 1706 | 42A07 | FSPFSGSDTGY |
| 1707 | 42A08 | FSTFSGSSISY |
| 1708 | 42A11 | FRTLAGSEMRY |
| 1709 | 42B06 | FRTVSGSGVRY |
| 1710 | 42B10 | FRPGAGHSNSY |
| 1711 | 42C01 | FRRASGTAMSY |
| 1712 | 42C03 | FTSASGTDLSY |
| 1713 | 42C07 | FRSANGSSKRY |
| 1714 | 42C08 | FKTIAGAGMRY |
| 1715 | 42C10 | FRYGSGSSLSY |
| 1716 | 42C11 | FRTVPGASMKY |
| 1717 | 42D05 | FRTVDGSAISY |
| 1718 | 42D06 | FRTVKGSGGSY |
| 1719 | 42D07 | FRTVSGSSRGY |
| 1720 | 42D08 | FRPGPGSQMAY |
| 1721 | 42E01 | FRTVAGSASGY |
| 1722 | 42E02 | FRTVSGSSYSY |
| 1723 | 42E05 | FINLKGSSMAY |
| 1724 | 42E06 | FRMVTGSYGGY |
| 1725 | 42E07 | FKSSYGLPMRY |
| 1726 | 42F01 | FKTVSGQSLRY |

| | | |
|---|---|---|
| 1727 | 42F08 | FRTVTGRAARY |
| 1728 | 42F10 | FGPAIGASRTY |
| 1729 | 42G05 | FRTVSGAPKSY |
| 1730 | 42G07 | FHTVSGSSMSY |
| 1731 | 42H05 | FRRLEGYSNRY |
| 1732 | 42H08 | FRTGSGSSMGY |
| 1733 | 42H11 | FTTVTGSSMSY |
| 1734 | 51A01 | YYWTERRPY |
| 1735 | 51A02 | YSWDDAHPY |
| 1736 | 51A03 | YRWMTRLTY |
| 1737 | 51A05 | YDWADAQPY |
| 1738 | 51B01 | YSWTDRLPY |
| 1739 | 51B04 | YRWATRLPY |
| 1740 | 51B11 | YKWSNRLPY |
| 1741 | 51C02 | YGWKTRQPY |
| 1742 | 51D01 | YRWPNRRGY |
| 1743 | 51D03 | YDWTTRQRY |
| 1744 | 51E02 | YNWSYAQPY |
| 1745 | 51E03 | YNWTDSLQY |
| 1746 | 51E05 | YSWTTSLPY |
| 1747 | 51F01 | YKWRSRSTY |
| 1748 | 51F02 | YSQTTRDPY |
| 1749 | 51F03 | YRWTARDTY |
| 1750 | 51F04 | YRWTSRLSY |
| 1751 | 51G02 | YSWTTRSRY |
| 1752 | 51G04 | YNWTSRYRY |
| 1753 | 51G10 | YSWKTRFPY |
| 1754 | 51H04 | YSWTTRYPY |
| 1755 | 51H05 | YEWTNALPY |
| 1756 | 52B01 | YSWITRSPY |
| 1757 | 52C04 | YSWTTRRQY |
| 1758 | 52D04 | YSWITRSPY |
| 1759 | 53A04 | YRWEESRQY |
| 1760 | 53A05 | YTWTTRLPY |
| 1761 | 53A09 | YRWEESRQY |
| 1762 | 53B05 | YSWTTRQPY |
| 1763 | 53B06 | YVWGTRLPY |
| 1764 | 53C03 | YEWTNALPY |
| 1765 | 53C04 | YRWEDALTY |

-continued

| | | |
|---|---|---|
| 1766 | 53H03 | YSWTTRYPY |
| 1767 | 53H04 | YSWIDSLRY |
| 1768 | 54B05 | YSWTTPRAY |

| SEQ ID NO: | Description | AASequence |
|---|---|---|
| 1769 | Anti-HSA sdAb clone 6C | EVQLVESGGGLVQPGNSLRLSCAASGFTFSRFGMSWVRQAPGKGLEWVSS ISGSGSDTLYADSVKGRFTISRDNAKTTLYLQMNSLRPEDTAVYYCTIGG SLSRSSQGTLVTVSS |
| 1770 | Anti-HSA sdAb clone 7A | EVQLVESGGGLVQPGNSLRLSCAASGFTFSKFGMSWVRQAPGKGLEWVSS ISGSGADTLYADSLKGRFTISRDNAKTTLYLQMNSLRPEDTAVYYCTIGG SLSKSSQGTLVTVSS |
| 1771 | Anti-HSA sdAb clone 7G | EVQLVESGGGLVQPGNSLRLSCAASGFTYSSFGMSWVRQAPGKGLEWVSS ISGSGSDTLYADSVKGRFTISRDNAKTTLYLQMNSLRPEDTAVYYCTIGG SLSKSSQGTLVTVSS |
| 1772 | Anti-HSA sdAb clone 8H | EVQLVESGGGLVQPGNSLRLSCAASGFTFSKFGMSWVRQAPGKGLEWVSS ISGSGTDTLYADSVKGRFTISRDNAKTTLYLQMNSLRPEDTAVYYCTIGG SLSRSSQGTLVTVSS |
| 1773 | Anti-HSA sdAb clone 9A | EVQLVESGGGLVQPGNSLRLSCAASGFTFSRFGMSWVRQAPGKGLEWVSS ISGSGSDTLYADSVKGRFTISRDNAKTTLYLQMNSLRPEDTAVYYCTIGG SLSKSSQGTLVTVSS |
| 1774 | Anti-HSA sdAb clone 10G | EVQLVESGGGLVQPGNSLRLSCAASGFTFSKFGMSWVRQAPGKGLEWVSS ISGSGRDTLYADSVKGRFTISRDNAKTTLYLQMNSLRPEDTAVYYCTIGG SLSVSSQGTLVTVSS |
| 1775 | wt anti-HSA | EVQLVESGGGLVQPGNSLRLSCAASGFTFSSFGMSWVRQAPGKGLEWVSS ISGSGSDTLYADSVKGRFTISRDNAKTTLYLQMNSLRPEDTAVYYCTIGG SLSRSSQGTLVTVSS |
| 1776 | Anti-HSA sdAb clone 6CE | EVQLVESGGGLVQPGNSLRLSCAASGFTFSRFGMSWVRQAPGKGLEWVSS ISGSGSDTLYAESVKGRFTISRDNAKTTLYLQMNSLRPEDTAVYYCTIGG SLSRSSQGTLVTVSS |
| 1777 | Anti-HSA sdAb clone 8HE | EVQLVESGGGLVQPGNSLRLSCAASGFTFSKFGMSWVRQAPGKGLEWVSS ISGSGTDTLYAESVKGRFTISRDNAKTTLYLQMNSLRPEDTAVYYCTIGG SLSRSSQGTLVTVSS |
| 1778 | Anti-HSA sdAb clone 10GE | EVQLVESGGGLVQPGNSLRLSCAASGFTFSKFGMSWVRQAPGKGLEWVSS ISGSGRDTLYAESVKGRFTISRDNAKTTLYLQMNSLRPEDTAVYYCTIGG SLSVSSQGTLVTVSS |
| 1779 | wt anti-HSA CDR1 | GFTFSSFGMS |
| 1780 | wt anti-HSA CDR2 | SISGSGSDTLYADSVK |
| 1781 | wt anti-HSACDR3 | GGSLSR |
| 1782 | CDR variant 1 | GFTFSRFGMS |
| 1783 | CDR variant 2 | GFTFSKFGMS |
| 1784 | CDR variant 3 | GFTYSSFGMS |
| 1785 | CDR variant 1 | SISGSGADTLYADSLK |
| 1786 | CDR variant 2 | SISGSGTDTLYADSVK |
| 1787 | CDR variant 3 | SISGSGRDTLYADSVK |
| 1788 | CDR variant 4 | SISGSGSDTLYAESVK |
| 1789 | CDR variant 5 | SISGSGTDTLYAESVK |
| 1790 | CDR variant 6 | SISGSGRDTLYAESVK |
| 1791 | CDR variant 1 | GGSLSK |
| 1792 | CDR variant 2 | GGSLSV |

| SEQ ID NO: | Description | AASequence |
|---|---|---|
| 1793 | Anti-CD3, clone 2B2 | EVQLVESGGGLVQPGGSLKLSCAASGFTFNKYAINWVRQAPGKGLEWVAR<br>IRSKYNNYATYYADQVKDRFTISRDDSKNTAYLQMNNLKTEDTAVYYCVR<br>HANEGNSYISYWAYWGQGTLVTVSSGGGGSGGGGSGGGGSQTVVTQEPSL<br>TVSPGGTVTLTCASSTGAVTSGNYPNWVQQKPGQAPRGLIGGTKFLVPGT<br>RARFSGSLLGGKAALTLSGVQPEDEAEYYCTLWYSNRWVEGGGTKLTVL |
| 1794 | Anti-CD3, clone 9F2 | EVQLVESGGGLVQPGGSLKLSCAASGFEFNKYAMNWVRQAPGKGLEWVAR<br>IRSKYNKYATYYADSVKDRFTISRDDSKNTAYLQMNNLKTEDTAVYYCVR<br>HGNEGNSYISYWAYWGQGTLVTVSSGGGGSGGGGSGGGGSQTVVTQEPSL<br>TVSPGGTVTLTCGSSFGAVTSGNYPNWVQQKPGQAPRGLIGGTKFLAPGT<br>RARFSGSLLGGKAALTLSGVQPEDEAEYYCVLWYDNRWVEGGGTKLTVL |
| 1795 | Anti-CD3, clone 5A2 | EVQLVESGGGLVQPGGSLKLSCAASGFTFNKYAMNWVRQAPGKGLEWVAR<br>IRSKYNNYATYYADSVKDRFTISRDDSKNTAYLQMNNLKTEDTAVYYCVR<br>HGNEGNSHISYWAYWGQGTLVTVSSGGGGSGGGGSGGGGSQTVVTQEPSL<br>TVSPGGTVTLTCGSSTGYVTSGNYPNWVQQKPGQAPRGLIGGTSFLAPGT<br>PARFSGSLLGGKAALTLSGVQPEDEAEYYCVLWYSNRWIFGGGTKLTVL |
| 1796 | Anti-CD3, clone 6A2 | EVQLVESGGGLVQPGGSLKLSCAASGFMFNKYAMNWVRQAPGKGLEWVAR<br>IRSKSNNYATYYADSVKDRFTISRDDSKNTAYLQMNNLKTEDTAVYYCVR<br>HGNEGNSYISYWATWGQGTLVTVSSGGGGSGGGGSGGGGSQTVVTQEPSL<br>TVSPGGTVTLTCGSSFGAVTSGNYPNWVQQKPGQAPRGLIGGTKLLAPGT<br>PARFSGSLLGGKAALTLSGVQPEDEAEYYCVLWYSNSWVFGGGTKLTVL |
| 1797 | Anti-CD3, clone 2D2 | EVQLVESGGGLVQPGGSLKLSCAASGFTFNTYAMNWVRQAPGKGLEWVAR<br>IRSKYNNYATYYKDSVKDRFTISRDDSKNTAYLQMNNLKTEDTAVYYCVR<br>HGNEGNSPISYWAYWGQGTLVTVSSGGGGSGGGGSGGGGSQTVVTQEPSL<br>TVSPGGTVTLTCGSSTGAVVSGNYPNWVQQKPGQAPRGLIGGTEFLAPGT<br>RARFSGSLLGGKAALTLSGVQPEDEAEYYCVLWYSNRWVEGGGTKLTVL |
| 1798 | Anti-CD3, clone 3F2 | EVQLVESGGGLVQPGGSLKLSCAASGFTYNKYAMNWVRQAPGKGLEWVAR<br>IRSKYNNYATYYADEVKDRFTISRDDSKNTAYLQMNNLKTEDTAVYYCVR<br>HGNEGNSPISYWAYWGQGTLVTVSSGGGGSGGGGSGGGGSQTVVTQEPSL<br>TVSPGGTVTLTCGSSKGAVTSGNYPNWVQQKPGQAPRGLIGGTKELAPGT<br>RARFSGSLLGGKAALTLSGVQPEDEAEYYCTLWYSNRWVEGGGTKLTVL |
| 1799 | Anti-CD3, clone 1A2 | EVQLVESGGGLVQPGGSLKLSCAASGNTFNKYAMNWVRQAPGKGLEWVAR<br>IRSKYNNYETYYADSVKDRFTISRDDSKNTAYLQMNNLKTEDTAVYYCVR<br>HTNEGNSYISYWAYWGQGTLVTVSSGGGGSGGGGSGGGGSQTVVTQEPSL<br>TVSPGGTVTLTCGSSTGAVTSGYYPNWVQQKPGQAPRGLIGGTYFLAPGT<br>RARFSGSLLGGKAALTLSGVQPEDEAEYYCVLWYSNRWVEGGGTKLTVL |
| 1800 | Anti-CD3, clone 1C2 | EVQLVESGGGLVQPGGSLKLSCAASGFTFNNYAMNWVRQAPGKGLEWVAR<br>IRSKYNNYATYYADVKDRFTISRDDSKNTAYLQMNNLKTEDTAVYYCVR<br>HGNEGNSQISYWAYWGQGTLVTVSSGGGGSGGGGSGGGGSQTVVTQEPSL<br>TVSPGGTVTLTCGSSTGAVTDGNYPNWVQQKPGQAPRGLIGGIKFLAPGT<br>RARFSGSLLGGKAALTLSGVQPEDEAEYYCVLWYSNRWVEGGGTKLTVL |
| 1801 | Anti-CD3, clone 2E4 | EVQLVESGGGLVQPGGSLKLSCAASGFTENKYAYNWVRQAPGKGLEWVAR<br>IRSKYNNYATYYADSVKDRFTISRDDSKNTAYLQMNNLKTEDTAVYYCVR<br>HGNEGNSYISYWAYWGQGTLVTVSSGGGGSGGGGSGGGGSQTVVTQEPSL<br>TVSPGGTVTLTCGESTGAVTSGNYPNWVQQKPGQAPRGLIGGTKILAPGT<br>RARFSGSLLGGKAALTLSGVQPEDEAEYYCVLWYSNRWVEGGGTKLTVL |
| 1802 | Anti-CD3, clone 10E4 | EVQLVESGGGLVQPGGSLKLSCAASGFTFNKYPMNWVRQAPGKGLEWVAR<br>IRSKYNNYATYYADSVKDRFTISRDDSKNTAYLQMNNLKNEDTAVYYCVR<br>HGNENNSYISYWAYWGQGTLVTVSSGGGGSGGGGSGGGGSQTVVTQEPSL<br>TVSPGGTVTLTCGSSTGAVTKGNYPNWVQQKPGQAPRGLIGGTKMLAPGT<br>RARFSGSLLGGKAALTLSGVQPEDEAEYYCALWYSNRWVEGGGTKLTVL |
| 1897 | Anti-CD3, clone 2H2 | EVQLVESGGGLVQPGGSLKLSCAASGFTFNGYAMNWVRQAPGKGLEWVAR<br>IRSKYNNYATYYADEVKDRFTISRDDSKNTAYLQMNNLKTEDTAVYYCVR<br>HGNEGNSPISYWAYWGQGTLVTVSSGGGGSGGGGSGGGGSQTVVTQEPSL<br>TVSPGGTVTLTCGSSAVVSGNYPNWVQQKPGQAPRGLIGGTEFLAPGT<br>RARFSGSLLGGKAALTLSGVQPEDEAEYYCVLWYSNRWVEGGGTKLTVL |
| 1802 | Anti-CD3, clone 2A4 | EVQLVESGGGLVQPGGSLKLSCAASGNTFNKYAMNWVRQAPGKGLEWVAR<br>IRSKYNNYATYYADSVKDRFTISRDDSKNTAYLQMNNLKTEDTAVYYCVR<br>HGNEGDSYISYWAYWGQGTLVTVSSGGGGSGGGGSGGGGSQTVVTQEPSL<br>TVSPGGTVTLTCGSSTGAVTHGNYPNWVQQKPGQAPRGLIGGTKVLAPGT<br>RARFSGSLLGGKAALTLSGVQPEDEAEYYCVLWYSNRWVEGGGTKLTVL |

-continued

| | | |
|---|---|---|
| 1898 | Anti-CD3, clone 10B2 | EVQLVESGGGLVQPGGSLKLSCAASGFTFNNYAMNWVRQAPGKGLEWVAR<br>IRSGYNNYATYYADSVKDRFTISRDDSKNTAYLQMNNLKTEDTAVYYCVR<br>HGNEGNSYISYWAYWGQGTLVTVSSGGGGSGGGGSGGGGSQTVVTQEPSL<br>TVSPGGTVTLTCGSYTGAVTSGNYPNWVQQKPGQAPRGLIGGTKFNAPGT<br>RARFSGSLLGGKAALTLSGVQPEDEAEYYCVLWYANRWVEGGGTKLTVL |
| 1804 | Anti-CD3, clone 1G4 | EVQLVESGGGLVQPGGSLKLSCAASGFEFNKYAMNWVRQAPGKGLEWVAR<br>IRSKYNNYETYYADSVKDRFTISRDDSKNTAYLQMNNLKTEDTAVYYCVR<br>HGNEGNSLISYWAYWGQGTLVTVSSGGGGSGGGGSGGGGSQTVVTQEPSL<br>TVSPGGTVTLTCGSSSGAVTSGNYPNWVQQKPGQAPRGLIGGTKFGAPGT<br>RARFSGSLLGGKAALTLSGVQPEDEAEYYCVLWYSNRWVEGGGTKLTVL |
| 1805 | wt anti-CD3 | EVQLVESGGGLVQPGGSLKLSCAASGFTFNKYAMNWVRQAPGKGLEWVAR<br>IRSKYNNYATYYADSVKDRFTISRDDSKNTAYLQMNNLKTEDTAVYYCVR<br>HGNEGNSYISYWAYWGQGTLVTVSSGGGGSGGGGSGGGGSQTVVTQEPSL<br>TVSPGGTVTLTCGSSTGAVTSGNYPNWVQQKPGQAPRGLIGGTKFLAPGT<br>RARFSGSLLGGKAALTLSGVQPEDEAEYYCVLWYSNRWVEGGGTKLTVL |
| 1806 | Anti-CD3, clone 2G5 | EVQLVESGGGLVQPGGSLKLSCAASGFTFNKYALNWVRQAPGKGLEWVAR<br>IRSKYNNYATEYADSVKDRFTISRDDSKNTAYLQMNNLKTEDTAVYYCVR<br>HGNEGNSPISYWAYWGQGTLVTVSSGGGGSGGGGSGGGGSQTVVTQEPSL<br>TVSPGGTVTLTCGSSTGAVTSGNYPNWVQQKPGQAPRGLIGGTNFLAPGT<br>PERFSGSLLGGKAALTLSGVQPEDEAEYYCVLWYSNRWAFGGGTKLTVL |
| 1807 | Anti-CD3, clone 8A5 | EVQLVESGGGLVQPGGSLKLSCAASGFTFNEYAMNWVRQAPGKGLEWVAR<br>IRSKYNNYATYYADDVKDRFTISRDDSKNTAYLQMNNLKTEDTAVYYCVR<br>HGNEGNSGISYWAYWGQGTLVTVSSGGGGSGGGGSGGGGSQTVVTQEPSL<br>TVSPGGTVTLTCGSSTGAVTVGNYPNWVQQKPGQAPRGLIGGTEFLAPGT<br>RARFSGSLLGGKAALTLSGVQPEDEAEYYCVLWYSNRWVEGGGTKLTVL |

| Linkers | | |
|---|---|---|
| SEQ ID NO: | Description | AA Sequence |
| 1808 | Linker | GGGGSGGGS |
| 1809 | Linker | (GS)$_n$ |
| 1810 | Linker | (GGS)$_n$ |
| 1811 | Linker | (GGGS)$_n$ |
| 1812 | Linker | (GGSG)$_n$ |
| 1813 | Linker | (GGSGG)$_n$ |
| 1814 | Linker | (GGGGS)$_n$ |
| 1815 | Linker | (GGGGG)$_n$ |
| 1816 | Linker | (GGG)$_n$ |
| 1817 | Linker | (GGGGSGGGGSGGGGSGGGGS) |
| 1818 | Linker | GGGGSGGGGSGGGGS |
| 1819 | 6X Histidine | HHHHHH |

| CD3 Binding Domain CDR Sequences | | |
|---|---|---|
| SEQ ID NO: | CD3 Binding Domain CDR | Sequence |
| 1820 | HC CDR1 variant 1 | GNTFNKYAMN |
| 1821 | HC CDR1 variant 2 | GFEFNKYAMN |
| 1822 | HC CDR1 variant 3 | GFMFNKYAMN |
| 1823 | HC CDR1 variant 4 | GFTYNKYAMN |

| | | |
|---|---|---|
| 1824 | HC CDR1 variant 5 | GFTFNNYAMN |
| 1825 | HC CDR1 variant 6 | GFTFNGYAMN |
| 1826 | HC CDR1 variant 7 | GFTFNTYAMN |
| 1827 | HC CDR1 variant 8 | GFTFNEYAMN |
| 1828 | HC CDR1 variant 9 | GFTFNKYPMN |
| 1829 | HC CDR1 variant 10 | GFTFNKYAYN |
| 1830 | HC CDR1 variant 11 | GFTFNKYAIN |
| 1831 | HC CDR1 variant 12 | GFTFNKYALN |
| 1832 | HC CDR2 variant 1 | RIRSGYNNYATYYADSVK |
| 1833 | HC CDR2 variant 2 | RIRSKSNNYATYYADSVK |
| 1834 | HC CDR2 variant 3 | RIRSKYNKYATYYADSVK |
| 1835 | HC CDR2 variant 4 | RIRSKYNNYETYYADSVK |
| 1836 | HC CDR2 variant 5 | RIRSKYNNYATEYADSVK |
| 1837 | HC CDR2 variant 6 | RIRSKYNNYATYYKDSVK |
| 1838 | HC CDR2 variant 7 | RIRSKYNNYATYYADEVK |
| 1839 | HC CDR2 variant 8 | RIRSKYNNYATYYADAVK |
| 1840 | HC CDR2 variant 9 | RIRSKYNNYATYYADQVK |
| 1841 | HC CDR2 variant 10 | RIRSKYNNYATYYADDVK |
| 1842 | HC CDR3 variant 1 | HANFGNSYISYWAY |
| 1843 | HC CDR3 variant 2 | HTNFGNSYISYWAY |
| 1844 | HC CDR3 variant 3 | HGNFNNSYISYWAY |
| 1845 | HC CDR3 variant 4 | HGNFGDSYISYWAY |
| 1846 | HC CDR3 variant 5 | HGNFGNSHISYWAY |
| 1847 | HC CDR3 variant 6 | HGNFGNSPISYWAY |
| 1848 | HC CDR3 variant 7 | HGNFGNSQISYWAY |
| 1849 | HC CDR3 variant 8 | HGNFGNSLISYWAY |

| | | |
|---|---|---|
| 1850 | HC CDR3 variant 9 | HGNFGNSGISYWAY |
| 1851 | HC CDR3 variant 10 | HGNFGNSYISYWAT |
| 1852 | LC CDR1 variant 1 | ASSTGAVTSGNYPN |
| 1853 | LC CDR1 variant 2 | GESTGAVTSGNYPN |
| 1854 | LC CDR1 variant 3 | GSYTGAVTSGNYPN |
| 1855 | LC CDR1 variant 4 | GSSFGAVTSGNYPN |
| 1856 | LC CDR1 variant 5 | GSSKGAVTSGNYPN |
| 1857 | LC CDR1 variant 6 | GSSSGAVTSGNYPN |
| 1858 | LC CDR1 variant 7 | GSSTGYVTSGNYPN |
| 1859 | LC CDR1 variant 8 | GSSTGAVVSGNYPN |
| 1860 | LC CDR1 variant 9 | GSSTGAVTDGNYPN |
| 1861 | LC CDR1 variant 10 | GSSTGAVTKGNYPN |
| 1862 | LC CDR1 variant 11 | GSSTGAVTHGNYPN |
| 1863 | LC CDR1 variant 12 | GSSTGAVTVGNYPN |
| 1864 | LC CDR1 variant 13 | GSSTGAVTSGYYPN |
| 1865 | LC CDR2 variant 1 | GIKFLAP |
| 1866 | LC CDR2 variant 2 | GTEFLAP |
| 1867 | LC CDR2 variant 3 | GTYFLAP |
| 1868 | LC CDR2 variant 4 | GTSFLAP |
| 1869 | LC CDR2 variant 5 | GTNFLAP |
| 1870 | LC CDR2 variant 6 | GTKLLAP |
| 1871 | LC CDR2 variant 7 | GTKELAP |
| 1872 | LC CDR2 variant 8 | GTKILAP |
| 1873 | LC CDR2 variant 9 | GTKMLAP |
| 1874 | LC CDR2 variant 10 | GTKVLAP |
| 1875 | LC CDR2 variant 11 | GTKFNAP |

| | | |
|---|---|---|
| 1876 | LC CDR2 variant 12 | GTKFGAP |
| 1877 | LC CDR2 variant 13 | GTKFLVP |
| 1878 | LC CDR3 variant 1 | TLWYSNRWV |
| 1879 | LC CDR3 variant 2 | ALWYSNRWV |
| 1880 | LC CDR3 variant 3 | VLWYDNRWV |
| 1881 | LC CDR3 variant 4 | VLWYANRWV |
| 1882 | LC CDR3 variant 5 | VLWYSNSWV |
| 1883 | LC CDR3 variant 6 | VLWYSNRWI |
| 1884 | LC CDR3 variant 7 | VLWYSNRWA |
| 1890 | Exemplary anti-DLL3 trispecific protein (anti-CD3:anti-ALB:anti-DLL3 configuration) (CAT) | EVQLVESGGGLVQPGGSLKLSCAASGFTFNKYAINWVRQAPGKGLEWVARIRSKYNNYA TYYADQVKDRFTISRDDSKNTAYLQMNNLKTEDTAVYYCVRHANFGNSYISYWAYWGQG TLVTVSSGGGGSGGGGSGGGGSQTVVTQEPSLTVSPGGTVTLTCASSTGAVTSGNYPNW VQQKPGQAPRGLIGGTKFLVPGTPARFSGSLLGGKAALTLSGVQPEDEAEYYCTLWYSN RWVFGGGTKLTVLGGGGSGGGGSEVQLVESGGGLVQPGNSLRLSCAASGFTFSKFGMSWV RQAPGKGLEWVSSISGSGRDTLYADSVKGRFTISRDNAKTTLYLQMNSLRPEDTAVYYC TIGGSLSVSSQGTLVTVSSGGGGSGGGGSEVQLVESGGGLVQPGGSLTLSCAASSSSVSL LSLAWYRQAPGKKRELVAGISDDGSIVYMDSVKGRFTISRDNAKNSVYLQMNSLRAEDT AVYYCYAYSWITRSPYWGQGTLVTVSSHHHHHH |
| 1891 | Exemplary anti-DLL3 trispecific Protein (anti-DLL3 anti-:ALB: anti-CD3 configuration) (TAC) | EVQLVESGGGLVQPGGSLTLSCAASSSSVSLLSLAWYRQAPGKKRELVAGISDDGSIVY MDSVKGRFTISRDNAKNSVYLQMNSLRAEDTAVYYCYAYSWITRSPYWGQGTLVTVSSG GGGSGGGGSEVQLVESGGGLVQPGNSLRLSCAASGFTFSKFGMSWVRQAPGKGLEWVSSI SGSGRDTLYADSVKGRFTISRDNAKTTLYLQMNSLRPEDTAVYYCTIGGSLSVSSQGTL VTVSSGGGGSGGGGSEVQLVESGGGLVQPGGSLKLSCAASGFTFNKYAINWVRQAPGKGL EWVARIRSKYNNYATYYADQVKDRFTISRDDSKNTAYLQMNNLKTEDTAVYYCVRHANF GNSYISYWAYWGQGTLVTVSSGGGGSGGGGSGGGGSQTVVTQEPSLTVSPGGTVTLTCA SSTGAVTSGNYPNWVQQKPGQAPRGLIGGTKELVPGTPARFSGSLLGGKAALTLSGVQP EDEAEYYCTLWYSNRWVFGGGTKLTVLHHHHHH |

```
DLL3 Protein UniProtKB Accession Q9NYJ7 (SEQ ID NO: 1885)
>sp|Q9NYJ7|DLL3_HUMAN Delta-like protein 3 OS = Homo sapiens OX = 9606 GN = DLL3
PE = 1 SV = 1
MVSPRMSGLLSQTVILALIFLPQTRPAGVFELQIHSFGPGPGPGAPRSPCSARLPCRLFF
RVCLKPGLSEEAAESPCALGAALSARGPVYTEQPGAPAPDLPLPDGLLQVPFRDAWPGTF
SFIIETWREELGDQIGGPAWSLLARVAGRRRLAAGGPWARDIQRAGAWELRFSYARCEP
PAVGTACTRLCRPRSAPSRCGPGLRPCAPLEDECEAPLVCRAGCSPEHGFCEQPGECRCL
EGWTGPLCTVPVSTSSCLSPRGPSSATTGCLVPGPGPCDGNPCANGGSCSETPRSFECTC
PRGFYGLRCEVSGVTCADGPCFNGGLCVGGADPDSAYICHCPPGFQGSNCEKRVDRCSLQ
PCRNGGLCLDLGHALRCRCRAGFAGPRCEHDLDDCAGRACANGGTCVEGGGAHRCSCALG
FGGRDCRERADPCAARPCAHGGRCYAHFSGLVCACAPGYMGARCEFPVHPDGASALPAAP
PGLRPGDPQRYLLPPALGLLVAAGVAGAALLLVHVRRRGHSQDAGSRLLAGTPEPSVHAL
PDALNNLRTQEGSGDGPSSVDWNRPEDVDPQGIYVISAPSIYAREVATPLFPPLHTGRA
GQRQHLLFPYPSSILSVK 51X5 (SEQ ID NO: 1886)
EVQLVESGGGLVQPGGSLTLSCAASLSSVSVLSIAWYRQAPGKKRELVAGISTDGSTVYIDSVKGRFTISRDNAKNSVYL
QMNSLRAEDTAVYYCYAYSWTTSLPYWGQGTLVTVSS

51X5 CDR1 (SEQ ID NO: 1887)
LSSVSVLSIA

51X5 CDR2 (SEQ ID NO: 1888)
GISTDGSTVYIDSVKG

51X5 CDR3 (SEQ ID NO: 1889)
YSWTTSLPY
```

```
>NP_058637.1 delta-like protein 3 isoform 1 precursor [Homo sapiens]
(SEQ ID No. 1892)
MVSPRMSGLLSQTVILALIFLPQTRPAGVFELQIHSFGPGPGPGAPRSPCSARLPCRLFFRVCLKPGLSE
EAAESPCALGAALSARGPVYTEQPGAPAPDLPLPDGLLQVPFRDAWPGTFSFIIETWREELGDQIGGPAW
SLLARVAGRRRLAAGGPWARDIQRAGAWELRFSYRARCEPPAVGTACTRLCRPRSAPSRCGPGLRPCAPL
EDECEAPLVCRAGCSPEHGFCEQPGECRCLEGWTGPLCTVPVSTSSCLSPRGPSSATTGCLVPGPGPCDG
NPCANGGSCSETPRSFECTCPRGFYGLRCEVSGVTCADGPCFNGGLCVGGADPDSAYICHCPPGFQGSNC
EKRVDRCSLQPCRNGGLCLDLGHALRCRCRAGFAGPRCEHDLDDCAGRACANGGTCVEGGGAHRCSCALG
FGGRDCRERADPCAARPCAHGGRCYAHFSGLVCACAPGYMGARCEFPVHPDGASALPAAPPGLRPGDPQR
YLLPPALGLLVAAGVAGAALLLVHVRRRGHSQDAGSRLLAGTPEPSVHALPDALNNLRTQEGSGDGPSSS
VDWNRPEDVDPQGIYVISAPSIYAREVATPLFPPLHTGRAGQRQHLLFPYPSSILSVK DLL3 Protein Sequence (SEQ ID NO: 1893)
RSPCSARLPCRLFFRVCLKPGLSEEAAESPCALGAALSARGPVYTEQPGAPAPDLPLPDGLLQVPFRDAWPGTFSFIIET
WREELGDQIGGPAWSLLARVAGRRRLAAGGPWARDIQRAGAWELRFSYRARCEPPAVGTACTRLCRPRSAPSRCGPGLRP
CAPLEDECEAPLVCRAGCSPEHGFCEQPGECRCLEGWTGPLCTVPVSTSSCLSPRGPSSATTGCLVPGPGPCDGNPCANG
GSCSETPRSFECTCPRGFYGLRCEVSGVTCADGPCFNGGLCVGGADPDSAYICHCPPGFQGSNCEKRVDRCSLQPCRNGG
LCLDLGHALRCRCRAGFAGPRCEHDLDDCAGRACANGGTCVEGGGAHRCSCALGFGGRDCRERADPCAARPCAHGGRCYA
HFSGLVCACAPGYMGARCEFPVHPDGASALPAAPPGLRPGDPQRYL
```

SEQUENCE LISTING

The patent contains a lengthy sequence listing. A copy of the sequence listing is available in electronic form from the USPTO web site (https://seqdata.uspto.gov/?pageRequest=docDetail&DocID=US11807692B2). An electronic copy of the sequence listing will also be available from the USPTO upon request and payment of the fee set forth in 37 CFR 1.19(b)(3).

What is claimed is:

1. A method of treating a cancer overexpressing a DLL3 protein in a subject in need thereof, comprising administering to the subject an effective amount of a DLL3 targeting trispecific protein, wherein the DLL3 targeting trispecific protein comprises:
   (a) a first domain (A), which is a single chain variable fragment that specifically binds to a human CD3;
   (b) a second domain (B), which is a single domain antibody that specifically binds to a human serum albumin protein; and
   (c) a third domain (C), which is a single domain antibody that specifically binds to DLL3, wherein the third domain (C) comprises:
      (i) an amino acid sequence that is at least 80% identical to an amino acid sequence of SEQ ID No. 408, and wherein the third domain (C) comprises a CDR1 that has the amino acid sequence of SEQ ID No. 851, a CDR2 that has the amino acid sequence of SEQ ID No. 1293, and a CDR3 that has the amino acid sequence of SEQ ID No. 1735;
      (ii) an amino acid sequence that is at least 80% identical to an amino acid sequence of SEQ ID No. 425, and wherein the third domain (C) comprises a CDR1 that has the amino acid sequence of SEQ ID No. 867, a CDR2 that has the amino acid sequence of SEQ ID No. 1309, and a CDR3 that has the amino acid sequence of SEQ ID No. 1751;
      (iii) an amino acid sequence that is at least 80% identical to an amino acid sequence of SEQ ID No. 432, and wherein the third domain (C) comprises a CDR1 that has the amino acid sequence of SEQ ID No. 874, a CDR2 that has the amino acid sequence of SEQ ID No. 1316, and a CDR3 that has the amino acid sequence of SEQ ID No. 1758;
      (iv) an amino acid sequence that is at least 80% identical to an amino acid sequence of SEQ ID No. 430, and wherein the third domain (C) comprises a CDR1 that has the amino acid sequence of SEQ ID No. 872, a CDR2 that has the amino acid sequence of SEQ ID No. 1314, and a CDR3 that has the amino acid sequence of SEQ ID No. 1756;
      (v) an amino acid sequence that is at least 80% identical to an amino acid sequence of SEQ ID No. 431, and wherein the third domain (C) comprises a CDR1 that has the amino acid sequence of SEQ ID No. 873, a CDR2 that has the amino acid sequence of SEQ ID No. 1315, and a CDR3 that has the amino acid sequence of SEQ ID No. 1757; or
      (vi) an amino acid sequence that is at least 80% identical to an amino acid sequence of SEQ ID No. 1886, and wherein the third domain (C) comprises a CDR1 that has the amino acid sequence of SEQ ID No. 1887, a CDR2 that has the amino acid sequence of SEQ ID No. 1888, and a CDR3 that has the amino acid sequence of SEQ ID No. 1889.

2. The method of claim 1, wherein the cancer comprises a solid tumor.

3. The method of claim 2, wherein the solid tumor comprises a tumor of an adrenal gland, liver, kidney, bladder, breast, gastric, ovary, cervix, uterus, esophagus, colorectum, prostate, pancreas, lung, thyroid, skin, or a head and neck, or wherein the solid tumor comprises a carcinoma, a sarcoma, or a glioblastoma.

4. The method of claim 1, wherein the cancer is metastatic.

5. The method of claim 1, wherein the DLL3 targeting trispecific protein is administered to the subject in combination with an anti-cancer agent, an anti-diarrheal agent, an anti-emetic agent, an analgesic, an opioid, a non-steroidal anti-inflammatory agent, or a combination thereof.

6. A method of treating a cancer overexpressing a DLL3 protein in a subject in need thereof, comprising administering to the subject an effective amount of a DLL3 targeting trispecific protein that comprises an amino acid sequence that is at least 80% identical to an amino acid sequence of SEQ ID No. 1890 or SEQ ID No. 1891, and wherein the DLL3 targeting trispecific protein comprises a single domain antibody that specifically binds to DLL3, and wherein the single domain antibody comprises a CDR1 that has the amino acid sequence of SEQ ID No. 874, a CDR2 that has the amino acid sequence of SEQ ID No. 1316, and a CDR3 that has the amino acid sequence of SEQ ID No. 1758.

7. The method of claim 6, wherein the cancer comprises a solid tumor.

8. The method of claim 7, wherein the solid tumor comprises a tumor of an adrenal gland, liver, kidney, bladder, breast, gastric, ovary, cervix, uterus, esophagus, colorectum, prostate, pancreas, lung, thyroid, skin, or a head and neck, or wherein the solid tumor comprises a carcinoma, a sarcoma, or a glioblastoma.

9. The method of claim 6, wherein the cancer is metastatic.

10. The method of claim 6, wherein the DLL3 targeting trispecific protein is administered to the subject in combination with an anti-cancer agent, an anti-diarrheal agent, an anti-emetic agent, an analgesic, an opioid, a non-steroidal anti-inflammatory agent, or a combination thereof.

11. A method of treating a cancer overexpressing a DLL3 protein in a subject in need thereof, comprising administering to the subject an effective amount of a DLL3 single domain antibody that comprises a CDR1 that has the amino acid sequence of SEQ ID No. 874, a CDR2 that has the amino acid sequence of SEQ ID No. 1316, and a CDR3 that has the amino acid sequence of SEQ ID No. 1758.

12. The method of claim 11, wherein the DLL3 single domain antibody comprises a sequence that is at least 80% identical to the amino acid sequence of SEQ ID No. 432.

13. The method of claim 11, wherein the cancer comprises a solid tumor.

14. The method of claim 13, wherein the solid tumor comprises a tumor of an adrenal gland, liver, kidney, bladder, breast, gastric, ovary, cervix, uterus, esophagus, colorectum, prostate, pancreas, lung, thyroid, skin, or a head and neck, or wherein the solid tumor comprises a carcinoma, a sarcoma, or a glioblastoma.

15. The method of claim 11, wherein the cancer is metastatic.

16. The method of claim 11, wherein the DLL3 single domain antibody is administered to the subject in combination with an anti-cancer agent, an anti-diarrheal agent, an anti-emetic agent, an analgesic, an opioid, a non-steroidal anti-inflammatory agent, or a combination thereof.

17. A method of treating a cancer overexpressing a DLL3 protein in a subject in need thereof, comprising administering to the subject an effective amount of a DLL3 targeting trispecific protein that comprises:
(a) a first domain (A), which is a single chain variable fragment that specifically binds to a human CD3;
(b) a second domain (B), which is a single domain antibody that specifically binds to a human serum albumin protein; and
(c) a third domain (C), which is a single domain antibody that specifically binds to a DLL3 protein, wherein the third domain (C) comprises a CDR1 that has the amino acid sequence of SEQ ID No. 874, a CDR2 that has the amino acid sequence of SEQ ID No. 1316, and a CDR3 that has the amino acid sequence of SEQ ID No. 1758;
wherein the cancer comprises a tumor of an adrenal gland, liver, kidney, bladder, breast, gastric, ovary, cervix, uterus, esophagus, colorectum, prostate, pancreas, lung, thyroid, skin, or a head and neck, or wherein the cancer comprises a carcinoma, a sarcoma, or a glioblastoma.

18. The method of claim 17, wherein the DLL3 targeting trispecific protein is administered to the subject in combination with an anti-cancer agent, an anti-diarrheal agent, an anti-emetic agent, an analgesic, an opioid, a non-steroidal anti-inflammatory agent, or a combination thereof.

19. The method of claim 17, wherein the domains are linked in the order $H_2N$-(A)-(B)—(C)—COOH, $H_2N$-(A)-(C)—(B)—COOH, $H_2N$—(B)-(A)-(C)—COOH, $H_2N$—(B)—(C)-(A)-COOH, $H_2N$—(C)—(B)-(A)-COOH, or $H_2N$—(C)-(A)-(B)—COOH, or by linkers L1 and L2, in the order $H_2N$-(A)-L1-(B)-L2-(C)—COOH, $H_2N$-(A)-L1-(C)-L2-(B)—COOH, $H_2N$—(B)-L1-(A)-L2-(C)—COGH, $H_2N$—(B)-L1-(C)-L2-(A)-COOH, $H_2N$—(C)-L1-(B)-L2-(A)-COOH, or $H_2N$—(C)-L1-(A)-L2-(B)—COOH.

20. The method of claim 19, wherein the linkers L1 and L2 are each, independently, selected from the group consisting of $(GS)_n$ (SEQ ID No. 1809), $(GGS)_n$ (SEQ ID No. 1810), $(GGGS)_n$ (SEQ ID No. 1811), $(GGSG)_n$ (SEQ ID No. 1812), $(GGSGG)_n$ (SEQ ID No. 1813), and $(GGGGS)_n$ (SEQ ID No. 1814), wherein n is 1, 2, 3, 4, 5, 6, 7, 8, 9, or 10; or wherein the linkers L1 and L2 each, independently comprise the sequence of GGGGSGGGS (SEQ ID No. 1808).

* * * * *